(12) United States Patent
Liu et al.

(10) Patent No.: US 9,085,605 B2
(45) Date of Patent: Jul. 21, 2015

(54) CHEMICAL SYNTHESIS AND ANTI-TUMOR AND ANTI-METASTATIC EFFECTS OF DUAL FUNCTIONAL CONJUGATE

(75) Inventors: Gang Liu, Xuanwu District Beijing (CN); Nan Zhao, Xuanwu District Beijing (CN); Yao Ma, Xuanwu District Beijing (CN)

(73) Assignee: Shenzhen Salubris Pharmaceuticals Co., Ltd., Guangdong Province (CN)

( * ) Notice: Subject to any disclaimer, the term of this patent is extended or adjusted under 35 U.S.C. 154(b) by 0 days.

(21) Appl. No.: 13/699,869

(22) PCT Filed: May 27, 2011

(86) PCT No.: PCT/CN2011/074817
§ 371 (c)(1),
(2), (4) Date: Feb. 11, 2013

(87) PCT Pub. No.: WO2011/147330
PCT Pub. Date: Dec. 1, 2011

(65) Prior Publication Data
US 2013/0143826 A1 Jun. 6, 2013

(30) Foreign Application Priority Data
May 27, 2010 (CN) .......................... 2010 1 0184541

(51) Int. Cl.
| | | |
|---|---|---|
| A61K 38/06 | (2006.01) | |
| A61K 38/07 | (2006.01) | |
| C07K 5/02 | (2006.01) | |
| A61K 31/337 | (2006.01) | |
| A61K 47/48 | (2006.01) | |
| C07D 405/12 | (2006.01) | |
| C07D 409/12 | (2006.01) | |
| C07D 305/14 | (2006.01) | |

(52) U.S. Cl.
CPC ............. *C07K 5/0215* (2013.01); *A61K 31/337* (2013.01); *A61K 47/48023* (2013.01); *A61K 47/48038* (2013.01); *A61K 47/48338* (2013.01); *C07D 305/14* (2013.01); *C07D 405/12* (2013.01); *C07D 409/12* (2013.01)

(58) Field of Classification Search
CPC ....................................................... A61K 38/00
See application file for complete search history.

(56) References Cited

U.S. PATENT DOCUMENTS

| | | | |
|---|---|---|---|
| 4,317,771 | A | 3/1982 | Shiba et al. |
| 4,606,857 | A | 8/1986 | Hasegawa et al. |
| 4,801,578 | A | 1/1989 | Monsigny et al. |
| 6,191,290 | B1 | 2/2001 | Safavy |
| 7,459,281 | B2 | 12/2008 | Salamone et al. |
| 2005/0143446 | A1 | 6/2005 | Holton |
| 2005/0182098 | A1 | 8/2005 | Holton et al. |
| 2005/0280268 | A1 | 12/2005 | Dehn et al. |
| 2006/0236763 | A1 | 10/2006 | Terada et al. |
| 2007/0120295 | A1 | 5/2007 | Zeyfang et al. |
| 2007/0249707 | A1 | 10/2007 | Holton |
| 2010/0099644 | A1 | 4/2010 | Lee et al. |

FOREIGN PATENT DOCUMENTS

| | | |
|---|---|---|
| CN | 1609118 A | 4/2005 |
| CN | 1712399 A | 12/2005 |
| WO | WO94/00156 A1 | 1/1994 |
| WO | WO97/10259 A1 | 3/1997 |
| WO | WO2008/080291 A1 | 7/2008 |
| WO | WO2008/107174 A1 | 9/2008 |
| WO | WO2009/111271 A1 | 9/2009 |
| WO | WO2010/091650 A1 | 8/2010 |

OTHER PUBLICATIONS

Gang Iiu, Chemical and biological research of anti-tumor drug paclitaxel and immunoenhancer muramyl dipeptide conjugate. Chinese Doctoral Dissertation & Master's Thesis Full-text Database (Doctor) Medicine and Health Science, Nov. 15, 2006.*
Sporn et at., Chemoprevention of Cancer, Carcinogenesis, 2000, vol. 21, 525-530.*
Auerbach et al., Cancer and Metastasis Reviews, 2000, 19, pp. 167-172.*
Gura, Science, 1997, 278 (5340): 1041-1042, encloses 1-5.*
Jain, Scientific American, Jul. 1994, 58-65.*
Cancer Druq Design and Discovery Neidle, Stephen, ed. (Elsevier/Academic Press, 2008) p. 431.*
Liu et al., CN1712399, published on Dec. 28, 2005, English abstract translation.*
Paclitaxel, European Pharmacopoeia 7.0 Jan. 2009: 1794, p. 2657.
Docetaxel Trihydrate, European pharmacopoeia 7.0, Jan. 2010:2449, p. 1881-1882.
A. Galelli, P. Lefrancier, and L. Chedid; Colony-stimulating activity induced by synthetic muramyl peptides: variation with chemical structure and association with anti-infectious activity; Infection and Immunity; 1984, 46, 495-500.
A. H. Ding, F. Porteu, E. Sanchez, and C.F. Nathan; Shared actions of endotoxin and taxol on TNF receptors and TNF release; Science; 1990, 20, 370-372.
A. M. Kolodziejczyk, A. S. Kolodziejczyk, S. Stoev; New convenient synthesis of immunostimulating peptides containingmeso-diaminopimelic acid Syntheses of FK-565 and FK-156; International Journal of Peptide and Protein Research; 1992, 39(4), 382-387.

(Continued)

*Primary Examiner* — Marcela M Cordero Garcia
*Assistant Examiner* — Kaipeen Yang
(74) *Attorney, Agent, or Firm* — Finnegan, Henderson, Farabow, Garrett & Dunner, LLP

(57) ABSTRACT

The present invention discloses chemical synthesis, anti-tumor and anti-metastatic effects of a dual functional conjugate as shown by formula I. Specifically, paclitaxel or docetaxol is linked with muramyl dipeptide derivative to form a conjugate, thus dual anti-tumor and anti-metastatic effects are achieved by combination of chemotherapy and immunotherapy. The present invention also discloses that paclitaxel or docetaxol and muramyl dipeptide derivative conjugate is synthesized by combination of solid-phase and solution-phase synthesis, and said conjugate can be used in manufacture of anti-tumor medicaments as proved by reliable bioassays.

35 Claims, 35 Drawing Sheets

(56) References Cited

OTHER PUBLICATIONS

Adam A., Lederer E.; Muramyl peptides: immunomodulators, sleep factors, and vitamins; Med. Res. Rev., 1984, 4(2), 111-152.
Adam A., Petit J. F., Chedid L.; Influence of a synthetic adjuvant (MDP) on qualitative and quantitative changes of serum globulins; Immunology; 1978, 35(6), 963-970.
Adam A., Ciorbaru, R., Ellouz, F., Petit, J.F. and Lederer, E.; Adjuvant activity of monomeric bacterial cell wall peptidoglycans; Biochem. Biophys. Res. Commun.; 1974, 56(6), 561-567.
Akihito T. et al.. Muramyl dipeptide-lys stimulates the function of human dendritic cells. Journal of leukocyte Biology, 70(5), 2001, 723-729.
Alexandre A. Vetcher, MarekNapierala, Ravi R. Iyer, Paul D. Chastain, Jack D. Griffith, and Robert D.; Wells sticky DNA, a long GAA•GAA•TTC triplex that is formed intramolecularly, in the sequence of intron 1 of the frataxin gene; J. Biol. Chem.; 2002, 277, 39217-39227.
Allen, J. N.; Moore, S. A.; Wewers, M. D. Taxol enhances butdoes not induce interleukin 1 beta and tumor necrosis factor alphaproduction. J. Lab. Clin. Med. 1993, 122, 374-381.
Almand, B.; Clark, J. I; Nikitina, E.; van Beynen, J.; English,N. R.; Knight, S. C.; Carbone, D. P.; Gabrilovi, D. I. Increasedproduction of immature myeloid cells in cancer patients: a mechanismof immunisuppression in cancer. J. Immunol. 2001, 166, 678-689.
Anton V. Gorbachen, Nancy A. Dilulio, and Robert L.; Fairchild IL-12 augments CD81 T cell development for contact hypersensitivity responses and circumvents Anti-CD154 antibody-mediated inhibition; The Journal of Immunology, 2001, 167, 156-162.
B. Bragg and A. Matus; Phosphorylation determines the binding of microtubule-a-ssociated protein 2 (MAP2) to microtubules in living cells; J. Cell Biol.; 1991, 114 (4), 735-743.
Balkwill, F. TNF-R in promotion and progression of cancer.Cancer Metastasis Rev. 2006, 25, 709-416.
Bhalla, K.; Ibrado, A. M.; Tourkina, E.; Tang, C.; Mahoney,M. E.; Huang, Y. Taxol induced internucleosomal DNA fragmentationassociated with programmed cell. Leukemia 1993, 7, 563-568.
Byrd-Leifer, C. A.; Block, E. F.; Takeda, K. Akira, S.; Ding, A. The role of MyD88 and TLR4 in the LPS-mimetic activity of Taxol. Eur.J. Immunol. 2001, 31, 2448-2457.
C. L. Contel, N. Temime, D. J. Charron, and M.A. Parant; Modulation of lipopolysaccaharide-induced cytokine gene expression in mouse bone marrow-derived macrophages by muramyl dipeptide; The Journal of Immunology; 1993, 150, 4541-4549.
Carboni, J., Singh, C., Tepper, M.; Cancer Institute Workshop on Taxol and Taxus, Alenandria, V. A.; NCI, 1992.
Cassidy, P. B.; Moos, P. J.; Kelly, R. C.; Fitzpatrick, F. A.Cyclooxygenase-2 induction by paclitaxel, docetaxel and taxaneanalogsin human monocytes and murine macrophages: structureactivityrelationships and their implications. Clin. Cancer Res. 2002, 8, 846-855.
Chomel J. J., Simon-Lavoine N., Thouvenot D., Valette M., Choay J., Chedid L., Aymard M.; Prophylatic and therapeutic effects of murabutide in OF1 mice infected with influenza A and B viruses; International Journal of Immunopharmacology; 1985, 7(3), 346-347.
Christian Bogdan and Aihao Ding; Taxol, a microtubule-stabilizing antineoplastic agent, induces expression of tumor necrosis factor a and interleukin-1 in macrophages; Journal of Leukocyte Biology; 1992, 52, 119-121.
David L. Morse, Heather Gray, Claire M. Payne, and Robert J. Gillies; Docetaxel induces cell death through mitotic catastrophe in human breast cancer cells; Mol Cancer Ther; 2005, 4, 1495-1504.
Deborah A. Eppstein, Noelene E. Byars, Anthony C. Allison; New adjuvants for vaccines containing purified protein antigens; Advanced Drug Delivery Reviews 1990, 4, 233-253.
Deutsch, H. M.; Glinski, J. A.; Hernandez, M.; Haugwitz, R. D.;Narayanan, V. L.; Suffness, M.; Zalkow, L. H. Synthesis of congeners andprodrugs. 3. Water-soluble prodrugs of Taxol with potent antitumoractivity. J. Med. Chem. 1989, 32, 788-792.

Diaz-Montero, C. M.; Salem, M. L.; Nishimura, M. I.; Garett-Mayer, E.; Cole, D. J.; Montero, A. J. Increased circulating myeloid-derivedsuppressor cells correlate with clinical cancer stage, metastatictumor burden and doxorubicin-cyclophosphamide chemotherapy. CancerImmunol. Immunother. 2009, 58, 49-59.
Dietrich F. M., Hochkeppel H. K., Lukas B.; Enhancement of host resistance against virus infections by MTP-PE, a synthetic lipophilic muramyl peptide—increased survival in mice and guinea pigs after single drug administration prior to infection, and the effect of MTP-PE on interferon levels in sera and lungs; Int. J. Immunopharmacol; 1986, 8, 931-932.
E. C. A. Darcissac, V. Vidal, M. Guillaume, J. J. Thebault, G. M. Bahr; Clinical tolerance and profile of cyotkine induction in healthy volunteers following the simultaneous administration of IFN-α and the synthetic immunomodulator murabutide; Journal of Interferon and Cytokine Research; 2001, 21(9), 655-661.
Edith C. A. Darcissac, George M. Bahr, Philippe R. Pouillart, Gilles J. Riveau, Monique A. Parant; Selective potentiation of cytokine expression in human whole blood by mirabutide, a muramyl dipeptide analogue; Cytokine, 1996, 8, 658-666.
Ellouz F., Adam A., Ciorbaru R., et al; Minimal structural requirements for adjuvant activity of bacterial peptidoglycan derivatives; Biochem. Biophys. Res. Commun.; 1974, 59, 1319-1325.
F. Audibert, L. Chédid, P. Lefrancier, J. Choay; Distinctive adjuvanticity of synthetic analogs of mycobacterial water-soluble components; Cellular Immunology; 1976, 21, 243-249.
Fitzpatrick, F. A.; Wheeler, R. The immunopharmacologyofpaclitaxel (Taxol), docetaxel (Taxotere), and related agents. Int. Immunopharmacol.2003, 3, 1699-1714.
Gang Iiu, Chemical and biological research of antitumor drug paclitaxel and immunoenhancer muramyl dipeptide conjugate, Chinese Doctoral Dissertation & Master's Thesis Full-text Database (Doctor) Medicine and Health Science, Nov. 15, 2006, 2006, No. 11E079-85, ISSN:1671-6779.
George M. Bahr, Edith Darcissac, Dorian Bevec, Peter Dukor, Louis Chedid; Immunopharmacological activities and clinical development of muramyl peptides with particular emphasis on murabutide; International Journal of Immunopharmacology; 1995 17(2), 117-131.
George M. Bahr, Philippe R. Pouillart, Louis A. Chedid; Enhancement in vivo of the anti-inflammatory and antitumor activities of type I interferon by association with the synthetic immunomodulator murabutide; Journal of Interferon and Cytokine Research; 1996, 16(4), 297-306.
George M. Bahr, Edith Darcissac, Philippe R. Pouillart, Louis A. Chedid; Synergistic effects between recombinant interleukin-2 and the synthetic immunomodulator murabutide: selective enhancement of cytokine release and potentiation of antitumor activity; Journal of Interferon and Cytokine Research; 1996, 16(2), 169-178.
Gilles J. Riveau, Beatrice G. Brunel-Riveau, Francoise M. Audibert, Louis A. Chedid; Influence of a muramyl dipeptide on human blood leukocyte functions and their membrane antigens; Cellular Immunology; 1991, 134, 147-156.
Grown, J.; O' Leary, M. The taxanes: and update. Lancet 2000,355, 1176-1178.
Gupta, G. P.; Massague, J. Cancer metastasis: building a framework. Cell 2006, 127, 679-695.
He, W.; Liu, Q.; Wang, L.; Chen, W.; Li, N.; Cao, X. TLR4signaling promotes immune escape of human lung cancer cells byinducing immunosuppressive cytokines and apoptosis resistance. Mol.Immunol. 2007, 44, 2850-2859.
Hong-Zhen Yang, Song Xu, Xue-Yan Liao, Suo-De Zhang, Zheng-Lun Liang, Bai-He Liu, Jin-Ye Bai, Chao Jiang, Jian Ding, Gui-Fang Cheng, and Gang Liu; A novel immunostimulator, N2-[α-O-Benzyl-N-(acetylmuramyl)-l-alanyl-d-isoglutaminyl]N6-trans-(m-nitrocinnamoyl)-l-lysine, and its adjuvancy on the hepatitis B surface antigen; J. Med. Chem.; 2005, 48(16), 5112-5122.
Horwitz, S. B.; Lothstein, L.; Manfredi, J. J.; Mellado, W.;Parness, J.; Roy, S. N.; Schiff, P. B.; Sorbara, L.; Zeheb, R. Taxol:mechanisms of action and resistance. Ann. N.Y. Acad. Sci. 1986,466, 733-744.

(56) References Cited

OTHER PUBLICATIONS

Huang, B.; Lei, Z.; Zhao, J.; Gong, W.; Liu, J.; Chen, Z.; Liu, Y.;Li, D.; Yuan, Y.; Zhang, G. M.; Feng, Z. H. CCL2/CCR2pathwaymediates recruitment of myeloid suppressor cells to cancers. Cancer Lett.2007, 252, 86-92.

Ichiro Azuma, Tsukasa Seya; Development of immunoadjuvants for immunotherapy of cancer; International Immunopharmacology; 2001, 1(7), 1229-1392.

Joyce, J. A.; Pollard, J.W. Microenvironmental regulation ofmetastasis. Nat. Rev. Cancer 2009, 9, 239-252.

Kawasaki, K.; Akashi, S.; Shimazu, R.; Yoshida, T.; Miyake, K.;Nishijima, M. Mouse Toll-like receptor 4. MD-2 complex mediateslipopolysaccharide-mimetic signal transduction by Taxol. J. Biol. Chem.2000, 275, 2251-2254.

Kenji Namba, Eiko Yamamura, Hironobu Nitanai, Tsuyoshi Otani, Ichiro Azuma; Romurtide, a synthetic muramyl dipeptide derivative, promotes megakaryocytopoiesis through stimulation of cytokine production in nonhuman primates with myelosuppression; Vaccine, 1997, 15(4), 405-413.

Kim, S.; Takahashi, H; Lin, W. W.; Descargues, P.; Grivennikov,S.; Kim, Y.; Luo, J. L.; Karin, M. Carcinoma-produced factors activatemyeloid cells through TLR2 to stimulate metastasis. Nature 2009,457, 102-106.

L. A. Chedid, M. A. Parant, F. M. Audibert, G. J. Riveau, F. J. Parant, E. Lederer, J. P. Choay, and P. L. Lefrancier; Biological activity of a new synthetic muramyl peptide adjuvant devoid of pyrogenicity; Infection and Immunity; 1982, 35, 417-424.

Lee, L. F.; Schuerer-Maly, C. C.; Lofquist, A. K.; van Haaften-Day, C.; Ting, J. P.; White, C. M.; Martin, B. K.; Haskill, J. S. Taxoldependent transcriptional activation of IL-8 expression in a subset ofhuman ovarian cancer. Cancer Res. 1996, 56, 1303-1308.

Li, X.; Yu, J.; Xu, S; Wang, N.; Yang, H.; Yan, Z.; Cheng, G.; Liu,G. Chemical conjugation of muramyl dipeptide and paclitaxel to explorethe combination of immunotherapy and chemotherapy for cancer.Glycoconjugate J. 2008, 25, 415-425.

Liebes L., Walsh C. M., Chachoua A., et al; Modulation of monocyte functions by muramyl triptidephosphatidylethanolamine in a phase II study in patients with metastatic melanoma; J. Natl. Cancer. Inst.; 1992, 84, 694-699.

Mansukhlal C. Wani, Harold Lawrence Taylor, Monroe E. Wall, Philip Coggon, Andrew T. McPhail; Plant antitumor agents. VI. Isolation and structure of taxol, a novel antileukemic and antitumor agent from Taxusbrevifolia; J. Am. Chem. Soc.; 1971, 93(9), 2325-2327.

Manthey, C. L.; Qureshi, N.; Stutz, P. L.; Vogel, S. N. Lipopolysaccharideantagonists block Taxol-induced signaling in murinemacrophages. J. Exp. Med. 1993, 178, 695-702.

Mantovani, A.; Garlanda, C.; Allavena, P. Molecular pathwaysand targets in cancer-related inflammation. Ann. Med. 2010, 42, 161-170.

Mehlen, P.; Puisieux, A. Metastasis: a question of life or death.Nat Rev. Cancer 2006, 6, 449-458.

Meyers Paul A., Schwartz Cindy L., et al; A randomized, prospective trial of the addition of ifosfamide and/or muramyl tripeptide to cisplatin, doxorubicin, and high-dose methotrexate; J. Clin. Oncol.; 2005, 23(9), 2004-2011.

Meyers, P. A. Muramyl tripeptide (mifamurtide) for the treatmentof osteosarcoma. Expert Rev Anticancer Ther. 2009, 9, 1035-1049.

Moos, P. J.; Muskardin, D. T.; Fitzpatrick, F. A. Effect of Taxoland taxotere on gene expression in macrophages: induction of theprostaglandinHsynthase-2 isoenzyme. J. Immunol. 1999, 162, 467-473.

Nardin A. Lefebvre M. L., Labroquere K., Faure O., Abastado J. P.; Liposomal muramyl tripeptide phosphatidylethanolamine: tTargeting and activating macrophages for adjuvant treatment of osteosarcoma; Current Cancer Drug Targets; 2006, 6, 123-133.

P. Walder, E. Buchar, Z. Machková, T. Vrba, M. Flegel, I. Janků, K. Mas'ek; Pharmacokinetic profile of the immunomodulating compound adamantylamide dipeptide(AdDP), a muramyl dipeptide derivative in mice; Immuno-pharmacology and Immunotoxicology, 1991, 13(1 and 2), 101-119.

Pablo D. Becker, Ricardo S. Corral, Carlos A. Guzmán, Saul Grinstein; Adamantylamide dipeptide as effective immunoadjuvant in rabbits and mice; Vaccine; 2001, 19(32), 4579-4903

Parant, M. A.; Audibert, F. M.; Chedid, L. A.; Level, M. R.;Lefrancier, P. L.; Choay, J. P.; Lederer, E. Immunostimulant activities ofa lipophilic muramyl dipeptide derivative and of desmuramylpeptidolipidanalogs. Infect. Immun. 1980, 27, 826-831.

Peter B. Schiff and Susan B. Horwitz; Taxol stabilizes microtubules in mouse fibroblast cells; Proc. Natl. Acad. Sci. USA; 1980, 77(3), 1561-1565.

Philippe R. Pouillart, Francoise M. Audibert, Louis A. Chedid, Pierre L. Lefrancier, George M. Bahr; Enhancement by muramyl peptides of the protective response of interferon-α/β against encephalomyocarditis virus infection; International Journal of Immunopharmacology; 1996, 18(3), 183-192.

Shoemaker, R. H. The NCI60 human tumour cell line anticancerdrug screen. Nat. Rev. Cancer 2006, 6, 813-823.

Sinha, P.; Celemnts, V. K.; Bunt, S. K.; Albelda, S. M.; Ostrand-Resenberg, S. Cross-talk between myeloid-derived suppressor cells andmacrophages subverts tumor immunity toward a type 2 response. J.Immunol. 2007, 179, 977-983.

Steeg, P. S. Tumor metastasis: mechanistic insights and clinicalchallenges. Nat. Med. 2006, 12, 895-904.

Subbaramaiah, K.; Hart, J. C.; Norton, L.; Dannenberg, A. J.Microtubule-interfering agents stimulate the transcription of cyclooxygenase-2. Evidence for involvement of ERK1/2 and p38mitogenactivatedprotein kinase pathways. J. Biol. Chem. 2000,275, 14838-14845.

Szajnik, M.; Szczepanski, M. J.; Czystowska1, M.; Elishaev, E.;Mandapathil, M.; Nowak-Markwitz, E.; Spaczynski, M.; Whiteside1,T. L. TLR4 signaling induced by lipopolysaccharide or paclitaxelregulates tumor survival and chemoresistance in ovarian cancer. Oncogene2009, 28, 4353-4363.

Tosjiyuki Harada, Shigeaki Ogura, Koichi Yamazaki, Ichiro Kinoshita, Tomoolth, Hiroshi Isobe, Katsushige Yamashiro, HitoshiDosaka-Akita, Masaharu Nishimura; Predictive value of expression of P53, Bcl-2 and lung resistance-related protein for response to chemotherapy in non-small cell lung cancers; Cancer Science; 2005, 94(4), 394-399.

Tsavaris, N.; Kosmas, C.; Vadiaka, M.; Kanelopoulos, P. Boulamatsis, D. Immune changes in patients with advanced breastcancer undergoing chemotherapy with taxanes. Br. J. Cancer 2002,87, 21-27.

Wang, A. C.; Su, Q. B.; Wu, F. X.; Zhang, X. L.; Liu, P. S. Role ofTLR4 for paclitaxel chemotherapy in human epitherlial ovarian cancercells. Eur. J. Clin. Invest. 2009, 39, 157-164.

Wang, J.; Kobayashi, M.; Han, M.; Choi, S.; Takano, M.;Hashino, S.; Tanaka, J.; Kondoh, T.; Kawamura, K.; Hosokawa, M.MyD88 is involved in the signalling pathway for Taxol induced apoptosisand TNF-R expression in human myelomonocytic cells. Br. J. Haematol. 2002, 118, 638-645.

Wani, M. C.; Taylor, H. L.; Wall, M. E.; Coggon, P.; McPhail,A. T. Plant antitumor agents. VI. Isolation and structure of Taxol, a novelantileukemic and antitumor agent from Taxusbrevifolia. J. Am. Chem.Soc. 1971, 93, 2325-2327.

Watson, J. M.; Kingston, D. G.; Chordia, M. D.; Chaudhary,A. G.; Rinehart, C. A.; Haskill, J. S. Identification of the structural regionof Taxol that may be responsible for cytokine gene induction andcytotoxicity in human ovarian cancer cells. Cancer Chemother. Pharmacol.1998, 41, 391-397.

WolfertMargreet A. et al.. The origin of the synergistic effect of muramyl dipeptide with endotoxin and peptidoglycan. J. Bio. Chem. 277(42), 2002, 39179-39186.

Wu, Y.; Zhou, B. P. Inflammation: a driving force speeds cancermetastasis. Cell Cycle 2009, 8, 3267-3273.

Wu,Y.; Zhou, B. P. TNF-a/NF-kB/Snail pathway in cancer cellmigration and invasion. Br. J. Cancer 2010, 102, 639-644.

Y. Osada, T. Otani, M. Sato, t. Une, K. Matsumoto, and H. Ogawa; Polymorphonuclear leukocyte activation by a synthetic muramyl dipeptide analog; Infection and Immunity; 1982, 38, 848-854.

(56) References Cited

OTHER PUBLICATIONS

Yang, L.; DeBusk, L. M.; Fukada, K.; Fingleton, B.; Green-Jarvis, B.; Shyr, Y.; Matrisian, L. M.; Carbone, D. P.; Lin, P. C. Expansionof myeloid immune suppressor Gr♭ CD11b♭ cells in tumor-bearinghost directly promotes tumor angiogenesis. Cancer Cell 2004,6, 409-421.

Yang, L.; Huang, J.; Ren, X.; Gorska, A. E.; Chytil, A.; Aakre, M.;Carbone, D. P.; Matrisian, L. M.; Richamond, A.; Lin, P. C.; Moses, H.L.Abrogation of TGF-β signaling in mammary carcinomas recruits Gr-1♭ CD11b♭ myeloid cells that promote metastasis. Cancer Cell 2008, 13, 23-25.

Young, M. R.; Lathers, D. M. Myeloid progenitor cells mediateimmune suppression in patients with head and neck cancers. Int. J.Immunopharmacol. 1999, 21, 241-252.

Yu Q, Gao J. X., He X. S., et a1; Docetaxcel induces apoptosis and regulates expressions of bax an d bcl-2 protein in human breast carcinoma MCF-7 Cells;Cancer Res. Pre. Treatment, 2006, 33(6), 388-390.

Zaks-Zilberman, M.; Zaks, T. Z.; Vogel, S. N. Induction of proinflammatory and chemokine genes by lipopolysaccharide andpaclitaxel (Taxol) in murine and human breast cancer cell lines. Cytokine2001, 15, 156-165.

Bhattacharya, D.; Thio, C. L. Review of Hepatitis B Therapeutics. Clin. Infect. Dis. 2010, 51, 1201.

Marie-Louise, M.; Qiang, D.; Maryline, M. B. Therapeutic vaccines and immune-based therapies for the treatment of chronic hepatitis B: Perspectives and challenges. J. Hepatol. 2011, 54, 6, 1286.

Singh, M.; O' Hagan, D. Advances in vaccine adjuvants. Nat. Biotechnol. 1999, 17, 1075.

Hui, C. K.; Lau, G. K. K. Advances in immunomodulating therapy of HBV invection, Int. J. Med. Sci. 2005, 2, 24.170.

Kotani, S.; Watanabe, Y.; Kinoshita, F.; Shimono, T.; Morisaki, I.; Shiba, T.;Kusumoto, S.; Tarumi, Y.; Ikenaka, K. Biken J. Immunoadjuvant activities of synthetic N-acetyl-muramyl-peptides or -amino acids. 1975, 18, 105.

Carelli, C.; Audibert, F.; Chedid, L. Persistent enchancement of cell-mediated and antibody immune responses after administration of muramyl dipeptide derivatives with antigen in metabolizable oil. Infect. Immun. 1981, 33, 312.

Riveau, G.; Masek, K.; Parant, M.; Chedid, L.Central pyrogenic activity of muramyl dipeptide. J. Exp. Med. 1980, 152, 869.

Ghada, M.; Anthony, W. C.; Jean-Philippe, D.; Gillian, M. B. Synthesis and Immunostimulating Properties of Lipophilic Ester and Ether Muramyl Peptide Derivatives. J. Med. Chem. 1996,39, 4483.

Parant, M.; Parant, F.; Chedid, L.; Yapo, A.; Petit, J. F.; Lederer, E.Fate of the synthetic immunoadjuvant, muramyl dipeptide (14C-labelled) in the mouse. Int. J.Immunopharmacol. 1979, 1, 35.

Chen, Y. Z.; Liu, G.; Senju, S.; Wang, Q.; Irie, A.; Haruta, M.; Matsui, M.; Yasui, F.;Kohara, M.; Nishimura, Y. Improved electrical performance of NILC poly-Si TFTs manufactured using H2SO4 and HCI solution. Int. J. Immunopathol. Pharmacol. 2010, 23, 165.

Pristovsek, P.; Kidric, J.; Hadzi, D. Proposal of a 3D Peptide Pharmacophore of Muramyl Dipeptide-Type Immunostimulants. 1. Conformational Search of Active and Inactive Analogues. J. Chem. Inf. Comput. Sci. 1997, 37, 971.

Pristovsek, P.; Kidric, J.; Hadzi, D.Bioactive Conformations of Small Peptides: A Method for Selection of Candidates Based on Conformations of Active and Inactive Analogs and Its Application to Muramyl Dipeptide. J. Chem. Inf. Comput. Sci. 1995, 35, 633.

Inohara, N.; Ogura, Y.; Fontalba, A.; Gutierrez, O.; Pons, F.; Crespo, J.; Fukase, K.;Inamura, S.; Kusumoto, S.; Hashimoto, M.; Foster, S. J.; Moran, A. P.; Fernandez-Luna, J. L.; Nunez, G.Host Recognition of Bacterial Muramyl Dipeptide Mediated through NOD2. J. Biol. Chem. 2003, 278, 5509.

Giradin, S. E.; Boneca, I. G.; Viala, J.; Chamaillard, M.; Labigne, A.; Thomas, G.;Philpott, D. J.; Sansonetti, P. J. Nod2 Is a General Sensor of Peptidoglycan through Muramyl Dipeptide (MDP) . J. Biol. Chem. 2003, 278, 8869.

Kobiyashi, K. S.; Chamaillard, M.; Ogura, Y.; Henegariu, O.; Inohara, N.; Nunez,G.; Flavell, R. A. Nod2-Dependent Regulation of Innate and Adaptive Immunity in the Intestinal Tract.Science 2005, 307, 731.

Uehori, J.; Fukase, K.; Akazawa, T.; Uematsu, S.; Akria, S.; Funami, K.; Shingai,M.; Matsumoto, M.; Azuma, I.; Toyohsima, K.; Kusumoto, S.; Seya, T.Dendritic cell maturation induced by muramyl dipeptide (MDP) derivatives: MonoacylatedMDP confers TLR2/TLR4 activation. J. Immunol.2005, 174, 7096.

Fidler, I.J., Kleinerman, E.S.: Therapy of cancer metastasis bysystemic activation of macrophages: from the bench to the clinic. Res. Immunol. 144, 284-298 (1993).

Killion, J.J., Fidler, I.J.: Therapy of cancer metastasis by tumoricidalactivation of tissue macrophages using liposome-encapsulatedimmunomodulators. Pharmacol. Ther. 78, 141-154 (1998).

Georg, G.I., Chen, T.T., Ojima, I., Wyas, D.M., (eds.): TaxaneAnticancer Agents: Basic Science and Current Status. (Developedfrom Symposia sponsored by the Divisions of Chemical Healthand Safety, Medicinal Chemistry, and Organic Chemistry at the207th National Meeting of the American Chemical Society, SanDiego, California, Mar. 13-17, 1994.) [In: ACS Symp. Ser., 1995; 583], pp. 353.

Schiff, P.B., Fant, J., Horwithz, S.B.: Promotion of microtubuleassembly in vitro by taxol. Nature 277, 665-667(1979).

Ding, A.H., Porteu, F., Sanchez, E., Nathan, C.F.: Shared actionsof endotoxin and taxol on TNF receptors and TNF release.Science 248, 370-372(1990).

Kikelj, D., Pecar, S., Kotnik, V., Stalc, A., Wraber-Herzog, B.,Simci, S., Ihan, A., Klamfer, L., Povsic, L., Grahek, R., Suhadolc, E.,Hocevar, M., Hoenig, H., Rogi-Kohlenprath, R.: N-{trans-2-[[2'-(Acetylamino)cyclohexyl]oxy]acetyl}-L-alanyl-D-glutamic acid: anovel immunologically active carbocyclic muramyl dipeptide analog.J. Med. Chem. 41, 530-539 (1998).

Inohara, N., Ogura Y ., Fontalba, A., Gutierrez, O., Pons, F.,Crespo, J., Fukase, K., Inamura, S., Kusumoto, S., Hashimoto,M., Foster, S.J., Moran, A.P., Fernandez-Luna, J.L., Nunez, G.:Host recognition of bacterial muramyl dipeptide mediated throughNOD2. Implications for Crohn's disease. J. Biol. Chem. 278,5509-5512 (2003).

Uehara, A., Yang, S., Fujimoto, Y., Fukase, K., Kusumoto, S.,Shibata, K., Sugawara, S., Takada, H.: Muramyldipeptideanddiaminopimelic acid-containing desmuramylpeptides in combinationwith chemically synthesized toll-like receptor agonistssynergistically induced production of interleukin-8 in a NOD2-and NOD1-dependent manner, respectively, in human monocyticcells in culture. Cell. Microbiol. 7, 53-61 (2005).

Uehara, A., Sugawara, Y., Kurata, S., Fujimoto, Y., Fukase, K.,Kusumoto, S., Satta, Y., Sasano, T., Sugawara, S., Takada, H.:Chemically synthesized pathogen-associated molecular patternsincrease the expression of peptidoglycan recognition proteins viatoll-like receptors, NOD1 and NOD2 in human oral epithelialcells. Cell. Microbiol. 7, 675-686(2005).

Yang, S., Tamai, R., Akashi, S., Takeuchi, O., Akira, S.,Sugawara, S., Takada, H.: Synergistic effect of muramyldipeptidewith lipopolysaccharide or lipoteichoic acid to induce inflammatorycytokines in human monocytuc cells in culture. Infect.Immun. 69, 2045-2053 (2001).

Traub, S., Kubasch, N., Morath, S., Kresse, M., Hartung, T.,Schmidt, R.R., Hermann, C.: Structural requirements of syntheticmuropeptides to synergize with lipopolysaccharide in cytokineinduction. J. Biol. Chem. 279, 8694-8700 (2004).

Liu, G., Zhang, S.D., Xia, S.Q., Ding, Z.K.: Solid-phase synthesisof muramyl dipeptide (MDP) derivatives using a multipinmethod. Bioorg. Med. Chem. Lett. 10, 1361-1363 (2000).

Zhang, S.D., Liu, G., Xia, S.Q., Wu, P., Zhang, L.: "Meshed-bag-gathered-bunch" method for solid-phase synthesis of smallmolecular diverse compounds. J. Comb. Chem. 4, 131-137(2002).

Nicolaou, K.C., Dai, W.M., Guy, R.K.: Chemistry and biology oftaxol. Agnew. Chem., Int. Ed. Engl. 33, 15-44 (1994).

Ojima, I., Lin, S., Slater, J.C., Wang, T., Pera, P., Bernacki, R.J.,Ferlini, C., Scambia, G.: Syntheses and biological activity of C-3'-difluoromethyl-taxoids. Bioorg. Med. Chem. 8, 1619-1628 (2000).

(56) References Cited

OTHER PUBLICATIONS

Kingston, D.G.I.: Recent advances in the chemistry of taxol. J.Nat. Prod. 63, 726-734 (2000).

Ojima, I., Lin, S., Wang, T.: Recent advances in the medicincalchemistry of taxoids with novel beta-amino acid side chains. Curr.Med. Chem. 6, 927-954 (1999) http://www.google.cn/books?hl=zh-CN&lr=&id=dzJ6W8waltAC&oi=fnd&pg=PA927&dq=Recent+advances+in+the+medicinal+chemistry+of+taxoids+with+novel+amino+acid+side+chains&ots=19IN5AqQvW&sig=VIHA__rwxlQjCwQtDaSayBOzvU24&redir_esc=y.

Matsumoto, K., Ogawa, H., Kusama, T., Nagase, O., Sawaki, N.,Inage, M., Kusumoto, S., Shiba, T., Azuma, I.: Stimulation ofnonspecific resistance to infection induced by 6-O-acyl muramyldipeptide analogs in mice. Infect. Immun. 32, 748-785(1981).

Azuma, I., Okumura,H., Saiki, I., Kiso, M., Hasegawa, A., Tanio, Y., Yamamura, Y.: Adjuvant activity of carbohydrate analogs of Nacetylmuramyl-L-alanyl-D-isoglutamine on the induction ofdelayed-type hypersensitivity to azobenzenearsonate-N-acetyl-Ltyrosine guinea pigs. Infect. Immun. 33, 834-839(1981).

Yang, H.Z., Xu, S., Liao, X.Y., Zhang, S.D., Liang, Z.L., Liu, B.H. ,Bai, J.Y., Jiang, C., Ding, J., Cheng, G.F., Liu, G.: A novelimunostimulator, N2-[α-O-Benzyl-N-(acetylmuramyl)-L-alanyl-D-isoglutaminyl]-N6-trans-(m-nitrocinnamoyl)-L-lysince, and itsadjuvancy on the hepatitis B surface antigen. J. Med. Chem. 48,5112-5122 (2005).

Bourzat, J.D., Commercon, A.: A practical access to chrialphenylisoserinates, preparation of Taxotere analogs. Tetrahedron Lett. 34, 6049-6052 (1993).

Lin, S., Fang, K., Hashimoto, M., Nakanishi, K., Ojima, I.:Design and synthesis of a novel photoaffinity taxoid as a potentialprobe for the study of paclitaxel-microtubules interactions. TetrahedronLett. 41, 4287-4290 (2000).

Gross, P.H., Rimpler, M.: Muramyl peptides. 1. Stereochemicallypure derivatives on muramic and isomuramic acids. LiebigsAnn. Chem. 1, 37-45 (1986).

Denis, J.N., Greene, A.E., Guenard, D., Gueritte-Voegelein, F.,Mangatal, L., Potier, P.: Highly efficient, practical approach tonatural taxol. J. Am. Chem. Soc. 110, 5917-5919(1988).

English abstract for CN1712399A, 2005.

English abstract for CN1609118A, 2005.

English abstract: Gang Iiu, Chemical and biological research of anti-tumor drug paclitaxel and immunoenhancer muramyl dipeptide conjugate, Chinese Doctoral Dissertation Master's Thesis Full-text Database (Doctor) Medicine and Health Science, Nov. 15, 2006, No. 11E079-85, ISSN:1671-6779.

\* cited by examiner

| National Cancer Institute Developmental TherapeuticS Program In-Vitro Test Results In-Vitro | | | | | | | | | | | | | | |
|---|---|---|---|---|---|---|---|---|---|---|---|---|---|---|
| NSC: D – 747905/1 | | | Experiment ID: 0808NS92 | | | | | | Test Type: 08 | | | Units: molar | | |
| Report Date : 5 October 2008 | | | Test date: 18 August 2008 | | | | | | QNS : | | | MC : | | |
| COMI : T-M-220 (75984) | | | Stain reagent: SRB Dual-Pass Related | | | | | | SSPL | | OX3W | | | |
| Concentration Log10 | | | | | | | | | | | | | | |
| | Time | | Mean optical densities | | | | | Percent Growth | | | | | | |
| Panel / cell line | Zero | Control | -8.5 | -7.5 | 6.5 | -5.5 | -4.5 | -8.5 | -7.5 | -6.5 | 5.5 | -4.5 | GI50 | TGI | LC50 |
| Leukemia | | | | | | | | | | | | | | | |
| CCRF-CEM | 0.221 | 1.127 | 0.291 | 0.283 | 0.246 | 0.229 | 0.243 | 8 | 7 | 3 | 1 | 4 | <1.04E-8 | >3.25E-5 > | 3.25E-5 |
| HL-60(TB) | 0.702 | 2.368 | 0.634 | 0.738 | 0.592 | 0.571 | 0.625 | -10 | 2 | -16 | -19 | -18 | <8.93E-9 | 3.06E-8 > | 3.25E-5 |
| K-562 | 0.148 | 1.177 | 0.236 | 0.311 | 0.188 | 0.155 | 0.164 | 9 | 15 | 4 | 2 | 3 | <9.66E-9 | >3.25E-5 > | 3.25E-5 |
| MOLT-4 | 0.328 | 1.109 | 0.601 | 0.732 | 0.510 | 0.421 | 0.380 | 35 | 52 | 23 | 12 | 10< | <1.88E-8 | >3.25E 5 > | 3.25E-5 |
| RPMI-8226 | 0.349 | 1.043 | 0.343 | 0.334 | 0.304 | 0.283 | 0.278 | -2 | -4 | 1-3 | .-19 | -10 | <6.60E-9 | 1 67E-6 > | 3.25E-5 |
| SR | 0.224 | 0.475 | 0.230 | 0.234 | 0.206 | 0.196 | 0.195 | 2 | 4 | -8 | -13 | 2 | <3.253E-9 | . > | 3.25E-5 |
| Non-small cell lung cancer | | | | | | | | | | | | | | | |
| A549/ATCC | 0.185 | 1.105 | 0.927 | 0.418 | 0.353 | 0.343 | 0.318 | 81 | 25 | 18 | 17 | 14 | 1.16E-8 | >3.25E-5 > | 3.25E-5 |
| EKVX | 0.578 | 1.721 | 1.617 | 1.126 | 0.979 | 1 039 | 1 051 | 91 | 48 | 35 | 40 | 41 | 2 91E-8 | >3.25E-5 > | 3 25E-5 |
| HOF-62 | 0.861 | 1.564 | 1.509 | 1.367 | 1.110 | 1.072 | 1.094 | 92 | 72 | 35 | 30 | 33 | 1.30E-7 | >3.25E-5 > | 3.25E-5 |
| NCI-H226 | 0.835 | 1.587 | 1.520 | 1.396 | 1.212 | 1.308 | 1.272 | 91 | 75 | 50 | 63 | 58 | >3.25E-5 | >3.25E-5 > | 3.25E-5 |
| NCI-H23 | 0.711 | 1.834 | 1.763 | 1.100 | 1.041 | 1.101 | 1.000 | 94 | 35 | 29 | 35 | 26 | 1.79E-8 | >3.25E-5 > | 3.25E-5 |
| NCI-H322M | 0.603 | 1.495 | 1.467 | 0.847 | 0.830 | 0.787 | 0.808 | 97 | 27 | 25 | 21 | 23 | 1.54E-8 | >3.25E-5 > | 3.25E-5 |
| NCI-H460 | 0.201 | 1.566 | 1.291 | 0.372 | 0.256 | 3.253 | 0.242 | 80 | 12 | 5 | 5 | 3 | 9.01 E-9 | >3 25E-5 > | 3.25E-5 |
| NCI H522 | 0.423 | 1.460 | 1.234 | 0.549 | 0 511 | 0.498 | 0.461 | 78 | 12 | 8 | 7 | 4 | 8.67E 9 | >3 25E-5 > | 3.25E-5 |
| Colon Cancer | | | | | | | | | | | | | | | |
| COLO 205 | 0.302 | 0.923 | 0.836 | 0.249 | 0.184 | 0.190 | 0.155 | 86 | -18 | -39 | -37 | -49 | 7.22E-9 | 2 19E-8 > | 3.25E-5 |
| HCC-2998 | 0.459 | 1.314 | 1.108 | 0.535 | 0.369 | 0.476 | 0.533 | 76 | 9 | -20 | 2 | 9 | 7.91 E-9 | > | 3.25E-5 |
| HCT-116 | 0.214 | 1.609 | 1.146 | 0.308 | 0.266 | 0.268 | 0.247 | 67 | 7 | 4 | 4- | 2 | 6.19E-9 | >3.25E-5 > | 3.25E-5 |
| HCT-15 | 0.283 | 1.346 | 1.290 | 1.171 | 0.858 | 0.466 | 0.448 | 95 | 84 | 54 | 17 | 15 | 4.10E-7 | >3.25E-5 > | 3.25E-5 |
| HI29 | 0.220 | 1.349 | 0.866 | 0.282 | 0 .232 | 0.228 | 0.190 | 57 | 5 | 1 | 1 | -14 | 4.49E-9 | 3.62E-6 > | 3.25E-5 |
| KM12 | 0.208 | 0.966 | 0.767 | 0.258 | 0.202 | 0.226 | 0.181 | 72 | 6 | -3 | 2 | -13 | 7.00C-9 | > | 3.25E-5 |
| SW-520 | 0.182 | 1.212 | 0.986 | 0.537 | 0 531 | 0 604 | 0 565 | 78 | 34 | 34 | 41 | 37 | 1 43E-8 | >3.25E-5 > | 3 25E-5 |
| CNS cancer | | | | | | | | | | | | | | | |
| SF-268 | 0.380 | 1.123 | 0.986 | 0.639 | 0.550 | 0.538 | 0.516 | 82 | 35 | 23 | 21 | 18 | 1.54E-8 | >3.25E-5 > | 3.25E-5 |
| SF-295 | 0.624 | 2.176 | 2.378 | 1.371 | J.747 | 0.712 | 0.692 | 94 | 48 | 8 | 6 | 4 | 2.95E-8 | >3.25E-5 > | 3.25E-5 |
| SF-530 | 0.774 | 1.923 | 1.772 | 0.881 | 0.400 | 3.400 | 0.440 | 87 | 9 | -37 | -37 | -43 | 9.70E-9 | 5.17E-8 > | 3.25E-5 |
| SNB-19 | 0.638 | 1.644 | 1.551 | 1.157 | 3.887 | 0.918 | U.844 | 91 | 52 | 25 | 28 | 20 | 3.72E-8 | >3.25E-5 > | 3.25E-5 |
| SNB-75 | 0.560 | 1.070 | 0.358 | 0.500 | 0.337 | 0.374 | 0.403 | 57 | -u | -42 | -36 | -31 | 4.04E-9 | 2.07E-0 > | 3.20E-5 |
| U251 | 0 213 | 0 988 | 0 816 | 0 377 | 0 328 | 0 316 | 0.325 | 78 | 20 | 15 | 13 | 14 | 9 92E-9 | >3 ?5E-5 > | 3.25E-5 |
| Melanoma | | | | | | | | | | | | | | | |
| LOX IMVI | 0.254 | 1.326 | 0.944 | 0.540 | 0.522 | 0.600 | 0.628 | 64 | 27 | 25 | 32 | 35 | 7.81E-9 | >3 25E-5 > | 3.25E-5 |
| MAUVE-3M | 0.450 | 0.737 | 0.696 | 0.674 | 0.552 | 0.587 | 0.610 | 86 | 78 | 36 | 48 | 56 | | >3 25E-5 > | 3.25E-5 |
| M14 | 0.435 | 1.536 | 1.352 | 0.703 | 0.285 | 0.469 | 0.582 | 83 | 24 | -35 | 3 | 13 | 1.19E-8 | > | 3.25E-5 |
| SK-MEL-2 | 0.569 | 1.431 | 1.334 | 0.660 | 0.573 | 0.642 | 0.654 | 89 | 11 | , | 8 | 10 | 1.02E-8 | >3 25E-5 > | 3.25E-5 |
| SK-MEL-28 | 0.364 | 1.004 | 0.939 | 0.684 | 0.706 | 0.762 | 0.717 | 90 | 50 | 53 | 62 | 55 | | >3 25E 5 > | 3.25E-5 |
| SK-MEL-5 | 0.867 | 2.704 | 2.741 | 1.760 | 1.236 | 1.329 | 1.201 | 102 | 49 | 20 | 25 | 18 | 3.06E-8 | >3 25E-5 > | 3.25E-5 |
| UACC-257 | 0.549 | 1.275 | 1.165 | 0.885 | 0.898 | 0.922 | 0.887 | 85 | 46 | 48 | 51 | 47 | | >3 25E-5 > | 3.25E-5 |
| UACC-62 | 0.590 | 1'.736 | 1.471 | 0.921 | 0.779 | 0.872 | 0.967 | 77 | 29 | 16 | 25 | 33 | 1.18E-8 | >3 25E-5 > | 3.25E-5 |
| Ovarian Cancer | | | | | | | | | | | | | | | |
| IGROV1 | 0.128 | 0.427 | 0.334 | 0.198 | 0.164 | 0.177 | 0.150 | 69 | 23 | 12 | 16 | 7 | 8.43E-9 | >3.25E-5 > | 3.25E 5 |
| OVCAR-3 | 0.303 | 0.823 | 0.755 | 0.311 | 0.226 | 0.225 | 0.190 | 87 | 1 | -26 | -26 | -37 | 8.78E-9 | 3.67E-8 > | 3.25E-5 |
| OVCAR-4 | 0.375 | 1.400 | 1.393 | 0.928 | 0 851 | 0.855 | 0.822 | 99 | 54 | 46 | 47 | 44 | 1.07E-7 | >3.25E-5 > | 3.25E-5 |
| OVCAR-5 | 0 545 | 1 423 | 1 427 | 0 756 | 0.682 | 0 732 | 0.773 | 101 | 24 | 16 | 21 | 26 | 1.49E-8 | >3 25E-5 > | 3 25F-5 |
| OVCAR-8 | 0.384 | 1.727 | 1.645 | 0.843 | 0.612 | 0.666 | 0.680 | 94 | 34 | 17 | 21 | 22 | 1.76E-8 | >3 25E-5 > | 3.25E-5 |
| SK-OV-3 | 0.527 | 1.067 | 1.006 | 0.639 | 0.578 | 0.561 | 0.528 | 89 | 30 | 9 | 6 | | 1.48E-8 | >3 25E-5 > | 3.25E-5 |
| Renal cancer | | | | | | | | | | | | | | | |

Figure 1A

| | | | | | | | | | | | | | | |
|---|---|---|---|---|---|---|---|---|---|---|---|---|---|---|
| 736-0 | 0.741 | 2.272 | 2.097 | 1.729 | 1.112 | 0.932 | 0.975 | 89 | 65 | 24 | 12 | 15 | 7.46E-8 | >3.25E-5 > 3.25E-5 |
| A498 | 0.808 | 1.434 | 1.430 | 1.170 | 0.841 | 0.921 | 0.948 | 99 | 58 | 5 | 18 | 22 | 4.58E-8 | >3.25E-5 > 3.25E-5 |
| ACHN | 0.287 | 1.153 | 1.146 | 1.030 | 0.793 | 0.631 | 0.650 | 99 | 86 | 58 | 40 | 42 | 9.15E 7 | >3.25E 5 > 3.25E 5 |
| CAKI-1 | 0.505 | 1.960 | 1.917 | 1.813 | 1.396 | o.903 | U.890 | 98 | 91 | 62 | 28 | 27 | 7.14E-8 | >3.25E-5 > 3.25E-5 |
| RXF 393 | 0.432 | 0.793 | 0.746 | 0.516 | 0.345 | 3.377 | 0.384 | 87 | 23 | -20 | -13 | -11 | 1.23E-8 | 1.11E-7 > 3.25E-5 |
| SN12C | 0.312 | 1 056 | 0.902 | 0 575 | 0 495 | 0 510 | 0 529 | 79 | 35 | 25 | 27 | 29 | 1.50E-8 | >3.25E-5 > 3 25E-5 |
| TK-10 | 0.564 | 1.104 | 1.084 | 1.009 | 0.750 | 3.695 | 0.661 | 96 | 82 | 34 | 24 | 18 | 1.53E-7 | >3.25E-5 > 3.25E-5 |
| UO-31 | 0.286 | 1.002 | 0.940 | 0.912 | 0.709 | 0.503 | 0.436 | 91 | 87 | 59 | 30 | 21 | 6.68E-7 | >3.25E-5 > 3.25E-5 |
| Prostate Cancer | | | | | | | | | | | | | | |
| DU-145 | 0.239 | 0.814 | 0.801 | 0.218 | 0.143 | 0.127 | 0.088 | 98 | -9 | -40 | -47 | -63 | 9.11E-9 | 2 68E-8 5.06E-6 |
| Breast cancer | | | | | | | | | | | | | | |
| MCF7 | 0.244 | 1.372 | 0.901 | 0.397 | 0.379 | 0.384 | 0.372 | 58 | 14 | 12 | 12 | 11 | 4.97E-9 | >3.25E-5 > 3.25E-5 |
| NCI/ADR-RES | 0.498 | 1.735 | 1.799 | 1.565 | 1.290 | 0.988 | 0.939 | 105 | 86 | 64 | 40 | 36 | 1.22E-6 | >3.25E-5 > 3 25E-5 |
| MDA-MB-231 /ATCC0. | 530 | 1.011 | 0.998 | 0.629 | 0.604 | 0.489 | 0.516 | 97 | 20 | 15 | -8 | -3 | 1.34E-8 | 1.50E-6 > 3.25E-5 |
| HS 576T | 0.561 | 1.109 | 0.975 | 0.695 | 0.589 | 0.590 | 0.543 | 75 | 24 | 5 | 5 | -3 | 1.03E-8 | 1.33E-5 > 3.25E-5 |
| MDA-MR-435 | 0.483 | 2.065 | 1.419 | 0.272 | 0.290 | 0.434 | 0.504 | 59 | -44 | -40 | -10 | 1 | 3 99E-9 | > 3.25E-5 |
| BT-549 | 0.882 | 1.497 | 1.331 | 0.996 | 0.907 | 0.858 | 0.821 | 73 | 18 | 4 | -3 | -7 | 8.58E-9 | 1 28E-6 > 3.25E-5 |
| T-47D | 0.542 | 1.184 | 1.131 | 0.732 | 0.690 | 0.703 | 0.642 | 92 | 30 | 23 | 25 | 16 | 1.53E-8 | >3 25E-5 > 3.25E-5 |
| MDA-MB-468 | 0.580 | 1.156 | 1.064 | 0.461 | 0.437 | 0.434 | 0.361 | 84 | -21 | -25 | -25 | -38 | 6.68E-9 | 2 07E-8 > 3.25E-5 |

Figure 1B

| National Cancer Institute Developmental TherapeuticS Program In-Vitro Test Results In-Vitro | | | | | | | | | | | | | | |
|---|---|---|---|---|---|---|---|---|---|---|---|---|---|---|
| NSC D – 747906/1 | | | Experiment ID: 0808NS92 | | | | Test Type: 08 | | | | | Units: molar | | |
| Report Date : 5 October 2008 | | | Test date: 18 августа 2008 | | | | QNS : | | | | | MC : | | |
| COMI : T-M-222 (75985) | | | Stain reagent: SRB Dual-Pass Related | | | | SSPL | | | OX3W | | | | |

| | Time | | Mean optical densities | | Concentration Log10 | | Percent Growth | | | | | | | |
|---|---|---|---|---|---|---|---|---|---|---|---|---|---|---|
| Panel / cell line | Zero | Control | -8.5 | -7.5 | 6.5 | -5.5 | -4.5 | -8.5 | 7.5 | -6.5 | 5.5 | -4.5 | GI50 | TGI | LC50 |
| Leukemia | | | | | | | | | | | | | | | |
| CCRF-CEM | 0 221 | 1.127 | 0.291 | 0.283 | 0.246 | 0229 | 0.243 | 8 | 7 | 3 | 1 | 2 | 3.25E-9 > | 3.25E-5 > | 3.25E-5 |
| HL-60(TB) | 0.702 | 2.368 | 0.634 | 0.738 | 0.592 | 0.571 | 0.625 | -10 | 2 | -16 | -19 | -11 | 3.25E-9 > | 3.25E-5 > | 3.25E-5 |
| K-562 | 0 148 | 1.177 | 0.236 | 0.311 | 0.188 | 0 166 | 0.164 | 9 | 16 | 4 | 2 | 2 | 3.25E-9 > | 3.25E-5 > | 3.25E-5 |
| MOLT-4 | 0.328 | 1.109 | 0.601 | 0.732 | 0.510 | 0.421 | 0.380 | 35 | 52 | 23 | 12 | 7 | 3.25E-8 < | 3.25E 9 > | 3.25E-5 |
| RPMI-8226 | 0.349 | 1.043 | 0.343 | 0.334 | 0.304 | 0.283 | 0.278 | -2 | -4 | -13 | -19 | -20 | 3.25E-9 | 6.96E-8 > | 3.25E-5 |
| SR | 0 224 | 0.457 | 0.230 | 0.234 | 0.206 | 0196 | 0195 | 2 | 4 | -8 | 13 | -13 | 3.25E-9 | . > | 3.25E-5 |
| Non-small cell lung cancer | | | | | | | | | | | | | | | |
| A549/ATCC | 0.185 | 1.066 | 0.339 | 0.376 | 0.325 | 0.326 | 0.341 | 17 | 22 | 16 | 16 | 18 | <3.25E-9 > | 3.25E-5 > | 3.25E-5 |
| EKVX | 0.578 | 1.835 | 1.076 | 1.167 | 0.898 | 0.960 | 0.795 | 40 | 47 | 25 | 30 | 17 | <3 25E-9 > | 3.25E-5 > | 3 25E-5 |
| HOF-62 | 0.861 | 1.601 | 1.249 | 1 365 | 1.098 | 1.057 | 1.054 | 52 | 68 | 32 | 26 | 26 | 1.30E-7 > | 3.25E-5 > | 3.25E-5 |
| NCI-H226 | 0.835 | 1.644 | 1.397 | 1439 | 1.256 | 1.300 | 1.276 | 69 | 75 | 52 | 57 | 55 | >3.25E-5 > | 3.25E-5 > | 3.25E-5 |
| NCI-H23 | 0.711 | 1.766 | 0.969 | 1.237 | 1.077 | 1.047 | 1.062 | 24 | 50 | 35 | 32 | 33 | <3.25E-9 > | 3.25E-5 > | 3.25E-5 |
| NCI-H322M | 0.603 | 1.446 | 0.810 | 0.863 | 0.750 | 0.731 | 0.650 | 24 | 31 | 17 | 15 | 6 | <3.25E-9 > | 3.25E-5 > | 3.25E-5 |
| NCI-H460 | 0.201 | 1.660 | 0.282 | 0.364 | 0.267 | 0.261 | 0.278 | 6 | 11 | 4 | 4 | 5 | <3.25 E-9 > | 3.25E-5 > | 3.25E-5 |
| NCI H522 | 0.423 | 1.445 | 0 462 | 0.487 | 0.446 | 0.444 | 0.470 | 4 | 6 | 2 | 2 | 5 | <3.25E 9 > | 3.25E-5 | 3.25E 5 |
| Colon Cancer | | | | | | | | | | | | | | | |
| COLO 205 | 0.302 | 0.862 | 0.200 | 0.246 | 0.171 | 0.142 | 0.139 | -34 | -19 | -44 | -53 | -54 | <3.25E-9 < | 3. 25E-9 | 1.57E-6 |
| HCC-2998 | 0.459 | 1.276 | 0.463 | 0.578 | 0.399 | 0.427 | 0.450 | . | 15 | -13 | -7 | -2 | <3.25 E-9 | 1.09E-7 > | 3.25E-5 |
| HCT-116 | 0.214 | 1.649 | 0.294 | 0.310 | 0.243 | 0.234 | 0.270 | 6 | 7 | 2 | 1 | 4 | <3.25E-9 > | 3.25E-6 > | 3.25E-5 |
| HCT-15 | 0.283 | 1.377 | 1.259 | 1 269 | 0.865 | 0.477 | 0.411 | 89 | 90 | 53 | 18 | 12 | <3.99E-7 > | 3.25E-5 > | 3.25E-5 |
| HT29 | 0.220 | 1.287 | 0.227 | 0.260 | 0.216 | 0.213 | 0.211 | 1 | 4 | -2 | -3 | -4 | <3.25E-9 | 1.43E-7 > | 3.25E-5 |
| KM12 | 0.208 | 1.006 | 0.229 | 0.216 | 0.199 | 0.216 | 0.201 | 3 | 1 | -5 | 1 | -3 | <3.25E-9 | | > 3.25E-5 |
| SW-520 | 0.182 | 1.153 | 0.406 | 0.425 | 0.423 | 0.507 | 0.572 | 23 | 25 | 25 | 33 | 40 | <3 25E-8 > | 3.25E-5 > | 3.25E-5 |
| CNS cancer | | | | | | | | | | | | | | | |
| SF-268 | 0.380 | 1.122 | 0.540 | 0.556 | 0.463 | 0.486 | 0.393 | 22 | 24 | 11 | 14 | 2 | <3.25E-9 > | 3.25E-5 > | 3.25E-5 |
| SF-295 | 0.624 | 2.106 | 0.787 | 1.492 | 0.611 | 0.588 | 0.537 | 11 | 59 | -6 | -6 | -14 | | 2.99E-5 > | 3.25E-5 |
| SF-539 | 0.774 | 2.033 | 0.627 | 1.032 | 0 432 | 0.457 | 0.518 | -19 | 20 | -44 | -41 | -3 | <3.25E-9 | 3.25E-8 > | 3.25E-5 |
| SNB-19 | 0.638 | 1.593 | 0.911 | 1.135 | 0.816 | 0.842 | 0.858 | 29 | 52 | 19 | 21 | 23 | > | 3 25r-5 > | 3.25E-5 |
| SNB-75 | 0.580 | 1.092 | 0.416 | 0.657 | 0.393 | 0.401 | 0.466 | -28 | 15 | -32 | -31 | -20 | <3.25E-9 | | > 3.25E-5 |
| U251 | 0.213 | 1.032 | 0.368 | 0.377 | 0.302 | 0 321 | 0.326 | 19 | 20 | 11 | 13 | 14 | <3.25E-9 > | 3.25E-5 > | 3.25E-5 |
| Melanoma | | | | | | | | | | | | | | | |
| LOX IMVI | 0.254 | 1.460 | 0.593 | 0.625 | 0.549 | 0.644 | 0.714 | 28 | 31 | 24 | 32 | 38 | 3.25E-9 > | 3.25E-5 > | 3.25E-5 |
| MAUVE-3M | 0.450 | 0.712 | 0.510 | 0.544 | 0.509 | 0.563 | 0.610 | 23 | 36 | 22 | 43 | 61 | > | 3.25E-5 > | 3.25E-5 |
| M14 | 0.435 | 1.507 | 0.464 | 0.724 | 0.318 | 0.414 | 0.630 | 3 | 27 | -27 | -5 | 18 | <3.25E-9 | > | 3.25E-5 |
| SK-MEL-2 | 0.569 | 1.416 | 0.703 | 0.787 | 0.613 | 0.633 | 0.743 | 16 | -27 | 5 | 7 | 21 | <3.99E-9 > | 3.25E-5 > | 3.25E-5 |
| SK-MEL-28 | 0.364 | 0.988 | 0.624 | 0.645 | 0.685 | 0.683 | 0.653 | 42 | 5 | 51 | 51 | 46 | > | 3.25E 5 > | 3.25E-5 |
| SK-MEL-5 | 0.867 | 2.659 | 1.109 | 1.544 | 0.923 | 0.926 | 1.042 | 13 | 3 | 3 | 3 | 10 | <3.25E-9 > | 3.25E-5 > | 3.25E-5 |
| UACC-257 | 0.549 | 1.206 | 0.847 | 0.795 | 0.810 | 0.835 | 0.781 | 45 | 40 | 40 | 43 | 35 | <3.25E-9 > | 3.25E-5 > | 3.25E-5 |
| UACC-62 | 0.590 | 1.855 | 0 926 | 0.970 | 0.855 | 0.900 | 0.965 | 27 | 21 | 21 | 24 | 30 | <3.25E-9 > | 3.25E-5 > | 3.25E-5 |
| Ovarian Cancer | | | | | | | | | | | | | | | |
| OVCAR-3 | 0.303 | 0.874 | 0.265 | 0.268 | 0.224 | 0.224 | 0.130 | -13 | -12 | -26 | -26 | -57 | <3.25E-9 < | 3.25E-9 | 1.91E-5 |
| OVCAR-4 | 0.375 | 1.385 | 0.900 | 0.927 | 0.876 | 0.852 | 0.821 | 52 | 55 | 50 | 47 | 44 | 2.74E-7 > | 3.25E-5 > | 3.25E-5 |
| OVCAR-5 | 0.545 | 1.379 | 0.712 | 0.798 | 0.666 | 0.638 | 0.675 | 20 | 30 | 15 | 11 | 16 | <3.25E-9 > | 3.25E-5 > | 3.25E-5 |
| OVCAR-8 | 0.384 | 1.628 | 0.711 | 0.807 | 0.588 | 0 590 | 0.695 | 26 | 34 | 16 | 17 | 25 | <3.25E-9 > | 3.25E-5 > | 3.25E-5 |
| SK-OV-3 | 0.527 | 1.064 | 0.568 | 0.664 | 0.543 | 0.542 | 0.545 | 8 | 25 | 3 | 3 | 3 | <3.25E-9 > | 3.25E-5 > | 3.25E-5 |
| Renal cancer | | | | | | | | | | | | | | | |
| 736-0 | 0.741 | 2.278 | 1.507 | 1.811 | 1.119 | 0.937 | 1.127 | 50 | 70 | 25 | 13 | 25 | | > 3.25E-5 > | 3.25E-5 |

Figure 2A

| | | | | | | | | | | | | | | | | | |
|---|---|---|---|---|---|---|---|---|---|---|---|---|---|---|---|---|---|
| A498 | 0.808 | 1.442 | 0.960 | 1.068 | 0.811 | 0.884 | 0.917 | 24 | 41 | . | 12 | 17 | <3.25E-9 | > | 3.25E-5 | > | 3.25E-5 |
| ACHN | 0.287 | 1.156 | 1.040 | 1.073 | 0.801 | 0.650 | 0.626 | 87 | 90 | 59 | 42 | 39 | 1.09E-6 | > | 3.25E 5 | > | 3.25E 5 |
| CAKI-1 | 0.505 | 2.028 | 1.683 | 1.822 | 1.319 | 0.857 | 0.577 | 77 | 86 | 53 | 23 | 5 | 4.21E-9 | > | 3.25E-5 | > | 3.25E-5 |
| RXF 393 | 0.432 | 0.759 | 0.396 | 0.491 | 0.350 | 0.354 | 0.367 | -8 | 18 | -19 | -19 | -15 | 3.25E-9 | | . | > | 3.25E-5 |
| SN12C | 0.312 | 1.134 | 0.546 | 0.583 | 0.482 | 0.508 | 0.549 | 28 | 33 | 21 | 24 | 29 | 3.25E-9 | > | 3 75F-5 | > | 3 25E-5 |
| TK-10 | 0.564 | 1.083 | 0.782 | 0.979 | 0.638 | 0.596 | 0.525 | 42 | 80 | 14 | 6 | -7 | 3.25E-9 | | 9.46E-6 | > | 3.25E-5 |
| UO-31 | 0.236 | 1.005 | 0.819 | 0.883 | 0.814 | 0.498 | 0.433 | 74 | 83 | 73 | 29 | 20 | 3.25E-9 | > | 3.25E-5 | > | 3.25E-5 |
| Prostate Cancer | | | | | | | | | | | | | | | | | |
| DU-145 | 0.239 | 0.864 | 0.175 | 0.192 | 0.129 | 0.139 | 0.112 | -27 | 20 | -46 | -42 | -53 | <3.25E-9 | | 3 25E-9 | | 1.69E-5 |
| Breast cancer | | | | | | | | | | | | | | | | | |
| MCF7 | 0.244 | 1.279 | 1.347 | 0.352 | 0.335 | 0.353 | 0.363 | 10 | 10 | 9 | 11 | 11 | <3.25E-9 | > | 3.25E-5 | > | 3.25E-5 |
| NCI/ADR-RES | 0.498 | 1.682 | 0.509 | 1.609 | 0.326 | 0.873 | 0.523 | 85 | 94 | 70 | 32 | 2 | 1.08E-6 | > | 3.25E-5 | > | 3.25E-5 |
| MDA-MB-231/ATCC | 0.530 | 1.184 | 0.782 | 0.775 | 0.618 | 0.578 | 0.655 | 38 | 37 | 13 | 7 | 19 | <3.25E-9 | > | 3.25E-5 | > | 3.25E-5 |
| HS 576T | 0.561 | 1.044 | 0.498 | 0.571 | 0.483 | 0.457 | 0.470 | -11 | 2 | -14 | -19 | -16 | 3.25E-9 | | | > | 3 25E-5 |
| MDA-MR-435 | 0.483 | 1.883 | 0.095 | 0.099 | 0.128 | 0.215 | 0.343 | -80 | -80 | -74 | -56 | -29 | <3.25E-9 | < | 3.25E-9 | | |
| BT-549 | 0.882 | 1.349 | 0.831 | 0.986 | 0.773 | 0746 | 0.680 | -6 | 22 | -12 | -15 | 22 | <3.25E- | | | > | 3.25E-5 |
| T-47D | 0 542 | 1.151 | 0.664 | 0.701 | 0.630 | 0.665 | 0.728 | 20 | 26 | 14 | -20 | 30 | <3.25E- | > | 3.25E-9 | > | 3.25E-5 |
| MDA-MB-468 | 0.580 | 1.162 | 0.407 | 0.447 | 0.422 | 0 388 | 0.353 | -30 | -23 | -27 | -33 | | | < | 3.25E-9 | | 3.25E-5 |

Figure 2B

| National Cancer Institute Developmental Therapeutics Program In-Vitro Test Results In-Vitro | | | | | | | | | | | | | | | | |
|---|---|---|---|---|---|---|---|---|---|---|---|---|---|---|---|---|
| NSC D – 747903/1 | | | Experiment ID: 0808NS92 | | | | | Test Type: 08 | | | | | Units: molar | | | |
| Report Date : 5 October 2008 | | | Test date: 18 August 2008 | | | | | ONS : | | | | | MC : | | | |
| COMI : T-M-213 (75982) | | | Stain reagent: SRB Dual-Pass Related | | | | | SSPL | | OX3W | | | | | | |

| | Time | | Mean optical densities | | | | | Percent Growth | | | | | | | | |
|---|---|---|---|---|---|---|---|---|---|---|---|---|---|---|---|---|
| Panel / cell line | Zero | Control | -8.5 | -7.5 | 6.5 | -5.5 | -4.5 | -8.5 | 7.5 | -6.5 | 5.5 | -4.5 | GI50 | | TGI | LC50 |
| Leukemia | | | | | | | | | | | | | | | | |
| CCRF-CEM | 0.221 | 1.118 | 1.069 | 0.277 | 0.253 | 0.260 | 0.332 | 95 | 6 | 4 | 4 | 12 | 1.04E-8 | > | 3.25E-5 > | 3.25E-5 |
| HL-60(TB) | 0 702 | 2.185 | 2.065 | 0.748 | 0.624 | 0.663 | 0.669 | 92 | 3 | -11 | -6 | -5 | 9.63E-9 | | 5.37E-8 > | 3.25E-5 |
| K-562 | 0 148 | 1.151 | 0.977 | 0.296 | 0.225 | 0.223 | 0.207 | 83 | 15 | 8 | 7 | 6 | 9.82E-9 | > | 3 25E-5 > | 3.25E-5 |
| MOLT-4 | 0.328 | 1.198 | 1.206 | 0.645 | 0.476 | 0.426 | 0.412 | 101 | 36 | 17 | 11 | 10 | 2.00E-8 | | 3 25E 5 > | 3.25E-5 |
| RPMI-8226 | 0.349 | 1.015 | 0.730 | 0.340 | 0.332 | 0.320 | 0.331 | 57 | -3 | -5 | -8 | -5 | 4.28E-9 | | 2.94E-8 > | 3.25E-5 |
| SR | 0 224 | 0.544 | 0.460 | 0.231 | 0.221 | 0.227 | 0.218 | 74 | 2 | -2 | 1 | -3 | 6.97E-9 | | . > | 3.25E-5 |
| Non-small cell lung cancer | | | | | | | | | | | | | | | | |
| A549/ATCC | 0.185 | 0.923 | 0.818 | 0.357 | 0,280 | 0.280 | 0.316 | 86 | 23 | 13 | 13 | 18 | 1.21E-8 | > | 3.25E-5 > | 3.25E-5 |
| EKVX | 0.578 | 1.627 | 1.567 | 1.085 | 0.946 | 0.959 | 1.001 | 94 | 48 | 35 | 36 | 40 | 2.99E-8 | > | 3.25E-5 > | 3 25E-5 |
| HOF-62 | 0.861 | 1.576 | 1.484 | 1 309 | 1.046 | 0.992 | 1.049 | 87 | 63 | 26 | 18 | 26 | 7.15E-8 | | 325E-5 | 3.25E-5 |
| NCI-H226 | 0.835 | 1.667 | 1.619 | 1 449 | 1.294 | 1.442 | 1.458 | 94 | 74 | bb | 73 | 75 | > 3.25E-5 | | 325E-5 > | 3.25E-5 |
| NCI-H23 | 0.711 | 1.641 | 1.554 | 0.965 | 1.006 | 0.978 | 1.173 | 91 | 27 | 32 | 29 | 50 | 1.43E-8 | > | 3.25E-5 > | 3.25E-5 |
| NCI-H322M | 0.603 | 1.504 | 1.488 | 0.922 | 0.881 | 0.849 | 1.001 | 98 | 35 | 31 | 27 | 44 | 1.90E-8 | > | 3.25E-5 > | 3.25E-5 |
| NCI-H460 | 0.201 | 1.542 | 1.098 | 0.343 | 0.253 | 0.252 | 0.255 | 67 | 11 | 4 | 4 | 4 | 6.48E-9 | > | 3.25E-5 > | 3.25E-5 |
| NCI H522 | 0.423 | 1.323 | 1.107 | 0.388 | 0.360 | 0 394 | 0.396 | 76 | -8 | -15 | -7 | -7 | 6.61E-9 | | 2.59E-8 | 3.25E 5 |
| Colon Cancer | | | | | | | | | | | | | | | | |
| COLO 205 | 0.302 | 0.744 | 0.647 | 0.194 | 0.211 | 0.216 | 0.178 | 78 | -36 | -30 | -29 | -41 | 5.73E-9 | | 1.58E-8 > | 3.25E-5 |
| HCC-2998 | 0.459 | 1.196 | 1.083 | 0.498 | 0.354 | 0.487 | 0.573 | 85 | 5 | -23 | 4 | 15 | 8.88E-9 | | . > | 3.25E-5 |
| HCT-116 | 0.214 | 1.520 | 1.032 | 0.292 | 0.227 | 0.238 | 0.247 | 63 | 6 | 1 | 2 | 3 | 5.42E-9 | > | 325E-5 > | 3.25E-5 |
| HCT-15 | 0.283 | 1.256 | 1.230 | 1.176 | 0.768 | 0.445 | 0.366 | 97 | 92 | 50 | 17 | 9 | 3.22E-7 | > | 325E-5 > | 3.25E-5 |
| HI29 | 0.220 | 1.281 | 0.740 | 0.243 | 0.208 | 0.197 | 0.232 | 49 | 3 | -6 | -10 | 1 | < 3.25E-9 | | . > | 3.25E-5 |
| KM12 | 0.208 | 0.956 | 0.714 | 0.264 | 0.229 | 0.252 | 0.280 | 68 | 7 | 3 | 6 | 10 | 6.39E-9 | > | 3.25E-5 > | 3.25E-5 |
| SW-520 | 0.182 | 1.059 | 0.344 | 0.456 | 0.450 | 0.529 | 0.566 | 75 | 31 | 31 | 40 | 44 | 1.22E-3 | > | 3.25E-5 > | 3.25E-5 |
| CNS cancer | | | | | | | | | | | | | | | | |
| SF-268 | 0.380 | 1.082 | 0.936 | 0.588 | 0.500 | 0 526 | 0.565 | 79 | 30 | 17 | 21 | 26 | 1.26E-8 | > | 3 25E-5 > | 3.25E-5 |
| SF-295 | 0.624 | 2.016 | 1.905 | 1.244 | 0.673 | 0.670 | 0.709 | 92 | 45 | 4 | 3 | 6 | 2.49E-8 | > | 3 25E-5 > | 3.25E-5 |
| SF-539 | 0.774 | 1.882 | 1.719 | 0.903 | 0 421 | 0.485 | 0.515 | 85d | 12 | -46 | -40 | -34 | 9.80E-9 | | 519E-8 > | 3.25E-5 |
| SNB-19 | 0.638 | 1.499 | 1.397 | 1.030 | 0.747 | 0.801 | 0.813 | 88 | 45 | 13 | 19 | 20 | 2.54E-8 | > | 3 25E-5 > | 3.25E-5 |
| SNB-75 | 0.580 | 1.025 | 0.805 | 0.475 | 0,335 | 0.380 | 0.437 | 51 | -18 | -42 | -35 | -25 | 3.32E-9 | | 1.77E-8 > | 3.25E-5 |
| U251 | 0/213 | 0/ 947 | 0.795 | 0.353 | 0.284 | 0.296 | 0.317 | 79 | 19 | 10 | 11 | 14 | 9.96E-9 | > | 3.25E-5 > | 3.25E-5 |
| Melanoma | | | | | | | | | | | | | | | | |
| LOX IMVI | 0.254 | 1.351 | 0.987 | 0.584 | 0.526 | 0.596 | 0.668 | 67 | 30 | 25 | 31 | 38 | 9.32E-9 | > | 3 25E-5 > | 3.25E-5 |
| MAUVE-3M | 0.450 | 0.730 | 0.666 | 0.521 | 0.515 | 0.556 | 0.573 | 77 | 25 | 23 | 38 | 44 | 1.08E-8 | > | 3 25E-5 > | 3.25E-5 |
| M14 | 0.435 | 1.468 | 1.278 | 0.773 | 0.397 | 0 843 | 0.642 | 82 | 33 | -9 | 39 | 20 | 1.44E-8 | | . > | 3.25E-5 |
| SK-MEL-2 | 0.569 | 1.343 | 1.268 | 0.585 | 0.528 | 0.561 | 0.659 | 90 | 2 | -7 | -1 | 12 | 9.31E-9 | | . > | 3.25E-5 |
| SK-MEL-28 | 0.364 | 0.934 | 0.867 | 0.673 | 0,665 | 0.741 | 0.755 | 88 | 54 | 53 | 66 | 69 | > 3.25E-5 | > | 3 25E 5 > | 3.25E-5 |
| SK-MEL-5 | 0.867 | 2.575 | 2.611 | 1.342 | 0,967 | 1.046 | 1,132 | 102 | 28 | 6 | 10 | 15 | 1.63E-8 | > | 3 25E-5 > | 3.25E-5 |
| UACC-257 | 0.549 | 1.115 | 1.054 | 0.767 | 0.770 | 0.808 | 0.769 | 89 | 39 | 39 | 46 | 39 | 1.93E-3 | > | 3 25E-5 > | 3.25E-5 |
| UACC-62 | 0.590 | 1.858 | 1.580 | 1.076 | 0.911 | 0.987 | 1.209 | 78 | 38 | 25 | 31 | 49 | 1.65E-8 | > | 3 25E-5 > | 3.25E-5 |
| Ovarian Cancer | | | | | | | | | | | | | | | | |
| OVCAR-3 | 0.303 | 0.803 | 0.692 | 0.296 | 0.247 | 0.265 | 0,282 | 78 | -2 | -19 | -13 | -7 | 7.21 E-9 | | 3.03E-8 > | 3.25E-5 |
| OVCAR-4 | 0.375 | 1.357 | 1.332 | 0.949 | 0.911 | 0.959 | 0.871 | 97 | 58 | 55 | 59 | 51 | > 3.25E-5 | > | 3.25E-5 > | 3.25E-5 |
| OVCAR-5 | 0 545 | 1.382 | 1.361 | 0.690 | 0.630 | 0.687 | 0.829 | 97 | 17 | 10 | 17 | 34 | 1.27E-8 | > | 3.25E-5 > | 3.25E-5 |
| OVCAR-8 | 0.384 | 1.492 | 1.436 | 0.758 | 0.566 | 0.571 | 0.678 | 95 | 34 | 16 | 17f | 27 | 1.76E-8 | > | 3.25E-5 > | 3.25E-5 |
| SK-OV-3 | 0.527 | 1.007 | 0.941 | 0.577 | 0.492 | 0.495 | 0.556 | 86 | 10 | -7 | -6 | 6 | 9.76E-9 | | > | 3.25E-5 |

Figure 3A

| | | | | | | | | | | | | | | | | |
|---|---|---|---|---|---|---|---|---|---|---|---|---|---|---|---|---|
| Renal cancer | | | | | | | | | | | | | | | | |
| 736-0 | 0.741 | 2.178 | 2.070 | 1.770 | 1.047 | 0.921 | 1.211 | 93 | 72 | 21 | 12 | 33 | 8.73E-8 | > | 3.25E-5 | > | 3.25E-5 |
| A498 | 0.808 | 1.352 | 1.334 | 1.157 | 0.723 | 0.883 | 0.987 | 97 | 64 | -11 | 14 | 33 | 5.03E-8 | | . | > | 3.25E-5 |
| ACHN | 0.287 | 1.114 | 1.139 | 1.061 | 0.758 | 0.603 | 0.586 | 103 | 94 | 57 | 38 | 36 | 7.62E-7 | > | 3.25E-5 | > | 3.25E-5 |
| CAKI-1 | 0.505 | 1.870 | 1.822 | 1.750 | 1.397 | 0.900 | 0.813 | 97 | 91 | 63 | 29 | 23 | 8.58E-7 | > | 3.25E-5 | > | 3.25E-5 |
| RXF 393 | 0.432 | 0.700 | 0.644 | 0.442 | 0.292 | 0.321 | 0.357 | 79 | 4 | -33 | -26 | -17 | 7.87E-9 | | 4.08E-8 | > | 3.25E-5 |
| SN12C | 0.312 | 1.073 | 0.958 | 0.581 | 0.509 | 0.536 | 0.582 | 85 | 35 | 26 | 29 | 35 | 1.64E-8 | > | 3.25E-5 | > | 3.25E-5 |
| TK-10 | 0.564 | 1.092 | 1.059 | 0.939 | 0.816 | 0.681 | 0.662 | 94 | 71 | 48 | 22 | 19 | 2.57E-7 | > | 3.25E-5 | > | 3.25E-5 |
| UO-31 | 0.286 | 0.957 | 0.892 | 0.895 | 0.710 | 0.508 | 0.443 | 90 | 91 | 63 | 33 | 23 | 8.88E-7 | > | 3.25E-5 | > | 3.25E-5 |
| Prostate Cancer | | | | | | | | | | | | | | | | |
| DU-145 | 0.239 | 0.817 | 0.764 | 0.212 | 0.158 | 0.163 | 0.151 | 91 | -11 | -34 | -32 | -37 | 8.16E-9 | | 2.52E-8 | > | 3.25E-5 |
| Breast cancer | | | | | | | | | | | | | | | | |
| MCF7 | 0.244 | 1.177 | 0.701 | 0.348 | 0.315 | 0.281 | 0.210 | 49 | 11 | 8 | 4 | -14 | < 3.25E-9 | | 5.38E-6 | > | 3.25E-5 |
| NCI/ADR-RES | 0.498 | 1.599 | 1.701 | 1.428 | 1.227 | 1.015 | 0.886 | 109 | 84 | 66 | 47 | 35 | 2.25E-6 | > | 3.25E-5 | > | 3.25E-5 |
| MDA-MB-231/ATCC | 0.530 | 1.123 | 1.095 | 0.734 | 0.590 | 0.534 | 0.638 | 95 | 34 | 10 | 1 | 18 | 1.80E-8 | > | 3.25E-5 | > | 3.25E-5 |
| HS 576T | 0.561 | 0.978 | 0.920 | 0.655 | 0.564 | 0.583 | 0.553 | 86 | 22 | 1 | 5 | -2 | 1.20E-8 | | 1.93E-5 | > | 3.25E-5 |
| MDA-MR-435 | 0.483 | 1.897 | 1.060 | 0.222 | 0.241 | 0.358 | 0.439 | 41 | -54 | -50 | -26 | -9 | < 3.25E-9 | | 8.75E-9 | | . |
| BT-549 | 0.882 | 1.497 | 1.318 | 1.075 | 0.916 | 1.011 | 0.924 | 71 | 31 | 5 | 21 | 7 | 1.09E-8 | > | 3.25E-5 | > | 3.25E-5 |
| T-47D | 0.542 | 1.137 | 1.056 | 0.672 | 0.712 | 0.702 | 0.658 | 36 | 22 | 29 | 27 | 19 | 1.19E-8 | > | 3.25E-5 | > | 3.25E-5 |
| MDA-MB-468 | 0.580 | 1.187 | 1.089 | 0.491 | 0.454 | 0.445 | 0.417 | 84 | -15 | -22 | -28 | -28 | 7.13E-9 | | 2.27E-8 | > | 3.25E-5 |

Figure 3B

| National Cancer Institute Developmental TherapeuticS Program In-Vitro Test Results In-Vitro | | | | | | | | | | | | | | |
|---|---|---|---|---|---|---|---|---|---|---|---|---|---|---|
| NSC D – 747904/1 | | | Experiment ID: 0808NS392 | | | | | Test Type: 08 | | | | Units: molar | | |
| Report Date : 5 October 2008 | | | Test date: 18 August 2008 | | | | | ONS : | | | | MC : | | |
| COMI : T-M-219 (75983) | | | Stain reagent: SRB Dual-Pass Related | | | | | SSPL | | | 0X3W | | | |

| | Time | | Mean optical densities | | | | | Concentration Log10 Percent Growth | | | | | | |
|---|---|---|---|---|---|---|---|---|---|---|---|---|---|---|
| Panel / cell line | Zero | Control | -8.5 | -7.5 | 6.5 | -5.5 | -4.5 | -8.5 | 7.5 | -6.5 | 5.5 | -4.5 GI50 | TGI | LC50 |
| Leukemia | | | | | | | | | | | | | | |
| CCRF-CEM | 0.221 | 1.118 | 1.018 | 0.258 | 0.239 | 0.223 | 0.254 | 89 | 4 | 2 | . | 4    9.34E-9 | > 3.25E-5 | > 3.25E-5 |
| HL-60(TB) | 0 702 | 2.185 | 2.108 | 0.644 | 0.556 | 0.543 | 0.631 | 95 | -8 | -21 | -23 | -10  8.84E-9 | 2.70E-8 | > 3.25E-5 |
| K-562 | 0 148 | 1.151 | 0.877 | 0.285 | 0.193 | 0.182 | 0.188 | 73 | 14 | 4 | 3 | 4    7.87E-9 | 3.25E-5 | > 3.25E-5 |
| MOLT-4 | 0.328 | 1.198 | 1.040 | 0.602 | 0.446 | 0.423 | 0.425 | 82 | 31 | 14 | -1 | 11   1.39E-8 | > 3.25E-5 | > 3.25E-5 |
| RPMI-8226 | 0.349 | 1.015 | 0.581 | 0.327 | 0.298 | 0.281 | 0.277 | 35 | -6 | -15 | -19 | -21 < 3.25E-9 | 2.28E-8 | > 3.25E-5 |
| SR | 0.224 | 0.544 | 0.393 | 0.205 | 0.177 | 0.194 | 0.202 | 53 | -8 | -21 | -3 | -10  3.61 E-9 | 2.36E-8 | > 3.25E-5 |
| Non-small cell lung cancer | | | | | | | | | | | | | | |
| A549/ATCC | 0.185 | 0.923 | 0.679 | 0.332 | 0.280 | 0.288 | 0.314 | 67 | 20 | 13 | 14 | 17   7.46E-9 | > 3.25E-5 | > 3.25E-5 |
| EKVX | 0.578 | 1.627 | 1.518 | 1.037 | 0.928 | 0,950 | 0.992 | 90 | 44 | 33 | 35 | 39   2.37E-8 | > 3.25E-5 | > 3.25E-5 |
| HOF-62 | 0.861 | 1.576 | 1.503 | 1.293 | 1.023 | 1.023 | 1.087 | 90 | 60 | 23 | 23 | 32   6.12E-8 | > 3.25E-5 | > 3.25E-5 |
| NCI-H226 | 0.835 | 1.667 | 1.655 | 1.409 | 1.294 | 1.289 | 1.314 | 99 | 69 | 55 | 55 | 58 > 3.25E-5 | > 3.25E-5 | > 3.25E-5 |
| NCI-H23 | 0,711 | 1.641 | 1.546 | 1.032 | 1.064 | 1.030 | 1.007 | 90 | 34 | 38 | 34 | 32   1.70E-8 | > 3.25E-5 | > 3.25E-5 |
| NCI-H322M | 0.603 | 1.504 | 1.474 | 0.881 | 0.816 | 0.800 | 0.758 | 97 | 31 | 24 | 22 | 17   1.66E-8 | > 3.25E-5 | > 3.25E-5 |
| NCI-H460 | 0.201 | 1.542 | 0.922 | 0.321 | 0.271 | 0.251 | 0.288 | 54 | 9 | 5 | 4 | 6    3.94E-9 | > 3.25E-5 | > 3.25E-5 |
| NCI H522 | 0.423 | 1.323 | 0.965 | 0.397 | 0.372 | 0.354 | 0.390 | 60 | -6 | -12 | -16 | -8   4.63E-9 | 2.63E-8 | > 3.25E-5 |
| Colon Cancer | | | | | | | | | | | | | | |
| COLO 205 | 0,302 | 0.744 | 0.612 | 0.195 | 0.129 | 0.135 | 0,135 | 70 | -36 | -57 | -55 | -55  5.04E-9 | 1.50E-8 | 1.50E-7 |
| HCC-2998 | 0.459 | 1.196 | 0.983 | 0.620 | 0.468 | 0.477 | 0.424 | 71 | 22 | 1 | 2 | -8   8.70E-9 | 5.68E-6 | > 3.25E-5 |
| HCT-116 | 0.214 | 1.520 | 0.945 | 0.296 | 0.229 | 0.226 | 0.333 | 56 | 6 | 1 | 1 | 9    4.29E-9 | > 3.25E-5 | > 3.25E-5 |
| HCT-15 | 0.283 | 1.256 | 1.294 | 1.182 | 0.752 | 0.495 | 0.371 | 104 | 92 | 48 | 22 | 9    2.95E-7 | > 3.25E-5 | > 3.25E-5 |
| HI29 | 0.220 | 1.281 | 0.637 | 0.232 | 0.207 | 0.201 | 0.204 | 39 | 1 | -6 | -9 | -8 < 3.25E-9 | 4.59E-8 | > 3.25E-5 |
| KM12 | 0.208 | 0.956 | 0.640 | 0.198 | 0.225 | 0.196 | 0.238 | 58 | -5 | 2 | -6 | 4    4.32E-9 | . | > 3.25E-5 |
| SW-520 | 0.182 | 1.059 | 0.682 | 0.369 | 0.392 | 0.415 | 0.508 | 57 | 21 | 24 | 27 | 37   5.12E-9 | > 3.25E-5 | > 3.25E-5 |
| CNS cancer | | | | | | | | | | | | | | |
| SF-268 | 0.380 | 1.082 | 0.903 | 0.540 | 0.493 | 0.483 | 0.535 | 75 | 23 | 16 | 15 | 22   9.67E-9 | > 325E-5 | > 3.25E-5 |
| SF-295 | 0.624 | 2.016 | 1.769 | 1.075 | 0.641 | 0.576 | 0.644 | 82 | 32 | 1 | -8 | 1    1.44E-8 | . | > 3.25E-5 |
| SF-539 | 0.774 | 1.882 | 1.624 | 0.665 | 0.395 | 0.410 | 0.514 | 77 | -14 | -49 | -47 | -34  6.40E-9 | 2.27E-8 | > 3.25E-5 |
| SNB-19 | 0.638 | 1.499 | 1.349 | 0.913 | 0.758 | 0.752 | 0.830 | 83 | 32 | 14 | 13 | 22   1.43E-8 | > 3.25E-5 | > 3.25E-5 |
| SNB-75 | 0.580 | 1.025 | 0,760 | 0.423 | 0.328 | 0.335 | 0.415 | 40 | -27 | -43 | -42 | -29 < 3.25E-9 | 1.29E-8 | > 3.25E-5 |
| U251 | 0.213 | 0.947 | 0.699 | 0.323 | 0.280 | 0.272 | 0.292 | 66 | 15 | 9 | 8 | 11   6.73E-9 | > 3.25E-5 | > 3.25E-5 |
| Melanoma | | | | | | | | | | | | | | |
| LOX IMVI | 0.254 | 1.351 | 0.862 | 0.555 | 0.538 | 0.561 | 0.686 | 55 | 27 | 26 | 28 | 39   5.08E-9 | > 3.25E-5 | > 3.25E-5 |
| MAUVE-3M | 0.450 | 0.730 | 0.661 | 0.516 | 0.535 | 0.538 | 0.603 | 75 | 23 | 30 | 31 | 55   . | > 3.25E-5 | > 3.25E-5 |
| M14 | 0.435 | 1.468 | 1.334 | 0.569 | 0.264 | 0.304 | 0.706 | 87 | 13 | -39 | -30 | 26   1.03E-8 | . | > 3.25E-5 |
| SK-MEL-2 | 0.569 | 1.343 | 1.148 | 0.587 | 0.525 | 0.536 | 0.703 | 75 | 2 | -8 | -6 | 17   7.15E-9 | . | > 3.25E-5 |
| SK-MEL-28 | 0.364 | 0.934 | 0.778 | 0.606 | 0.632 | 0.614 | 0.,619 | 73 | 42 | 47 | 44 | 45   1.83E-8 | > 3.25E-5 | > 3.25E-5 |
| SK-MEL-5 | 0.867 | 2.575 | 2.440 | 1.260 | 0,967 | 0.990 | 1.178 | 92 | 23 | 6 | 7 | 18   1.32E-8 | > 3.25E-5 | > 3.25E-5 |
| UACC-257 | 0.549 | 1.115 | 0.966 | 0.745 | 0.748 | 0.745 | 0.747 | 74 | 35 | 35 | 35 | 35   1.31E-3 | > 3.25E-5 | > 3.25E-5 |
| UACC-62 | 0.590 | 1.858 | 1.601 | 0.936 | 0.848 | 0.851 | 0.941 | 80 | 27 | 20 | 21 | 28   1.20E-8 | > 3.25E-5 | > 3.25E-5 |
| Ovarian Cancer | | | | | | | | | | | | | | |
| OVCAR-3 | 0.303 | 0.803 | 0.642 | 0.253 | 0,225 | 0.225 | 0.195 | 68 | -17 | -26 | -26 | -36  5.28E-9 | 2.07E-8 | > 3.25E-5 |
| OVCAR-4 | 0.375 | 1.357 | 1.267 | 0.896 | 0.842 | 0.821 | 0.822 | 91 | 53 | 48 | 45 | 46   1.16E-7 | > 3.25E-5 | > 3.25E-5 |
| OVCAR-5 | 0 545 | 1.382 | 1.267 | 0 773 | 0.705 | 0.676 | 0.660 | 86 | 27 | 19 | 16 | 14   1.34E-8 | > 3.25E-5 | > 3.25E-5 |
| OVCAR-8 | 0.384 | 1.492 | 1.307 | 0.688 | 0.508 | 0.488 | 0.661 | 83 | 27 | 11 | 9 | 25   1.28E-8 | > 3.25E-5 | > 3.25E-5 |
| SK-OV-3 | 0.527 | 1.007 | 0.871 | 0.589 | 0.496 | 0.502 | 0.536 | 72 | 13 | -6 | -5 | 2    7.57E-9 | . | > 3.25E-5 |
| Renal cancer | | | | | | | | | | | | | | |

Figure 4A

| | | | | | | | | | | | | | | | | |
|---|---|---|---|---|---|---|---|---|---|---|---|---|---|---|---|---|
| 736-0 | 0.741 | 2.178 | 2.072 | 1.672 | 1.001 | 0.873 | 1.314 | 93 | 65 | 18 | 9 | 40 | 6.73E-8 | | 3.25E-5 | > | 3.25E-5 |
| A498 | 0.808 | 1.352 | 1.263 | 0.944 | 0.759 | 0.752 | 0.858 | 84 | 25 | -6 | -7 | 9 | 1.21E-8 | | . | > | 3.25E-5 |
| ACHN | 0.287 | 1.114 | 1.149 | 1.043 | 0.746 | 0.614 | 0.595 | 104 | 91 | 55 | 40 | 37 | 7.13E-7 | > | 3.25E-5 | > | 3.25E-5 |
| CAKI-1 | 0.505 | 1.870 | 1.787 | 1.724 | 1.218 | 0.894 | 0.671 | 94 | 89 | 52 | 28 | 12 | 4.03E-7 | > | 3.25E-5 | > | 3.25E-5 |
| RXF 393 | 0.432 | 0.700 | 0.610 | 0.412 | 0.293 | 0.285 | 0.307 | 66 | -5 | -32 | -34 | -29 | 5.54E-9 | | 2.80E-8 | > | 3.25E-5 |
| SN12C | 0.312 | 1.073 | 0.935 | 0.548 | 0.480 | 0.476 | 0.564 | 82 | 31 | 22 | 22 | 33 | 1.37E-8 | > | 3.25E-5 | > | 3.25E-5 |
| TK-10 | 0.564 | 1.092 | 1.006 | 0.938 | 0.659 | 0.613 | 0.592 | 84 | 71 | 18 | 9 | 5 | 3.04E-3 | > | 3.25E-5 | > | 3.25E-5 |
| UO-31 | 0.286 | 0.957 | 0.870 | 0.834 | 0.657 | 0.492 | 0.408 | 87 | 82 | 55 | 31 | 18 | 5.33E-7 | > | 3.25E-5 | > | 3.25E-5 |
| Prostate Cancer | | | | | | | | | | | | | | | | | |
| DU-145 | 0.239 | 0.817 | 0.768 | 0.197 | 0.147 | 0.124 | 0.130 | 92 | -18 | -38 | -48 | -46 | 7.79E-9 | | 2.23E-8 | > | 3.25E-5 |
| Breast cancer | | | | | | | | | | | | | | | | | |
| MCF7 | 0.244 | 1.177 | 0.603 | 0.352 | 0.338 | 0.332 | 0.337 | 38 | 12 | 10 | 9 | 10 | <3.25E-9 | > | 3.25E-5 | > | 3.25E-5 |
| NCI/ADR-RES | 0.498 | 1.599 | 1.570 | 1.588 | 1.322 | 1.109 | 0.331 | 97 | 99 | 75 | 55 | -34 | 3.74E-6 | | 1.37E-5 | > | 3.25E-5 |
| MDA-MB-231/ATCC | 0.530 | 1.123 | 1.131 | 0.671 | 0.558 | 0.598 | 0.598 | 101 | 24 | 5 | 11 | 11 | 1.49E-8 | > | 3.25E-5 | > | 3.25E-5 |
| HS 576T | 0.561 | 0.978 | 0.777 | 0.509 | 0.504 | 0.434 | 0.379 | 52 | -9 | -10 | 23 | -33 | 3.49E-9 | | 2.29E-8 | > | 3.25E-5 |
| MDA-MR-435 | 0.483 | 1.897 | 0.783 | 0.137 | 0.166 | 0.204 | 0.388 | 21 | -72 | -66 | -58 | -20 | <3.25E-9 | | 5.50E-9 | | . |
| BT-549 | 0.882 | 1.497 | 1.294 | 0.993 | 0.872 | 0.825 | 0.757 | 67 | 18 | -1 | -6 | -14 | 7.23E-9 | | 2.82E-7 | > | 3.25E-5 |
| T-47D | 0.542 | 1.137 | 0.992 | 0.673 | 0.660 | 0.641 | 0.717 | 76 | 22 | 20 | 17 | 29 | 9.76E-9 | > | 3.25E-5 | > | 3.25E-5 |
| MDA-MB-468 | 0.580 | 1.187 | 0.968 | 0.460 | 0.459 | 0.459 | 0.407 | 64 | -21 | -21 | -21 | -30 | 4.75E-9 | | 1.85E-8 | > | 3.25E-5 |

Figure 4B

| National Cancer Institute Developmental Therapeutics Program In-Vitro Test Results In-Vitro | | | | | |
|---|---|---|---|---|---|
| NSC D – 747908/1 | Experiment ID : 0808NS92 | | Test Type: 08 | | Units: molar |
| Report Date : 5 October 2008 | Test date: 18 August 2008 | | QNS : | | MC : |
| COMI : T-M-233(75987) | Stain reagent: SRB Dual-Pass Related | | SSPL | 0X3W | |

| | Time | | Concentration Log10 Mean optical densities | | | | | | Percent Growth | | | | | | |
|---|---|---|---|---|---|---|---|---|---|---|---|---|---|---|---|
| Panel / cell line | Zero | Control | -8.5 | -7.5 | 6.5 | -5.5 | -4.5 | -8.5 | 7.5 | -6.5 | 5.5 | -4.5 | GI50 | TGI | LC50 |
| Leukemia | | | | | | | | | | | | | | | |
| CCRF-CEM | 0.221 | 1.127 | 1.011 | 0.288 | 0.274 | 0.275 | 0.259 | 87 | 7 | 6 | 6 | 4 | 9.50E-9 > | 3.25E-5 | > 3.25E-5 |
| HL-60(TB) | 0.702 | 2.368 | 2.316 | 0.630 | 0.576 | 0.588 | 0.613 | 97 | -10 | -18 | -16 | -13 | 8.90E-9 | 2.61E-8 | > 3.25E-5 |
| K-562 | 0.148 | 1.177 | 0.891 | 0.242 | 0.207 | 0.191 | 0.177 | 72 | 9 | 6 | 4 | 3 | 7.31E-9 > | 3.25E-5 | > 3.25E-5 |
| MOLT-4 | 0.328 | 1.109 | 1.259 | 0.670 | 0.526 | 0.473 | 0,446 | 119 | 44 | 25 | 19 | 15 | 2.69E-8 > | 3.25E-5 | > 3.25E-5 |
| RPMI-8226 | 0.349 | 1.043 | 0.603 | 0.333 | 0.336 | 0.323 | 0.308 | 37 | -5 | -4 | -7 | -12 | < 3.25E-9 | 2.50E-8 | > 3.25E-5 |
| SR | 0.224 | 0.457 | 0.384 | 0.233 | 0.219 | 0.219 | 0.203 | 69 | 4 | -2 | -2 | -9 | 6.30E-9 | 1.40E-7 | > 3.25E-5 |
| Non-small cell lung cancer | | | | | | | | | | | | | | | |
| A549/ATCC | 0.185 | 1.066 | 0.851 | 0.378 | 0.320 | 0.323 | 0.326 | 76 | 22 | 15 | 16 | 16 | 9.74E-9 > | 3.25E-5 | > 3.25E-5 |
| EKVX | 0.578 | 1.835 | 1.656 | 1.132 | 1.036 | 1.087 | 1.051 | 86 | 44 | 36 | 41 | 38 | 2.35E-3 > | 3.25E-5 | > 3 25E-5 |
| HOF-62 | 0 861 | 1.601 | 1.527 | 1 336 | 1.100 | 1 088 | 1.069 | 90 | 64 | 32 | 31 | 28 | 9 05E-8 > | 3.25E-5 | > 3.25E-5 |
| NCI-H226 | 0.835 | 1.644 | 1.556 | 1.401 | 1.251 | 1 285 | 1.311 | 89 | 70 | 51' | 30 | 59 | > 3.25E-5 > | 3.25E-5 | > 3.25E-5 |
| NCI-H23 | 0.711 | 1.766 | 1.644 | 0.987 | 0.937 | 1.022 | 1.109 | 88 | 26 | 21' | 29 | 38 | 1.34E-8 > | 3.25E-5 | > 3.25E-5 |
| NCI-H322M | 0.603 | 1.446 | 1.369 | 0.866 | 0.861 | 0.830 | 0.848 | 91 | 31 | 31J | 27 | 29 | 1.57E-8 > | 3.25E-5 | > 3.25E-5 |
| NCI-H460 | 0.201 | 1.660 | 1.095 | 0.331 | 0,266 | 0,265 | 0.267 | 61 | 9 | 4 | 4 | 4 | 5.34E-9 > | 3.25E-5 | > 3.25E-5 |
| NCI H522 | 0.423 | 1.445 | 1.183 | 0.516 | 0.446 | 0.462 | 0.466 | 75 | 9 | 2 | 4 | 4 | 7.74E-9 > | 3.25E-5 | > 3.25E 5 |
| Colon Cancer | | | | | | | | | | | | | | | |
| COLO 205 | 0.302 | 0.862 | 0.753 | 0.218 | 0.173 | 0.152 | 0.161 | 80 | -28 | -43 | -50 | -47 | 6.21E-9 | 1.80E-8 | > 3.25E-5 |
| HCC-2998 | 0.459 | 1.276 | 1.055 | 0.519 | 0.373 | 0.429 | 0,482 | 73 | 7 | -19 | -7 | 3 | 7.26E-9 | . | > 3.25E-5 |
| HCT-116 | 0.214 | 1.649 | 0.945 | 0 303 | 0.267 | 0.266 | 0.296 | 51 | 6 | 4 | 4 | 6 | 3.41E-9 > | 3.25E-5 | > 3.25E-5 |
| HCT-15 | 0.283 | 1.377 | 1.307 | 1.270 | 0.898 | 0.484 | 0.447 | 94 | 90 | 56 | 18 | 15 | 4.74E-7 > | 3.25E-5 | > 3.25E-5 |
| HI29 | 0.220 | 1.287 | 0.707 | 0.242 | 0.201 | 0.213 | 0.205 | 46 | 2 | -9 | -3 | -7 | < 3.25E-9 | 4.98E-8 | > 3.25E-5 |
| KM12 | 0.208 | 1.006 | 0.682 | 0.253 | 0.229 | 0.266 | 0.242 | 59 | 6 | 3 | 7 | 4 | 4.87E-9 > | 3.25E-5 | > 3.25C-5 |
| SW-520 | 0.182 | 1.153 | 0.313 | 0.481 | 0.482 | 0.632 | 0.612 | 65 | 31 | 31 | 46 | 44 | 8.92E-9 > | 3.25E-5 | > 3 25E-5 |
| CNS cancer | | | | | | | | | | | | | | | |
| SF-268 | 0.380 | 1.122 | 0.984 | 0.571 | 0.520 | 0.539 | 0.555 | 81 | 26 | 19 | 21 | 24 | 1.19E-S > | 3.25E-5 | > 3.25E-5 |
| SF-295 | 0.624 | 2.106 | 1.947 | 1 203 | 0.696 | 0694 | 0.690 | 89 | 39 | 5 | 5 | 4 | 1.97E-8 > | 3.25E-5 | > 3 25E-5 |
| SF-539 | 0.774 | 2.033 | 1.804 | 0.822 | 0.501 | 0 503 | 0.560 | 82 | 4 | -35 | -35 | -26 | 8.31E-9 | 4.07E-8 | > 3.25E-5 |
| SNB-19 | 0.638 | 1.593 | 1.476 | 1.023 | 0.824 | 0.850 | 0,854 | 88 | 40 | 19 | 22 | 23 | 2.03E-8 > | 3.25E-5 | > 3.25E-5 |
| SNB-75 | 0.580 | 1.092 | 0.869 | 0.514 | 0.376 | 0.402 | 0.449 | 56 | -11 | -35 | -31 | -23 | 4.04E-9 | 2.21E-8 | > 3.25E-5 |
| U251 | 0.213 | 1.032 | 0.325 | 0 369 | 0.327 | 0.335 | 0.336 | 75 | 19 | 14 | 15 | 15 | 9.05E-9 > | 3.25E-5 | > 3.25E-5 |
| Melanoma | | | | | | | | | | | | | | | |
| LOX IMVI | 0.254 | 1.460 | 0.915 | 0.602 | 0.584 | 0.676 | 0.729 | 55 | 29 | 27 | 35 | 39 | 4.97E-9 > | 3.25E-5 | > 3.25E-5 |
| MAUVE-3M | 0.450 | 0.712 | 0.649 | 0.501 | 0.516 | 0.600 | 0.632 | 76 | 20 | 25 | 57 | 70 | > | 3.25E-5 | > 3.25E-5 |
| M14 | 0.435 | 1.507 | 1.289 | 0630 | 0.303 | 0.541 | 0.689 | 80 | 18 | -30 | 10 | 24 | 9.87E-9 | . | > 3.25E-5 |
| SK-MEL-2 | 0 569 | 1.416 | 1.349 | 0.671 | 0.571 | 0.653 | 0.700 | 92 | 12 | . | 10 | 15 | 1.09E-8 > | 325E-5 | > 3.25E-5 |
| SK-MEL-28 | 0.364 | 0.988 | 0.887 | 0.678 | 0.670 | 0.809 | 0,758 | 84 | 50 | 49 | 71 | 63 | > | 3.25E-5 | > 3.25E-5 |
| SK-MEL-5 | 0.867 | 2.659 | 2.677 | 1.385 | 0.968 | 1.073 | 1.158 | 101 | 29 | 6 | 11 | 16 | 1.66E-8 > | 3.25E-5 | > 3.25L-0 |
| UACC-257 | 0.549 | 1.206 | 1.127 | 0.861 | 0.840 | 0.873 | 0.850 | 38 | 47 | 44 | 49 | 46 | 2.81E-3 > | 3.25E-5 | > 3.25E-5 |
| UACC-62 | 0.590 | 1.855 | 1.525 | 0.981 | 0.350 | 0.963 | 1.046 | 74 | 31 | 21' | 29 | 36 | 1.17E-8 > | 325E-5 | > 3.25E-5 |
| Ovarian Cancer | | | | | | | | | | | | | | | |
| OVCAR-3 | 0.303 | 0.874 | 0.677 | 0.311 | 0.245 | 0.223 | 0.228 | 65 | 1 | -19 | -25 | -25 | 5.65E-9 | 3.80E-8 | > 3.25E-5 |
| OVCAR-4 | 0.375 | 1.385 | 1.379 | 0.959 | 0.874 | 0.877 | 0.844 | 99 | 58 | 49 | 50 | 46 | 2.78E-7 > | 3.25E-5 | > 3 25E-5 |
| OVCAR-5 | 0 545 | 1.379 | 1.324 | 0.697 | 0.651 | 0.666 | 0.725 | 93 | 18 | 13 | 14 | 22 | 1.23E-8 > | 3.25E-5 | > 3.25E-5 |
| OVCAR-8 | 0.384 | 1.628 | 1.579 | 0.814 | 0.628 | 0.669 | 0.733 | 96 | 35 | 20 | 23 | 28 | 1.82E-8 > | 325E-5 | > 3.25E-5 |
| SK-OV-3 | 0.527 | 1.064 | 0.977 | 0.664 | 0.534 | 0.549 | 0.524 | 84 | 25 | 1' | 4 | -1 | 1.23E-8 | 2.36E-5 | > 3.25E-5 |

Figure 5A

| | | | | | | | | | | | | | | | | |
|---|---|---|---|---|---|---|---|---|---|---|---|---|---|---|---|---|
| Renal cancer | | | | | | | | | | | | | | | | |
| 736-0 | 0.741 | 2.278 | 2.135 | 1.652 | 1.019 | 1.022 | 1.193 | 91 | 59 | 18 | 18 | 29 | 5.46E-8 | > | 3.25E-5 | > 3.25E-5 |
| A498 | 0.808 | 1.442 | 1.383 | 1.111 | 0.797 | 0.920 | 0.995 | 91 | 46 | -1 | 16 | 29 | 2.88E-3 | | . | > 3.25E-5 |
| ACHN | 0.237 | 1.156 | 1.176 | 1.040 | 0.781 | 0.630 | 0.632 | 102 | 87 | 57 | 39 | 40 | 7.99E-7 | > | 3.25E-5 | > 3.25E-5 |
| CAKI-1 | 0.505 | 2.028 | 1.886 | 1.864 | 1.407 | 0.888 | 0.809 | 91 | 89 | 59 | 25 | 20 | 6.07E-7 | > | 3.25E-5 | > 3.25E-5 |
| RXF 393 | 0.432 | 0.759 | 0.695 | 0.459 | 0.317 | 0.339 | 0.369 | 80 | 8 | -27 | -22 | -15 | 8.56E-9 | | 5.55E-8 | > 3.25E-5 |
| SN12C | 0.312 | 1.134 | 0.940 | 0.546 | 0.499 | 0.540 | 0.562 | 76 | 28 | 23 | 28 | 30 | 1.15E-8 | > | 3.25E-5 | > 3.25F-5 |
| TK-10 | 0.564 | 1.083 | 1.027 | 0.893 | 0.691 | 0.640 | 0.628 | 89 | 63 | 24 | 15 | 12 | 7.13E-3 | > | 3.25E-5 | > 3.25E-5 |
| UO-31 | 0.286 | 1.005 | 0.983 | 0.883 | 0.726 | 0.485 | 0.427 | 98 | 83 | 61 | 28 | 20 | 6.99E-7 | > | 3.25E-5 | > 3.25E-5 |
| Prostate Cancer | | | | | | | | | | | | | | | | |
| DU-145 | 0.239 | 0.864 | 0.780 | 0.192 | 0.132 | 0.125 | 0.122 | 87 | -20 | -45 | -48 | -49 | 7.16E-9 | | 2.11E-8 | > 3.25E-5 |
| Breast cancer | | | | | | | | | | | | | | | | |
| MCF7 | 0.244 | 1.279 | 0.693 | 0.359 | 0.344 | 0.355 | 0.331 | 43 | 11 | 10 | 11 | 8 | <3.25E-9 | > | 3.25E-5 | > 3.25E-5 |
| NCI/ADR-RES | 0.498 | 1.682 | 1.671 | 1.542 | 1.205 | 0.786 | 0.680 | 99 | 83 | 60 | 24 | 15 | 6.10E-7 | > | 3.25E-5 | > 3.25E-5 |
| MDA-MB-231 /ATCC | 0.530 | 1.184 | 1.135 | 0.749 | 0.590 | 0.550 | 0.622 | 93 | 33 | 9 | 3 | 14 | 1.70E-8 | > | 3.25E-5 | > 3.25E-5 |
| HS 576T | 0.561 | 1.044 | 0.913 | 0.587 | 0.547 | 0.513 | 0.525 | 73 | 5 | 2 | -9 | -7 | 7.07E-9 | | 1.55E-7 | > 3.25E-5 |
| MDA-MR-435 | 0.483 | 1.883 | 0.937 | 0.269 | 0.258 | 0.434 | 0.525 | 32 | -44 | -47 | -10 | 3 | <3.25E-9 | | . | > 3.25E-5 |
| BT-549 | 0.832 | 1.349 | 1.165 | 0.837 | 0.771 | 0.708 | 0.759 | 61 | -5 | -13 | -20 | -14 | 4.72E-9 | | 2.71E-8 | > 3.25E-5 |
| T-47D | 0.542 | 1.151 | 1.021 | 0.651 | 0.694 | 0.699 | 0.679 | 79 | 18 | 25 | 26 | 23 | 9.63E-9 | > | 325E-5 | > 3.25E-5 |
| MDA-MB-468 | 0.580 | 1.162 | 1.016 | 0.425 | 0.386 | 0.413 | 0.398 | 75 | -27 | -33 | -29 | -31 | 5.72E-9 | | 1.77E-8 | > 3.25E-5 |

Figure 5B

| National Cancer Institute Developmental Therapeutics Program In-Vitro Test Results In-Vitro | | | | | | | | | | | | | | |
|---|---|---|---|---|---|---|---|---|---|---|---|---|---|---|
| NSC D – 749484/1 | | | | Experiment ID: 0903NS66 | | | | | Test Type: 08 | | | Units: molar | | |
| Report Date : 11 марта 2010 | | | | Test date: 30 марта 2009 | | | | | QNS : | | | MC : | | |
| COMI : T-M-220 (82279) | | | | Stain reagent: SRB Dual-Pass Related | | | | | SSPL | | 0X3W | | | |

| | Time | | Mean optical densities | | | | Concentration Log10 Percent Growth | | | | | | | |
|---|---|---|---|---|---|---|---|---|---|---|---|---|---|---|---|
| Panel / cell line | Zero | Control | -8.5 | -7.5 | 6.5 | -5.5 | -4.5 | -8.5 | 7.5 | -6.5 | 5.5 | -4.5 | GI50 | TGI | LC50 |
| Leukemia | | | | | | | | | | | | | | | |
| CCRF-CEM | 0.646 | 1.658 | 1.565 | 0.853 | 0.821 | 0.896 | 0.825 | 91 | 20 | 17 | 25 | 18 | 1.90E-8 | > 5.00E-5 | > 5.00E-5 |
| HL-60(TB) | 0 592 | 1.750 | 1.072 | 0.467 | 0.429 | 0.458 | 0.486 | 41 | -21 | -28 | -23 | -18 | < 5.00E-9 | 229E-8 | > 5.00E-5 |
| K-562 | 0.266 | 1.774 | 1.010 | 0.469 | 0. 411 | 0.422 | 0.422 | 49 | 13 | 10 | 10 | 10 | <, 5.00E-9 | > 5.00E-5 | > 5.00E-5 |
| MOLT-4 | 0.667 | 1.914 | 1.637 | 1.014 | 0.968 | 1.219 | 0.,936 | 78 | 28 | 24 | 44 | 22 | 1.80E-8 | > 5.00E-5 | > 5.00E-5 |
| RPMI-8226 | 0.636 | 1.747 | 1.039 | 0.736 | 0.752 | 0.728 | 0.729 | 36 | 14 | 10 | 8 | 8 | < 5.00E-9 | > 5.00E-5 | > 5.00E-5 |
| SR | 0.262 | 0.675 | 0.369 | 0.283 | 0.274 | 0.275 | 0.243 | 26 | 5 | 3 | 3 | -7 | < 5 00E-9 | 9.73E-6 | > 5.00E-5 |
| Non-small cell lung cancer | | | | | | | | | | | | | | | |
| A549/ATCC | 0.291 | 1.490 | 1.006 | 0.770 | 0.709 | 0.849 | 0.785 | 60 | 40 | 35 | 47 | 4' | 1.54E-8 | > 5.00E-5 | > 5.00E-5 |
| EKVX | 0.353 | 1.415 | 1.085 | 0.783 | 0,788 | 0.657 | 0,833 | 69 | 40 | 41 | 47 | 45 | 2.31 E-8 | > 5.00E-5 | > 5.00E-5 |
| HOF-62 | 0.509 | 1.394 | 1.192 | 0.922 | 0.792 | 0.908 | 0.838 | 77 | 47 | 32 | 45 | 37 | 3.88E-8 | > 5.00E-5 | > 5.00E-5 |
| HOP-92 | 0.872 | 1.341 | 1.212 | 1.177 | 1.160 | 1.170 | 1.054 | 72 | 65 | 61 | 64 | 39 | 1.76E-5 | > 5.00E-5 | > 5.00E-5 |
| NCI-H226 | 0.580 | 1.379 | 1.202 | 1.058 | 0,938 | 1.040 | 0,871 | 78 | 60 | 45 | 58 | 36 | . | > 5.00E-5 | > 5.00E-5 |
| NCI-H23 | 0.323 | 1.135 | 0.824 | 0.578 | 0,505 | 0.670 | 0.641 | 62 | 31 | 22 | 43 | 39 | 1.21E-8 | > 5.00E-5 | > 5.00E-5 |
| NCI-H322M | 0.508 | 1.339 | 1.036 | 0.733 | 0.712 | 0.741 | 0.900 | 64 | 27 | 25 | 28 | 47 | 1.18E-3 | > 5.00E-5 | > 5.00E-5 |
| NCI-H460 | 0.203 | 1.881 | 0.703 | 0.386 | 0 345 | 0.412 | 0.348 | 30 | 11 | 8 | 12 | 9 | < 5.00E-9 | > 5.00E-5 | > 5.00E-5 |
| NCI H522 | 0.606 | 1.530 | 1.149 | 0.779 | 0.745 | 0.896 | 0.849 | 59 | 19 | 15 | 31 | 26 | 8.27E-9 | > 5.00E-5 | > 5.00E-5 |
| Colon Cancer | | | | | | | | | | | | | | | |
| COLO 205 | 0.294 | 0.968 | 0.442 | 0.211 | 0.194 | 0.220 | 0.185 | 22 | -28 | -34 | -25 | -37 | < 5.00E-9 | 1 36E-8 | > 5.00E-5 |
| HCC-2998 | 1.219 | 2.929 | 2.623 | 1.222 | 0,879 | 0.985 | 0.987 | 82 | - | -28 | -19 | -19 | 1.23E-8 | 5.06E-8 | > 5.00E-5 |
| HCT-116 | 0.188 | 1.370 | 0.504 | 0.348 | 0.254 | 0.436 | 0.411 | 27 | 13 | 6 | 21 | 19 | < 5.00E-9 | > 5.00E-5 | > 5.00E-5 |
| HCT-15 | 0.469 | 2.275 | 2.271 | 1.965 | 1.135 | 0.849 | 0.821 | 100 | 83 | 37 | 21 | 19 | 2.59E-7 | > 5.00E-5 | > 5.00E-5 |
| HI29 | 0.210 | 1.369 | 0.610 | 0.293 | 0.284 | 0.303 | 0.270 | 34 | 7 | 6 | 8 | 5 | < 5.00E-9 | > 5.00E-5 | > 5.00E-5 |
| KM12 | 0,188 | 0.740 | 0.301 | 0.199 | 0.188 | 0.253 | 0.243 | 20 | 2 | . | 12 | 10 | < 5.00E-9 | . | > 5.00E-5 |
| SW-520 | 0.213 | 1.244 | 0.806 | 0.631 | 0.656 | 0.786 | 0.660 | 57 | 41 | 43 | 56 | 43 | | > 5.00E-5 | > 5.00E-5 |
| CNS cancer | | | | | | | | | | | | | | | |
| SF-268 | 0.397 | 1.046 | 0.805 | 0.594 | 0.530 | 0.678 | 0.596 | 63 | 30 | 21 | 43 | 31 | 1.25E-8 | > 5.00E-5 | > 5.00E-5 |
| SF-295 | 0.731 | 2.771 | 2.348 | 1.527 | 1.072 | 1.164 | 1.282 | 79 | 39 | 17 | 71 | 27 | 2.67E-8 | 5.00E-5 | > 5.00E-5 |
| SNB-19 | 0.717 | 1.386 | 1.301 | 1 226 | 1.173 | 1.300 | 1.246 | 87 | 76 | 68 | 87 | 79 | > 5.00E-5 | 5.00E-5 | > 5.00E-5 |
| SNB-75 | 0 557 | 1.255 | 0.901 | 0.602 | 0.551 | 0.690 | 0.641 | 49 | 6 | -1 | 19 | 12 | < 5.00E-9 | . | > 5.00E-5 |
| U251 | 0.288 | 1.347 | 0.866 | 0.587 | 0.536 | 0.602 | 0.483 | 55 | 28 | 23 | 30 | 18 | 7.45E-9 | > 5.00E-5 | > 5.00E-5 |
| Melanoma | | | | | | | | | | | | | | | |
| LOX IMVI | 0.274 | 1.563 | 1.027 | 0.951 | 0.911 | 1.014 | 0.824 | 58 | 52 | 49 | 57 | 43 | . | > 5.00E-5 | > 5.00E-5 |
| MAUVE-3M | 0.556 | 1.091 | 0.901 | 0.867 | 0.910 | 0.985 | 0,986 | 64 | 58 | 66 | 80 | 60 | > 5.00E-5 | > 5.00E-5 | > 5.00E-5 |
| M14 | 0.243 | 0.942 | 0.635 | 0.287 | 0.248 | 0.475 | 0.447 | 56 | 6 | 1 | 33 | 29 | 6.62E-9 | > 5.00E-5 | > 5.00E-5 |
| MDA-MB-435 | 0.372 | 2.112 | 0.640 | 0.378 | 0.529 | 0.617 | 0.662 | 15 | . | 9 | 14 | 17 | < 5.00E-9 | > 5.00E-5 | > 5.00E-5 |
| SK-MEL-2 | 0.652 | 1.553 | 1.421 | 0.969 | 0.912 | 1.023 | 0.852 | 85 | 35 | 29 | 41 | 22 | 2.53E-8 | > 5.00E-5 | > 5.00E-5 |
| SK-MEL-28 | 0.615 | 1.531 | 1.305 | 1.236 | 1.219 | 1.274 | 1.077 | 75 | 68 | 66 | 72 | 50 | > 5.00E-5 | > 5.00E-5 | > 5.00E-5 |
| SK-MEL-5 | 0.345 | 2.011 | 1.045 | 0.636 | 0.750 | 0.786 | 0.571 | 42 | 20 | 24 | 26 | 14 | < 5.00E-9 | > 5.00E-5 | > 5.00E-5 |
| UACC-257 | 0.681 | 1.564 | 1.488 | 1.416 | 1.369 | 1.424 | 1.332 | 91 | 83 | 78 | 84 | 74 | > 5.00E-5 | > 5.00E-5 | > 5.00E-5 |
| UACC-62 | 0.559 | 2.150 | 1.576 | 1.036 | 0.905 | 1.122 | 1.074 | 64 | 30 | 22 | 35 | 32 | 1.29E-8 | > 5.00E-5 | > 5.00E-5 |
| Ovarian Cancer | | | | | | | | | | | | | | | |
| IGROV1 | 0.511 | 1.372 | 1.134 | 0.992 | 0.943 | 0.952 | 0.779 | 72 | 56 | 50 | 51 | 31 | 5.76E-6 | > 5.00E-5 | > 5.00E-5 |
| OVCAR-3 | 0.362 | 0.832 | 0.566 | 0.273 | 0.244 | 0.253 | 0.246 | 43 | -25 | -33 | -30 | -32 | < 5.00E-9 | 2.17E-B | > 5.00E-5 |
| OVCAR-4 | 0.344 | 1.087 | 0.924 | 0.694 | 0.672 | 0.726 | 0.665 | 78 | 47 | 44 | 51 | 43 | . | > 5.00E-5 | > 5.00E-5 |

Figure 6A

| | | | | | | | | | | | | | | | |
|---|---|---|---|---|---|---|---|---|---|---|---|---|---|---|---|
| OVCAR-5 | 0.361 | 0.948 | 0.776 | 0.556 | 0.518 | 0.582 | 0.525 | 71 | 33 | 27 | 38 | 28 | 1.78E-8 | >5.00E-5 | >5.00E-5 |
| OVCAR-8 | 0.464 | 1.593 | 1.283 | 0.958 | 0.925 | 1.019 | 1.021 | 73 | 44. | 41 | 49 | 49 | 3.04E-8 | >5.00E-5 | >5.00E-5 |
| NCI/ADR-RES | 0.511 | 1.718 | 1.729 | 1.616 | 1.192 | 0.601 | 0.486 | 101 | 92 | 56 | 7 | -5 | 6.77E-7 | 1.99E-5 | >5.00E-5 |
| SK-OV-3 | 0.475 | 0.964 | 0.775 | 0.612 | 0.534 | 0.594 | 0.603 | 61 | 28 | 12 | 24 | 26 | 1.10E-8 | >5.00E-5 | >5.00E-5 |
| Renal cancer | | | | | | | | | | | | | | | |
| 786-0 | 0.584 | 1.989 | 1.754 | 1.402 | 1.001 | 1.438 | 1.428 | 83 | 58 | 30 | 61 | 60 | . | >5.00E-5 | >5.00E-5 |
| A498 | 1.019 | 1.608 | 1.488 | 1.274 | 1.199 | 1.295 | 1.307 | 80 | 43 | 31 | 47 | 49 | 3.28E-3 | >5.00E-5 | >5.00E-5 |
| ACHN | 0.292 | 1.210 | 1.180 | 0.930 | 0.751 | 0.785 | 0.747 | 97 | 75 | 50 | 54 | 50 | . | >500E-5 | >5.00E-5 |
| CAKI-1 | 0.612 | 2.918 | 2.734 | 2.146 | 1.594 | 1.397 | 1.439 | 92 | 67 | 43 | 34 | 36 | 2.45E-7 | >5.00E-5 | >5.00E-5 |
| RXF 393 | 0.326 | 0.799 | 0.644 | 0.539 | 0.464 | 0.533 | 0.507 | 67 | 45 | 29 | 44 | 38 | 3.00E-8 | >5.00E-5 | >5.00E-5 |
| SN12C | 0.403 | 1.488 | 1.143 | 0.891 | 0.830 | 1.022 | 0.940 | 68 | 45 | 39 | 57 | 50 | . | >5.00E-5 | >5.00E-5 |
| TK-10 | 0.608 | 1.387 | 1.249 | 0.933 | 0.855 | 0.901 | 0.859 | 82 | 48 | 32 | 38 | 32 | 4.41E-8 | >5.00E-5 | >5.00E-5 |
| UO-31 | 0.738 | 1.508 | 1.430 | 1.324 | 1.145 | 1.098 | 0.946 | 90 | 76 | 53 | 47 | 27 | 1.49E-6 | >5.00E-5 | >5.00E-5 |
| Prostate Cancer | | | | | | | | | | | | | | | |
| PC-3 | 0.258 | 0.979 | 0.632 | 0.468 | 0.449 | 0.476 | 0.445 | 52 | 29 | 26 | 30 | 26 | 6.02E-9 | >5.00E-5 | >5.00E-5 |
| DU-145 | 0.454 | 1.307 | 1.017 | 0.409 | 0.263 | 0.295 | 0.329 | 66 | -10 | -42 | -35 | -28 | 8.10E-9 | 3.69E-8 | >5.00E-5 |
| Breast cancer | | | | | | | | | | | | | | | |
| MCF7 | 0.305 | 1.641 | 0.755 | 0.506 | 0.471 | 0.488 | 0.473 | 34 | 15 | 12 | 14 | 13 | <5.00E-9 | >5.00E-5 | >5.00E-5 |
| MDA-MB-231/ATCC | 0.450 | 1.130 | 1.070 | 0.755 | 0.667 | 0.778 | 0.664 | 91 | 45 | 32 | 48 | 31 | 3.85E-3 | >5.00E-5 | >5.00E-5 |
| HS 578T | 0.493 | 0.944 | 0.691 | 0448 | 0.378 | 0458 | 0.504 | 44 | -9 | -23 | -7 | 2 | <5.00E-9 | . | >5.00E-5 |
| BT-549 | 1.094 | 2.240 | 1.953 | 1.273 | 1.252 | 1.588 | 1.449 | 75 | 16 | 14 | -43 | 31 | 1.32E-8 | >5.00E-5 | >5.00E-5 |
| T-47D | 0.445 | 0.931 | 0.674 | 0.568 | 0.526 | 0.615 | 0.616 | 47 | 25 | 17 | 35 | 35 | <5.00E-9 | >5.00E-5 | >5.00E-5 |
| MDA-MB-468 | 0.521 | 1.402 | 1.065 | 0.658 | 0.679 | 0.771 | 0.713 | 62 | 16 | 18 | 28 | 22 | 8.98E-9 | >5.00E-5 | >5.00E-5 |

Figure 6B

| Chemical | MW | Pharmacology original screened model | Inhibition (%) | | | | | | IC$_{50}$ (µM) |
|---|---|---|---|---|---|---|---|---|---|
| | | | 0.0001 µM | 0.001 µM | 0.01 µM | 0.1 µM | 1 µM | 1.0 µM | |
| Taxol | 853 | Normal cell HELF | 10.96 | 15.32 | 12.56 | 42.15 | 56.96 | 71.09 | 0.5701 |
| | | Anti-colon cancer HCT-8 | 13.58 | 10.33 | 19.75 | 34.03 | 50.70 | 64.98 | 1.1030 |
| | | Anti-liver cancer BEL-7402 | 5.18 | 6.09 | 9.17 | 53.60 | 70.04 | 73.57 | 0.307 |
| | | Anti-ovarian cancer A278 | 11.14 | 15.57 | 9.68 | 36.92 | 69.85 | 66.15 | 0.4855 |
| | | Anti-lung Cancer A549 | 3.83 | 14.47 | 35.92 | 62.02 | 63.86 | 58.90 | 0.0573 |
| | | Anti-gastric cancer BGC-823 | 7.51 | 13.92 | 78.63 | 86.40 | 85.49 | 79.33 | 0.0029 |
| | | Anti-breast Cancer MCF-7 | 13.38 | 13.11 | 21.37 | 51.88 | 69.81 | 70.95 | 0.2219 |
| | | Anti-cervical cancerHeLa | -12.33 | 25.81 | 72.40 | 81.18 | 79.66 | 72.40 | 0.0016 |
| | | Anti-nasopharyngeal cancer KB | 4.19 | 64.75 | 87.98 | 96.19 | 90.86 | 94.56 | 0.0005 |
| | | Anti-kidney cancer KeTr3 | 17.62 | 19.09 | 18.22 | 59.54 | 62.63 | 79.15 | 0.1900 |
| MTC-301 | 1425 | Normal cell HELF | 7.08 | 12.30 | 15.08 | 25.41 | 41.57 | 63.42 | 2.9240 |
| | | Anti-colon cancer HCT-8 | 10.26 | 12.38 | 9.52 | 20.38 | 32.41 | 61.51 | 5.3620 |
| | | Anti-liver cancer BEL-7402 | 1.76 | 4.93 | 7.37 | 18.14 | 63.15 | 75.37 | 0.6529 |
| | | Anti-ovarian cancer A278 | 8.61 | 10.49 | 13.73 | 24.13 | 45.11 | 58.66 | 3.6750 |
| | | Anti-lung Cancer A549 | -3.38 | 2.86 | 8.21 | 44.31 | 68.34 | 66.97 | 0.1988 |
| | | Anti-gastric cancer BGC-823 | 7.27 | 12.43 | 40.41 | 83.14 | 83.62 | 82.82 | 0.0120 |
| | | Anti-breast Cancer MCF-7 | -4.52 | 4.99 | 10.60 | 27.18 | 56.53 | 69.28 | 0.8326 |
| | | Anti-cervical cancerHeLa | -3.31 | -24.81 | 17.88 | 60.61 | 69.82 | 65.73 | .0270 |
| | | Anti-nasopharyngeal cancer KB | 7.02 | 2.14 | 30.48 | 89.39 | 88.35 | 99.84 | 0.0176 |
| | | Anti-kidney cancer KeTr3 | 13.90 | 9.27 | 4.23 | 20.65 | 5812 | 70.65 | 1.1810 |
| MTC-302 | 1423 | Normal cell HELF | -1.43 | 4.96 | -2.35 | 20.42 | 56.32 | 64.02 | 1.1080 |
| | | Anti-colon cancer HCT-8 | -1.40 | -4.56 | 7.20 | 20.24 | 50.14 | 60.33 | 1.4640 |
| | | Anti-liver cancer BEL-7402 | 1.59 | -4.82 | 1.18 | 29.47 | 70.39 | 75.52 | 0.2855 |
| | | Anti-ovarian cancer A278 | 5.33 | 3.35 | 2.65 | 18.10 | 63.15 | 65.66 | 0.8811 |
| | | Anti-lung Cancer A549 | -0.90 | -7.19 | 21.83 | 47.93 | 64.49 | 69.55 | 0.1457 |
| | | Anti-gastric cancer BGC-823 | -0.30 | -0.55 | 66.73 | 76.74 | 72.28 | 79.30 | 0.0054 |
| | | Anti-breast Cancer MCF-7 | 1.20 | -10.58 | 5.48 | 29.59 | 59.06 | 64.59 | 0.7297 |
| | | Anti-cervical cancerHeLa | -9.32 | -17.91 | 60.51 | 70.38 | 76.69 | 75.43 | 0.0081 |
| | | Anti-nasopharyngeal cancer KB | -7.52 | -0.28 | 51.84 | 77.35 | 75.41 | 78.74 | 0.0064 |
| | | Anti-kidney cancer KeTr3 | 8.79 | 10.46 | 8.56 | 43.02 | 61.42 | 79.96 | 0.3894 |
| MTC-303 | 1445 | Normal cell HELF | 3.38 | 1.11 | -1.64 | 21.71 | 64.39 | 64.52 | 0.5706 |
| | | Anti-colon cancer HCT-8 | 5.21 | 3.23 | -1.13 | 9.51 | 49.35 | 62.23 | 2.1110 |
| | | Anti-liver cancer BEL-7402 | -4.00 | 1.09 | -5.44 | 46.42 | 83.73 | 79.22 | 0.0978 |
| | | Anti-ovarian cancer A278 | 16.63 | 17.42 | 5.51 | 24.47 | 63.51 | 61.56 | 1.2630 |
| | | Anti-lung Cancer A549 | 20.00 | 19.98 | 36.90 | 56.73 | 69.47 | 70.21 | 0.0589 |
| | | Anti-gastric cancer BGC-823 | 9.16 | 15.34 | 77.56 | 80.50 | 91.07 | 87.28 | 0.0037 |
| | | Anti-breast Cancer MCF-7 | -8.18 | -6.20 | 3.90 | 23.57 | 55.58 | 57.46 | 0.8809 |
| | | Anti-cervical cancerHeLa | 5.92 | 3.90 | 79.38 | 87.62 | 95.47 | 92.25 | 0.0043 |
| | | Anti-nasopharyngeal cancer KB | 14.84 | 17.93 | 40.89 | 87.52 | 94.26 | 95.88 | 0.0113 |
| | | Anti-kidney cancer KeTr3 | 33.86 | -7.74 | 19.81 | 51.53 | 81.49 | 78.93 | 0.0976 |
| MTC-304 | 1461 | Normal cell HELF | -2.72 | -2.99 | 4.69 | 16.13 | 64.68 | 62.63 | 0.7312 |
| | | Anti-colon cancer HCT-8 | 4.08 | 3.81 | 10.54 | 17.50 | 46.99 | 72.56 | 1.5500 |
| | | Anti-liver cancer BEL-7402 | -2.46 | -5.42 | -12.84 | 22.51 | 75.36 | 84.16 | 0.2627 |
| | | Anti-ovarian cancer A278 | 2.85 | 19.62 | 11.25 | 22.00 | 56.27 | 66.18 | 1.1880 |
| | | Anti-lung Cancer A549 | 13.33 | 22.42 | 27.50 | 58.01 | 71.42 | 63.35 | 0.0782 |
| | | Anti-gastric cancer BGC-823 | 10.32 | 17.89 | 86.82 | 90.49 | 94.66 | 96.46 | 0.0031 |
| | | Anti-breast Cancer MCF-7 | -11.05 | -3.03 | 4.54 | 16.52 | 57.44 | 56.65 | 1.0080 |
| | | Anti-cervical cancerHeLa | 10.14 | 9.73 | 58.63 | 85.16 | 86.69 | 88.81 | 0.0060 |
| | | Anti-nasopharyngeal cancer KB | -5.15 | 17.07 | 23.45 | 78.49 | 89.66 | 97.54 | 0.0281 |
| | | Anti-kidney cancer KeTr3 | 6.95 | 24.81 | 16.39 | 37.61 | 70.10 | 72.77 | 0.3392 |

Figure 7

| Chemical | MW | Pharmacology original screened model | Inhibition (%) | | | | | | IC$_{50}$ (μM) |
|---|---|---|---|---|---|---|---|---|---|
| | | | 0.0001 μM | 0.001 μM | 0.01 μM | 0.1 μM | 1 μM | 1.0 μM | |
| MTC-305 | 1461 | Normal cell HELF | -0.29 | -12.62 | 2.24 | 18.78 | 57.59 | 59.44 | 1.000 |
| | | Anti-colon cancer HCT-8 | 6.02 | 5.41 | 11.13 | 23.62 | 48.55 | 57.87 | 2.3870 |
| | | Anti-liver cancer BEL-7402 | -6.45 | -5.79 | -8.87 | 26.41 | 83.17 | 82.88 | 0.1811 |
| | | Anti-ovarian cancer A278 | 11.39 | 7.89 | 9.76 | 17.55 | 49.16 | 58.65 | 2.8580 |
| | | Anti-lung Cancer A549 | 15.61 | -7.70 | 28.15 | 40.56 | 52.36 | 59.55 | 0.8078 |
| | | Anti-gastric cancer BGC-823 | 6.80 | 14.41 | 75.58 | 81.22 | 82.47 | 81.35 | 0.0035 |
| | | Anti-breast Cancer MCF-7 | 2.06 | -12.59 | 3.72 | 22.75 | 56.91 | 56.04 | 1.0720 |
| | | Anti-cervical cancer HeLa | 11.09 | -20.79 | 57.51 | 73.79 | 73.18 | 79.30 | 0.0088 |
| | | Anti-nasopharyngeal cancer KB | 1.69 | 6.24 | 49.50 | 89.67 | 85.94 | 94.11 | 0.0092 |
| | | Anti-kidney cancer KeTr3 | 8.41 | -14.03 | 8.36 | 35.34 | 70.78 | 70.99 | 0.2333 |
| MTC-306 | 1427 | Normal cell HELF | -14.8 | -11.4 | -7.1 | 22.9 | 65.3 | 63.3 | 0.3940 |
| | | Anti-colon cancer HCT-8 | -6.8 | -9.1 | 1.9 | 3.4 | 47.2 | 54.8 | 2.4380 |
| | | Anti-liver cancer BEL-7402 | 10.7 | 10.1 | 6.2 | 28.5 | 78.0 | 79.2 | 0.2573 |
| | | Anti-ovarian cancer A278 | -3.8 | 8.7 | 11.5 | 38.1 | 59.4 | 78.6 | 0.3126 |
| | | Anti-lung Cancer A549 | 3.7 | -4.6 | 35.7 | 60.1 | 59.7 | 59.7 | 0.1190 |
| | | Anti-gastric cancer BGC-823 | 9.9 | 15.4 | 61.9 | 80.1 | 75.8 | 81.2 | 0.0046 |
| | | Anti-breast Cancer MCF-7 | 6.1 | 18.6 | 19.7 | 42.6 | 55.7 | 65.8 | 0.7353 |
| | | Anti-cervical cancer HeLa | 3.9 | 30.5 | 87.3 | 94.8 | 93.3 | 94.4 | 0.0017 |
| | | Anti-nasopharyngeal cancer KB | 2.8 | 28.9 | 79.6 | 88.8 | 83.9 | 91.9 | 0.0020 |
| | | Anti-kidney cancer KeTr3 | -0.3 | 9.2 | 22.1 | 72.4 | 87.6 | 89.2 | 0.0367 |
| MTC-307 | 1427 | Normal cell HELF | -26.4 | -8.7 | -19.8 | 15.9 | 61.3 | 68.4 | 0.4437 |
| | | Anti-colon cancer HCT-8 | -18.2 | -28.1 | -0.6 | 7.8 | 48.4 | 55.3 | 1.2680 |
| | | Anti-liver cancer BEL-7402 | -3.2 | 1.7 | 3.8 | 16.8 | 82.5 | 83.2 | 0.2712 |
| | | Anti-ovarian cancer A278 | -17.9 | 5.5 | -0.8 | 31.6 | 63.6 | 64.4 | 0.3482 |
| | | Anti-lung Cancer A549 | 2.3 | -11.9 | 22.4 | 43.0 | 64.5 | 50.5 | 0.4811 |
| | | Anti-gastric cancer BGC-823 | 9.5 | 8.9 | 46.9 | 71.1 | 72.8 | 79.2 | 0.0035 |
| | | Anti-breast Cancer MCF-7 | -5.2 | 6.9 | 64.9 | 26.8 | 58.3 | 66.6 | 0.8300 |
| | | Anti-cervical cancer HeLa | -9.9 | 12.3 | 63.9 | 86.0 | 91.6 | 89.6 | 0.0040 |
| | | Anti-nasopharyngeal cancer KB | -2.4 | 16.3 | 63.9 | 84.0 | 84.1 | 88.0 | 0.0036 |
| | | Anti-kidney cancer KeTr3 | -8.0 | 1.1 | -14.0 | 54.1 | 78.4 | 96.7 | 0.0930 |
| MTC-308 | 1445 | Normal cell HELF | -11.7 | -14.4 | -5.3 | 7.6 | 48.7 | 51.6 | 2.2770 |
| | | Anti-colon cancer HCT-8 | -3.8 | -12.7 | 0.7 | -10.7 | 37.9 | 50.8 | 4.6000 |
| | | Anti-liver cancer BEL-7402 | -2.8 | -13.0 | -9.2 | 3.2 | 75.0 | 78.0 | 0.3802 |
| | | Anti-ovarian cancer A278 | 3.9 | 6.8 | 13.7 | 28.1 | 67.5 | 69.8 | 0.4262 |
| | | Anti-lung Cancer A549 | -0.6 | -9.2 | 27.2 | 33.4 | 45.8 | 47.9 | IC$_{50}$>10 |
| | | Anti-gastric cancer BGC-823 | 5.7 | 19.6 | 64.4 | 67.2 | 68.6 | 74.2 | 0.0030 |
| | | Anti-breast Cancer MCF-7 | -3.8 | -1.8 | 13.2 | 30.2 | 39.1 | 57.7 | 2.8470 |
| | | Anti-cervical cancer HeLa | 11.7 | 7.2 | 74.9 | 91.7 | 85.4 | 92.0 | 0.0048 |
| | | Anti-nasopharyngeal cancer KB | 12.4 | 7.4 | 69.6 | 81.7 | 81.7 | 85.5 | 0.0056 |
| | | Anti-kidney cancer KeTr3 | 13.7 | 10.7 | 12.2 | 52.5 | 72.3 | 84.0 | 0.1674 |

Figure 8

| Chemical | MW | Pharmacology original screened model | inhibition (%) | | | | | | IC$_{50}$ (μM) |
|---|---|---|---|---|---|---|---|---|---|
| | | | 0.0001 μM | 0.001 μM | 0.01 μM | 0.1 μM | 1 μM | 1.0 μM | |
| Docetaxel | 807.0 | Normal cell HELF | 11.34 | 34.32 | 41.71 | 58.04 | 52.13 | 95.04 | 0.240 |
| | | Anti-colon cancer HCT-8 | 8.71 | 21.64 | 42.36 | 47.20 | 50.81 | 90.76 | 0.664 |
| | | Anti-liver cancer BEL-7402 | 7.90 | 23.85 | 35.01 | 48.61 | 43.76 | 86.10 | 0.859 |
| | | Anti-ovarian cancer A278 | 6.56 | 22.47 | 14.51 | 42.21 | 38.95 | 90.52 | 2.724 |
| | | Anti-lung Cancer A549 | 28.32 | 33.98 | 35.83 | 38.56 | 28.29 | 84.61 | 28.050 |
| | | Anti-gastric cancer BGC-823 | 93.44 | 83.33 | 82.50 | 80.55 | 77.29 | 85.99 | 0<IC$_{50}$<0.001 |
| | | Anti-breast Cancer MCF-7 | 26.93 | 34.07 | 43.06 | 48.19 | 45.62 | 82.02 | 0.609 |
| | | Anti-cervical cancerHeLa | 76.05 | 79.34 | 83.76 | 83.62 | 82.65 | 93.87 | 0<IC$_{50}$<0.001 |
| | | Anti-nasopharyngeal cancer KB | 8272 | 85.99 | 88.43 | 87.03 | 88.38 | 97.63 | 0<IC$_{50}$<0.001 |
| | | Anti-kidney cancer KeTr3 | 17.19 | 48.71 | 74.79 | 75.79 | 74.91 | 84.79 | 0.006 |
| MDC-403 | 1399.0 | Normal cell HELF | 7.32 | 25.92 | 51.61 | 58.04 | 61.98 | 96.85 | 0.161 |
| | | Anti-colon cancer HCT-8 | 16.01 | 15.60 | 39.00 | 53.38 | 56.96 | 87.29 | 0.577 |
| | | Anti-liver cancer BEL-7402 | 7.92 | 14.14 | 33.16 | 51.96 | 46.22 | 69.87 | 1.288 |
| | | Anti-ovarian cancer A278 | 2.85 | 11.47 | 29.03 | 37.60 | 38.95 | 69.11 | 8.643 |
| | | Anti-lung Cancer A549 | 32.59 | 28.56 | 41.29 | 32.41 | 30.54 | 73.49 | 95.930 |
| | | Anti-gastric cancer BGC-823 | 69.26 | 83.33 | 82.90 | 81.30 | 78.98 | 98.06 | 0<IC$_{50}$<0.001 |
| | | Anti-breast Cancer MCF-7 | 25.01 | 27.35 | 41.29 | 45.34 | 48.65 | 67.71 | 2.808 |
| | | Anti-cervical cancerHeLa | 50.77 | 62.29 | 76.50 | 74.70 | 77.80 | 96.80 | 0<IC$_{50}$<0.001 |
| | | Anti-nasopharyngeal cancer KB | 70.63 | 82.85 | 84.17 | 83.86 | 84.28 | 98.52 | 0<IC$_{50}$<0.001 |
| | | Anti-kidney cancer KeTr3 | 8.27 | 24.81 | 69.82 | 74.49 | 72.04 | 98.56 | 0.031 |
| MDC404 | 1315.0 | Normal cell HELF | 3.47 | 4.63 | 51.17 | 62.82 | 66.11 | 92.81 | 0.185 |
| | | Anti-colon cancer HCT-8 | 8.33 | 4.42 | 24.26 | 41.13 | 57.04 | 79.28 | 2.355 |
| | | Anti-liver cancer BEL-7402 | -2.88 | 1.51 | 26.72 | 43.64 | 48.89 | 68.72 | 2.258 |
| | | Anti-ovarian cancer A278 | -4.35 | 2.83 | 27.70 | 40.76 | 44.56 | 73.01 | 3.858 |
| | | Anti-lung Cancer A549 | 27.12 | 23.80 | 36.41 | 36.24 | 29.66 | 71.68 | 0<IC$_{50}$<0.001 |
| | | Anti-gastric cancer BGC-823 | 55.48 | 79.41 | 83.59 | 82.07 | 81.90 | 99.46 | 0<IC$_{50}$<0.001 |
| | | Anti-breast Cancer MCF-7 | 18.13 | 20.70 | 37.12 | 43.79 | 43.03 | 66.52 | 8.303 |
| | | Anti-cervical cancerHeLa | 30.20 | 55.62 | 77.47 | 76.54 | 74.46 | 94.70 | 0.002 |
| | | Anti-nasopharyngeal cancer KB | 60.16 | 76.01 | 83.99 | 83.91 | 89.86 | 98.28 | 0<IC50<0.001 |
| | | Anti-kidney cancer KeTr3 | -1.97 | 10.63 | 69.72 | 74.77 | 75.35 | 99.36 | 0.036 |
| MDC405 | 1315.0 | Normal cell HELF | 6.97 | 27.23 | 43.85 | 56.35 | 54.30 | 92.19 | 0.522 |
| | | Anti-colon cancer HCT-8 | 5.08 | 11.58 | 44.60 | 66.29 | 65.48 | 77.74 | 0.265 |
| | | Anti-liver cancer BEL-7402 | 7.00 | 19.93 | 37.71 | 37.27 | 35.21 | 69.95 | 23.020 |
| | | Anti-ovarian cancer A278 | -6.27 | 11.22 | 27.52 | 45.13 | 42.45 | 73.99 | 3.993 |
| | | Anti-lung Cancer A549 | 32.34 | 36.45 | 36.83 | 35.72 | 29.68 | 70.47 | 61.140 |
| | | Anti-gastric cancer BGC-823 | 13.03 | 51.16 | 73.09 | 73.70 | 73.60 | 82.04 | 0.007 |
| | | Anti-breast Cancer MCF-7 | 18.16 | 26.26 | 39.62 | 46.39 | 38.88 | 59.38 | 47.270 |
| | | Anti-cervical cancerHeLa | 82.48 | 85.63 | 88.24 | 85.03 | 3.97 | 96.00 | 0<IC$_{50}$<0.001 |
| | | Anti-nasopharyngeal cancer KB | 67.06 | 79.57 | 81.75 | 86.16 | 87.71 | 98.48 | 0<IC$_{50}$<0.001 |
| | | Anti-kidney cancer KeTr3 | 6.00 | 28.22 | 68.28 | 73.41 | 71.72 | 98.42 | 0.037 |

Figure 9

| Chemical | MW | Pharmacology original screened model | Inhibition (%) | | | | | | IC$_{50}$ (μM) |
|---|---|---|---|---|---|---|---|---|---|
| | | | 0.0001 μM | 0.001 μM | 0.01 μM | 0.1 μM | 1 μM | 1.0 μM | |
| MDC-406 | 1381.0 | Normal cell HELF | 1.76 | 19.02 | 36.62 | 52.03 | 53.52 | 81.61 | 1.142 |
| | | Anti-colon cancer HCT-8 | 8.64 | 15.40 | 37.32 | 69.55 | 64.03 | 76.41 | 0.352 |
| | | Anti-liver cancer BEL-7402 | 0.61 | 22.26 | 36.91 | 43.30 | 39.75 | 62.97 | 6.561 |
| | | Anti-ovarian cancer A278 | -2.13 | 7.08 | 28.91 | 41.90 | 39.99 | 69.92 | 6.739 |
| | | Anti-lung Cancer A549 | 34.82 | 33.73 | 35.38 | 30.47 | 32.03 | 69.34 | >100 |
| | | Anti-gastric cancer BGC-823 | 46.61 | 52.05 | 73.51 | 73.60 | 70.86 | 76.45 | 0.001<IC$_{50}$<0.01 |
| | | Anti-breast Cancer MCF-7 | 20.02 | 26.19 | 38.95 | 45.59 | 44.49 | 67.11 | 38.200 |
| | | Anti-cervical cancerHeLa | 82.16 | 84.01 | 86.73 | 84.10 | 84.24 | 97.24 | 0<IC$_{50}$<0.001 |
| | | Anti-nasopharyngeal cancer KB | 70.63 | 78.00 | 80.85 | 78.35 | 82.58 | 99.18 | 0<IC$_{50}$<0.001 |
| | | Anti-kidney cancer KeTr3 | 4.19 | 21.51 | 65.00 | 71.25 | 70.00 | 95.30 | 0.054 |
| MDC-407 | 1381.0 | Normal cell HELF | 13.59 | 23.10 | 45.14 | 54.98 | 58.08 | 74.00 | 0.649 |
| | | Anti-colon cancer HCT-8 | 9.44 | 13.38 | 40.84 | 60.24 | 66.06 | 82.28 | 0.500 |
| | | Anti-liver cancer BEL-7402 | 2.35 | 13.41 | 34.47 | 48.80 | 39.91 | 70.11 | 2.386 |
| | | Anti-ovarian cancer A278 | 1.84 | 8.02 | 27.16 | 45.25 | 41.90 | 79.73 | 4.290 |
| | | Anti-lung Cancer A549 | 32.86 | 33.81 | 33.39 | 32.87 | 35.63 | 56.70 | >100 |
| | | Anti-gastric cancer BGC-823 | 68.51 | 65.70 | 71.29 | 73.70 | 74.26 | 80.08 | 0<IC$_{50}$<0.001 |
| | | Anti-breast Cancer MCF-7 | 23.85 | 26.70 | 41.91 | 45.27 | 45.06 | 54.32 | 35.620 |
| | | Anti-cervical cancerHeLa | 76.33 | 83.99 | 86.38 | 85.78 | 73.46 | 96.53 | 0<IC$_{50}$<0.001 |
| | | Anti-nasopharyngeal cancer KB | 71.15 | 75.84 | 81.71 | 82.01 | 85.08 | 98.14 | 0<IC$_{50}$<0.001 |
| | | Anti-kidney cancer KeTr3 | 5.99 | 17.32 | 65.58 | 73.02 | 73.93 | 97.38 | 0.064 |
| MDC-408 | 1399.0 | Normal cell HELF | 1.5 | 10.1 | 46.2 | 61.3 | 68.4 | 79.6 | 0.226 |
| | | Anti-colon cancer HCT-8 | 5.3 | 9.6 | 39.2 | 48.2 | 73.7 | 72.0 | 0.609 |
| | | Anti-liver cancer BEL-7402 | 0.8 | 12.5 | 30.4 | 43.9 | 53.1 | 72.8 | 2.458 |
| | | Anti-ovarian cancer A278 | -1.7 | 12.3 | 38.7 | 52.2 | 57.0 | 68.9 | 1.048 |
| | | Anti-lung Cancer A549 | 22.8 | 36.9 | 46.9 | 51.3 | 50.1 | 75.7 | 0.402 |
| | | Anti-gastric cancer BGC-823 | 19.0 | 68.5 | 69.6 | 75.6 | 76.6 | 94.3 | 0.003 |
| | | Anti-breast Cancer MCF-7 | 11.5 | 23.3 | 42.2 | 54.4 | 54.0 | 57.7 | 2.756 |
| | | Anti-cervical cancerHeLa | 44.2 | 80.2 | 81.2 | 81.0 | 86.4 | 88.3 | 0.001<IC$_{50}$<0.01 |
| | | Anti-nasopharyngeal cancer KB | 19.4 | 64.9 | 80.5 | 86.3 | 86.1 | 97.2 | 0.004 |
| | | Anti-kidney cancer KeTr3 | 7.5 | 20.6 | 60.5 | 74.2 | 84.1 | 95.8 | 0.059 |

Figure 10

CHEMICAL SYNTHESIS AND ANTI-TUMOR AND ANTI-METASTATIC EFFECTS OF DUAL FUNCTIONAL CONJUGATE

FIELD

The present invention relates to a series of conjugates of paclitaxel and muramyl dipeptide derivatives, or docetaxel and muramyl dipeptide derivatives, and synthesis, use in cancer treatment thereof. The invention belongs to the field of medical technology.

BACKGROUND

Paclitaxel (also can be called TAXOL®), isolated from *Taxus brevifolia*[1], was found to show anti-tumor activity by US National Cancer Institute (NCI). Premier mechanistic study indicated that paclitaxel is a mitotic inhibitor, which arrest the growth of cancer cells at G2 and M stage by promoting polymerization and depolymerization of cancer cell microtubule, then preventing formation of spindle in cancer cell[2]. Further mechanistic study indicated paclitaxel can also be used as bacterium lipopolysaccharide (LPS) analogue, which exerts its anti-tumor effect by affecting or changing the function of macrophages in immune system, for example, by inducing the expression of tumor necrosis factor α (TNF-α) and interleukin-1 (IL-1) in maerophages[3, 4]. Furthermore, it shows anti-tumor effect by activating MAP-2 kinase, and/or promoting tyrosine phosphorylation of cancer cells[5, 6].

Muramyl dipeptide (N-acetylmuramyl-L-alanyl-D-isoglutamine, MDP) is the minimal structural unit shows immunoadjuvant activity among mycobacterium cell wall peptidoglycans[7, 8]. MDP, injected at the same time with or before the injection of antigen, will enhance immune response or change immune response type. Furthermore, Muramyl dipeptide shows other activities, such as nonspecific resistance to infection caused by, for example, *pneumobacillus, colibacillus, pseudomonas aeruginosa, mononucleosis listeria*, and/or *tritirachium album* etc, nonspecific resistance to, for example, fibrosarcoma and hepatoma etc, and immunoregulation[9-13]. Studies also indicated that MDP together with lipopolysaccharide (LPS) can significantly stimulates the cytokines expression of macrophage[14-16].

Based on these, we expected that paclitaxel together with muramyl dipeptide may show synergistic effect as well. We are the first to propose the new idea that bonding chemotherapy drug paclitaxel and immunostimulants muramyl dipeptide to form a series of conjugates. Biological tests are carried out to prove effectiveness of the new idea, which—combines chemotherapy and immunotherapy to realize anti-tumor and anti-metastatic effects[17].

Applicants disclosed two types of conjugates in our previous patent application[18], which were obtained by bonding muramyl dipeptide with paclitaxel 2'-hydroxy (2'-O-MTC, Structure 1), or with 3'-amino of 3'-N benzoyl paclitaxel (3'-N-MTC, Structure 1). In in vitro tests, Applicants found that 2'-O-MTC conjugate not only maintained anticancer activity of paclitaxel, but also assisted macrophages to produce αTNF- and IL-1 significantly, which means it potentially can inhibit metastasis. However, the activity of 3'-N-MTC conjugate was not significant. Based on that, we preliminarily determined the optimal position of conjugates for bonding would be paclitaxel's 2'-hydroxyl group. Unfortunately, 2'-O-MTC conjugate did not show desired results in vivo, which might depend on the physicochemical properties or the pharmaceutical properties of the molecule. To continue this design concept used in the new drug discovery, Applicants optimized the 2'-O-MTC conjugate by simplifing structures of muramyl dipeptide molecules, and obtained a new series of 2'-O-MTC analogues showing significant anti-tumor and anti-metastasis activities in vivo, which means they can be developed as antitumor drugs. Disclosed herein are the aforementioned new series of 2'-O-MTC analogues.

Structure I shows the two conjugates of muramyl dipeptide with paclitaxel disclosed in Applicants' previous patent application

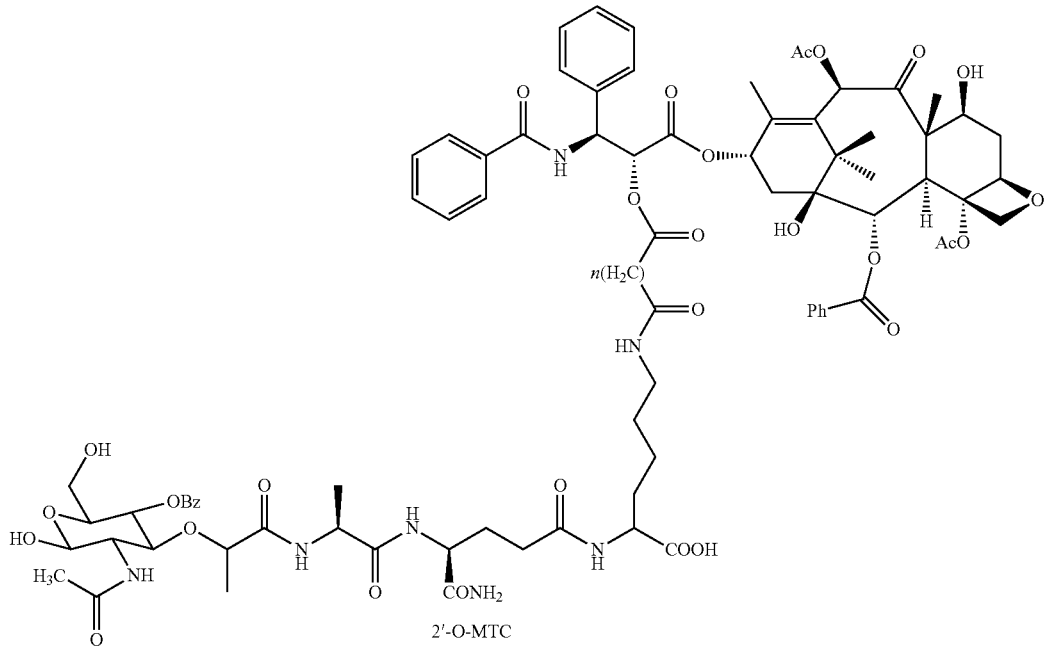

2'-O-MTC

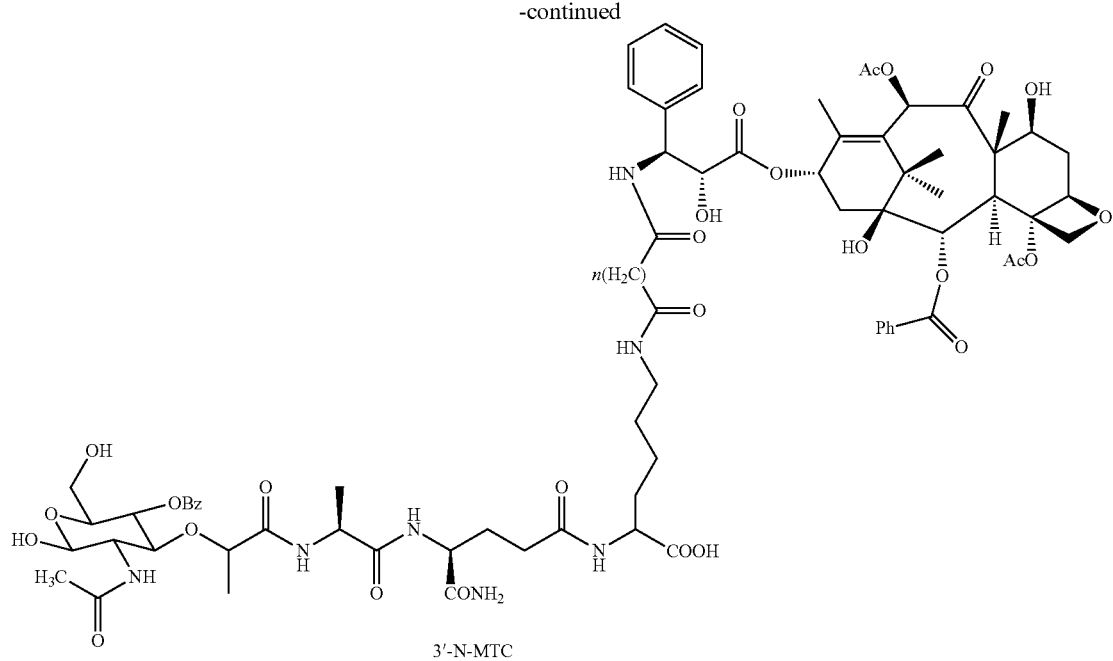

3'-N-MTC

Paclitaxel is a taxanes antineoplastic drug, while docetaxel (Structure 2), a semisynthetic derivative of Paclitaxel, is another important member of taxanes antineoplastic drug which shows inhibitory activities against terminal breast cancer, non-small cell lung cancer, ovarian cancer, pancreatic cancer, liver cancer, head and neck tumors. Current research indicated that docetaxel induces the apoptosis of cancer cell by promoting microtubule to form stable polymer, inhibiting depolymerization[19], and furthermore inhibiting mitosis and proliferation of cancer cell[20]. Research also discovered that docetaxel can make the tumor cell stop at G2/M stage by up regulating Bax protein expression and down regulating Bcl-2 protein expression[21]. Based on this, the disclosure of this application involves replacing paclitaxel in the original conjugates with docetaxel to form conjugates of docetaxel-muramyl dipeptides (MDC), which also showed anti-tumor activities.

Structure 2

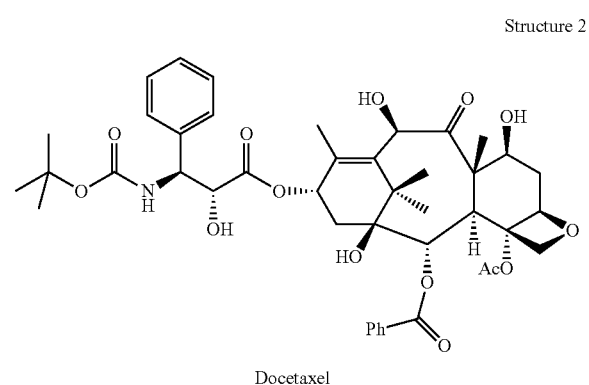

Docetaxel

Muramyl dipeptide shows broad biological activities, and attracts great interest when discovered. However, muramyl dipeptide shows several side effects, such as immunogen induced allergic reactions, fever, inflammation and sleepiness, which limit its clinical application. In order to find muramyl dipeptide analog with higher activity and fewer side effects, scientists have synthesized hundreds of muramyl dipeptide simplifiers or analogues, and studied their biological activities. L-threonine-Muramyl dipeptide is obtained by replacing L-alanine in muramyl dipeptide molecule with L-threonine, which shows higher immunoadjuvant activity than that of the muramyl dipeptide, but pyrogen is 100 times lower. When used as a vaccine adjuvant, L-threonine-Muramyl dipeptide doesn't stimulate macrophages and anti-inflammatory effects, but stimulates the immune response of the administered antigen, so it can be an ideal vaccine adjuvant because its activity and side effect can be effectively separated[22].

Murabutide is obtained by introducing muramyl dipeptide to long lipotropic chain. Murabutide can enhance non-specific anti-bacterial and anti-viral infection of host immune system, and induce activity of colony stimulating factor, Also, it is well tolerated by human[23-26]. Compared to other exogenous immunomodulators, Murabutide is non-pyrogenicity and promotes cytokines, both synergetically and selectively, to release Th1 cytokine, and Murabutide does not cause inflammatory response[27, 28]. Furthermore, Murabutide combined with IFN-α or IL-2 can significantly enhance the anti-tumor activities of the cytokines, hence improve the anti-viral and anti-inflammatory effect of IFN-α[29, 30]. Murabutide can regulate function of macrophage[31]. It can also be used in the treatment of chronic hepatitis C (HCV), because of the synergistic effect shown in vitro when combined with IFN-α[32].

Muramyl tripeptidephosphatidylethanolamine (MTP-PE) is obtained by introducing lipophiliclong chain to muramyl dipeptides through phosphate bond. MTP-PE can activate monocytes and macrophages, then kill tumor cells. MTP-PE encapsulated in liposomes (L-MTP-PE), injected intravenously, is mainly directed to activate the macrophages in lung, liver and spleen[33], wherein its activities is increased by ten to hundreds times, and pyrogenicity is significantly reduced. Two hours after being intravenously injected to metastatic melanoma patients, tumor necrosis factor in plasma increased in sixteen times, and the level of neopterin and interleukin was effectively improved[34].

MDP-Lys (L18) is obtained by introducing lipophilic long chain to muramyl dipeptides through lysine. MDP-Lys (L18) can enhance the production of cytokines such as CSFs, IL-1, IL-6, tumor necrosis factor (TNF-α) etc, which play important role in regulation of the hematopoietic system[35, 36]. In addition, MDP-Lys (L8) has a strong anti-infection, anti-tumor activity[37].

MDP-C is obtained by introducing aromatic conjugate system to muramyl dipeptides through lysine. MDP-C can induce macrophage to generate cytotoxic activity against P388 leukemia cells, it can also induce Tlymphocytes (CTLs) to generate cytotoxic activity against mastocytoma P815. It is reported that the MDP-C stimulates mouse bone marrow dendritic cells (BMDCs) to produce cytokines IL-2 and IL-12 (interleukin), and it also can be used as effective immunopotentiator for it shows activity on stimulating cytotoxic Tlymphocytes to produce interferon-γ. Low doses of MDP-C can significantly and synergistically promote proliferation of mouse spleen lymphocyte induced by Concanavalin A (ConA). In addition, MDP-C can increase the expression of bone marrow dendritic cell surface molecules, such as CD11c, MHC land cell adhesion molecule-1. Also, MDP-C, in vitro, can significantly enhance, through producing antibodies and specific hepatitis B virus surface antigen (HBsAg) Tcell response, the response of immune system to the HBsAg in hepatitis B virus transgenic mice[38, 39].

Adamantantylamide dipeptide (AdDP) is obtained by bonding carboxyl teminal of dipeptide fragment in muramyl dipeptide molecule with amantadine. AdDP is safe, and shows anti-virus infection activity. Compared with other MDP analogues, its bioavailability is higher[40]. AdDP can enhance the humoral immunity both in BALB/c mice and rabbit when administered with protein immunogen orally or peritoneally[41].

Chemists also obtained muramyl dipeptide sugar-free ring analogs by synthesis or isolating from natural product, such as FK-156 and FK-565. They show anti-infection, anti-viral and anti-tumor activities[42].

REFERENCE

[1] Mansukhlal C. Wani, Harold Lawrence Taylor, Monroe E. Wall, Philip Coggon, Andrew T. McPhail; Plant antitumor agents. VI. Isolation and structure of taxol, a novel antileukemic and antitumor agent from *Taxus brevifolia*; J. Am. Chem. Soc.; 1971, 93(9), 2325-2327.
[2] Peter B. Schiff and Susan B. Horwitz; Taxol stabilizes microtubules in mouse fibroblast cells; Proc. Natl. Acad. Sci. USA; 1980, 77(3), 1561-1565.
[3] A. H. Ding, F. Porteu, E. Sanchez, and C. F. Nathan; Shared actions of endotoxin and taxol on TNF receptors and TNF release; Science; 1990, 20, 370-372.
[4] Christian Bogdan and Aihao Ding; Taxol, a microtubule-stabilizing antineoplastic agent, induces expression of tumor necrosis factor a and interleukin-1 in macrophages; Journal of Leukocyte Biology; 1992, 52, 119-121.
[5] B. Brugg and A. Matus; Phosphorylation determines the binding of microtubule-associated protein 2 (MAP2) to microtubules in living cells; J. Cell Biol.; 1991, 114 (4), 735-743.
[6] Carboni, J., Singh, C., Tepper, M.; Cancer Institute Workshop on Taxol and Taxus, Alenandria, V. A.; NCI, 1992.
[7] Ellouz F., Adam A., Ciorbaru R., et al; Minimal structural requirements for adjuvant activity of bacterial peptidoglycan derivatives; Biochem. Biophys. Res. Commun.; 1974, 59, 1317-1325.
[8] Adam, A., Ciorbaru, R., Ellouz, F., Petit, J. F. and Lederer, E.; Adjuvant activity of monomeric bacterial cell wall peptidoglycans; Biochem. Biophys. Res. Commun.; 1974, 56(3), 561-567.
[9] F. Audibert, L. Chédid, P. Lefrancier, J. Choay; Distinctive adjuvanticity of synthetic analogs of mycobacterial water-soluble components; Cellular Immunology; 1976, 21, 243-249.
[10] M. A. Parant, F. M. Audibert, L. A. Chedid, M. R. Level, P. L. Lefrancier, J. P. Choay, and E. Lederer; Immunostimulant activities of a lipophilic muramyl dipeptide derivative and of desmuramyl peptidolipid analogs; Infect. Immun.; 1980, 27, 826-831.
[11] Adam A., Petit J. F., Chedid L.; Influence of a synthetic adjuvant (MDP) on qualitative and quantitative changes of serum globulins; Immunology; 1978, 35(6), 963-970.
[12] Dietrich F. M., Hochkeppel H. K., Lukas B.; Enhancement of host resistance against virus infections by MTP-PE, a synthetic lipophilic muramyl peptide—increased survival in mice and guinea pigs after single drug administration prior to infection, and the effect of MTP-PE on interferon levels in sera and lungs; Int. J. Immunopharmacol; 1986, 8, 931-932.
[13] Adam A., Lederer E.; Muramyl peptides: immunomodulators, sleep factors, and vitamins; Med. Res. Rev., 1984, 4(2), 111-152.
[14] Anton V. Gorbachev, Nancy A. Dilulio, and Robert L.; Fairchild IL-12 augments CD81 T cell development for contact hypersensitivity responses and circumvents Anti-CD154 antibody-mediated inhibition; The Journal of Immunology, 2001, 167, 156-162.
[15] Alexandre A. Vetcher, Marek Napierala, Ravi R. Iyer, Paul D. Chastain, Jack D. Griffith, and Robert D.; Wells sticky DNA, a long GAA-GAA-TTC triplex that is formed intramolecularly, in the sequence of intron 1 of the frataxin gene; J. Biol. Chem.; 2002, 277, 39217-39227.
[16] C. L. Contel, N. Temime, D. J. Charron, and M. A. Parant; Modulation of lipopolysaccharide-induced cytokine gene expression in mouse bone marrow-derived macrophages by muramyl dipeptide; The Journal of Immunology; 1993, 150, 4541-4549.
[17] Xuqin Li, Junli Yu, Song Xu, Nan Wang, Hongzhen Yang, Zheng Yan, Guifang Cheng, Gang Liu; Chemical conjugation of muramyl dipeptide and paclitaxel to explore the combination of immunotherapy and chemotherapy for cancer, Glycoconj J.; 2008, 25(5), 415-425.
[18] Patent No. 200510081265X.
[19] Toshiyuki Harada, Shigeaki Ogura, Koichi Yamazaki, Ichiro Kinoshita, Tomoo Itoh, Hiroshi Isobe, Katsushige Yamashiro, Hirotoshi Dosaka-Akita, Masaharu Nishimura; Predictive value of expression of P53, Bcl-2 and lung resistance-related protein for response to chemotherapy in non-small cell lung cancers; Cancer Science; 2005, 94(4), 394-399.
[20] David L. Morse, Heather Gray, Claire M. Payne, and Robert J. Gillies; Docetaxel induces cell death through mitotic catastrophe in human breast cancer cells; Mol Cancer Ther, 2005, 4, 1495-1504.
[21] Yu Q, Gao J. X., He X. S., et al; Docetaxcel induces apoptosis and regulates expressions of bax and bcl-2 protein in human breast carcinoma MCF-7 Cells; Cancer Res. Pre. Treatment, 2006, 33(6), 388-390.

[22] Deborah A. Eppstein, Noelene E. Byars, Anthony C. Allison; New adjuvants for vaccines containing purified protein antigens; Advanced Drug Delivery Reviews 1990, 4, 233-253.

[23] L. A. Chedid, M. A. Parant, F. M. Audibert, G. J. Riveau, F. J. Parant. E. Lederer, J. P. Choay, and P. L. Lefrancier, Biological activity of a new synthetic muramyl peptide adjuvant devoid of pyrogenicity; Infection and Immunity; 1982, 35, 417-424.

[24] Chomel J. J., Simon-Lavoine N., Thouvenot D., Valette M., Choay J., Chedid L., Aymard M.; Prophylactic and therapeutic effects of murabutide in OF1 mice infected with influenza A and B viruses; International Journal of Immunopharmacology; 1985, 7(3), 346-347.

[25] George M. Bahr, Edith Darcissac, Dorian Bevec, Peter Dukor, Louis Chedid; Immunopharmacological activities and clinical development of muramyl peptides with particular emphasis on murabutide; International Journal of Immunopharmacology; 1995 17(2), 117-131.

[26] A. Galelli, P. Lefrancier, and L. Chedid; Colony-stimulating activity induced by synthetic muramyl peptides: variation with chemical structure and association with anti-infectious activity; Infection and Immunity; 1984, 46, 495-500.

[27] George M. Bahr. Edith Darcissac, Philippe R. Pouillart, Louis A. Chedid; Synergistic effects between recombinant interleukin-2 and the synthetic immunomodulator murabutide: selective enhancement of cytokine release and potentiation of antitumor activity; Journal of Interferon and Cytokine Research; 1996, 16(2), 169-178.

[28] Edith C. A. Darcissac, George M. Bahr, Philippe R. Pouillart, Gilles J. Riveau, Monique A. Parant; Selective potentiation of cytokine expression in human whole blood by murabutide, a muramyl dipeptide analogue; Cytokine, 1996, 8, 658-666.

[29] George M. Bahr, Philippe R. Pouillart, Louis A. Chedid; Enhancement in vivo of the anti-inflammatory and antitumor activities of type I interferon by association with the synthetic immunomodulator murabutide; Journal of Interferon and Cytokine Research; 1996, 16(4), 297-306.

[30] Philippe R. Pouillart, Francoise M. Audibert, Louis A. Chedid, Pierre L. Lefrancier, George M. Bahr; Enhancement by muramyl peptides of the protective response of interferon-α/β against encephalomyocarditis virus infection; International Journal of Immunopharmacology; 1996, 18(3), 183-192.

[31] Gilles J. Riveau, Beatrice G. Brunel-Riveau, Francoise M. Audibert, Louis A. Chedid; Influence of a muramyl dipeptide on human blood leukocyte functions and their membrane antigens; Cellular Immunology; 1991, 134, 147-156.

[32] E. C. A. Darcissac, V. Vidal, M. Guillaume, J. J. Thebault, G. M. Bahr; Clinical tolerance and profile of cytokine induction in healthy volunteers following the simultaneous administration of IFN-α and the synthetic immunomodulator murabutide; Journal of Interferon and Cytokine Research; 2001, 21(9), 655-661.

[33] (a). Nardin A., Lefebvre M. L., Labroquere K., Faure O., Abastado J. P.; Liposomal muramyl tripeptide phosphatidylethanolamine: tTargeting and activating macrophages for adjuvant treatment of osteosarcoma; Current Cancer Drug Targets; 2006, 6, 123-133.

(b). Meyers Paul A., Schwartz Cindy L., et al; A randomized, prospective trial of the addition of ifosfamide and/or muramyl tripeptide to cisplatin, doxorubicin, and high-dose methotrexate; J. Clin. Oncol.; 2005, 23(9), 2004-2011.

[34] Liebes L., Walsh C. M., Chachoua A., et al; Modulation of monocyte functions by muramyl triptide phosphatidylethanolamine in a phase II study in patients with metastatic melanoma; J. Natl. Cancer. Inst.; 1992, 84, 694-699.

[35] Y. Osada, T. Otani, M. Sato, T. Une, K. Matsumoto, and H. Ogawa; Polymorphonuclear leukocyte activation by a synthetic muramyl dipeptide analog; Infection and Immunity; 1982, 38, 848-854.

[36] Kenji Namba, Eiko Yamamura, Hironobu Nitanai, Tsuyoshi Otani. Ichiro Azuma; Romurtide, a synthetic muramyl dipeptide derivative, promotes megakaryocytopoiesis through stimulation of cytokine production in nonhuman primates with myelosuppression; Vaccine, 1997, 15(4), 405-413.

[37] Ichiro Azuma, Tsukasa Seya; Development of immunoadjuvants for immunotherapy of cancer; International Immunopharmacology; 2001, 1(7), 1229-1392.

[38] Hong-Zhen Yang, Song Xu, Xue-Yan Liao, Suo-De Zhang, Zheng-Lun Liang, Bai-He Liu. Jin-Ye Bai, Chao Jiang, Jian Ding, Gui-Fang Cheng, and Gang Liu; A novel immunostimulator, $N_2$-[α-O-Benzyl-N-(acetylmuramyl)-1-alanyl-d-isoglutaminyl]-$N_6$-trans-(m-nitrocinnamoyl)-1-lysine, and its adjuvancy on the hepatitis B surface antigen; J. Med. Chem.; 2005, 48(16), 5112-5122.

[39] Patent No. CN1609118A.

[40] P. Walder, E. Buchar, Z. Machková, T. Vrba, M. Flegel, I. Janků, K. Mas'ek; Pharmacokinetic profile of the immunomodulating compound adamantylamide dipeptide (AdDP), a muramyl dipeptide derivative in mice; Immunopharmacology and Immunotoxicology, 1991, 13 (1 and 2), 101-119.

[41] Pablo D. Becker, Ricardo S. Corral, Carlos A. Guzmán, Saul Grinstein; Adamantylamide dipeptide as effective immunoadjuvant in rabbits and mice; Vaccine; 2001, 19(32), 4579-4903.

[42] A. M. Kolodziejczyk, A. S. Kolodziejczyk, S. Stoev; New convenient synthesis of immunostimulating peptides containingmeso-diaminopimelic acid Syntheses of FK-565 and FK-156; International Journal of Peptide and Protein Research; 1992, 39(4), 382-387.

DETAILED DESCRIPTION OF THE INVENTION

The technical problem to be solved by the present application is to provide a compound having anti-tumor and anti-metastasis synergy activities.

The second technical problem to be solved by the present application is to provide a method for the preparation of the compound.

The third technical problem to be solved by the present application is to provide pharmaceutical composition comprising the compounds.

A further technical problem to be solved in the present application is to apply the compound in the preparation of anti-tumor and anti-metastasis synergy drugs.

Provided is a compound of formula I, and/or a pharmaceutically acceptable salt thereof,

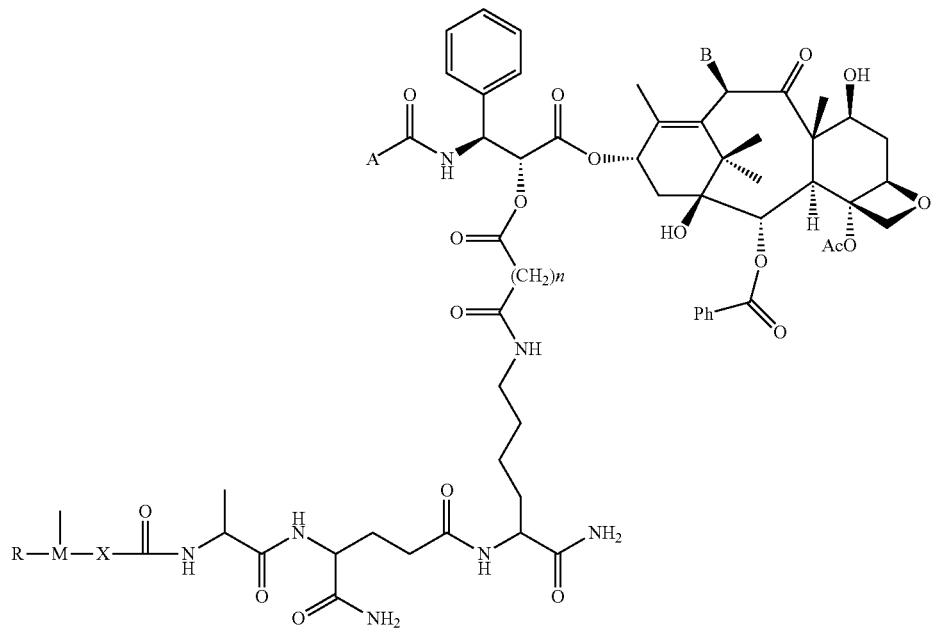

wherein, when A is phenyl, B is acetoxy; when A is tert-butoxy, B is hydroxy;

wherein, n=2, 3, 4, 5, 6, 7, 8, 9, 10, 11 or 12.

In a preferred embodiment, n=2, 3, 4, 5, 6, 7, 8, 9 or 10.

In another preferred embodiment, n=2, 3, 4, 5, 6, 7 or 8.

In a further preferred embodiment, n=2, 3, 4 or 5.

Wherein X is chosen from $C_{1-6}$alkyl, $C_{1-6}$alkylene and $C_{1-6}$alkyl comprising at least one heteroatom, wherein the at least one heteroatom is independently chosen from oxygen, sulfur and nitrogen; or X is a single bond, which means M is connected to carbonyl directly.

In a preferred embodiment, X is chosen from $C_{1-4}$alkyl, $C_{1-4}$alkylene and $C_{1-4}$alkyl comprising at least one heteroatom, wherein the at least one heteroatom is independently chosen from oxygen and sulfur; or X is a single bond, which means M is connected to carbonyl directly.

In another preferred embodiment, X is chosen from $C_{1-3}$alkyl, $C_{1-3}$alkylene and $C_{1-3}$alkyl comprising at least one heteroatom, wherein the at least one heteroatom is oxygen; or X is a single bond, which means M is connected to carbonyl directly.

In a further preferred embodiment, X is chosen from —C=C—, —$CH_2$—$CH_2$—, —O—$CH_2$— and single bond.

M can be substituted or unsubstituted aryl, substituted or unsubstituted heteroaryl, for example, M can be aryl or heteroaryl, the term "aryl" as disclosed herein refers to five to fourteen membered aromatic ring.

In one embodiment, M is chosen from five-membered aryl, six-membered aryl, nine-membered fused ring aryl, ten-membered fused ring aryl, thirteen-membered fused ring aryl and fourteen-membered fused ring aryl.

The term "five-membered aryl" as disclosed herein refers to

The term "six-membered aryl" as disclosed herein refers to

The term "nine-membered fused ring aryl" as disclosed herein refers to

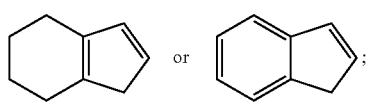 [SMILES: C1=CC2=C(C1)CCCC2 ; C1=Cc2ccccc2C1]

The term "ten-membered fused ring aryl" as disclosed herein refers to

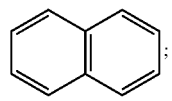

The term "heteroaryl" can be, for example, a heterocyclic aromatic ring comprising at least one, such as one, two, three, and four heteroatoms in the ring, wherein the at least one heteroatom is independently chosen from nitrogen, oxygen and sulfur.

For another example, the "heteroaryl" can be five to fourteen membered heterocyclic aromatic ring comprising at least one, such as one, two, three, and four heteroatoms in the ring, wherein the at least one heteroatom is independently chosen from nitrogen, oxygen and sulfur.

For a further example, the "heteroaryl" can be chosen from five-membered heterocyclicaromatic ring, six-membered heterocyclicaromatic ring, eight-membered fused heterocyclicaromatic ring, nine-membered fused heterocyclicaromatic ring, ten-membered fused heterocyclicaromatic ring, all of the aromatic ring mentioned above comprising at least one, such as one, two, three, and four heteroatoms in the ring, wherein the at least one heteroatom is independently chosen from nitrogen, oxygen and sulfur.

The term "five-membered heterocyclicaromatic ring" comprising at least one, for example one, two, three, or four heteroatoms in the ring, wherein the at least one heteroatom is independently chosen from nitrogen, oxygen and sulfur, the five-membered heterocyclicaromatic ring disclosed herein is chosen from

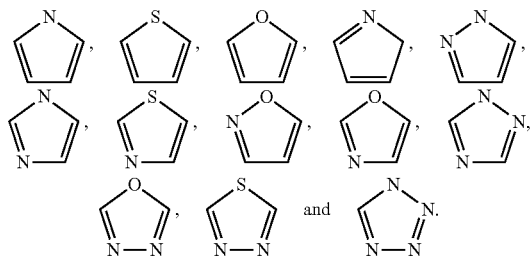

The term "six-membered heterocyclicaromatic ring" comprising at least one, for example one, two, three, or four heteroatoms in the ring, wherein the at least one heteroatom is independently chosen from nitrogen, oxygen and sulfur, the six-membered heterocyclicaromatic ring disclosed herein is chosen from

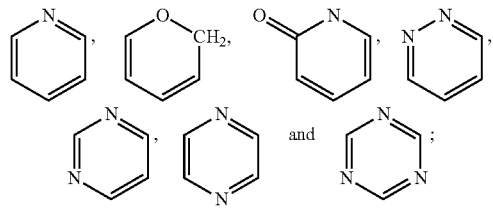

The term "eight-membered fused heterocyclicaromatic ring" comprising at least one, for example one, two, three, or four heteroatoms in the ring, wherein the at least one heteroatom is independently chosen from nitrogen, oxygen and sulfur, the eight-membered fused heterocyclicaromatic ring disclosed herein is chosen from

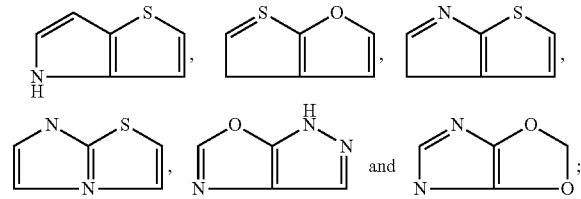

The term "nine-membered fused heterocyclicaromatic ring" comprising at least one, for example one, two, three, or four heteroatoms in the ring, wherein the at least one heteroatom is independently chosen from nitrogen, oxygen and sulfur, the nine-membered fused heterocyclicaromatic ring disclosed herein is chosen from

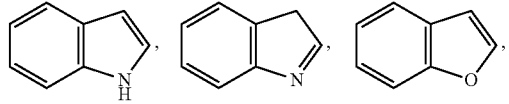

-continued

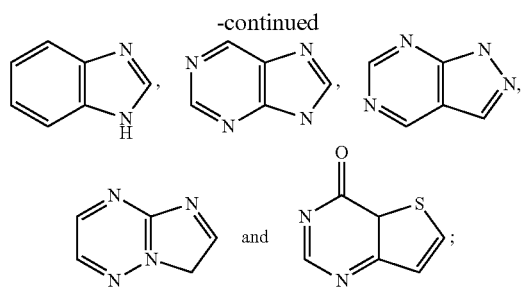

The term "ten-membered fused heterocyclicaromatic ring" comprising at least one, for example one, two, three, or four heteroatoms in the ring, wherein the at least one heteroatom is independently chosen from nitrogen, oxygen and sulfur, the ten-membered fused heterocyclicaromatic ring disclosed herein is chosen from

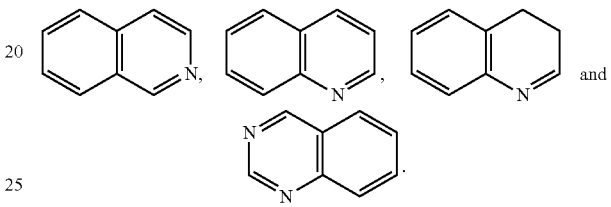

R refers to one or more groups, and R can be connected to M at any applicable point of attachment.

In one embodiment, R is chosen from hydrogen, substituted or unsubstituted straight or branched $C_{1-6}$alkyl, hydroxy, substituted or unsubstituted straight or branched $C_{1-6}$alkoxy, thiol, substituted or unsubstituted straight or branched $C_{1-6}$alkylthio, $C_{1-6}$alkoxy-$C_{1-6}$alkyl, amino, substituted or unsubstituted straight or branched $C_{1-6}$ alkylamino includes mono-alkylamino or di-alkylamino, aldehyde group, substituted or unsubstituted straight or branched $C_{1-6}$ alkylcarbonyl, carboxyl, substituted or unsubstituted straight or branched $C_{1-6}$ alkylcarboxyl, carbamoyl, substituted or unsubstituted straight or branched $C_{1-6}$ alkylamide, $C_{2-6}$ alkene, halogen, nitro and cyano;

The substituent(s) on substituted $C_1$-$C_6$straight chain or branched chain described herein is independently chosen from hydroxyl, thiol, amino, aldehyde group, carboxyl, carbamoyl, halogen, nitro and cyano;

In one embodiment, R is chosen from hydrogen, substituted or unsubstituted straight or branched $C_{1-4}$ alkyl, hydroxy, substituted or unsubstituted straight or branched $C_{1-4}$ alkoxy, $C_{1-4}$ alkoxy-$C_{1-4}$ alkyl, thiol, substituted or unsubstituted straight or branched $C_{1-4}$alkylthio, amino, substituted or unsubstituted straight or branched $C_{1-4}$ alkylamino includes mono-alkylamino or di-alkylamino, aldehyde group, substituted or unsubstituted straight or branched $C_{1-4}$alkylcarbonyl, carboxyl, substituted or unsubstituted straight or branched $C_{1-4}$alkylcarboxyl, carbamoyl, substituted or unsubstituted straight or branched $C_{1-4}$alkylamide, $C_{2-4}$alkene, halogen, nitro and cyano;

The substituent(s) on substituted straight or branched $C_{1-4}$ chain described herein is chosen from hydroxyl, thiol, amino, aldehyde group, carboxyl, carbamoyl, fluorine, chlorine, bromine, nitro and cyano;

In one embodiment, R is chosen from hydrogen, straight or branched $C_{1-4}$ alkyl, hydroxy, straight or branched $C_{1-4}$ alkoxy, thiol, straight or branched $C_{1-4}$alkylthio, amino, straight or branched $C_{1-4}$ alkylamino, halogen, nitro and cyano;

In one embodiment, R is chosen from hydrogen, hydroxyl, thiol, amino, fluorine, chlorine, bromine, nitro, cyano, methyl, ethyl, n-propyl, iso-propyl, methoxy, ethoxy, n-propoxy and iso-propoxy;

In one embodiment, the compound of formula I as disclosed herein is chosen from the compounds of formula IA as below:

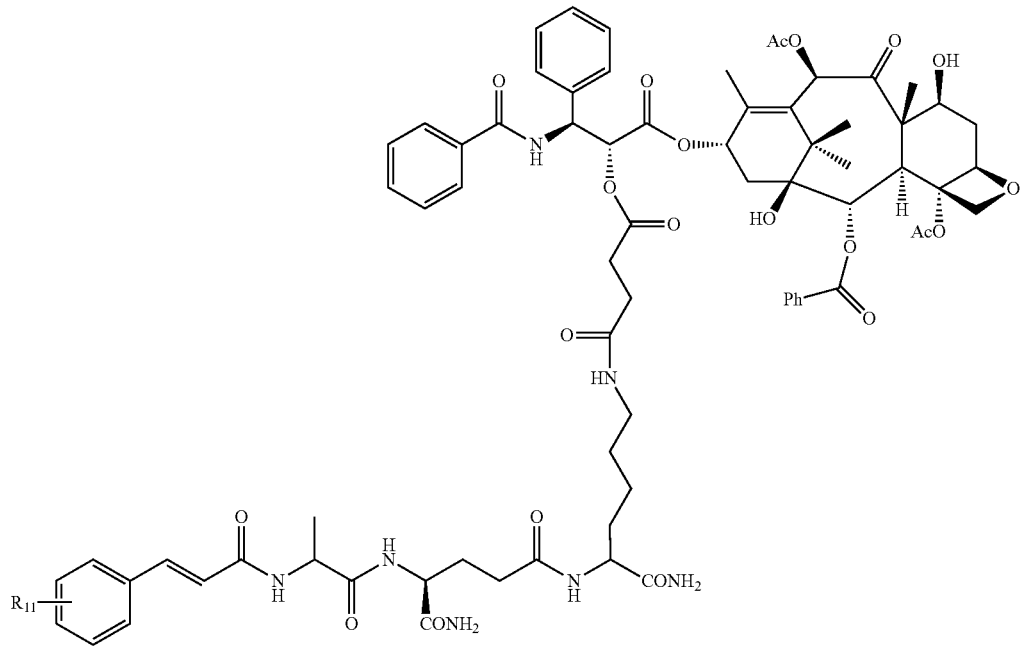

IA $R_{11}$ refers to one or more groups, and $R_{11}$ can be connected to phenyl at any applicable point of attachment. In one embodiment, $R_{11}$, is independently chosen from hydrogen, hydroxyl, thiol, amino, aldehyde group, carboxyl, carbamoyl, halogen, nitro, cyano, $C_{1-4}$ alkyl, $C_{1-4}$ alkoxy, $C_{1-4}$ alkylamino and $C_{1-4}$ alkoxy-$C_{1-4}$ alkyl.

In one embodiment, the compound of formula I as disclosed herein is chosen from compounds of formula IB as below:

$R_{12}$ refers to one or more groups, and $R_{12}$ can be connected to thienyl at any applicable point of attachment. In one embodiment, $R_{12}$ is independently chosen from hydrogen, hydroxyl, thiol, amino, aldehyde group, carboxyl, carbamoyl, halogen, nitro, cyano, $C_{1-4}$ alkyl, $C_{1-4}$ alkoxy, $C_{1-4}$ alkylamino and $C_{1-4}$ alkoxy-$C_{1-4}$ alkyl.

In one embodiment, the compound of formula I as disclosed herein is chosen from compounds of formula IC as below:

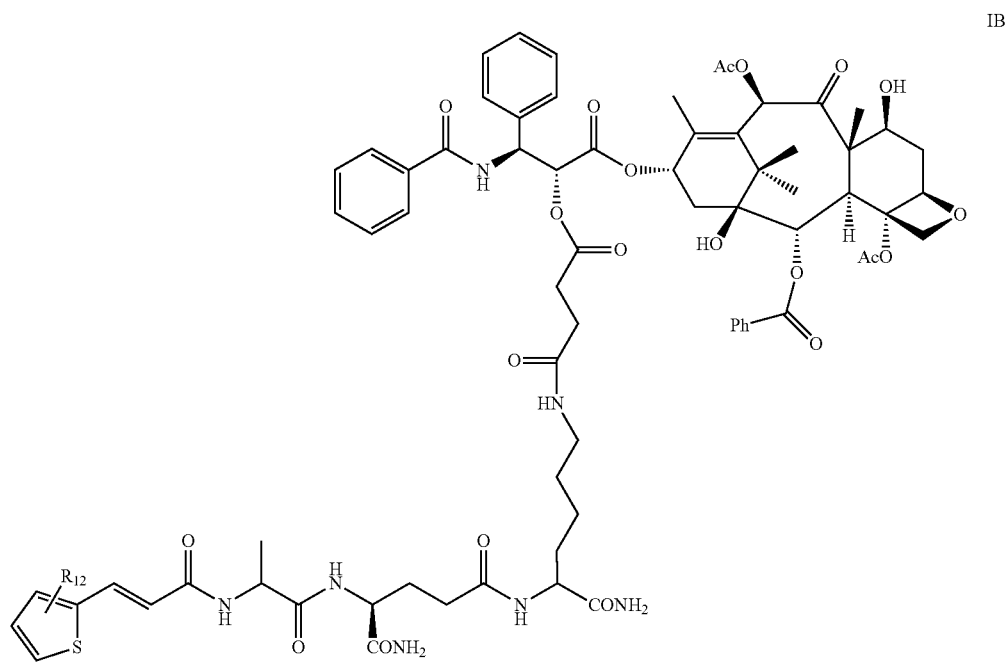

IB

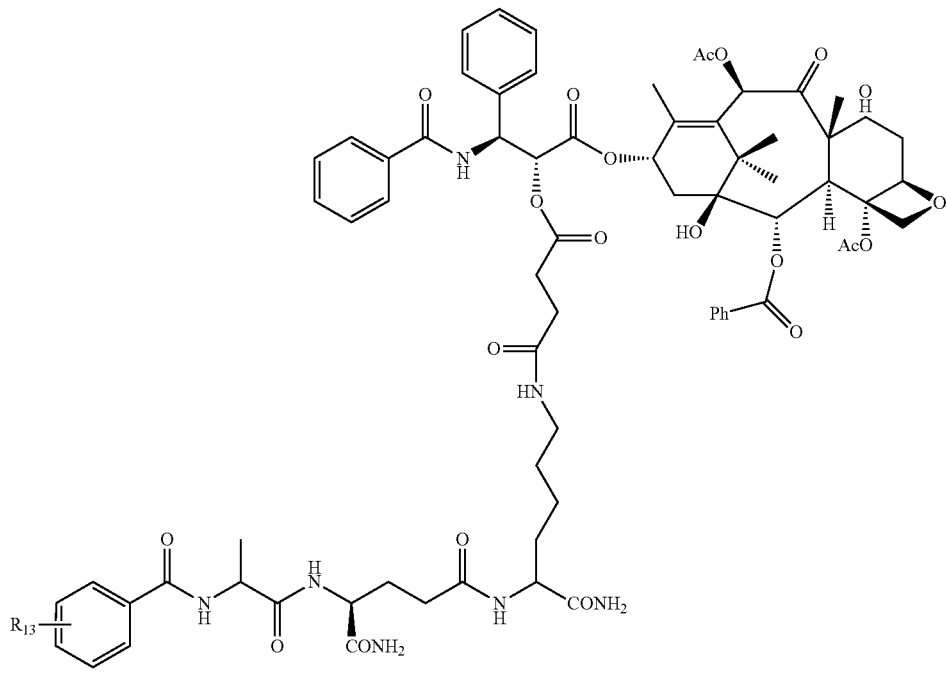

IC $R_{13}$ refers to one or more groups, and $R_{13}$ can be connected to phenyl at any applicable point of attachment. In one embodiment, $R_{13}$ is independently chosen from hydrogen, hydroxyl, thiol, amino, aldehyde group, carboxyl, carbamoyl, halogen, nitro, cyano, $C_{1-4}$ alkyl, $C_{1-4}$ alkoxy, $C_{1-4}$ alkylamino and $C_{1-4}$ alkoxy-$C_{1-4}$ alkyl.

In one embodiment, the compound of formula I as disclosed herein is chosen from compounds of formula ID as below:

$R_{14}$ refers to one or more groups, and $R_{14}$ can be connected to quinolyl at any applicable point of attachment. In one embodiment, $R_{14}$ is independently chosen from hydrogen, hydroxyl, thiol, amino, aldehyde group, carboxyl, carbamoyl, halogen, nitro, cyano, $C_{1-4}$ alkyl, $C_{1-4}$ alkoxy, $C_{1-4}$ alkylamino and $C_{1-4}$ alkoxy-$C_{1-4}$ alkyl.

In one embodiment, the compound of formula I as disclosed herein is chosen from compounds of formula IE as below:

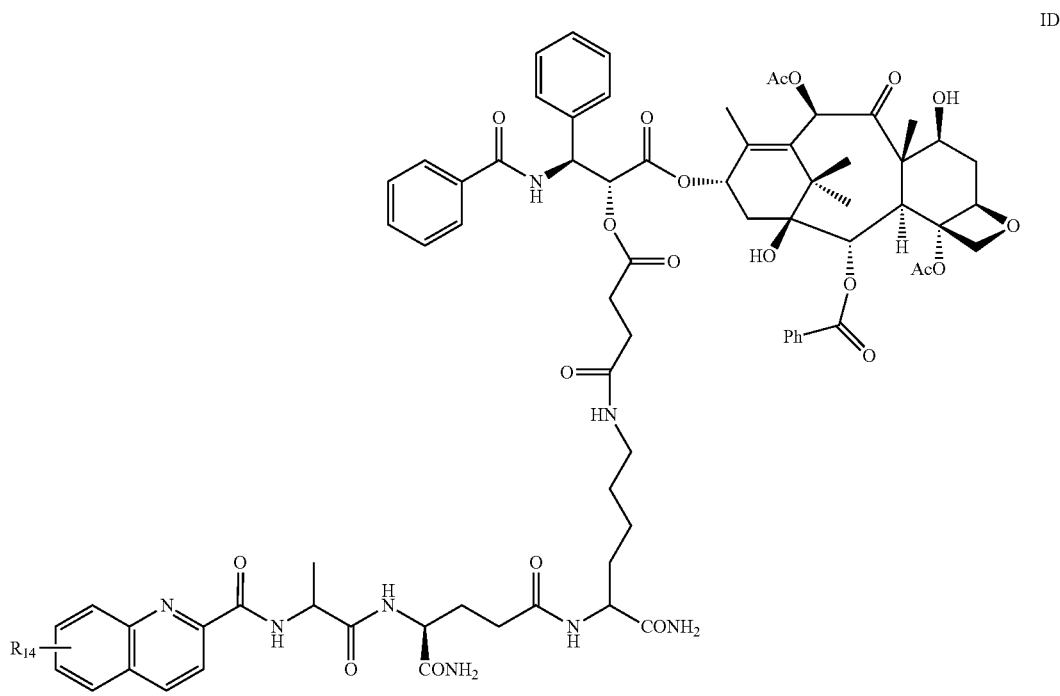

ID

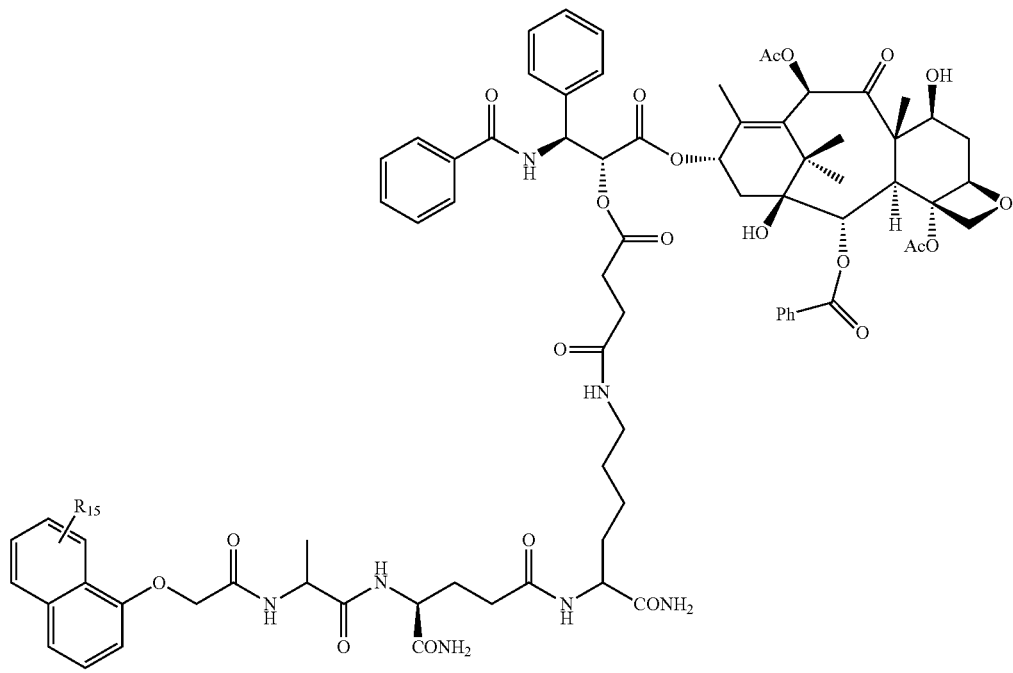

IE $R_{15}$ is one or more groups, and $R_{15}$ can be connected to naphthyl at any applicable point of attachment. In one embodiment, $R_{15}$ is chosen from hydrogen, hydroxyl, thiol, amino, aldehyde group, carboxyl, carbamoyl, halogen, nitro, cyano, $C_{1-4}$ alkyl, $C_{1-4}$ alkoxy, $C_{1-4}$ alkylamino and $C_{1-4}$ alkoxy-$C_{1-4}$ alkyl.

In one embodiment, the compound of formula I as disclosed herein is chosen from compounds of formula IF as below:

$R_{21}$ refers to one or more groups, and $R_{21}$ can be connected to phenyl at any applicable point of attachment. In one embodiment, $R_{21}$ is chosen from hydrogen, hydroxyl, thiol, amino, aldehyde group, carboxyl, carbamoyl, halogen, nitro, cyano, $C_{1-4}$ alkyl, $C_{1-4}$ alkoxy, $C_{1-4}$ alkylamino and $C_{1-4}$ alkoxy-$C_{1-4}$ alkyl.

In one embodiment, the straight or branched $C_{1-6}$ alkyl described herein refers to the straight or branched $C_{1-4}$ alkyl, or the straight or branched $C_{2-5}$ alkyl. In another embodiment,

IF

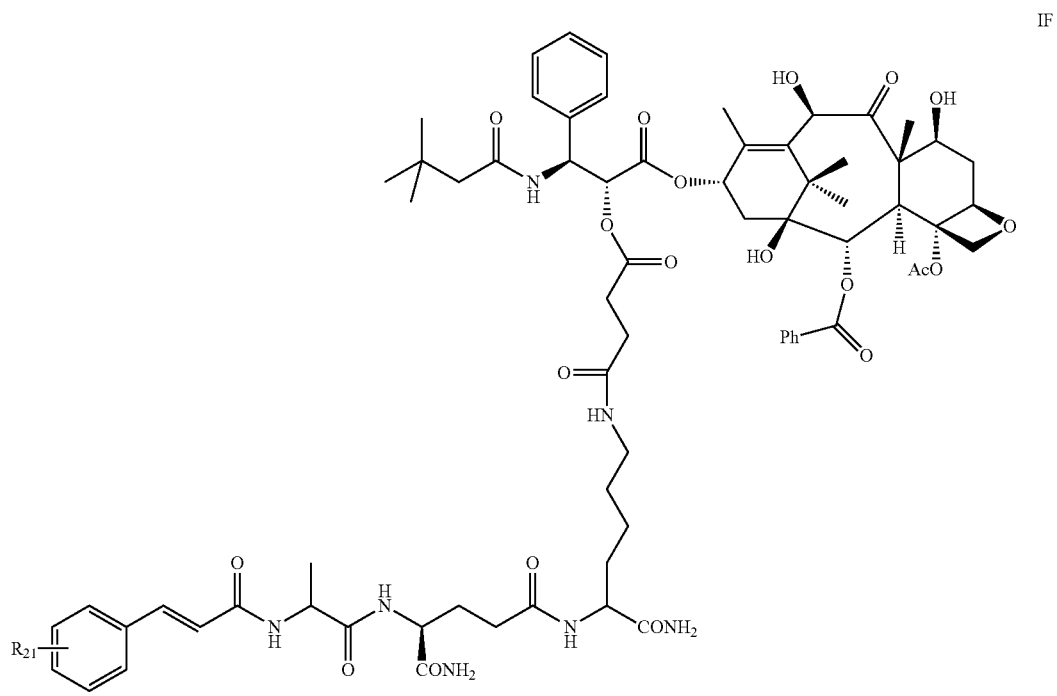

the straight or branched $C_{1-6}$alkyl is chosen from methyl, ethyl, n-propyl, iso-propyl, n-butyl, iso-butyl, tert-butyl, pentyl, neo-pentyl, iso-pentyl and hexyl. The straight or branched $C_{1-4}$ alkyl described herein is preferably chosen from methyl, ethyl, n-propyl, iso-propyl, n-butyl, and tert-butyl. The straight or branched $C_{2-5}$ alkyl described herein is preferably chosen from ethyl, n-propyl, iso-propyl, n-butyl, tert-butyl, pentyl, and iso-pentyl.

The substituent(s) on substituted straight or branched $C_{1-6}$ alkyl described herein can be chosen from hydroxyl, sulfydryl, amino, aldehyde group, carboxyl, carbamoyl, halogen, nitro and cyano.

The substituent(s) on substituted straight or branched $C_1$-$C_4$alkyl described herein can be chosen from hydroxyl, sulfydryl, amino, aldehyde group, carboxyl, carbamoyl, fluorine, chlorine, bromine, nitro and cyano.

The term "$C_{2-6}$ alkene" as disclosed herein refers to alkene having two, three, four, five or six carbon atoms. It can be straight chain or branched chain. For example, $C_{2-6}$ alkene can be chosen from vinyl, 1-propenyl, 2-propenyl, 1-butenyl, 2-butenyl, 1-pentenyl and 1-hexenyl, $C_{2-6}$ alkene is preferably chosen from $C_{2-4}$ alkene.

The term "alkoxy" as disclosed herein refers to —O-alkyl.

The term "halogen" as disclosed herein refers to fluorine, chlorine, bromine or iodine. In one embodiment, the halogenis preferably chosen from fluorine and chlorine.

The "R-M-X-CO-" group is most preferably chosen from p-chloro-cinnamoyl, p-hydroxy-cinnamoyl, p-methyl-cinnamoyl, 2,4-di-fluoro-cinnamoyl, 3-fluoro-4-chloro-cinnamoyl, 3-chloro-4-fluoro-cinnamoyl, 4-fluoro-cinnamoyl, 3-fluoro-cinnamoyl, 3,4-di-fluoro-cinnamoyl, 2-quinoline-acyl, 2-thienyl-acryloyl, 2-nitro-4-chloro-benzoyl and 2-naphthyloxy-acetyl.

The pharmaceutically acceptable salt of the conjugates disclosed above is part of the invention, the basic nitrogen atoms in the molecules of the conjugates in the present invention can form salts with acid, not be particularly limited, with any pharmaceutically acceptable acid such as inorganic acids, including, for example, hydrochloric acid, hydrobromic acid, sulfuric acid, phosphoric acid, nitric acid, and organic acids, including, for example, oxalic acid, fumaric acid, maleic acid, succinic acid, citric acid, tartaric acid, methanesulfonic acid and p-toluenesulfonic acid, etc.

The conjugates of muramyl dipeptide analogue and paclitaxel, or muramyl dipeptide analogue and docetaxel, and salts thereof can be synthesized by the general and exemplary methods as follows:
1. Paclitaxel-2'-O-alkane-di-acid monoester or docetaxel-2'-O-alkane-di-acid monoesterare synthesized by liquid-phase synthesis;
2. Muramyl dipeptide analogue (MDA) is synthesized by solid-phase or liquid-phase synthesis;
3. Conjugates of muramyl dipeptide analogue and paclitaxel, or muramyl dipeptide analogue and docetaxel are synthesized by liquid-phase synthesis.

The method for preparing paclitaxel-2'-O-alkane-di-acid monoester or docetaxel-2'-O-alkane-di-acid monoester through liquid-phase synthesis comprises the steps as follows:

1) Preparation of the paclitaxel-2'-O-alkane-di-acid monoester through liquid-phase synthesis (1) Paclitaxel, alkane-di-anhydride and 4-N,N-dimethyl pyridine (DMAP) are dissolved in pyridine, and are stirred for 4 h at room temperature (r.t);

(2) The solution of step (1) is diluted with ethylacetate (AcOEt), the AcOEt layer is washed with saturate $CuSO_4$ solution and $H_2O$ sequentially;

(3) At last, the AcOEt layer is separated and then concentrated under vacuum, abundant water is added into the residue, white solid precipitated, the paclitaxel-2'-O-alkane-di-acid monoester was obtained as white solid after filtration and lyophilization.

2) Preparation of the docetaxel-2'-O-alkane-di-acid monoester through liquid-phase synthesis (1) Docetaxel, alkane-di-anhydride and 4-N,N-dimethyl pyridine are dissolved in N,N-dimethylformamide (DMF), and are stirred for 2 h at r.t;

(2) The DMF solution is diluted with dichloromethane (DCM), then, the DCM layer is washed with HCl aqueous solution (2N) and $H_2O$ sequentially;

(3) At last, the DCM layer is separated and concentrated under vacuum, the residue is dissolved in a little methanol, then abundant water is added into the residue, white solid precipitated, docetaxel-2'-O-alkane-di-acid monoester is obtained as white solid after filtration and lyophilization.

The method for preparing the muramyl dipeptide analogue through solid-phase synthesis and liquid-phase synthesis comprises the steps as follows:
1) Solid-Phase Synthesis:
(1) Synthesis of amino acid intermediate Fmoc-D-iso-Gln-OH;
The route is shown below:

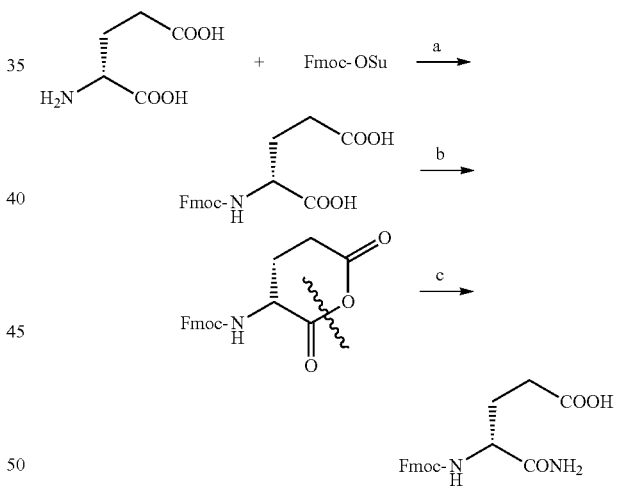

Reagents and conditions: (a) r.t, 3 d; (b) dicyclohexyl carbodiimide (DCC), 0° C., 5 h, r.t, 20 h; (c) $NH_3$; −10° C., 1.5 h.

(2) Then, by employing any one of amino resin such as Rink-Amide AM (loading 0.88 mmol/g) as carrier of solid phase, Fmoc-L-Lys(Boc)-COOH, Fmoc-D-iso-Gln-COOH, Fmoc-L-Ala-COOH and carboxylic acid are introduced to the resin by solid-phase synthesis; After the condensation reaction is completed, the muramyl dipeptide analogue is obtained by steps, such as washing the resin thoroughly, cleaving the crude product from the resins, and purifying the crude product, etc. Acylation involved herein are conventional amide condensation reaction, the condensation reaction is completed by adding the excess amount of reagents (such as amino acid or carboxylic acid) and superactive condensing agent (such as 2-(7-Aza-1H-benzotriazole-1-yl)-1,1, 3,3-tetramethyluronium hexafluorophosphate (HATU), 2-(1H-Benzotriazole-1-yl)-1,1,3,3-tetramethyluronium hexafluorophosphate (HBTU), Benzotriazol-1-yloxytris(dimethylamino)-phosphonium hexafluorophosphate (BOP), or Benzotriazol-1-yl-oxytripyrrolidinophosphonium hexafluorophosphate (PyBOP). The characteristic of the method is that the introduction of the carboxylic acid is not affected by structure (such as aromatic and non-aromatic, straight chain and branched chain), the steric hindrance, physicochemical property, electronic effect, the ring system and the line system, etc., So the three amino acids above can be replaced by any natural or unnatural amino acid, such as Fmoc-D-Lys(Boc)-COOH, Fmoc-L-iso-Gin-COOH, Fmoc-L-Gln-COOH, Fmoc-D-Gln-COOH or Fmoc-D-Ala-COOH. The route is shown as below:

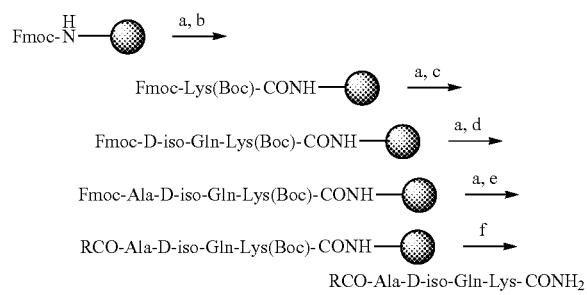

Reagents and conditions: (a) 20% piperidine/DMF; rt, 1 h; (b) Fmoc-Lys(Boc)-OH, HOBt, N,N'-Diisopropyl carbodiimide (DIC); r.t, 8 h; (C) Fmoc-D-iso-Gln-OH, HOBt, DIC; r.t, 12 h; (d) Fmoc-Ala-OH, HOBt, DIC; r.t, 8 h; (e) organic acid©, HOBt. DIC; r.t, 8 h; (f) 90% Trifluoroacetic acid(TFA)/H$_2$O, r.t, 2 h.

2) Liquid-Phase Synthesis:

(1) Synthesis of amino acid intermediate Boc-D-Glu(Obzl)-NH$_2$;

The route is shown below:

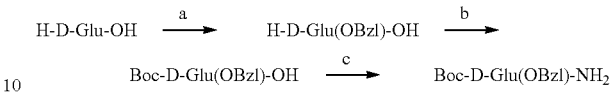

Reagents and conditions: (a) C$_6$H$_5$CH$_2$OH, BF$_3$.Et$_2$O; r.t, 15 h; (b) (Boc)$_2$O, NaHCO$_3$; r.t, 20 h; (c) HOSu, DCC, NH$_3$; −10° C., 1.5 h.

(2) Synthesis of amino acid intermediate Boc-Lys(Z)-NH$_2$;

The route is shown below:

Reagents and conditions: (a) HOSu, DIC, NH$_3$; −10° C., 1.5 h.

(3) Then, the dipeptide fragment Boc-Ala-D-Glu(OBzl)-NH$_2$ and the tripeptide fragment R-Ala-D-Glu(OBzl)-NH$_2$ are synthesized by the active ester method, and the protecting group Bzl in tripeptide is removed by using hydrobromic acid in acetic acid solution or under other feasible acid/basic conditions, the tetrapeptide R-Ala-D-iso-Gln-Lys(Z)-NH$_2$ is synthesized by the active ester method;

(4) At last, the protecting group Z is removed by using the mixture of boron trifluoride ethylether, TFA and ethanethiol (V/V/V=9:9:2) to obtain the crude product, and muramyl dipeptide analogue is obtained after purification.

The route is shown as below:

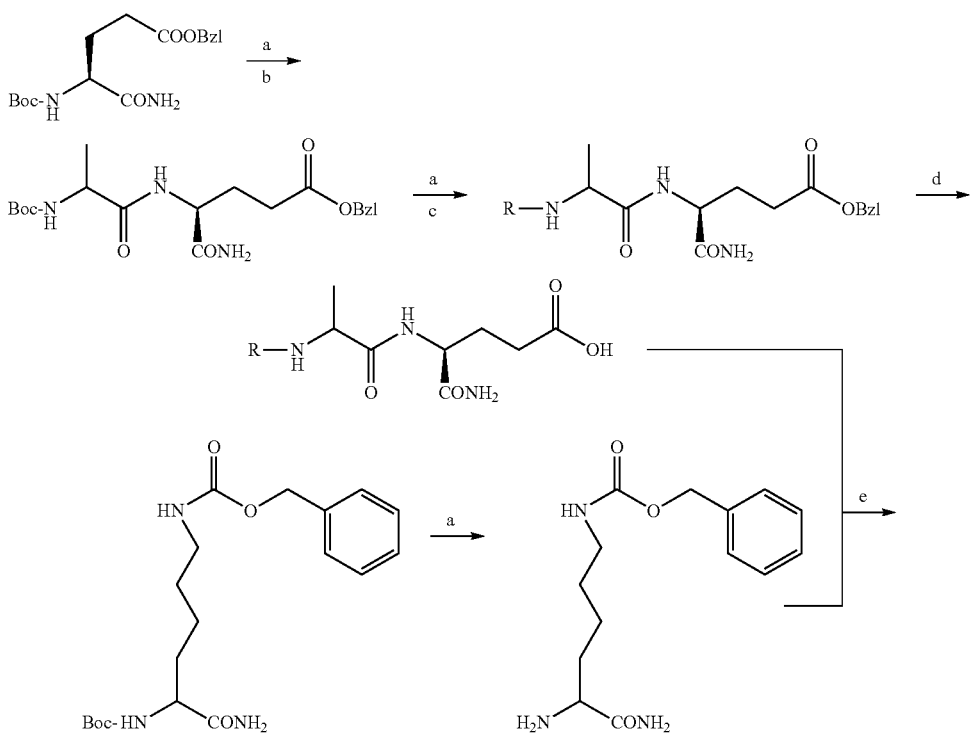

-continued

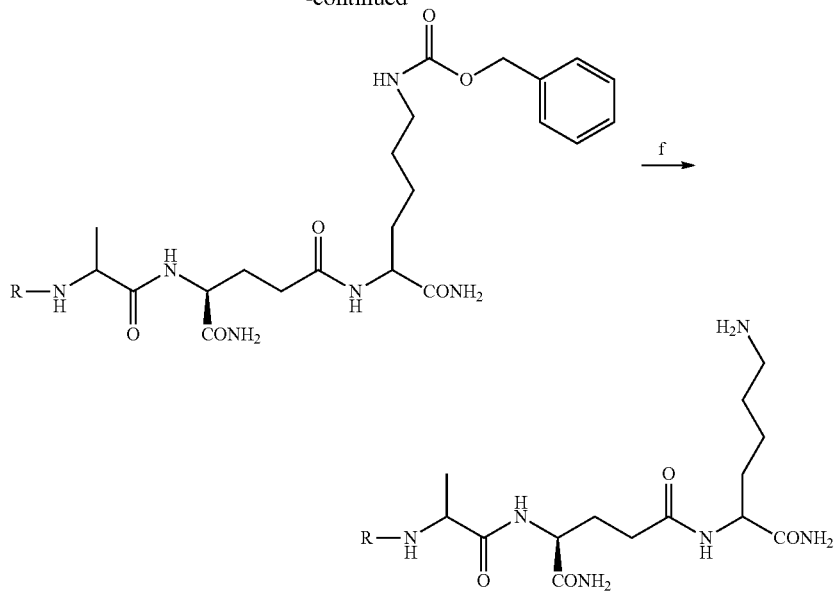

Reagents and conditions: (a) 50% TFA/DCM; r.t 1 h; (b) Boc-Ala-OH, HOSu, DIC; 0° C., 5 h, r.t, 20 h; (c) organic acid ©, HOSu, DIC; 0° C., 5 h, r.t, 20 h; (d) HBr/HOAc; r.t, 3 h; (e) HOSu, DIC; 0° C., 5 h, r.t, 20 h; (f) BF3.Et$_2$, TFA, EtSH (9:9:2); r.t 2 h.

The method for preparing the conjugates of muramyl dipeptide analogue and paclitaxel, or muramyl dipeptide analogue and docetaxel comprises the steps as follows:

1) First, paclitaxel-2'-O-alkane-di-acid monoester or docetaxel-2'-O-alkane-di-acid monoester, HOSu and DIC with certain molar ratio (2:1-1:2) are dissolved in dimethyl sulfoxide (DMSO) or DMF or N-methyl pyrrolidone, etc., the resulting solution is reacted for 1-10 hours at the temperature of −20° C. to 50° C.;

2) Then, the muramyl dipeptide analogue with mole numbers equal to that of paclitaxel-2'-O-alkane-di-acid monoester or docetaxel-2'-O-alkane-di-acid monoester is added to the solution of DMSO or DMF or N-methyl pyrrolidone, etc., the pH of the reaction system is adjusted to 6-8 by alkalescence reagent such as N-methyl morpholine, etc., the reaction is continued for 1-10 hours, the conjugate is obtained after reaction completed;

3) At last, any one solvent selected from water, methanol, ethanol, diethyl ether, petroleum ether, ethyl butyl ether is added to the reaction solution, and the solid precipitated is filtered, the crude product is purified to obtain the target product;

4) The method for purification includes preparative HPLC and recrystallization.

The route is shown as below:

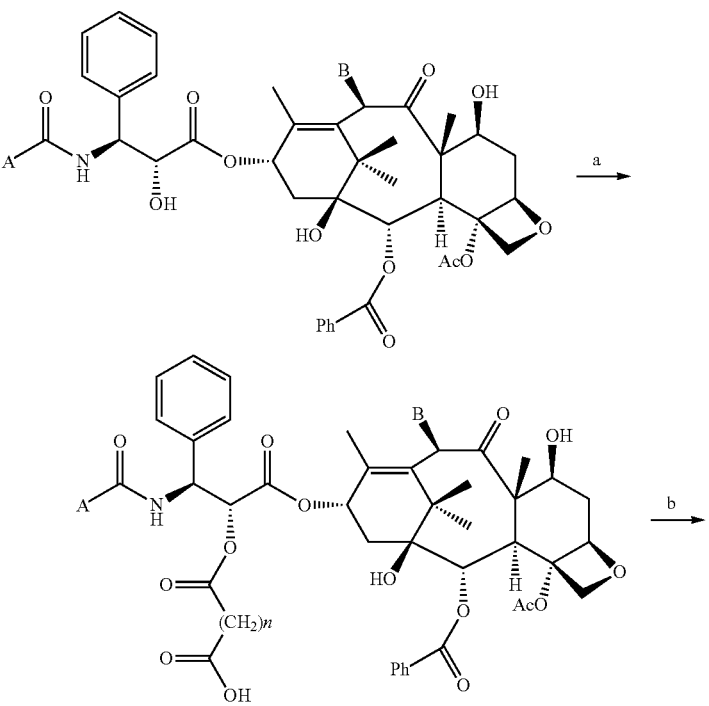

-continued

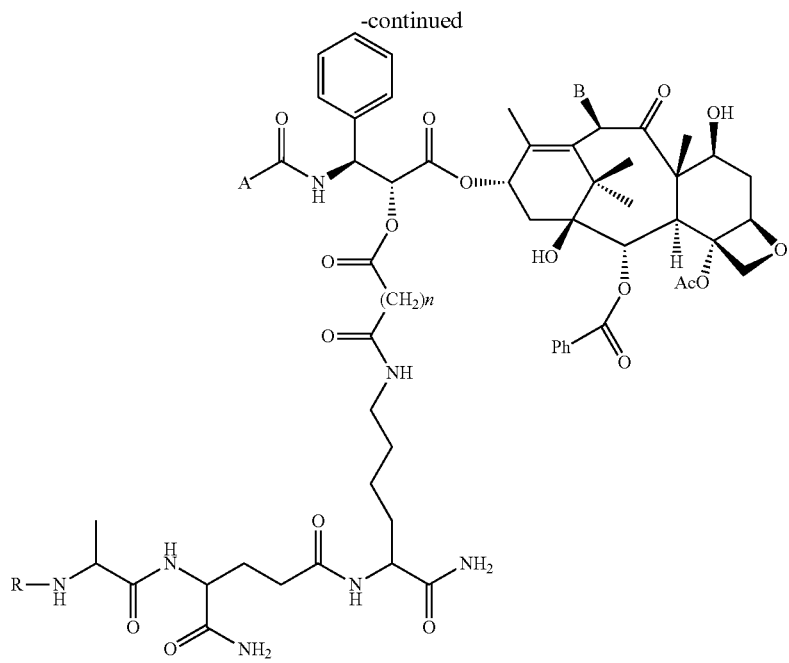

Reagents and conditions: (a) alkane-di-anhydride, DMAP, r.t, 4 h; (b) HOSu, 1-(3-Dimethylaminopropyl)-3-ethylcarbodiimide hydrochloride(EDC-HCl), DMSO, r.t, 20 h; MDA (muramyl dipeptide analogue) derivatives, r.t, 12 h.

The alkane diacid is chosen from $C_4$-$C_{14}$ alkane diacid, the alkane dianhydride is chosen from $C_4$-$C_{14}$alkane dianhydride.

The method for preparing the conjugates as disclosed in the present invention has mild reaction condition, short reaction time, stable yield, so that it is suitable for building compound library through, for example, combinatorial chemistry method, which also belong to the claim scope of the present invention.

People skilled in the art may adjust the steps mentioned above to improve the yield, they may design mutes based on the basic knowledge of the field, such as selecting the reactant, solvent and temperature. Also, they can, by using a variety of conventional protecting groups, avoid side reaction and thus increase the yield. These common reactions may be referenced in books on peptide synthesis chemistry such as 1) Gang LIU and Kit S. LAM, "One-bead one-compound combinatorial library method", Combinatorial Chemistry, A Practical Approach, Edited by Hicham Fenniri, OXFORD University Press, 2000, Chapter 2, pp 33-50; 2) Gang Liu, Xiaoyi Xiao, et al. Looking for combinatorial chemistry in drug research, Science Press, 2003, 6; 3) N. Leo Benoiton, Chemistry of Peptide Synthesis, published in 2005 by CRC press; 4) Miklos Bodanszky, Principles of Peptide Synthesis by Publisher of Springer Verlag (Edition: 2ND/REV). Such modifications or changes are within the scope of the present invention.

The conjugates disclosed in the present invention can be used in preparation of medicament for preventing and/or treating cancer. The cancer can be chosen from melanoma, gastric cancer, lung cancer, breast cancer, renal cancer, liver cancer, oral cavity epidermal carcinoma, cervical cancer, oophoroma, pancreatic cancer, prostatic cancer and colonic cancer.

The present invention therefore also relates to compositions comprising therapeutic amount of conjugate(s) disclosed in the present invention, and one or more pharmaceutically acceptable carriers and/or excipients. The pharmaceutically acceptable carriers include, for example, saline, buffered saline, dextrose, water, glycerol, ethanol, hereinafter discussed in more detail. If desired, the composition can also comprise a smaller amount of wetting or emulsifying agent(s), or pH buffering agent(s). The composition can be liquid solution, suspension, emulsion, tablets, pills, capsules, sustained release preparations or powders. The composition can be suppositories using traditional binders and carriers such as tricarboxylic acid glyceride. Oral preparation can use standard carriers such as mannitol, lactose, starch, magnesium stearate, sodium saccharin, cellulose and magnesium carbonate et al, in pharmaceutical grade. As required by different preparations, the related preparation may involve mixing, granulating and compressing or dissolving the active ingredients. Also, the composition may be prepared into nanoparticles.

The pharmaceutically acceptable carrier used herein can be solid or liquid.

The carrier or excipient can be a delayed-release material known to those skilled in the art, such as glyceryl monostearate or glyceryl distearate, and can also include waxes, ethyl cellulose, hydroxypropyl methyl cellulose, and methylmethacrylate etc. The recognized PHOSALPG-50 (phospholipid with 1,2-propanediol was concentrated, A. Nattermann & Cie. GmbH) in 0.01% Tween-80 used for the preparation of acceptable oral preparation of other conjugates, can be also employed in preparation of conjugates disclosed in the present invention.

Conjugates disclosed in the present invention can be administered in variety of pharmaceutical forms. If solid carrier is employed, the preparation can be tablet, hard capsule with powder or small pills in it, lozenge or sugar lozenge form. The amount of solid carrier can be widely ranged, but preferably from about 25 mg to about 1 g. If a liquid carrier is used, the preparation can be syrups, emulsions, soft gelatin capsules, sterile injectable solution or suspension or non-aqueous liquid suspension in the ampoule or vial.

Various release systems are known and can be used for the administration of conjugates or various preparations thereof, these preparations include tablets, capsules, injectable solutions, liposome capsules, microparticles, microcapsules etc. The method introduced includes but not limited to dermal, intradermal, intramuscular, intraperitoneal, intravenous, subcutaneous, intranasal, pulmonary, epidural, ophthalmic and oral (preferred) administration. Conjugates can be administrated through any convenient or suitable route, for example, injection or bolus injection, absorption through epithelial or mucosal route (e.g., oral mucosa, rectal and intestinal mucosa, etc.) or drug elution stent, or can be administered together with other biologically active agents, or can be administered systemically or locally. For treatment or prevention of nasal, bronchial or pulmonary diseases, the preferred route of administration is oral, nasal, or bronchial aerosol or nebulizer.

BRIEF DESCRIPTION OF DRAWINGS

FIGS. 1A and 1B The 50% growth inhibition ($GI_{50}$) and 50% lethal concentration ($LC_{50}$) of MTC-220 in 60 human origin tumor lines.

FIGS. 2A and 2B The 50% growth inhibition ($GI_{50}$) and 50% lethal concentration ($LC_{50}$) of MTC-302 in 60 human origin tumor lines.

FIGS. 3A and 3B The 50% growth inhibition ($GI_{50}$) and 50% lethal concentration ($LC_{50}$) of MTC-213 in 60 human origin tumor lines.

FIGS. 4A and 4B The 50% growth inhibition ($GI_{50}$) and 50% lethal concentration ($LC_{50}$) of MTC-219 in 60 human origin tumor lines.

FIGS. 5A and 5B The 50% growth inhibition ($GI_{50}$) and 50% lethal concentration ($LC_{50}$) of MTC-233 in 60 human origin tumor lines.

FIGS. 6A and 6B The 50% growth inhibition ($GI_{50}$) and 50% lethal concentration ($LC_{50}$) of MDC-400 in 60 human origin tumor lines.

FIG. 7 Anti-tumor activities of MTC-301, 302, 303 and 304 in 10 tumor cell lines in vitro.

FIG. 8 Anti-tumor activities of MTC-305, 306, 307 and 308 in 10 tumor cell lines in vitro.

FIG. 9 Anti-tumor activities of MDC-403, 404 and 405 in 10 tumor cell lines in vitro.

FIG. 10 Anti-tumor activities of MDC-406, 407 and 408 in 10 tumor cell lines in vitro.

DETAILED EXAMPLES

Figure 11:
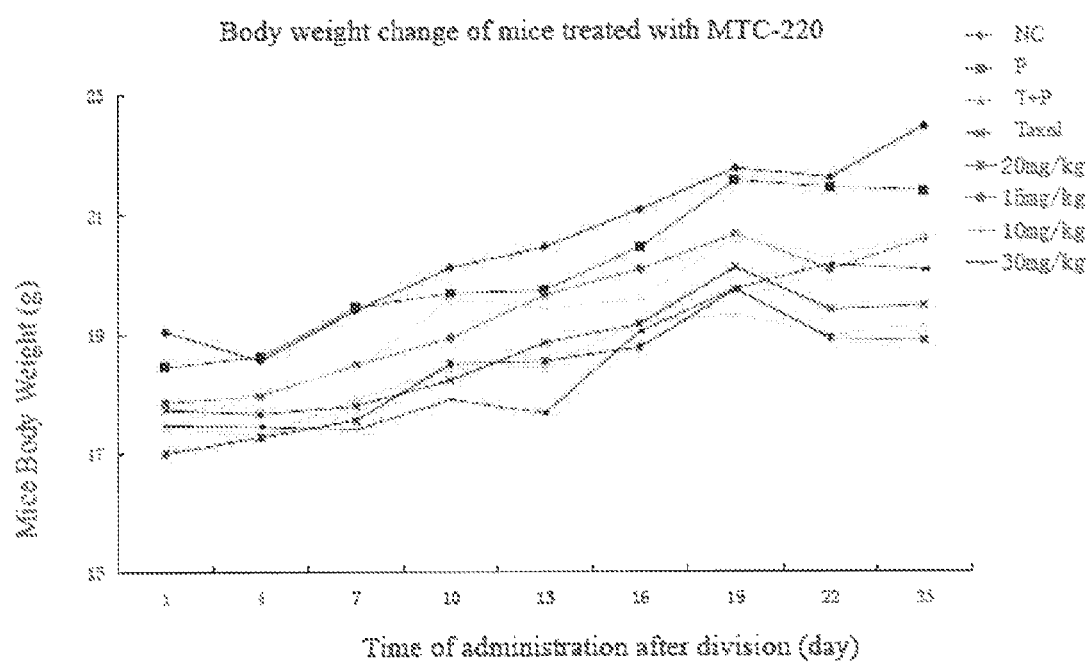
FIG. 11 The effect on body weight of MTC-220 in MDA-MB-231 tumor bearing mice.
Figure 12:
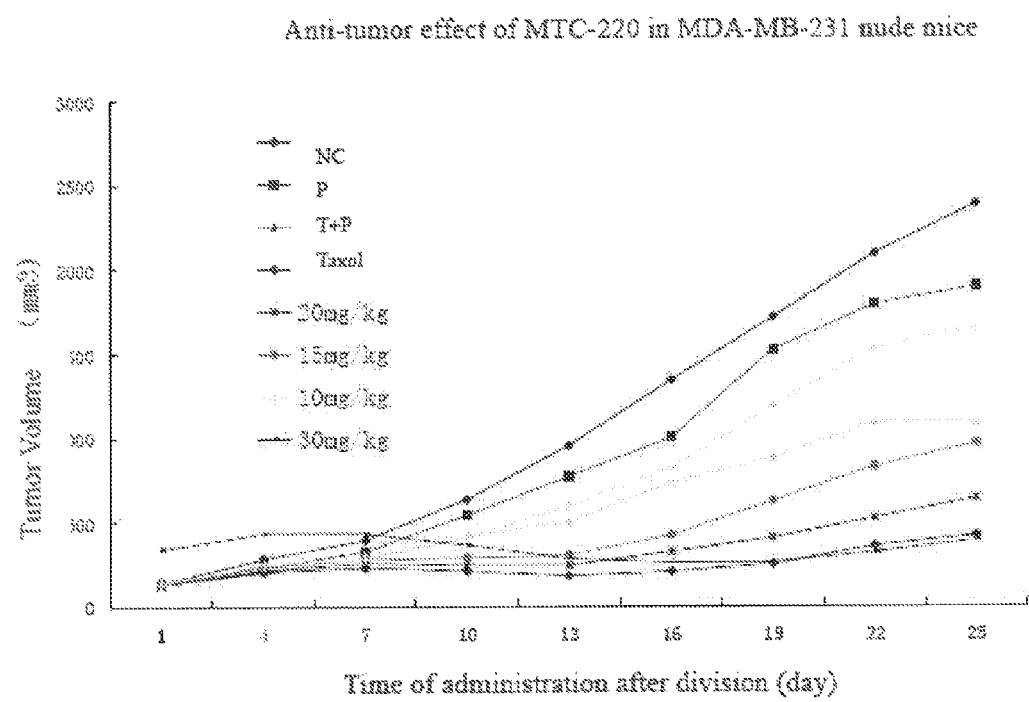
FIG. 12 The growth inhibition of MTC-220 in MDA-MB-231 tumor bearing mice.
Figure 13:
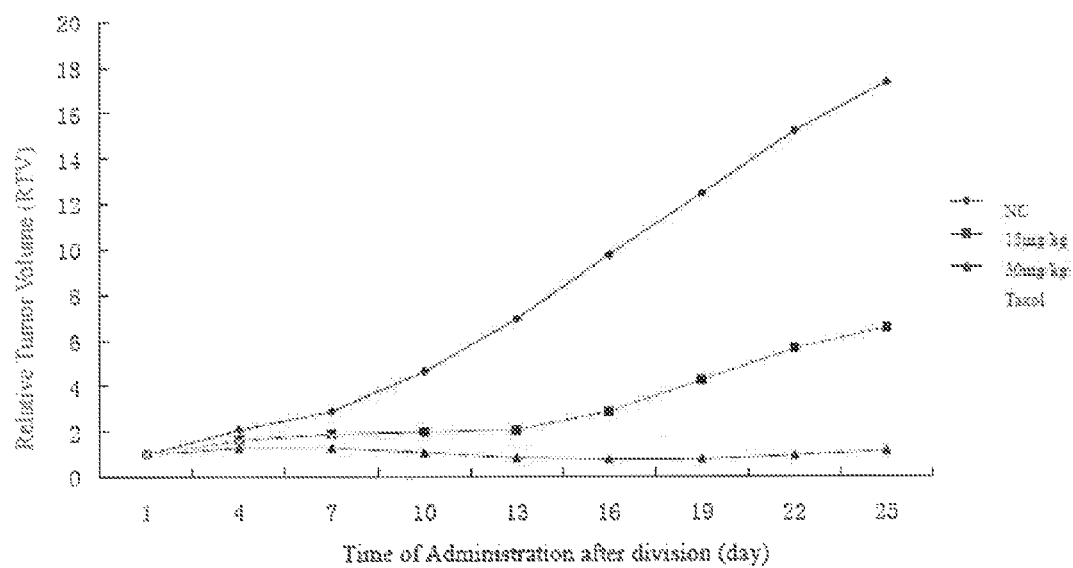
FIG. 13 The effect on RTV of MTC-220 in MDA-MB-231 tumor bearing mice which was treated with a same dose by different administration method.
Figure 14:
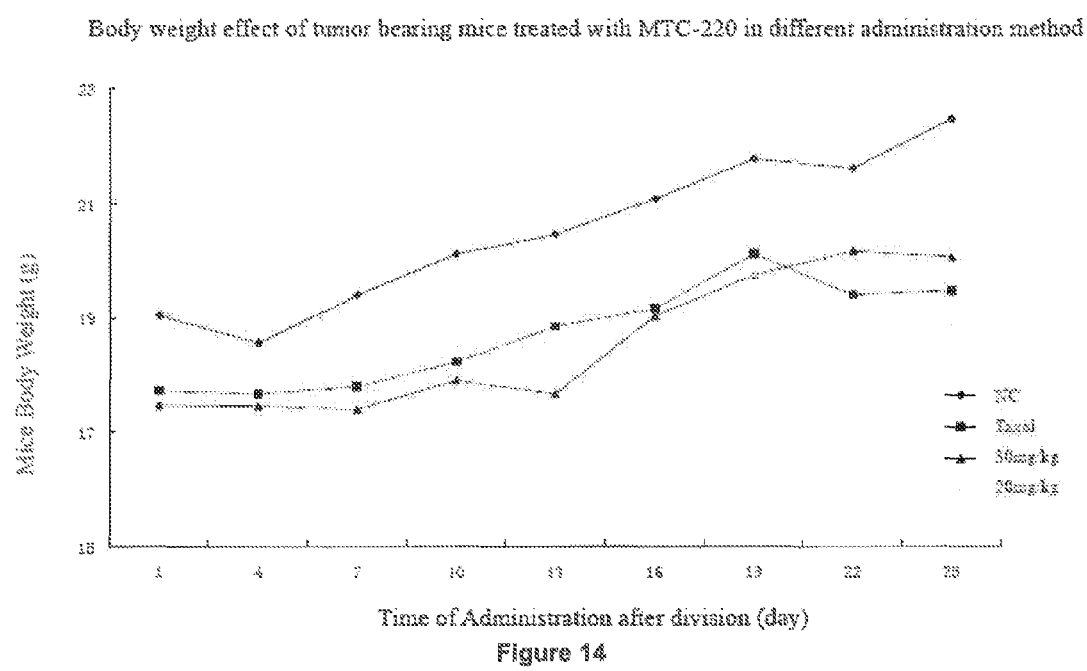
FIG. 14 The effect on body weight of MTC-220 in MDA-MB-231 tumor bearing mice which was treated with a same dose by different administration method.
Figure 15:
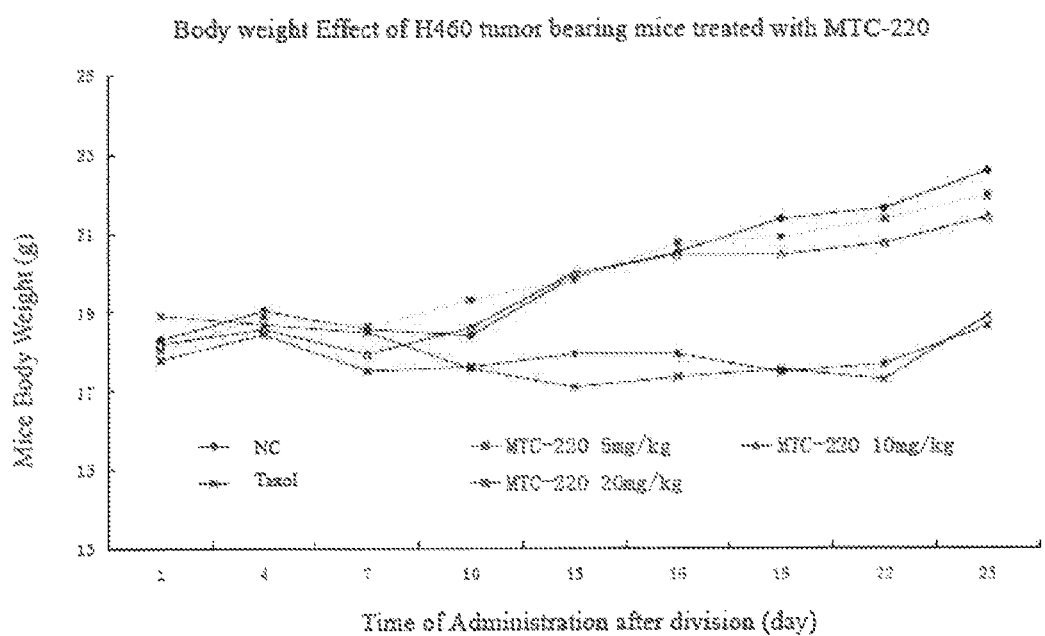
FIG. 15 The effect on body weight of MTC-220 in H460 tumor bearing mice.
Figure 16:
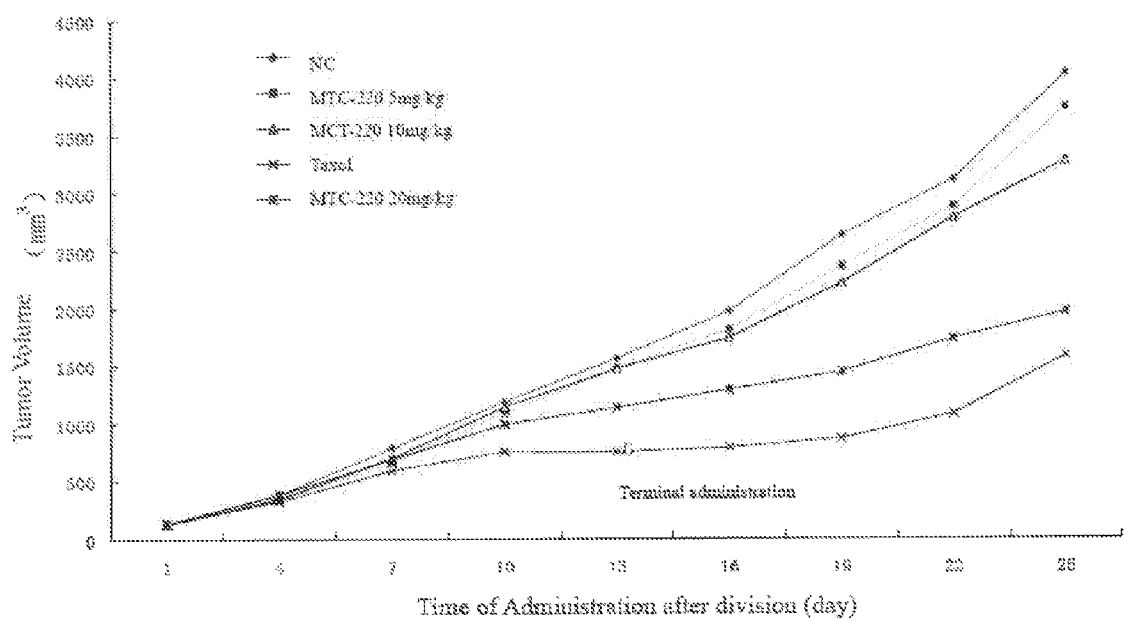
FIG. 16 The growth inhibition of MTC-220 in H460 tumor bearing mice.

The present disclosure is further illustrated by the following examples of synthesis of conjugates of Muramyl Dipeptide Analogue and paclitaxel, or of Muramyl Dipeptide Analogue and docetaxel and biological experiments thereof. Those skilled in the art should understand that these examples are merely for illustrative purposes, without limiting the scope of the present invention. The scope of the present invention is limited only by the claims. Under conditions without departing from the scope of the claims, people skilled in the art can modify or improve aspects of the present invention, such modifications and improvements also belong to the scope of protection of the present invention.

Also, unless otherwise specified, materials and the reagents used in the following examples are those commonly used in the field, which can be commercially available; the intermediates used can be commercially available or prepared by known methods; methods used are conventional methods known by those skilled in the art.

Example 1

Liquid-phase Synthesis of Paclitaxel 2'-O-succinic acid monoester (Synthetic method refer to CN200510081265)

Synthetic route was shown below

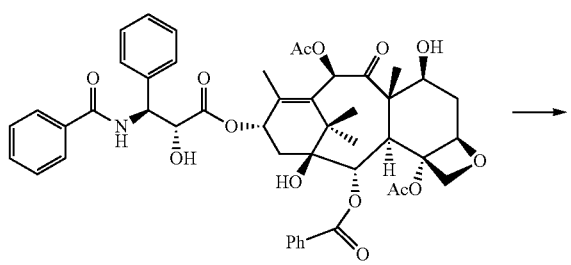

-continued

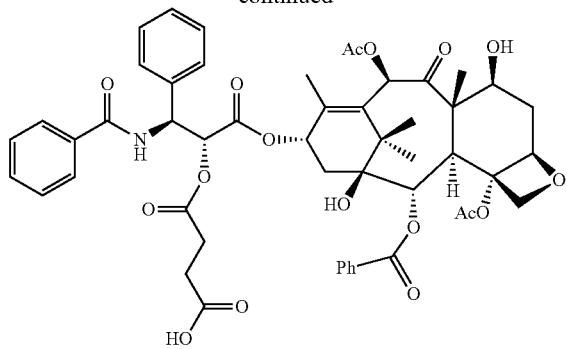

Reagents and conditions: succinic anhydride, DMAP, r.t, 4 h.

8.53 g (1.0 eq) Paclitaxel, 1.2 g (1.2 eq) succinic anhydride, 0.12 g (0.1 eq) 4-N,N-dimethyl pyridine were dissolved in pyridine, then stirred at r.t for 4 h. After the reaction completed, the pyridine solution was diluted with AcOEt. And then, the AcOEt layer was washed with saturated aqueous CuSO$_4$ solution, and H$_2$O sequentially. At last, the AcOEt layer was separated. The AcOEt solution was concentrated under vacuum, and then abundant water was added into the residue, white solid precipitated in the system. After filtation and lyophilization, 8.1 g target product was obtained with a yield of 85%, m.p.=178~180° C.

$^1$H-NMR (600 MHz, DMSO-d$_6$): 4.63 (1H, br.s, 1-OH), 5.40 (1H, d, J=8.4 Hz, 2-H), 3.58 (1H, d, J=8.4 Hz, 3-H), 4.90 (1H, d, J=10.8 Hz, 5-H), 1.62 (1H, t, J=14.4 Hz, 6-H$_a$), 2.31 (1H, m, 6-H$_b$), 4.10 (1H, dd, J=12.0 and 8.4 Hz, 7-H), 4.89 (1H, d, J=10.8 Hz, 7-OH), 6.29 (1H, s, 10-H), 5.81 (1H, t, J=10.8 Hz, 13-H), 1.51 (1H, m, 14-H$_a$), 1.81 (1H, m, 14-H$_b$), 0.99 (3H, s, 16-H), 1.02 (3H, s, 17-H), 1.75 (3H, s, 18-H), 1.49 (3H, s, 19-H), 3.98 (1H, d, J=10.2 Hz, 20-H$_a$), 4.02 (1H, d, J=10.2 Hz, 20-H$_b$), 2.10 (3H, s, 4-OCOCH$_3$), 2.23 (3H, s, 10-OCOCH$_3$), 5.35 (1H, d, J=10.8 Hz, 2'-H), 5.54 (1H, dd, J=10.8 and 10.2 Hz, 3'-H), 9.21 (1H, d, J=10.2 Hz, 3'-NH), 7.49 (2H, m, ph-o-H), 7.47 (2H, m, ph-m-H), 7.54 (1H, m, ph-p-H), 7.84 (2H, d, J=10.2 Hz, NBz-o-H), 7.43 (2H, m, NBz-m-H), 7.19 (1H, m, NBz-p-H), 7.97 (2H, d, J=9.6 Hz, OBz-o-H), 7.65 (2H, m, OBz-m-H), 7.72 (1H, m, OBz-p-H), 2.61 (2H, t, J=7.2 Hz, —CH$_2$—CH$_2$—COOH), 2.32 (2H, m, —CH$_2$—CH$_2$—COOH), 12.23 (1H, br.s, —CH$_2$—CH$_2$—COOH).

$^{13}$C-NMR (150 MHz, DMSO-d$_6$): 76.7 (1-C), 74.5 (2-C), 46.1 (3-C), 80.2 (4-C), 83.6 (5-C), 36.5 (6-C), 70.4 (7-C), 57.3 (8-C), 202.3 (9-C), 74.7 (10-C), 133.3 (11-C), 139.4 (12-C), 70.7 (13-C), 34.4 (14-C), 42.9 (15-C), 26.3 (16-C), 21.3 (17-C), 13.8 (18-C), 9.7 (19-C), 75.2 (20-C), 169.6 (2-OCO), 169.6, 22.5 (4-OCOCH$_3$), 168.7, 20.6 (10-OCOCH$_3$), 169.0 (1'-C), 74.7 (2'-C), 53.9 (3'-C), 166.4 (3'-NHCO), 137.3 (ph-q-C), 127.6 (ph-o-C), 128.3 (ph-m-C), 131.4 (ph-p-C), 129.9 (NBz-q-C), 127.4 (NBz-o-C), 128.6 (NBz-m-C), 128.2 (NBz-p-C), 134.3 (OBz-q-C), 129.5 (OBz-o-C), 128.6 (OBz-m-C), 133.4 (OBz-p-C), 172.9, 28.4, 30.9, 171.6 (—CO—CH$_2$—CH$_2$—COOH).

IR: 3471.3 ($\nu_{OH}$ and $\nu_{NH}$), 3065.2 ($\nu_{=C-H}$), 2957.5 ($\nu_{-C-H}$), 1717.3, 1642.0 ($\nu_{C=O}$), 1602.4, 1579.8, 1525.9 ($\nu_{C=C}$), 1487.4, 1370.4 ($\delta_{-C-H}$), 1241.4 ($\nu_{C-O-C}$), 978.6, 904.7, 948.5, 776.0, 708.3 ($\delta_{=CH}$).

ESI-MS: 954.75 [M+H]$^+$, 1929.13 [2M+Na]$^+$.

HR-MS(TOF): 954.3552 [M+H]$^+$, 976.3352 [M+Na]$^+$, C$_{51}$H$_{55}$NO$_{17}$.

Example 2-3

Solid-Phase Synthesis of Muramyl dipeptide Analogue MDA

Example 2

Synthesis of Fmoc-D-iso-Gln-OH

Synthetic route was shown below

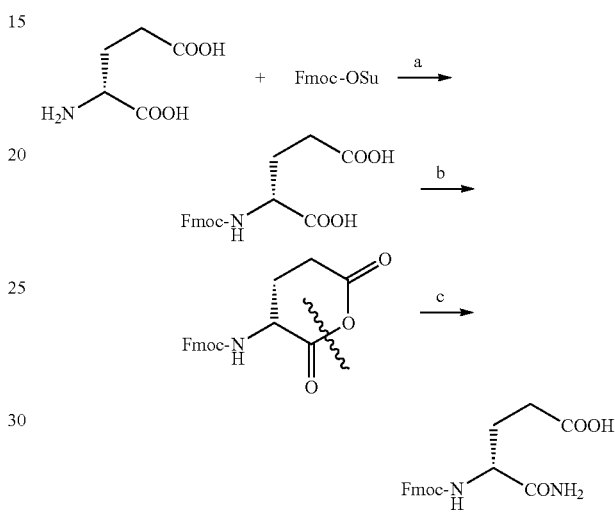

Reagents and conditions: (a) r.t, 3 d; (b) DCC, 0° C., 5 h, r.t, 20 h; (c) NH$_3$; −10° C., 1.5 h.

Steps 1

Synthesis of Fmoc-D-Glu-OH

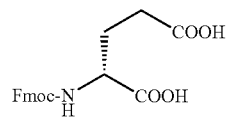

In an ice-water bath, a solution of D-glutamic acid (H-D-Glu-OH, 29.4 g, 1.0 eq) in a mixture of acetone and H$_2$O (V/V=1:1) was stirred. After the solid was fully dissolved, NaHCO$_3$ (23.3 g, 1.1 eq) was added in portions, then Fmoc-OSu (67.4 g, 1.0 eq) were added slowly and the reaction was stirred for additional 3 days at r.t. The mixture was then cooled in ice-water bath again, and pH was adjusted to 2-3 with 2.0N HCl. After removal of acetone under reduced pressure, the remaining solution was extracted with AcOEt (400 mL×4). The organic layer was separated and combined, dried with MgSO$_4$ overnight, and concentrated to a small volume under reduced pressure. Then residue was recrystallized with ethylacetate-cyclohexane system. After filtration, 59.8 g of target product was obtained as a white solid with a yield of 81%.

Steps 2

Synthesis of Fmoc-D-iso-Gln-OH

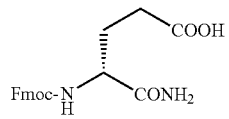

Fmoc-D-Glu-OH (59.8 g, 1.0 eq) was dissolved in anhydrous tetrahydrofuran (THF) (324 mL). DCC (40.1 g, 1.2 eq) was then added while stirring in ice-water bath. The reaction mixture was allowed to warm to r.t and stirring was maintained for additional 8 h to produce 1,3-dicyclohexylurea (DCU). The precipitates were filtered off, and washed with small amount THF. Dry ammonia gas was then bubbled through the filtrate which was stirred in a NaCl salt-ice bath. The reaction was completed after 1.5 h when no more white solid was precipitated. Still standing for 30 min, small amount MeOH was added to dissolve the solid. The mixture was cooled in an ice-water bath again. Then 2.0 N HCl was added carefully and slowly to adjust pH to 2-3. The solvent was evaporated under vacuum. The resulting solid was dissolved in AcOEt and then washed with diluted HCl, saturated aqueous $NaHCO_3$ solution, and $H_2O$ sequentially. The organic layer was separated and combined, then dried with $MgSO_4$ overnight, filtered and evaporated under vacuum. Then residue was recrystallized with ethylacetate-cyclohexane system. After filtration, 46.5 g target product was obtained with a yield of 78%. m.p.=204~205° C., $[\alpha]=-4.2°$ (C=10 mg/mL, DMF).

$^1$H-NMR (500 MHz, DMSO): 7.88 (2H, d, J=8.0 Hz), 7.72 (2H, m), 7.42 (2H, m), 7.40 (1H, m), 7.40 (1H, br.s), 7.32 (2H, m, 7.02 (1H, br.s), 4.27 (2H, m), 4.20 (1H, m), 3.93 (1H, dd, J=13.5 and 8.5 Hz), 2.25 (2H, m), 1.89 (1H, m), 1.73 (1H, m).

$^{13}$C-NMR (125 MHz, DMSO): 173.9, 173.4, 155.9, 143.8, 140.7, 127.6, 127.0, 125.3, 120.0, 65.6, 53.8, 46.6, 30.4, 27.2.

ESI-MS: 369.03 $[M+H]^+$, 759.98 $[2M+Na]^+$.

HR-MS(TOF): 369.1448 $[M+H]^+$, 759.2623 $[2M+Na]^+$, $C_{20}H_{20}N_2O_5$.

Example 3

Solid-Phase Synthesis of Muramyl Dipeptide Analogue Analogue MDA

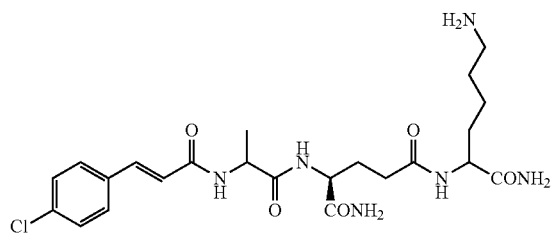 [SMILES: CC(NC(=O)/C=C/c1ccc(Cl)cc1)C(=O)N[C@@H](CCC(=O)NC(CCCCN)C(N)=O)C(N)=O]

Synthetic route was shown below

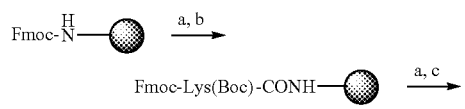

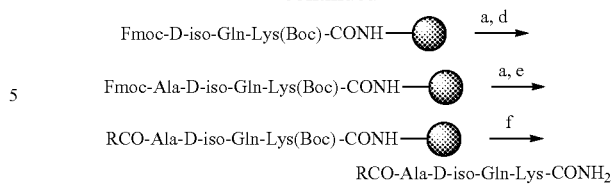

= Rink Amide-Am Resin

Reagents and conditions: (a) 20% piperidine/DMF; r.t, 1 h; (b) Fmoc-Lys(Boc)-OH, HOBt, DIC; r.t, 8 h; (C) Fmoc-D-iso-Gln-OH. HOBt, DIC; r.t, 12 h; (d) Fmoc-Ala-OH, HOBt, DIC; r.t, 8 h; (e) 4-chloro-cinnamic acid (R), HOBt, DIC; r.t, 8 h; (f) 90% $TFA/H_2O$, r.t, 2 h.

100.0 g Rink-amide-AM resin (loading 0.88 mmol/g, 1.0 eq) was put into a solid-phase reactor and vacuumed under reduced pressure for 1 h. Anhydrous DCM (500 mL) was added to swell the resin for 45 min and then removed. The Fmoc group of resin was removed by using of 20% (Volume percentage) piperidine/DMF for 1 h at r.t, followed by drainage of the liquid phase. The resin was washed thoroughly with DMF (500 mL×6) and DCM (500 mL×6) respectively. Fmoc-Lys(Boc)-COOH (61.8 g, 1.5 eq), HOBt (17.8 g, 1.5 eq), DIC (20.8 mL, 1.5 eq) and DMF (500 mL) were added into the reactor to introduce the first amino acid, which was bonded to the resin after reacting for 8 h at r.t. When it was negative by the ninhydrin method, the coupling reaction was completed. The liquid phase was removed, and the resin was thoroughly washed with DMF (500 mL×6) and DCM (500 mL×6) respectively. Then the Fmoc was removed by using 20% (Volume percentage) piperidine/DMF. Fmoc-D-iso-Gln-OH (48.5 g, 1.5 eq), HOBt (17.8 g, 1.5 eq), DIC (20.8 ml g, 1.5 eq), and DMF (500 mL) were sadded to introduce the second amino acid to the solid phase. The reaction was lasted 12 h and was monitored by ninhydrin method. When ninhydrin test indicted the reaction was complete, the liquid phase was removed, 500 mL 20% (Volume percentage) piperidine/DMF was added to remove Fmoc, removed the liquid phase again after 1 h, the resin was washed with DMF (500 mL*6) and DCM (500 mL*6) respectively. Fmoc-Ala-COOH (41 g, 1.5 eq), HOBt (17.8 g, 1.5 eq), DIC (20.8 mL, 1.5 eq) and 500 mL DMF were added to introduce the third amino acid. The reaction was lasted 12 h and was monitored by ninhydrin method. When ninhydrin test indicted the reaction was complete, the liquid phase was removed, 500 mL 20% (Volume percentage) piperidine/DMF was added to remove Fmoc, liquid phase was removed again after 1 h, the resin was washed with DMF (500 mL×6) and DCM (500 mL×6) respectively. Chlorocinnamic acid (24.1 g 1.5 eq), HOBt (17.8 g, 1.5 eq), DIC (20.8 mL, 1.5 eq) and 500 mL DMF were added to introduce the organic acid. The reaction was lasted 8 h and was monitored by ninhydrin method. When ninhydrin test indicted the reaction was complete, the liquid phase was removed, the resin was washed with DMF (500 mL×6) and DCM (500 mL×6) respectively. TFA water solution 90% (Volume percentage) was added to the reactor, the reaction was lasted for 2 h. Collected the liquid phase, another TFA water solution 90% (Volume percentage) was added to the reactor, the reaction was lasted for 2 h, collected the liquid phase again, the resin was washed with 200 mL DCM. TFA water solutions and DCM were combined and evaporated under vacuum. In ice bath, to the residue was added abundant diethylether, white solid precipitated, removed the supernatant. The white solid was grinded and washed with diethylether for several times, filtration gave crude product (39.8) with the yield 89%. The crude product was purified by ODS column chromatography with gradientelution, methanol/water to produce 35.88 g target product in 98.5% purity. m.p.=215~217° C., [α]=+37.7° (C=11.05 mg/mL, DMF).

$^1$H-NMR (600 MHz, DMSO-$d_6$): 7.47 (2H, d, J=8.4 Hz, 2 and 6-H), 7.57 (2H, d, J=8.4 Hz, 3 and 5-H), 7.39 (1H, d, J=15.9 Hz, 7-H), 6.75 (1H, d, J=15.9 Hz, 8-H), 8.39 (1H, d, J=6.6 Hz, 10-H), 4.38 (1H, m, 11-H), 1.26 (3H, m, 12-H), 8.21 (1H, d, J=8.4 Hz, 14-H), 4.14 (1H, m, 15-H), 6.98 (1H, s, 17-$H_a$), 7.41 (1H, s, 17-$H_b$), 1.71 (1H, m, 18-$H_a$), 1.97 (1H, m, 18-$H_b$), 2.15 (2H, t, J=7.2 Hz, 19-H), 7.90 (1H, d, J=8.4 Hz, 21-H), 4.11 (1H, m, 22-H), 7.10 (1H, s, 24-$H_a$), 7.30 (1H, s, 24-$H_b$), 1.46 (1H, m, 25-$H_a$), 1.63 (1H, m, 25-$H_b$), 1.27 (2H, m, 26-H), 1.53 (2H, m, 27-H), 2.73 (2H, m, 28-H), 7.75 (2H, br.s, 29-H).

$^{13}$C-NMR (150 MHz, DMSO-$d_6$): 134.0 (1-C), 129.0 (2 and 6-C), 129.2 (3 and 5-C), 133.8 (4-C), 137.6 (7-C), 122.7 (8-C), 164.7 (9-C), 48.8 (11-C), 18.1 (12-C), 172.4 (13-C), 52.2 (15-C), 173.8 (16-C), 27.7 (18-C), 31.7 (19-C), 171.6 (20-C), 52.1 (22-C), 173.3 (23-C), 31.3 (25-C), 22.4 (26-C), 26.8 (27-C), 38.7 (28-C).

IR: 3282.3, 3202.2 ($v_{OH}$ and $v_{NH}$), 3067.3 ($v_{=CH}$), 2938.0 ($v_{-CH}$), 1609.5 ($v_{C=O}$), 1537.5, 1450.2 ($v_{C=C}$), 1199.0, 1180.2, 1130.6 ($\delta_{-CH}$), 972.4, 820.4, 799.4, 720.0 ($\delta_{=CH}$ and $v_{C-Cl}$).

ESI-MS: 509.60 [M+H]$^+$, 1017.24 [2M+H]$^+$.
HR-MS(TOF): 509.2292 [M+H]$^+$, $C_{23}H_{33}ClN_6O_5$.

Example 4-10

Liquid-Phase Synthesis of Muramyl Dipeptide Analogue MDA

The synthetic route was shown below

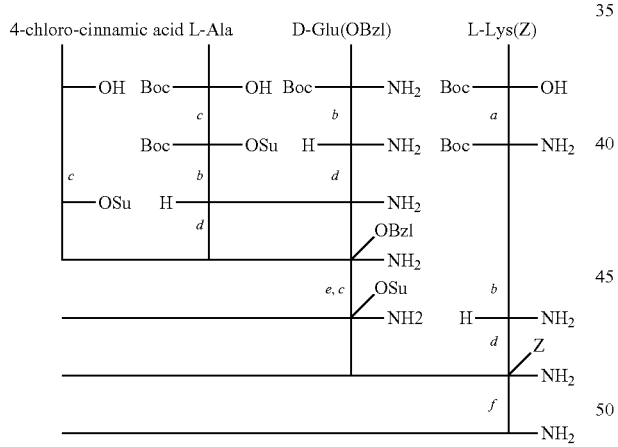

Reagents and conditions: (a) HOSu, DIC, NH$_3$; −10° C., 1.5 h; (b) 50% TFA/DCM; r.t 1 h; (c) HOSu, DIC; 0° C., 5 h, r.t, 20 h; (d) 0° C., 5 h, r.t, 24 h; (e) HBr/HOAc; r.t, 3 h; (f) BF$_3$.Et$_2$O, TFA, EtSH (9:9:2); r.t 2 h.

Example 4

Liquid-phase synthesis of Boc-D-Glu(OBzl)-NH$_2$

The synthetic route was shown as below:

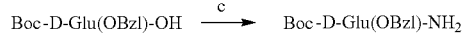

Reagents and conditions: (a) $C_6H_5CH_2OH$, BF$_3$.Et$_2$O; r.t, 15 h; (b) (Boc)$_2$O, NaHCO$_3$; r.t, 20 h; (c) HOSu, DCC, NH$_3$; −10° C., 1.5 h.

Step 1

Liquid-phase synthesis of H-D-Glu(OBzl)-OH

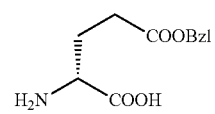

To a solution of 29.1 g (1.0 eq) H-D-Glu-OH in 205.6 mL (10.0 eq) benzyl alcohol which was stirred at r.t, 47.7 mL (2.0 eq) boron trifluoride etherate solution was added slowly, and 10 min later, all of the substrate was dissolved. The reaction was completed in 15 h, 616.8 mL (3 times of the volume of benzyl alcohol) THF was added, stirred and 55.1 mL (2.0 eq) triethylamine was added slowly. A large number of white viscous precipitate precipitated. The THF was removed under reduced pressure; the residue was cooled, after adding the proper amount of the AcOEt, the viscous precipitate turned to powder. 36.6 g target compound was obtained with yield of 78% after filtration and drying. m.p.=174~176° C.

Step 2

Liquid-phase synthesis of Boc-D-Glu(OBzl)-OH

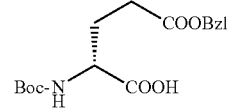

36.6 g (1.0 eq) H-D-Glu(OBzl)-OH was dissolved in 500 mL dioxane/water (v/v=1:1), 67.3 g (2.0 eq) Boc anhydride and 25.3 g sodium dicarbonate (2.0 eq) were added sequentially; and an oil bath heating was employed for dissolving all the substrates. The solution was stirred at r.t for 20 hours. After the completion of the reaction, the dioxane was removed under vacuum, and large number of viscous precipitate was obtained. The precipitate was diluted with 500 mL water, and stirred for another 30 minutes to fully dissolution. The pH of the solution was adjusted to 2~3 by 2 N HCl aqueous solution in ice bath, and the mixture became muddy, and was allowed to stand for 30 minutes.

The solution was extracted with AcOEt for 5 times, and the organic phase was combined, dried with MgSO$_4$ overnight. After filtration, the AcOEt was removed under vacuum, and 48.6 g yellow oily target compound was obtained with yield of 86%.

Step 3

Liquid-phase synthesis of Boc-D-Glu(OBzl)-NH$_2$

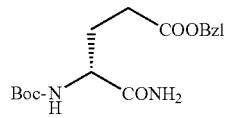

48.6 g (1.0 eq) Boc-D-Glu(OBzl)-OH was dissolved in tetrahydrofuran, 24.8 g (1.5 eq) HOSu and 44.5 g (1.5 eq) DCC were added sequentially. After stirring for 5 hours in ice bath, the reaction was warmed to r.t and stirred for another 20 hours. A large number of white precipitate (DCU) precipitated, the precipitate was filtered out and washed with little tetrahydrofuran. The filtrate was stirred in ice-salt bath, and anhydrous ammonia was introduced to the solution. After 15 minutes, a large number of white precipitate precipitated, and stirred the mixture for another 1.5 hours, no more white solid precipitated out, and the reaction was completed. The precipitate was filtered and washed with tetrahydrofuran, and yellow oil was obtained after removing the tetrahydrofuran filtrate under vacuum. The yellow oil was diluted with AcOEt; and the pH of the solution was adjusted to 7 with 2N HCl aqueous solution in ice bath, and the solution was allowed to stand for 30 minutes. The AcOEt layer was separated, and successively washed with diluted hydrochloric acid, saturated sodium bicarbonate and water. After that, the AcOEt layer was dried with MgSO$_4$ overnight. The mixture was filtered and the filtrate was evaporated to dryness under vacuum, and the residue was recrystallized with ethyl acetate-cyclo hexane to yield 34.2 g target compound with the yield of 75%, m.p.=122~123° C., [α]=−1.8° (C=9.8 mg/mL, DMF)

$^1$H-NMR (300 MHz, DMSO-d$_6$): 1.36 (9H, s, —C(CH$_3$)$_3$), 6.82 (1H, d, J=8.4 Hz, 4-H), 3.86 (1H, m, 5-H), 7.01 (1H, s, 7-H$_a$), 7.31 (1H, s, 7-H$_b$), 1.73 (1H, m, 8-H$_a$), 1.88 (1H, m, 8-H$_b$), 2.36 (2H, t, J=7.2 Hz, 9-H), 5.07 (2H, s, 11-H), 7.25-7.39 (5H, m, 12~16-H).

$^{13}$C-NMR (125 MHz, DMSO-d$_6$): 28.1 (1-C), 78.0 (2-C), 155.3 (3-C), 53.3 (5-C), 173.5 (6-C), 27.1 (8-C), 30.2 (9-C), 172.2 (10-C), 65.4 (11-C), 127.8 (12 and 16-C), 128.4 (13 and 15-C), 127.9 (14-C).

ESI-MS: 337.75 [M+H]$^+$, 673.32 [2M+H]$^+$.

HR-MS(TOF): 337.1754 [M+H]$^+$, 359.1572 [M+Na]$^+$, C$_{17}$H$_{24}$N$_2$O$_5$.

Example 5

Liquid-phase synthesis of Boc-Lys(Z)-NH

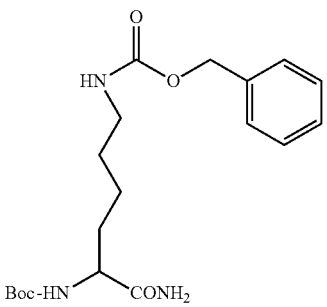

To a solution of 38.0 g (1.0 eq) Boc-Lys(Z)-OH in tetrahydrofuran, 13.8 g (1.2 eq) HOSu and 18.9 ml (1.2 eq) DIC were added, and the mixture was stirred in ice bath for 5 hours, and continued at r.t for 20 hours. A large number of white precipitate (DIU) was precipitated. The mixture was filtered, and the precipitate was washed with tetrahydrofuran. The filtrate was stirred in sodium chloride cryohydrate bath, and the anhydrous ammonia gas was introduced into the filtrate. 15 minutes later, a large number of white precipitate formed, and the reaction was continued for 1.5 hours, no more white precipitate formed, and the reaction was completed. The mixture was filtered, and the precipiate was washed with tetrahydrofuran. The filtrate was evaporated to dryness under vacuum and white solid residue was obtained. The residue was dissolved in AcOEt, the pH of the solution was adjusted to 7 with 2 N HCl aqueous solution in ice bath, and the solution was allowed to stand for 30 minutes. The AcOEt layer was separated, successively washed with diluted hydrochloric acid, saturated sodium bicarbonate aqueous solution and water, and dried with MgSO$_4$ overnight. The mixture was filtered, and the filtrate was evaporated to dryness under vacuum, the residue was recrystallized in AcOEt to obtain 35.0 g target compound with the yield of 92%, m.p.=137~138° C.

$^1$H-NMR (300 MHz, DMSO-d$_6$): 1.37 (9H, br.s, 1-H), 6.71 (1H, d, J=8.1 Hz, 4-H), 3.79 (1H, m, 5-H), 7.23 (2H, br.s, 7-H), 1.28 (2H, m, 8-H), 1.45 (2H, m, 9-H), 1.58 (2H, m, 10-H), 2.95 (2H, m, 11-H), 6.93 (1H, br.s, 12-H), 5.00 (2H, s, 14-H), 7.22-7.39 (5H, m, 16~20-H).

ESI-MS: 380.71 [M+H]$^+$, 759.50 [2M+H]$^+$.

HR-MS(TOF): 380.2201 [M+H]$^+$, 781.4102 [2M+Na]$^+$, C$_{19}$H$_{29}$N$_3$O$_5$.

Example 6

Liquid-phase synthesis of bipeptid fragment Boc-Ala-D-Glu(OBzl)-NH$_2$

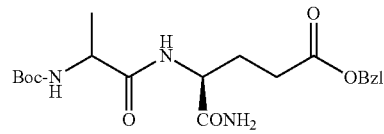

16.9 g (1.0 eq) Boc-Ala-OH was dissolved in tetrahydrofuran, 12.3 g (1.2 eq) HOSu and 16.9 mL (1.2 eq) DIC were added in sequence, the mixture was stirred in ice bath for 5 hours, and continued for 20 hours at r.t. A large amount of white precipitate (DIU) formed. The mixture was filtered, and the precipitate was washed with a small amount of tetrahydrofuran, and the filtrate containing (Boc-Ala-OSu) was collected for further use.

30 g (1.0 eq) Boc-D-Glu(OBzl)-NH$_2$ was dissolved in 100 mL trifluoroacetic acid-dichloromethane (v/v=1:1), and the solution was stirred for 1 hour at r.t to remove Boc group. After the completion of the reaction, the TFA was removed under vacuum; the residue was repeatedly grinded and washed in anhydrous ether, and evaporated to dryness, and re-dissolved in tetrahydrofuran. The pH of the solution was adjusted to 7~8 with N-methyl morpholine (NMM) in ice bath. The Boc-Ala-OSu solution was sparingly added to the solution in a few portions. The mixture was stirred for 5 hours in ice bath, and continued for 24 hours at r.t. After the completion of the reaction, the mixture was evaporated to dryness. The residue was dissolved in proper amount AcOEt and successively washed with diluted hydrochloric acid, saturated sodium bicarbonate aqueous solution and water. The AcOEt layer was separated, and dried with MgSO$_4$ overnight. The mixture was filtered and the filtrate was evaporated to dryness. The residue was recrystallized from methanol and water, the crystal was washed with a big amount of ether to obtained 29.4 g target compound. Yield: 81%, m.p.=134~135° C.

$^1$H-NMR (300 MHz, DMSO-$d_6$): 1.36 (9H, br.s, 1-H), 7.92 (1H, d, J=7.8 Hz, 4-H), 4.17 (1H, m, 5-H), 1.15 (3H, d, J=7.2 Hz, 6-H), 7.10 (1H, d, J=6.6 Hz, 8-H), 3.91 (1H, m, 9-H), 7.18 (1H, br.s, 11-H$_a$), 7.31 (1H, br.s, 11-H$_b$), 1.75 (1H, m, 12-H$_a$), 2.03 (1H, m, 12-H$_b$), 2.33 (2H, t, J=7.5 Hz, 13-H), 5.07 (2H, s, 15-H), 7.31-7.40 (5H, m, 17~21-H).

ESI-MS: 408.71 [M+H]$^+$, 815.44 [2M+H]$^+$.

HR-MS(TOF): 408.2137 [M+H]$^+$, 430.1955 [M+Na]$^+$, $C_{20}H_{29}N_3O_6$.

Example 7

Liquid-Phase Synthesis of Tripeptide Fragment

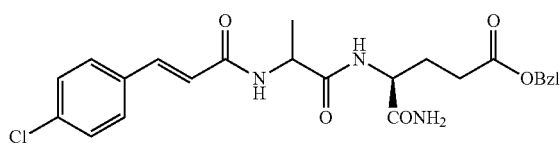

To a solution of 13.2 g (1.0 eq) 4-chloro cinnamic acid in tetrahydrofuran, 9.9 g (1.2 eq) HOSu and 13.6 mL (1.2 eq) DIC were added. The mixture was stirred for 5 hours in ice bath, continued for 20 hours at r.t. A large amount of white precipitate (DIU) formed. The mixture was filtered and the precipitate was washed with tetrahydrofuran; the filtrate (Ac-OSu) was collected for further use.

29.4 g (1.0 eq) Boc-Ala-D-Glu(OBzl)-NH$_2$ was dissolved in 100 mL trifluoroacetic acid-dichloromathane (v/v=1:1), and stirred for 1 hour to remove the Boc group. After completion of the reaction, TFA was removed under vacuum. The residue was repeatedly grinded, washed with ether, and evaporated to dryness and re-dissovled in tetrahydrofuran. The pH of the solution was adjusted to 7~8 with N-methyl morpholine (NMM) in ice bath. The Ac-OSu solution was sparingly added to the mixture in a few portions. The mixture was stirred for 5 hours in ice bath, then 24 hours at r.t, and refluxed for 2 hours. After completion of the reaction, the mixture was allowed to stand for 30 minutes and a large amount of viscous white precipitate formed. The mixture was filtered and the precipitate was washed with tetrahydrofuran. The precipitate was dissolved in AcOEt, and the solution was successfully washed with diluted hydrochloric acid, saturated sodium bicarbonate and water. The AcOEt layer was separated, and dried with MgSO$_4$ overnight. The mixture was filtered and the filtrate was evaporated to dryness. The residue was recrystallized in methanol-water, and washed with a large amount of anhydrous ether to obtain 26.8 g target compound. Yield: 79%, m.p.=226~228° C.

$^1$H-NMR (300 MHz, DMSO-$d_6$): 7.48 (2H, d, J=8.7 Hz, 2~6-H), 7.59 (2H, d, J=8.7 Hz, 3~5-H), 7.39 (1H, d, J=15.9 Hz, 7-H), 6.76 (1H, d, J=15.9 Hz, 8-H), 8.39 (1H, d, J=6.6 Hz, 10-H), 4.38 (1H, m, 11-H), 1.23 (3H, d, J=6.9 Hz, 12-H), 8.25 (1H, d, J=8.1 Hz, 14-H), 4.18 (1H, m, 15-H), 7.16 (1H, br.s, 17-H$_a$), 7.31 (1H, br.s, 17-H$_b$), 1.78 (1H, m, 18-H$_a$), 2.05 (1H, m, 18-H$_b$), 2.38 (2H, m, 19-H), 5.07 (2H, s, 21-H), 7.31-7.36 (5H, m, 23~27-H).

ESI-MS: 472.33 [M+H]$^+$, 943.17 [2M+H]$^+$.

HR-MS(TOF): 472.1635 [M+H]$^+$, 943.3174 [2M+H]$^+$, $C_{24}H_{26}ClN_3O_5$.

Example 8

Liquid-Phase Synthesis of Tripeptide Fragment

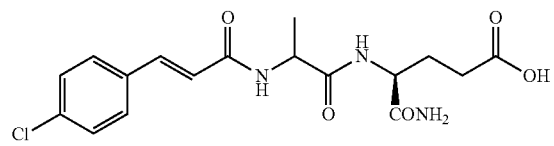 [SMILES: CC(NC(=O)/C=C/c1ccc(Cl)cc1)C(=O)N[C@@H](CCC(=O)O)C(N)=O]

26.8 g tripeptide fragment of example 7 was dissolved in hydrobromic acid/acetic acid solution. The solution was stirred for 2 hours to remove the protective group. After completion of the reaction, the solution was poured to ice water, and adjusted the pH of the mixture to 10~11 with 10% NaOH aqueous solution. After extracting with AcOEt, the pH of the solution was adjusted to 2~3 with 10% HCl aqueous solution. The water phase was extracted with AcOEt 3 times, and the organic layers were combined, washed with brine and dried over Na$_2$SO$_4$. The mixture was filtered and the filtrate was concentrated to a small amount of solution under vacuum. Adding ether, a large amount of white solid precipitated. The mixture was filtered, and the precipitate was dried to obtain 18.5 g target compound. Yield, 85%.

$^1$H-NMR (300 MHz, DMSO-$d_6$): 7.45 (2H, d, J=8.1 Hz, 2~6-H), 7.56 (2H, d, J=8.1 Hz, 3~5-H), 7.42 (1H, d, J=15.3 Hz, 7-H), 6.75 (1H, d, J=15.3 Hz, 8-H), 8.39 (1H, d, J=6.6 Hz, 10-H), 4.37 (1H, m, 11-H), 1.25 (3H, d, J=6.6 Hz, 12-H), 8.21 (1H, d, J=8.1 Hz, 14-H), 4.16 (1H, m, 15-H), 7.11 (1H, br.s, 17-H$_a$), 7.30 (1H, br.s, 17-H$_b$), 1.72 (1H, m, 18-H$_a$), 1.98 (1H, m, 18-H$_b$), 2.22 (2H, m, 19-H), 12.25 (1H, br.s, 21-H).

ESI-MS: 382.17 [M+H]$^+$, 785.04 [2M+Na]$^+$.

HR-MS(TOF): 382.1171 [M+H]$^+$, 785.2073 [2M+Na]$^+$, $C_{17}H_{20}ClN_3O_5$.

Example 9

Liquid-Phase Synthesis of Tetrapeptide Fragment

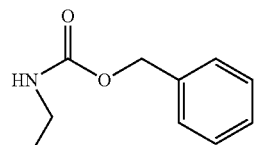
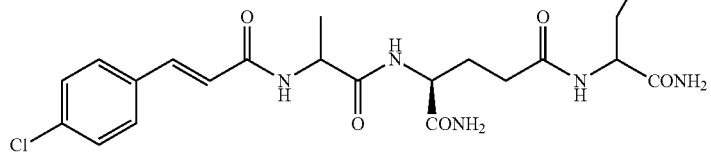

16.3 g (1.0 eq) tripeptide fragment of example 8 was dissolved in tetrahydrofuran, 5.9 g (1.2 eq) HOSu and 8.1 mL (1.2 eq) DIC were added in sequence. The mixture was stirred for 5 hours in ice bath, continued for 20 hours at r.t. A large amount of white solid (DIU) precipitated. The mixture was filtered and the precipitate was washed with a small amount of tetrahydrofuran, and the filtrate was collected for further use.

16.2 g (1.0 eq) Boc-Lys(Z)-NH, was dissolved in 100 mL trifluoroacetic acid-dichloromathane (v/v=1:1), and stirred for 1 hour to remove the Boc group. After completion of the reaction, the TFA was removed under vacuum, and the residue was repeatedly grinded and washed with ether, and evaporated to dryness. The residue was re-dissolved in tetrahydrofuran, and the pH was adjusted to 7~8 with N-methyl morpholine (NMM) in ice bath. The filtrate above was sparingly added to the solution in a few portions, and stirred in ice bath for 5 hours, and the reaction continued for 20 hours at r.t. A large amount of viscous white precipitate formed. The mixture was filtered and the precipitate was washed with a small amount of tetrahydrofuran. Then the precipitate was dried under vacuum, and 14.6 g target compounds was obtained with the yield of 74%, m.p.=195~196° C.

$^1$H-NMR (300 MHz, DMSO-d$_6$): 7.47 (2H, m, 2 and 6-H), 7.58 (2H, m, 3 and 5-H), 7.38 (1H, d, J=15.3 Hz, 7-H), 6.79 (1H, d, J=15.3 Hz, 8-H), 8.45 (1H, d, J=8.1 Hz, 10-H), 4.40 (1H, m, 11-H), 1.28 (3H, m, 12-H), 8.29 (1H, d, J=8.1 Hz, 14-H), 4.19 (1H, m, 15-H), 6.95 (1H, s, 17$_a$-H), 7.41 (1H, s, 17$_b$-H), 1.71 (1H, m, 18-H), 1.96 (1H, m, 18$_b$-H), 2.14 (2H, m, 19-H), 7.92 (1H, m, 21-H), 4.12 (1H, m, 22-H), 7.09 (1H, s, 24$_a$-H), 7.33 (1H, m, 24$_b$-H), 1.49 (1H, m, 25$_a$-H), 1.65 (1H, m, 25$_b$-H), 1.27 (2H, m, 26-H), 1.53 (2H, m, 27-H), 2.91 (2H, m, 28-H), 6.91 (1H, br.s, 29-H), 5.00 (2H, s, 31-H), 7.20-7.38 (5H, m, 33~37-H).

$^{13}$C-NMR (125 MHz, DMSO-d$_6$): 133.9 (1-C), 129.0 (2 and 6-C), 129.2 (3 and 5-C), 133.8 (4-C), 137.6 (7-C), 122.8 (8-C), 164.7 (9-C), 48.9 (11-C), 18.1 (12-C), 172.4 (13-C), 52.1 (15-C), 173.9 (16-C), 27.6 (18-C), 31.6 (19-C), 171.5 (20-C), 52.1 (22-C), 173.3 (23-C), 31.4 (25-C), 22.7 (26-C), 27.5 (27-C), 38.7 (28-C), 156.0 (30-C), 65.1 (31-C), 137.5 (32-C), 127.7 (33 and 37-C), 128.3 (34 and 36-C), 127.0 (35-C).

ESI-MS: 643.31 [M+H]$^+$.
HR-MS(TOF): 643.2635 [M+H]$^+$, 665.2451 [M+Na]$^+$, C$_{31}$H$_{39}$ClN$_6$O$_7$.

Example 10

Liquid-phase synthesis of Muramyl dipeptide Analogue MDA

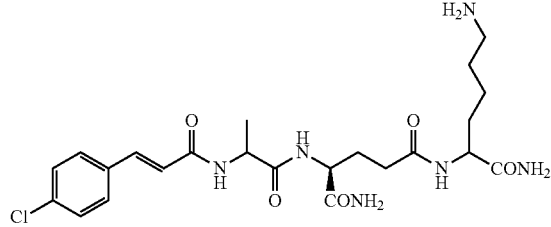 [SMILES: CC(NC(=O)/C=C/c1ccc(Cl)cc1)C(=O)N[C@@H](CCC(=O)NC(CCCCN)C(N)=O)C(N)=O]

14.6 g tripeptide fragment of example 9 was dissolved in a mixture of boron trifluoride diethyl etherate, trifluoacetic acid and ethanol (v:v:v=9:9:2). The mixture was stirred at r.t. for 2 hours. After completion of the reaction, the solvent was evaporated to dryness under vacuum. Large amount of ether was added to the residue in the ice bath, and white solid precipitated. The mixture was centrifuged, and the supernatant was separated. The precipitate was grinded and washed with large amount of ether repeatedly, and 8.3 g crude product was obtained with yield of 72%. The 8.3 g crude product was purified by ODS column chromatography with gradient elution method (methanol-water). The eluent was combined, and the solvent was removed under vacuum, and further dried by lypophilization, 6.8 g target compound was obtained with a purity of 98.5%. m.p.=215~217° C., [α]=+37.7° (C=11.05 mg/ml, DMF).

$^1$H-NMR (600 MHz, DMSO-d$_6$): 7.47 (2H, d, J=8.4 Hz, 2 and 6-H), 7.57 (2H, d, J=8.4 Hz, 3 and 5-H), 7.39 (1H, d, J=15.9 Hz, 7-H), 6.75 (1H, d, J=15.9 Hz, 8-H), 8.39 (1H, d, J=6.6 Hz, 10-H), 4.38 (1H, m, 11-H), 1.26 (3H, m, 12-H), 8.21 (1H, d, J=8.4 Hz, 14-H), 4.14 (1H, m, 15-H), 6.98 (1H, s, 17-H$_a$), 7.41 (1H, s, 17-H$_b$), 1.71 (1H, m, 18-H$_a$), 1.97 (1H, n, 18-H$_b$), 2.15 (2H, t, J=7.2 Hz, 19-H), 7.90 (1H, d, J=8.4 Hz, 21-H), 4.11 (1H, m, 22-H), 7.10 (1H, s, 24-H$_a$), 7.30 (1H, s, 24-H$_b$), 1.46 (1H, m, 25-H$_a$), 1.63 (1H, m, 25-H$_b$), 1.27 (2H, m, 26-H), 1.53 (2H, m, 27-H), 2.73 (2H, m, 28-H), 7.75 (2H, br.s, 29-H).

$^{13}$C-NMR (150 MHz, DMSO-d$_6$): 134.0 (1-C), 129.0 (2 and 6-C), 129.2 (3 and 5-C), 133.8 (4-C), 137.6 (7-C), 122.7 (8-C), 164.7 (9-C), 48.8 (11-C), 18.1 (12-C), 172.4 (13-C), 52.2 (15-C), 173.8 (16-C), 27.7 (18-C), 31.7 (19-C), 171.6 (20-C), 52.1 (22-C), 173.3 (23-C), 31.3 (25-C), 22.4 (26-C), 26.8 (27-C), 38.7 (28-C).

IR: 3282.3, 3202.2 ($v_{OH}$ and $v_{NH}$), 3067.3 ($v_{=CH}$), 2938.0 ($v_{—CH}$), 1609.5 ($v_{—C=O}$), 1537.5, 1450.2 ($v_{C=C}$), 1199.0, 1180.2, 1130.6 ($\delta_{—CH}$), 972.4, 820.4, 799.4, 720.0 ($\delta_{=CH}$ and $v_{C—Cl}$).

ESI-MS: 509.60 [M+H]$^+$, 1017.24 [2M+H]$^+$.
HR-MS(TOF): 509.2292 [M+H]$^+$, C$_{23}$H$_{33}$ClN$_6$O$_5$.

Example 11-22

Solid-Phase Synthesis of Muramyl Dipeptide Analogue

Example 11

Solid-Phase Synthesis of Muramyl Dipeptide MDA-201

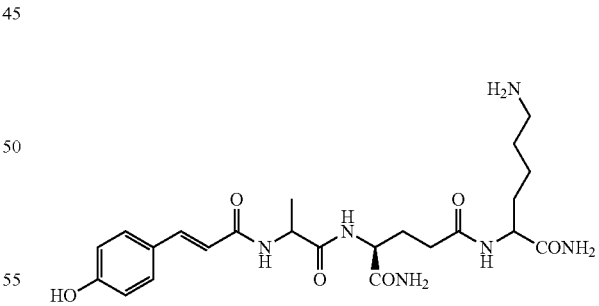

Solid-phase synthesis strategy was employed. Rink-Amide AM resin (loading 0.88 mmol/g) was chosen, Fmoc-Lys(Boc)-COOH, Fmoc-D-iso-Gln-COOH, Fmoc-Ala-COOH and p-hydroxycinnamic acid was introduced to the resin in sequence. After the completion of the condensation, the resin was sufficiently washed and the solvent was drained, and the resin was cleaved for 1 hour in 90% (volume percentage) TFA aqueous solution. The solvent was removed under vacuum, the residue was subjected to a large amount of ether in ice bath and white solid precipitated. The mixture was filtered, and the crude product was obtained, yield 85%. The crude product was purified by ODS column chromatography, and white solid with a purity of 98.5% was obtained through lypophilization. m.p.=143~144° C.

$^1$H-NMR (300 MHz, DMSO-$d_6$): 9.94 (1H, s, 1-OH), 6.79 (2H, d, J=8.7 Hz, 2 and 6-H), 7.59 (2H, d, J=8.7 Hz, 3 and 5-H), 7.36 (1H, d, J=15.9 Hz, 7-H), 6.51 (1H, d, J=15.9 Hz, 8-H), 8.25 (1H, d, J=6.3 Hz, 10-H), 4.34 (1H, m, 11-H), 1.24 (3H, m, 12-H), 8.17 (1H, d, J=8.4 Hz, 14-H), 4.12 (1H, m, 15-H), 6.98 (1H, s, 17-$H_a$), 7.31 (1H, s, 17-$H_b$), 1.72 (1H, m, 18-$H_a$), 1.98 (1H, m, 18-$H_b$), 2.15 (2H, m, 19-H), 7.89 (1H, d, J=7.8 Hz, 21-H), 4.11 (1H, m, 22-H), 7.10 (1H, s, 24-$H_a$), 7.31 (1H, s, 24-$H_b$), 1.48 (1H, m, 25-$H_a$), 1.63 (1H, m, 25-$H_b$), 1.25 (2H, m, 26-H), 1.50 (2H, m, 27-H), 2.74 (2H, m, 28-H), 7.76 (2H, br.s, 29-H).

$^{13}$C-NMR (125 MHz, DMSO-$d_6$): 159.0 (1-C), 115.8 (2 and 6-C), 129.3 (3 and 5-C), 125.8 (4-C), 139.2 (7-C), 118.2 (8-C), 165.5 (9-C), 48.9 (11-C), 17.9 (12-C), 172.6 (13-C), 52.2 (15-C), 173.8 (16-C), 27.6 (18-C), 31.7 (19-C), 171.6 (20-C), 52.1 (22-C), 173.3 (23-C), 31.3 (25-C), 22.4 (26-C), 26.7 (27-C), 38.7 (28-C).

IR: 3273.8, 3194.6 ($v_{OH}$ and $v_{NH}$), 3064.6 ($v_{=CH}$), 2943.4 ($v_{-CH}$), 1663.6 ($v_{C=O}$), 1605.7, 1537.3, 1515.0, 1450.4 ($v_{C=C}$), 1201.6, 11802, 1135.7 ($\delta_{-CH}$), 983.8, 835.0, 800.4, 721.6 ($\delta_{=CH}$).

ESI-MS: 491.39 [M+H]$^+$, 981.21 [2M+H]$^+$.
HR-MS(TOF): 491.2597 [M+H]$^+$, $C_{23}H_{34}N_6O_6$.

Example 12

Solid-Phase Synthesis of Muramyl Dipeptide MDA-202

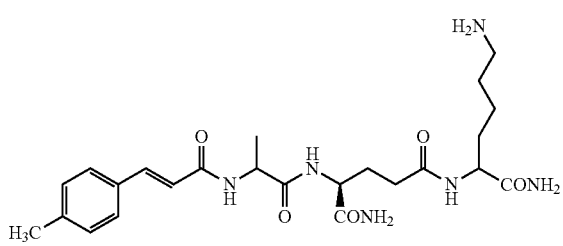 [SMILES: Cc1ccc(/C=C/C(=O)NC(C)C(=O)N[C@@H](CCC(=O)NC(CCCCN)C(N)=O)C(N)=O)cc1]

Solid-phase synthesis strategy was employed. Rink-Amide AM resin (loading 0.88 mmol/g) was chosen, Fmoc-Lys(Boc)-COOH, Fmoc-D-iso-Gln-COOH, Fmoc-Ala-COOH and 4-methylcinnamic acid were introduced to resin in sequence. After the completion of the condensation, the resin was sufficiently washed and the solvent was drained, and the resin was cleaved for 1 hour in 90% (volume percentage) TFA aqueous solution. The solvent was removed under vacuum, the residue was moved to an ice bath, and a large amount of ether was added to the residue, white solid precipitated immediately. The mixture was filtered, and the crude product was obtained, yield 86%. The crude product was purified by ODS column chromatography, and white solid with a purity of 98.5% was obtained through lypophilization. m.p.=150~151° C.

$^1$H-NMR (300 MHz, DMSO-$d_6$): 2.30 (3H, s, 1-$CH_3$), 7.44 (2H, d, J=8.1 Hz, 2 and 6-H), 7.21 (2H, d, J=8.1 Hz, 3 and 5-H), 7.37 (1H, d, J=15.9 Hz, 7-H), 6.69 (1H, d, J=15.9 Hz, 8-H), 8.35 (1H, d, J=6.6 Hz, 10-H), 4.37 (1H, m, 11-H), 1.25 (3H, m, 12-H), 8.21 (1H, d, J=8.1 Hz, 14-H), 4.12 (1H, m, 15-H), 6.99 (1H, s, 17-$H_a$), 7.32 (1H, s, 17-$H_b$), 1.73 (1H, m, 18-$H_a$), 1.97 (1H, m, 18-$H_b$), 2.16 (2H, m, 19-H), 7.90 (1H, d, J=7.8 Hz, 21-H), 4.10 (1H, m, 22-H), 7.11 (1H, s, 24-$H_a$), 7.34 (1H, s, 24-$H_b$), 1.49 (1H, m, 25-$H_a$), 1.63 (1H, m, 25-$H_b$), 1.28 (2H, m, 26-H), 1.51 (2H, m, 27-H), 2.74 (2H, m, 28-H), 7.80 (2H, br.s, 29-H).

$^{13}$C-NMR (125 MHz, DMSO-$d_6$): 20.9 (1-$CH_3$), 139.0 (2 and 6-C), 129.6 (2 and 6-C), 127.5 (3 and 5-C), 132.1 (4-C), 139.3 (7-C), 120.8 (8-C), 165.2 (9-C), 48.9 (11-C), 18.0 (12-C), 172.5 (13-C), 52.2 (15-C), 173.9 (16-C), 27.6 (18-C), 31.8 (19-C), 171.7 (20-C), 52.1 (22-C), 173.4 (23-C), 31.3 (25-C), 22.4 (26-C), 26.7 (27-C), 38.7 (28-C).

IR: 3278.8, 3199.9 ($v_{OH}$ and $v_{NH}$), 3063.3 ($v_{=CH}$), 2941.3 ($v_{-CH}$), 1656.3 ($v_{C=O}$), 1540.7, 1452.5 ($v_{C=C}$), 1202.2, 1184.1, 1135.3 ($\delta_{-CH}$), 984.0, 835.8, 813.6, 800.7, 721.6 ($\delta_{=CH}$).

ESI-MS: 489.48 [M+H]$^+$, 977.29 [2M+H]$^+$.
HR-MS(TOF): 489.2819 [M+H]$^+$, $C_{24}H_{36}N_6O_5$.

Example 13

Solid-Phase Synthesis of Muramyl Dipeptide MDA-203

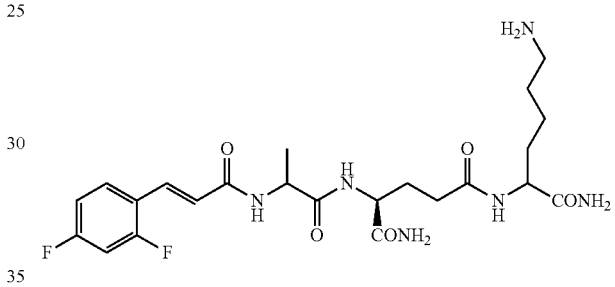

Solid-phase synthesis strategy was employed. Rink-Amide AM resin (loading 0.88 mmol/g) was chosen, Fmoc-Lys(Boc)-COOH, Fmoc-D-iso-Gln-COOH, Fmoc-Ala-COOH and 2,4-difluorocinnamic acid was introduced to resin in sequence. After the completion of the condensation, the resin was sufficiently washed and the solvent was drained, and the resin was cleaved for 1 hour in 90% (volume percentage) TFA aqueous solution. The solvent was removed under vacuum, the residue was moved to an ice bath, and a large amount of ether was added to the residue, a white solid precipitated immediately. The mixture was filtered, and the crude product was obtained with yield of 80%. The crude product was purified by ODS column chromatography, and white solid with a purity of 98.5% was obtained through lypophilization. m.p.=189~190° C.

$^1$H-NMR (300 MHz, DMSO-$d_6$): 7.35 (1H, m, 2-H), 7.72 (1H, dd, J=15.2 and 8.7 Hz, 5-H), 7.18 (1H, td, J=8.4 and 2.4 Hz, 6-H), 7.44 (1H, d, J=15.9 Hz, 7-H), 6.82 (1H, d, J=15.9 Hz, 8-H), 8.51 (1H, d, J=6.6 Hz, 10-H), 4.40 (1H, m, 11-H), 1.27 (3H, d, J=7.2 Hz, 12-H), 8.24 (1H, d, J=8.1 Hz, 14-H), 4.17 (1H, m, 15-H), 7.00 (1H, s, 17-$H_a$), 7.33 (1H, s, 17-$H_b$), 1.71 (1H, m, 18-$H_a$), 1.97 (1H, m, 18-$H_b$), 2.17 (2H, t, J=7.8 Hz, 19-H), 7.91 (1H, d, J=8.4 Hz, 21-H), 4.13 (1H, m, 22-H), 7.07 (1H, s, 24-$H_a$), 7.32 (1H, s, 24-$H_b$), 1.49 (1H, m, 25-$H_a$), 1.64 (1H, m, 25-$H_b$), 1.29 (2H, m, 26-H), 1.50 (2H, m, 27-H), 2.75 (2H, m, 28-H).

$^{13}$C-NMR (125 MHz, DMSO-$d_6$): 163.7 (m, 1-C), 104.7 (t, J=26.0 Hz, 2-C), 159.6 (m, 3-C), 118.5 (m, 4-C), 130.6 (m, 5-C), 112.4 (d. J=18.4 Hz, 6-C), 137.4 (s, 7-C), 124.3 (s, 8-C), 164.7 (s, 9-C), 48.9 (11-C), 18.0 (12-C), 172.2 (13-C), 52.1

(15-C), 173.2 (16-C), 27.6 (18-C), 31.7 (19-C), 171.6 (20-C), 52.0 (22-C), 172.3 (23-C), 31.3 (25-C), 22.4 (26-C), 26.8 (27-C), 38.7 (28-C).

IR: 3279.8, 3198.2 ($v_{OH}$ and $v_{NH}$), 3066.7 ($v_{=CH}$), 2939.5 ($v_{-CH}$), 1656.2 ($v_{C=O}$), 1616.4, 1544.6, 1504.2, 1454.1 ($v_{C=C}$), 1202.1, 1181.7, 1138.8 ($v_{C-F}$ and $\delta_{-CH}$), 967.5, 836.7, 800.7, 721.4 ($v_{C-Cl}$ and $\delta_{=CH}$).

ESI-MS: 511.28 [M+H]$^+$, 1021.02 [2M+H]$^+$.

HR-MS(TOF): 511.2482 [M+H]$^+$, $C_{24}H_{36}N_6O_5$.

Example 14

Solid-Phase Synthesis of Muramyl Dipeptide MDA-204

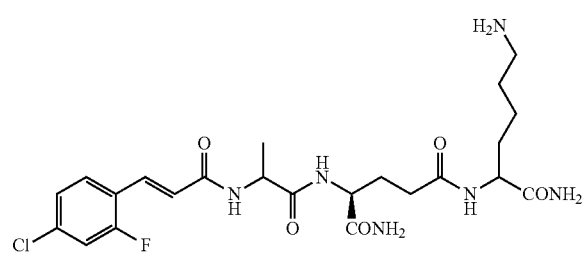 [SMILES: CC(NC(=O)/C=C/c1ccc(Cl)cc1F)C(=O)N[C@@H](CCC(=O)NC(CCCCN)C(N)=O)C(N)=O]

Solid-phase synthesis strategy was employed. Rink-Amide AM resin (loading 0.88 mmol/g) was chosen, Fmoc-Lys(Boc)-COOH, Fmoc-D-iso-Gln-COOH, Fmoc-Ala-COOH and 4-chloro-2-fluorocinnamic acid was introduced to the resin in sequence. After the completion of the condensation, the resin was sufficiently washed and the solvent was drained, and the resin was cleaved for 1 hour in 90% (volume percentage) TFA aqueous solution. The solvent was removed under vacuum, the residue was subjected to a large amount of ether in ice bath, a white solid precipitated immediately. The mixture was filtered, and the crude product was obtained with yield of 88%. The crude product was purified by ODS column chromatography, and white solid with a purity of 98.5% was obtained through lyophilization. m.p.=149~150° C.

$^1$H-NMR (300 MHz, DMSO-d$_6$): 7.54 (1H, dd, J=10.8 and 1.8 Hz, 2-H), 7.69 (1H, t, J=8.7 Hz, 5-H), 7.36 (1H, dd, J=10.5 and 2.1 Hz, 6-H), 7.44 (1H, d, J=15.9 Hz, 7-H), 6.87 (1H, d, J=15.9 Hz, 8-H), 8.57 (1H, d, J=6.6 Hz, 10-H), 4.40 (1H, m, 11-H), 1.27 (3H, d, J=7.2 Hz, 12-H), 8.27 (1H, d, J=8.1 Hz, 14-H), 4.13 (1H, m, 15-H), 6.99 (1H, s, 17-H$_a$), 7.35 (1H, s, 17-H$_b$), 1.72 (1H, m, 18-H$_a$), 1.98 (1H, m, 18-H$_b$), 2.17 (2H, t, J=7.8 Hz, 19-H), 8.08 (1H, d, J=8.1 Hz, 21-H), 4.10 (1H, m, 22-H), 7.12 (1H, s, 24-H$_a$), 7.32 (1H, s, 24-H$_b$), 1.49 (1H, m, 25-H$_a$), 1.64 (1H, m, 25-H$_b$), 1.29 (2H, m, 26-H), 1.51 (2H, m, 27-H), 2.74 (2H, m, 28-H).

$^{13}$C-NMR (125 MHz, DMSO-d$_6$): 135.1 (d, J=10.9 Hz, 1-C), 117.2 (d, J=25.8 Hz, 2-C), 160.7 (d, J=252.5 Hz, 3-C), 122.1 (d, J=11.6 Hz, 4-C), 130.8 (s, 5-C), 125.9 (d, J=3.0 Hz, 6-C), 137.3 (m, 7-C), 125.8 (d, J=6.3 Hz, 8-C), 164.6 (s, 9-C), 49.4 (11-C), 18.5 (12-C), 172.8 (13-C), 52.7 (15-C), 174.3 (16-C), 28.1 (18-C), 32.2 (19-C), 172.1 (20-C), 52.6 (22-C), 173.8 (23-C), 31.8 (25-C), 22.9 (26-C), 27.5 (27-C), 38.7 (28-C).

IR: 3358.7, 3284.3, 3199.3 ($v_{OH}$ and $v_{NH}$), 3067.3 ($v_{=CH}$), 2933.4 ($v_{-CH}$), 1654.7, 1642.5, 1642.5, 1622.9 ($v_{C=O}$), 1540.6, 1489.9, 1453.6 ($v_{C=C}$), 1202.4, 1129.9 ($v_{C-F}$ and $\delta_{-CH}$), 978.2, 815.0, 720.6, 690.2 ($v_{C-Cl}$ and $\delta_{=CH}$).

ESI-MS: 527.49 [M+H]$^+$, 1053.17 [2M+H]$^+$.

HR-MS(TOF): 527.2192 [M+H]$^+$, $C_{23}H_{32}ClFN_6O_5$.

Example 15

Solid-Phase Synthesis of Muramyl Dipeptide MDA-205

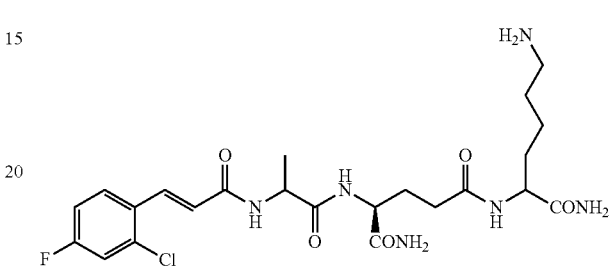

Solid-phase synthesis strategy was employed. Rink-Amide AM resin (loading 0.88 mmol/g) was chosen, Fmoc-Lys(Boc)-COOH, Fmoc-D-iso-Gln-COOH, Fmoc-Ala-COOH and 2-chloro-4-fluorocinnamic acid were introduced to resin in sequence. After the completion of the condensation, the resin was sufficiently washed and the solvent was drained, and the resin was cleaved for 1 hour in 90% (volume percentage) TFA aqueous solution. The solvent was removed under vacuum, the residue was subjected to a large amount of ether in ice bath, white solid precipitated immediately. The mixture was filtered, and the crude product was obtained with yield of 86%. The crude product was purified by ODS column chromatography, and white solid with a purity of 98.5% was obtained through lyophilization. m.p.=137~138° C.

$^1$H-NMR (300 MHz, DMSO-d$_6$): 7.55 (1H, dd, J=8.7 and 1.8 Hz, 2-H), 7.77 (1H, m, 5-H), 7.36 (1H, m, 6-H), 7.66 (1H, d, J=15.9 Hz, 7-H), 6.79 (1H, d, J=15.9 Hz, 8-H), 8.47 (1H, d, J=6.6 Hz, 10-H), 4.42 (1H, m, 11-H), 1.27 (3H, d, J=6.9 Hz, 12-H), 8.24 (1H, d, J=8.4 Hz, 14-H), 4.16 (1H, m, 15-H), 7.00 (1H, s, 17-H$_a$), 7.31 (1H, s, 17-H$_b$), 1.72 (1H, m, 18-H$_a$), 1.99 (1H, m, 18-H$_b$), 2.17 (2H, t, J=7.8 Hz, 19-H), 7.91 (1H, d, J=8.7 Hz, 21-H), 4.13 (1H, m, 22-H), 7.12 (1H, s, 24-H$_a$), 7.33 (1H, s, 24-H$_b$), 1.49 (1H, m, 25-H$_a$), 1.65 (1H, m, 25-H$_b$), 1.30 (2H, m, 26-H), 1.52 (2H, m, 27-H), 2.75 (2H, br.s, 28-H), 7.79 (2H, br.s, 29-H).

$^{13}$C-NMR (125 MHz, DMSO-d$_6$): 162.7 (d, J=250.0 Hz, 1-C), 115.9 (d, J=21.6 Hz, 2-C), 134.6 (d, J=10.0 Hz, 3-C), 129.9 (d, J=3.8 Hz, 4-C), 129.7 (d, J=10.0 Hz, 5-C), 117.7 (d, J=25.1 Hz, 3-C), 137.5 (7-C), 125.4 (8-C), 164.8 (9-C), 49.3 (11-C), 18.6 (12-C), 172.1 (13-C), 52.6 (15-C), 174.2 (16-C), 28.2 (18-C), 32.2 (19-C), 172.1 (20-C), 52.2 (22-C), 173.7 (23-C), 31.8 (25-C), 22.9 (26-C), 27.2 (27-C), 38.2 (28-C).

IR: 3279.8 ($v_{OH}$ and $v_{NH}$), 3066.0 ($v_{=CH}$), 2937.1 ($v_{-CH}$), 1776.1, 1656.3 ($v_{C=O}$), 1537.0, 1489.0, 1452.2 ($v_{C=C}$), 1238.1, 1201.1, 1181.0, 1135.6 ($v_{C-F}$ and $\delta_{-CH}$), 910.6, 835.5, 800.1, 721.3 ($v_{C-Cl}$ and $\delta_{=CH}$).

ESI-MS: 527.28 [M+H]$^+$, 1075.00 [2M+Na]$^+$.

HR-MS(TOF): 527.2201 [M+H]$^+$, $C_{23}H_{32}ClFN_6O_5$.

Example 16

Solid-Phase Synthesis of Muramyl Dipeptide MDA-206

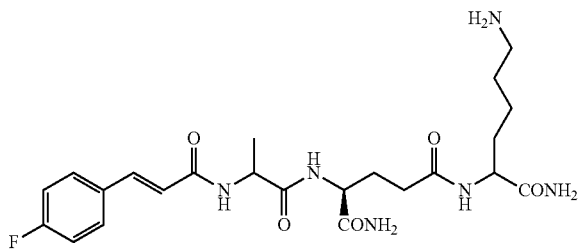 [SMILES: CC(NC(=O)/C=C/c1ccc(F)cc1)C(=O)N[C@@H](CCC(=O)NC(CCCCN)C(N)=O)C(N)=O]

Solid-phase synthesis strategy was employed. Rink-Amide AM resin (loading 0.88 mmol/g) was chosen, Fmoc-Lys(Boc)-COOH, Fmoc-D-iso-Gln-COOH, Fmoc-Ala-COOH and 4-fluorocinnamic acid were introduced in sequence. After the completion of the condensation, the resin was sufficiently washed and the solvent drained, and the resin was cleaved for 1 hour in 90% (volume percentage) TFA aqueous solution. The solvent was removed under vacuum, and the residue was subjected to a large amount of ether in ice bath, a white solid precipitated immediately. The mixture was filtered, and the crude product was obtained, yield 92%. The crude product was purified by ODS column chromatography, and white solid with a purity of 98.5% was obtained through lyophilization. m.p.=218~220° C.

$^1$H-NMR (300 MHz, DMSO-$d_6$): 7.26 (2H, t, J=8.7 Hz, 2 and 6-H), 7.63 (2H, dd, J=8.4 and 5.7 Hz, 3 and 5-H), 7.42 (1H, d, J=15.9 Hz, 7-H), 6.71 (1H, d, J=15.9 Hz, 8-H), 8.37 (1H, d, J=6.6 Hz, 10-H), 4.40 (1H, m, 11-H), 1.27 (3H, d, J=7.2 Hz, 12-H), 8.21 (1H, d, J=8.1 Hz, 14-H), 4.15 (1H, m, 15-H), 7.00 (1H, s, 17-$H_a$), 7.32 (1H, s, 17-$H_b$), 1.71 (1H, m, 18-$H_a$), 1.99 (1H, m, 18-$H_b$), 2.17 (2H, t, J=7.8 Hz, 19-H), 7.90 (1H, d, J=8.1 Hz, 21-H), 4.14 (1H, m, 22-H), 7.12 (1H, s, 24-$H_a$), 7.32 (1H, s, 24-$H_b$), 1.49 (1H, m, 25-$H_a$), 1.64 (1H, m, 25-$H_b$), 1.29 (2H, m, 26-H), 1.52 (2H, m, 27-H), 2.76 (2H, m, 28-H), 7.71 (2H, br.s, 29-H).

$^{13}$C-NMR (125 MHz, DMSO-$d_6$): 163.2 (d, J=245.8 Hz, 1-C), 116.4 (d, J=21.6 Hz, 2 and 6-C), 130.1 (d, J=8.5 Hz, 3 and 5-C), 131.9 (4-C), 138.3 (7-C), 122.2 (8-C), 165.3 (9-C), 49.3 (11-C), 18.5 (12-C), 172.8 (13-C), 52.6 (15-C), 174.2 (16-C), 27.2 (18-C), 32.2 (19-C), 172.1 (20-C), 52.5 (22-C), 173.7 (23-C), 31.8 (25-C), 22.9 (26-C), 27.2 (27-C), 38.5 (28-C).

IR: 3278.5, 3198.1 ($v_{OH}$ and $v_{NH}$), 3068.1 ($v_{=CH}$), 2931.9 ($v_{—CH}$), 1672.8, 1639.9 ($v_{C=O}$), 1614.9, 1539.4, 1509.6, 1451.7 ($v_{C=C}$), 1201.7, 1134.3 ($v_{C-F}$ and $\delta_{—CH}$), 971.4, 831.4, 800.6, 721.0 ($\delta_{=CH}$).

ESI-MS: 493.25 [M+H]$^+$, 1007.02 [2M+Na]$^+$.
HR-MS(TOF): 493.2580 [M+H]$_+$, 515.2381 [M+Na]$_+$, $C_{23}H_{33}FN_6O_5$.

Example 17

Solid-Phase Synthesis of Muramyl Dipeptide MDA-207

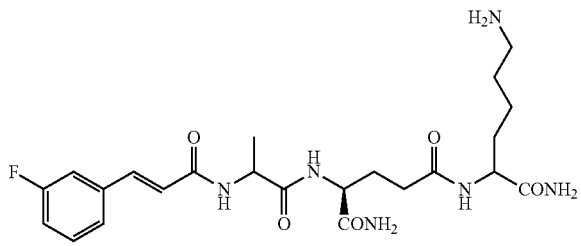 [SMILES: CC(NC(=O)/C=C/c1cccc(F)c1)C(=O)N[C@@H](CCC(=O)NC(CCCCN)C(N)=O)C(N)=O]

Solid-phase synthesis strategy was employed. Rink-Amide AM resin (loading 0.88 mmol/g) was chosen, Fmoc-Lys(Boc)-COOH, Fmoc-D-iso-Gln-COOH, Fmoc-Ala-COOH and 4-fluorocinnamic acid was introduced in sequence. After the completion of the condensation, the resin was sufficiently washed and the solvent was drained, and the resin was cleaved for 1 hour in 90% (volume percentage) TFA aqueous solution. The solvent was removed under vacuum, the residue was subjected to a large amount of ether in ice bath, and, a white solid precipitated immediately. The mixture was filtered, and the crude product was obtained, yield 75%. The crude product was purified by ODS column chromatography, and white solid with a purity of 98.5% was obtained through lyophilization. m.p.=195~196° C.

$^1$H-NMR (300 MHz, DMSO-$d_6$): 7.21 (1H, s, 2-H), 7.38 (1H, m, 3-H), 7.41 (1H, m, 5-H), 7.47 (1H, m, 6-H), 7.47 (1H, d, J=15.9 Hz, 7-H), 6.79 (1H, d, J=15.9 Hz, 8-H), 8.39 (1H, d, J=6.0 Hz, 10-H), 4.38 (1H, m, 11-H), 1.26 (3H, d, J=6.9 Hz, 12-H), 8.22 (1H, d, J=7.5 Hz, 14-H), 4.13 (1H, m, 15-H), 6.97 (1H, s, 17-$H_a$), 7.30 (1H, s, 17-$H_b$), 1.65 (1H, m, 18-$H_a$), 1.97 (1H, a, 18-$H_b$), 2.15 (2H, m, 19-H), 7.90 (1H, d, J=8.4 Hz, 21-H), 4.13 (1H, m, 22-H), 7.01 (1H, s, 24-$H_a$), 7.30 (1H, s, 24-$H_b$), 1.48 (1H, m, 25-$H_a$), 1.65 (1H, m, 25-$H_b$), 1.28 (2H, m, 26-H), 1.48 (2H, m, 27-H), 2.72 (2H, m, 28-H).

$^{13}$C-NMR (125 MHz, DMSO-$d_6$): 116.7 (d. J=21.0 Hz, 1-C), 162.9 (d, J=242.3 Hz, 2-C), 114.4 (d, J=21.4 Hz, 3-C), 137.9 (d, J=7.8 Hz, 4-C), 124.0 (d, J=22.6 Hz, 5-C), 131.4 (6-C), 138.1 (7-C), 124.0 (8-C), 165.1 (9-C), 49.3 (11-C), 18.6 (12-C), 172.8 (13-C), 52.6 (15-C), 174.3 (16-C), 28.2 (18-C), 32.2 (19-C), 172.0 (20-C), 52.5 (22-C), 173.7 (23-C), 31.8 (25-C), 22.9 (26-C), 27.2 (27-C), 38.5 (28-C).

IR: 3276.4, 3201.1 ($v_{OH}$ and $v_{NH}$), 3069.1 ($v_{=CH}$), 2938.1 ($v_{—CH}$), 1647.7 ($v_{C=O}$), 1539.0, 1448.0, 1421.8 (vC=C), 1200.8, 1180.2, 1134.1 ($v_{C-F}$ and $\delta_{—CH}$), 972.1, 834.9, 798.7, 721.2 ($\delta_{=CH}$).

ESI-MS: 493.25 [M+H]$^+$, 1007.09 [2M+Na]$^+$.
HR-MS(TOF): 493.2582 [M+H]$^+$, $C_{23}H_{33}FN_6O_5$.

Example 18

Solid-Phase Synthesis of Muramyl Dipeptide MDA-208

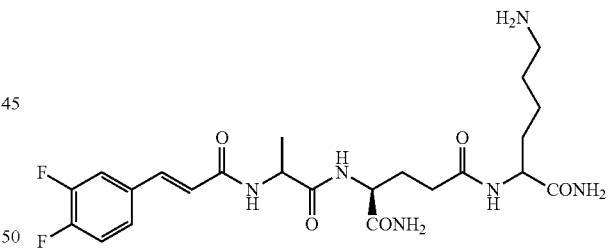

Solid-phase synthesis strategy was employed. Rink-Amide AM resin (loading 0.88 mmol/g) was chosen, Fmoc-Lys(Boc)-COOH, Fmoc-D-iso-Gln-COOH, Fmoc-Ala-COOH and 3,4-difluorocinnamic acid were introduced to the resin in sequence. After the completion of the condensation, the resin was sufficiently washed and the solvent was drained, and the resin was cleaved for 1 hour in 90% (volume percentage) TFA aqueous solution. The solvent was removed under vacuum, the residue was subjected to a large amount of ether in ice bath, and a white solid precipitated immediately. The mixture was filtered, and the crude product was obtained with yield of 95%. The crude product was purified by ODS column chromatography, and white solid with a purity of 98.5% was obtained through lyophilization. m.p.=139~140° C.

$^1$H-NMR (300 MHz, DMSO-$d_6$): 7.66 (1H, m, 3-H), 7.48 (1H, m, 5-H), 7.45 (1H, m, 6-H), 7.40 (1H, d, J=15.9 Hz, 7-H), 6.75 (1H, d, J=15.9 Hz, 8-H), 8.37 (1H, d, J=6.9 Hz,

10-H), 4.40 (1H, m, 11-H), 1.27 (3H, d, J=7.2 Hz, 12-H), 8.22 (1H, d, J=7.8 Hz, 14-H), 4.16 (1H, m, 15-H), 700 (1H, s, 17-H$_a$), 7.33 (1H, s, 17-H$_b$), 1.71 (1H, m, 18-H$_a$), 1.97 (1H, m, 18-H$_b$), 2.17 (2H, t, J=7.8 Hz, 19-H), 7.90 (1H, d, J=8.1 Hz, 21-H), 4.13 (1H, m, 22-H), 7.12 (1H, s, 24-H$_a$), 7.31 (1H, s, 24-H$_b$), 1.49 (1H, m, 25-H$_a$), 1.65 (1H, m, 25-H$_b$), 1.29 (2H, m, 26-H), 1.52 (2H, m, 27-H), 2.76 (2H, m, 28-H), 7.73 (2H, br.s, 29-H).

$^{13}$C-NMR (150 MHz, DMSO-d$_6$): 149.3 (dd, J=35.6 and 12.8 Hz, 1-C), 151.2 (dd, J=38.5 and 12.9 Hz, 2-C), 118.6 (d. J=17.5 Hz, 3-C), 133.3 (m, 4-C), 125.1 (m, 5-C), 116.7 (d, J=17.4 Hz, 6-C), 137.3 (s, 7-C), 123.8 (s, 8-C), 165.0 (9-C), 49.3 (11-C), 18.6 (12-C), 172.8 (13-C), 52.6 (15-C), 174.3 (16-C), 28.2 (18-C), 31.8 (19-C), 172.1 (20-C), 52.5 (22-C), 173.7 (23-C), 31.8 (25-C), 22.9 (26-C), 27.2 (27-C), 38.2 (28-C).

IR: 3275.8, 3196.4 ($\nu_{OH}$ and $\nu_{NH}$), 3064.8 ($\nu_{=CH}$), 2938.1 ($\nu_{-CH}$), 1673.1 ($\nu_{C=O}$), 1612.9, 1542.1, 1516.7, 1451.5 ($\nu_{C=C}$), 1201.6, 1135.4 ($\nu_{C-F}$ and $\delta_{-CH}$), 969.3, 834.3, 800.6, 721.2 ($\delta_{=CH}$).

ESI-MS: 511.30 [M+H]$^+$, 1021.09 [2M+H]$^+$.
HR-MS(TOF): 511.2479 [M+H]$^+$, C$_{23}$H$_{32}$F$_2$N$_6$O$_5$.

Example 19

Solid-Phase Synthesis of Muramyl Dipeptide MDA-113

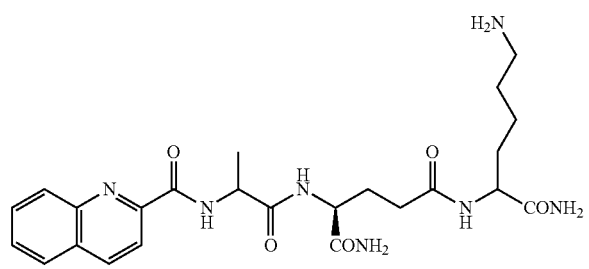 [SMILES: CC(NC(=O)c1ccc2ccccc2n1)C(=O)N[C@@H](CCC(=O)NC(CCCCN)C(N)=O)C(N)=O]

Solid-phase synthesis strategy was employed. Rink-Amide AM resin (loading 0.88 mmol/g) was chosen, Fmoc-Lys(Boc)-COOH, Fmoc-D-iso-Gln-COOH, Fmoc-Ala-COOH and 2-quinolinecarboxylic acid were introduced to resin in sequence. After the completion of the condensation, the resin was sufficiently washed and the solvent was drained, and the resin was cleaved for 1 hour in 90% (volume percentage) TFA aqueous solution. The solvent was removed under vacuum, the residue was subjected to a large amount of ether in ice bath, a white solid precipitated immediately. The mixture was filtered, and the crude product was obtained, yield 80%. The crude product was purified by ODS column chromatography, and MDA-113 as white solid with a purity of 98.5% was obtained through lypophilization.

Example 20

Solid-Phase Synthesis of Muramyl Dipeptide MDA-119

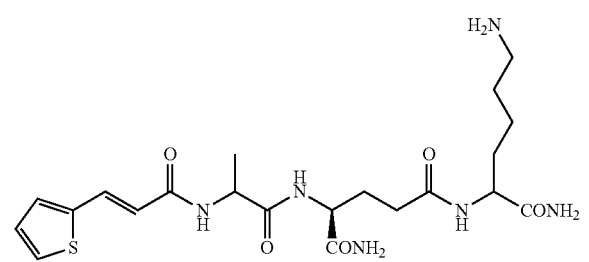 [SMILES: CC(NC(=O)/C=C/c1cccs1)C(=O)N[C@@H](CCC(=O)NC(CCCCN)C(N)=O)C(N)=O]

Solid-phase synthesis strategy was employed. Rink-Amide AM resin (loading 0.88 mmol/g) was chosen, Fmoc-Lys(Boc)-COOH, Fmoc-D-iso-Gln-COOH, Fmoc-Ala-COOH and 2-thienylacrylic acid were introduced in sequence. After the completion of the condensation, the resin was sufficiently washed and the solvent was drained, and the resin was cleaved for 1 hour in 90% (volume percentage) TFA aqueous solution. The solvent was removed under vacuum, the residue was subjected to a large amount of ether in ice bath, a white solid precipitated immediately. The mixture was filtered, and the crude product was obtained with yield of 83%. The crude product was purified by ODS column chromatography, and MDA-119 as white solid with a purity of 98.5% was obtained through lypophilization.

Example 21

Solid-Phase Synthesis of Muramyl Dipeptide MDA-130

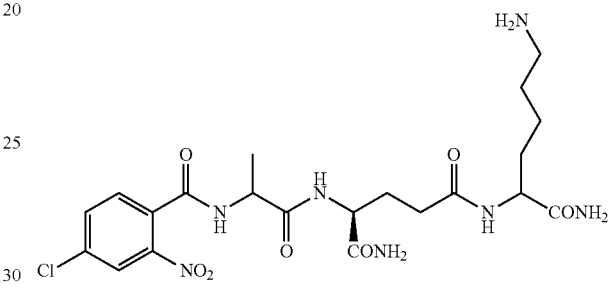

Solid-phase synthesis strategy was employed. Rink-Amide AM resin (loading 0.88 mmol/g) was chosen, Fmoc-Lys(Boc)-COOH, Fmoc-D-iso-Gln-COOH, Fmoc-Ala-COOH and 2-thienylacrylic acid were introduced in sequence. After the completion of the condensation, the resin was sufficiently washed and the solvent was drained, and the resin was cleaved for 1 hour in 90% (volume percentage) TFA aqueous solution. The solvent was removed under vacuum, the residue was subjected to a large amount of ether in ice bath, and, a white solid precipitated immediately. The mixture was filtered, and the crude product was obtained with yield of 81%. The crude product was purified by ODS column chromatography, and MDA-130 as white solid with a purity of 98.5% was obtained through lypophilization.

Example 22

Solid-Phase Synthesis of Muramyl Dipeptide MDA-133

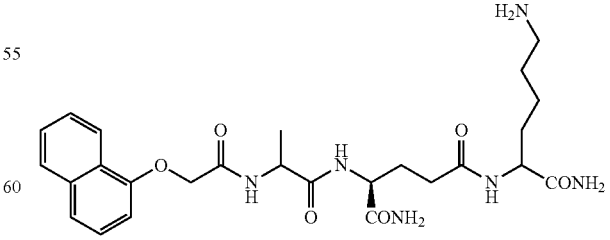

Solid-phase synthesis strategy was employed. Rink-Amide AM resin (loading 0.88 mmol/g) was chosen, Fmoc-Lys(Boc)-COOH, Fmoc-D-iso-Gln-COOH, Fmoc-Ala-COOH and 2-naphthoxyacetic acid were introduced in sequence. After the completion of the condensation, the resin was sufficiently washed and the solvent drained, and the resin was cleaved for 1 hour in 90% trifluoroacetic acid aqueous solution (Volume percentage). The solvent was removed under vacuum, the residue was subjected to a large amount of ether in ice bath, and, a white solid precipitated immediately. The mixture was filtered, and the crude product was obtained with yield of 88%. The crude product was purified by ODS column chromatography, and MDA-133 as white solid with a purity of 98.5% was obtained through lyophilization.

Example 23-35

Liquid-Phase Synthesis of MTC Conjugates

Example 23

Liquid-Phase Synthesis of Conjugate MTC-220

The synthetic route was shown below:

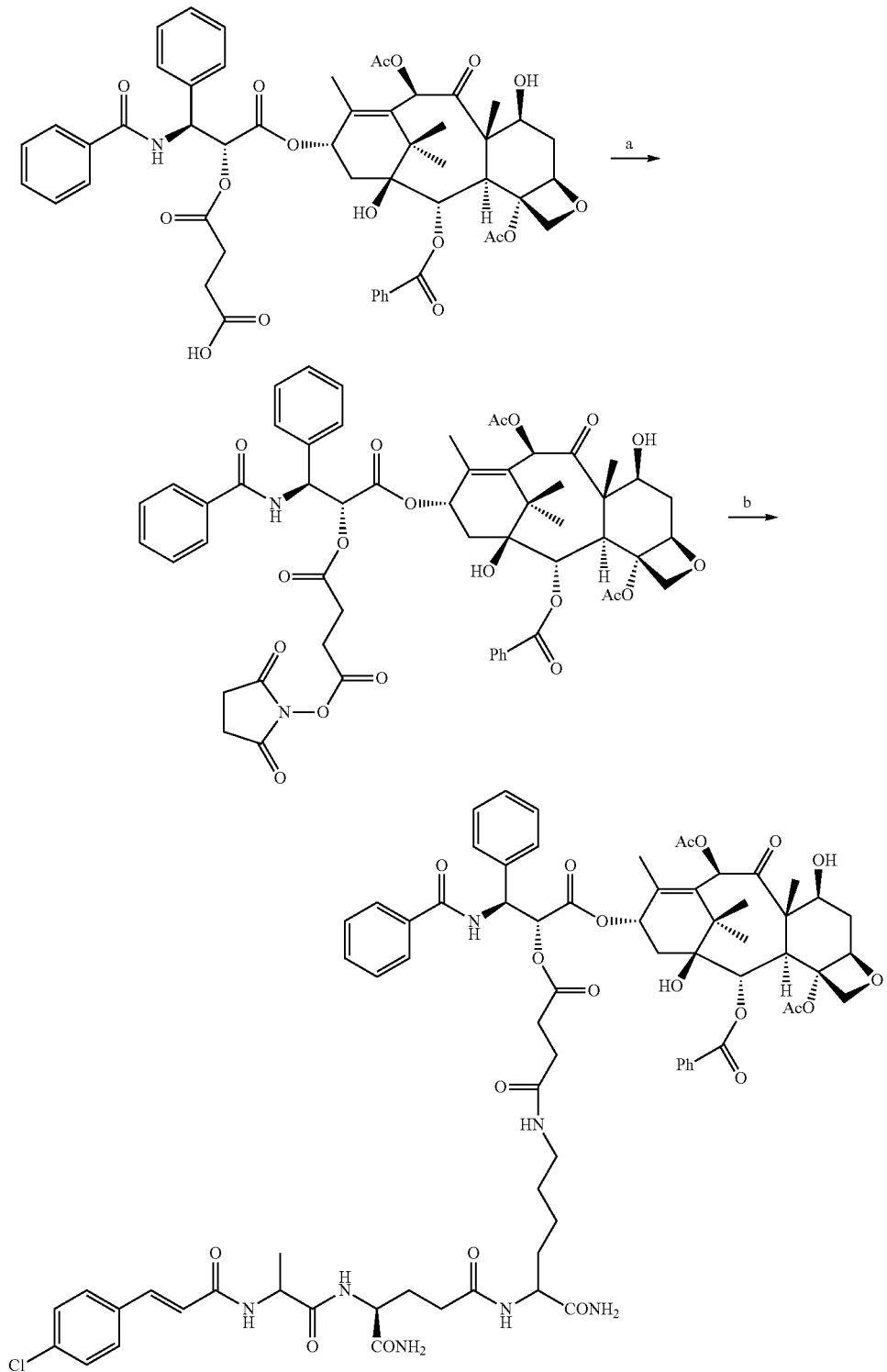

Reagents and conditions: (a) HOSu, EDC.HCl, DMSO, r.t, 20 h; (b) MDA, DMSO, r.t, 12 h.

9.53 g (1.0 eq) pcatiaxel-2'-O-succinic acid monoester, 1.15 g (1.0 eq) HOSu and 1.92 g (1.0 eq) EDC.HCl were dissolved in DMSO, and stirred at r.t for 20 hours. 5.08 g (1.0 eq) muramyl dipeptide analogue (MDA) was sparingly added to the mixture in a few portions. The pH of the mixture was adjusted to 7~8 with N-methyl morpholine, and continued to stir for 20 hours. After the completion of the reaction, plenty of water was added to the mixture, and a white solid precipitated. The mixture was filtered and the crude product was obtained. The crude product was purified by ODS column chromatography, 11.8 g solid product was obtained through lypophilization. Yield 82%, m.p.=180~181° C., [α]=−9.8° (C=10.1 mg/mL, DMF).

$^1$H-NMR (600 MHz, DMSO-$d_6$): 4.63 (1H, br.s, 1-OH), 5.42 (1H, d, J=7.2 Hz, 2-H), 3.58 (1H, d, J=7.2 Hz, 3-H), 4.90 (1H, m, 5-H), 1.62 (1H, m, 6-$H_a$), 2.30 (1H, m, 6-$H_b$), 4.12 (1H, m, 7-H), 4.91 (1H, m, 7-OH), 6.30 (1H, s, 10-H), 5.82 (1H, t, J=9.0 Hz, 13-H), 1.46 (1H, m, 14-$H_a$), 1.79 (1H, m, 14-$H_b$), 1.00 (3H, s, 16-H), 1.03 (3H, s, 17-H), 1.77 (3H, s, 18-H), 1.50 (3H, s, 19-H), 3.99 (1H, d, J=9.0 Hz, 20-$H_a$), 4.02 (1H, d, J=9.0 Hz, 20-$H_b$), 2.24 (3H, s, 4-OCOCH$_3$), 2.11 (3H, s, 10-OCOCH$_3$), 5.34 (1H, d, J=9.0 Hz, 2'-H), 5.54 (1H, t, J=9.0 Hz, 3'-H), 9.21 (1H, d, J=9.0 Hz, 3'-NH), 7.48 (2H, m, ph-o-H), 7.46 (2H, m, ph-m-H), 7.55 (1H, t, J=7.2 Hz, ph-p-H), 7.83 (2H, m, NBz-o-H), 7.44 (2H, m, NBz-m-H), 7.19 (1H, m, NBz-p-H), 7.98 (2H, d, J=7.2 Hz, OBz-o-H), 7.66 (2H, t, J=7.2 Hz, OBz-m-H), 7.74 (1H, t, J=7.2 Hz, OBz-p-H), 2.61 (2H, m, 22-H), 2.36 (2H, t, J=7.2 Hz, 23-H), 7.82 (1H, m, 25-H), 2.90 (1H, m, 26-$H_a$), 3.00 (1H, m, 26-$H_b$), 1.22 (2H, m, 27-H), 1.32 (2H, m, 28-H), 1.45 (1H, m, 29-$H_a$), 1.63 (1H, m, 29-$H_b$), 4.11 (1H, m, 30-H), 6.96 (1H, s, 32-$H_a$), 7.30 (1H, s, 32-$H_b$), 7.87 (1H, m, 33-H), 2.16 (2H, t, J=7.2 Hz, 35-H), 1.71 (1H, m, 36-$H_a$), 1.99 (1H, m, 36-$H_b$), 4.13 (1H, m, 37-H), 7.10 (1H, s, 39-$H_a$), 7.30 (1H, s, 39-$H_b$), 8.21 (1H, d, J=8.4 Hz, 40-H), 4.40 (1H, t, J=7.2 Hz, 42-H), 1.28 (3H, d, J=6.6 Hz, 43-H), 8.37 (1H, d, J=7.2 Hz, 44-H), 6.76 (1H, d, J=15.6 Hz, 46-H), 7.41 (1H, d, J=15.6 Hz, 47-H), 7.58 (2H, d, J=9.0 Hz, 49 and 53-H), 7.49 (2H, d, J=9.0 Hz, 50 and 52-H).

$^{13}$C-NMR (150 MHz, DMSO-$d_6$): 76.7 (1-C), 74.5 (2-C), 46.1 (3-C), 80.2 (4-C), 83.6 (5-C), 36.5 (6-C), 70.4 (7-C), 57.4 (8-C), 202.4 (9-C), 74.7 (10-C), 133.3 (11-C), 139.2 (12-C), 70.7 (13-C), 34.7 (14-C), 42.9 (15-C), 26.3 (16-C), 21.4 (17-C), 13.9 (18-C), 9.8 (19-C), 75.3 (20-C), 165.2 (2-OCO), 169.6, 22.5 (4-OCOCH$_3$), 168.8, 20.6 (10-OCOCH$_3$), 169.1 (1'-C), 74.4 (2'-C), 54.0 (3'-C), 166.4 (3'-NHCO), 137.3 (ph-q-C), 127.7 (ph-o-C), 128.3 (ph-m-C), 131.5 (ph-p-C), 129.9 (NBz-q-C), 127.4 (NBz-o-C), 129.0 (NBz-m-C), 128.2 (NBz-p-C), 134.3 (OBz-q-C), 129.6 (OBz-o-C), 128.7 (OBz-m-C), 133.5 (OBz-p-C), 172.0 (21-C), 28.8 (22-C), 29.5 (23-C), 170.0 (24-C), 38.5 (26-C), 28.5 (27-C), 22.9 (28-C), 31.6 (29-C), 52.3 (30-C), 173.9 (31-C), 171.5 (34-C), 31.7 (35-C), 27.7 (36-C), 52.1 (37-C), 173.3 (38-C), 172.3 (41-C), 48.8 (42-C), 18.1 (43-C), 164.7 (45-C), 122.7 (46-C), 137.6 (47-C), 133.8 (48-C), 129.0 (49 and 53-C), 129.2 (50 and 52-C), 133.9 (51-C).

IR: 3316.9 ($\nu_{OH}$ and $\nu_{NH}$), 3066.0 ($\nu_{=CH}$), 2935.0, 2873.1 ($\nu_{-CH}$), 1736.0, 1655.0 ($\nu_{C=O}$), 1537.3, 1492.9 ($\nu_{C=C}$), 1451.7, 1371.8 ($\delta_{-CH}$), 1241.5 ($\nu_{C-O-C}$), 980.2, 906.6, 822.6, 776.2, 708.9 ($\delta_{=CH}$).

ESI-MS: 1444.56 [M+H]$^+$, 1466.46 [M+Na]$^+$.
HR-MS(TOF): 1444.5645 [M+H]$^+$, 1466.5475 [M+Na]$^+$, $C_{74}H_{86}ClN_7O_{21}$.

Example 24

Liquid-Phase Synthesis of Conjugate MTC-301

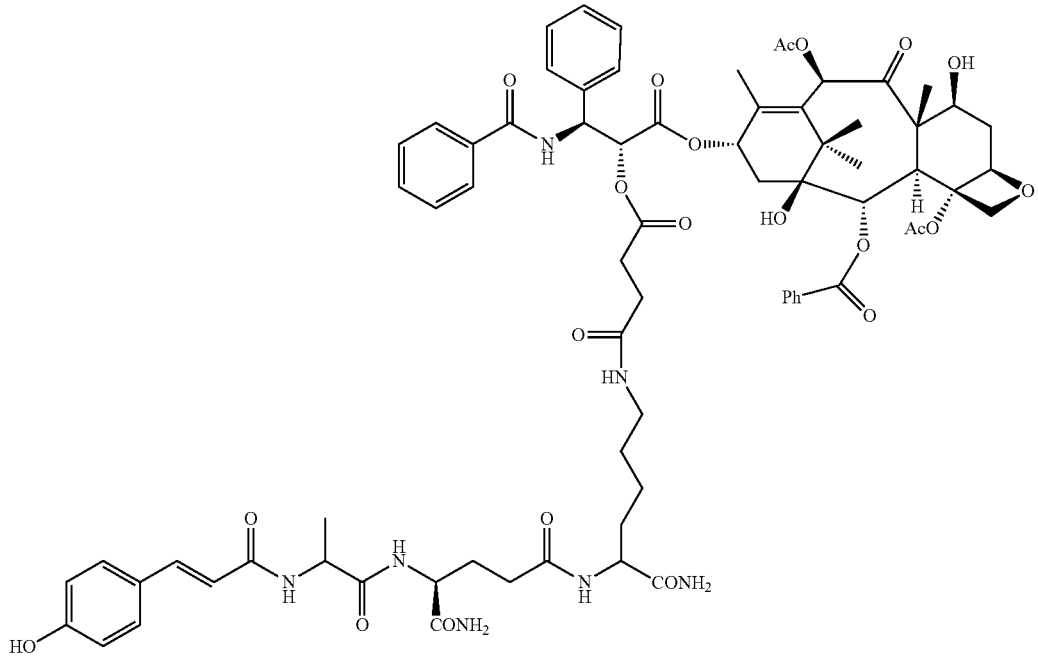

953 mg (1.0 eq) pcatiaxel-2'-O-succinic acid monoester, 115 mg (1.0 eq) HOSu and 192 mg (1.0 eq) EDC.HCl were dissolved in DMSO, and stirred at r.t for 4 hours. 490 mg (1.0 eq) muramyl dipeptide analogue MDA-201 was sparingly added to the mixture in a few portions. The pH of the mixture was adjusted to 7~8 with N-methyl morpholine, and continued to stir for 4 hours. After the completion of the reaction, plenty of water was added to the mixture, and white solid precipitated. The mixture was filtered and the crude product was obtained. The crude product was purified by ODS column chromatography, 11.8 g solid product was obtained through lyophilization. Yield, 83%, m.p.=179~180° C.

$^1$H-NMR (500 MHz, DMSO-$d_6$): 4.62 (1H, br.s, 1-OH), 5.40 (1H, d, J=7.0 Hz, 2-H), 3.56 (1H, d, J=7.0 Hz, 3-H), 4.89 (1H, m, 5-H), 1.62 (1H, m, 6-$H_a$), 2.31 (1H, m, 6-$H_b$), 4.12 (1H, m, 7-H), 4.92 (1H, m, 7-OH), 6.28 (1H, s, 10-H), 5.81 (1H, t, J=7.5 Hz, 13-H), 1.46 (1H, m, 14-$H_a$), 1.75 (1H, m, 14-$H_b$), 1.01 (3H, s, 16-H), 1.04 (3H, s, 17-H), 1.78 (3H, s, 18-H), 1.48 (3H, s, 19-H), 3.99 (1H, d, J=8.5 Hz, 20-$H_a$), 4.00 (1H, d, J=8.5 Hz, 20-$H_b$), 2.23 (3H, s, 4-OCOCH$_3$), 2.10 (3H, s, 10-OCOCH$_3$), 5.33 (1H, d, J=9.0 Hz, 2'-H), 5.52 (1H, t, J=9.0 Hz, 3'-H), 9.21 (1H, d, J=8.5 Hz, 3'-NH), 7.48 (2H, d, J=7.5 Hz, ph-o-H), 7.47 (2H, d, J=7.5 Hz, ph-m-H), 7.55 (1H, t, J=7.5 Hz, ph-p-H), 7.83 (2H, m, NBz-o-H), 7.43 (2H, m, NBz-m-H), 7.17 (1H, m, NBz-p-H), 7.98 (2H, d, J=7.5 Hz, OBz-o-H), 7.65 (2H, t, J=8.0 Hz, OBz-m-H), 7.74 (1H, t, J=7.5 Hz, OBz-p-H), 2.72 (2H, m, 22-H), 2.35 (2H, t, J=7.0 Hz, 23-H), 7.82 (1H, m, 25-H), 2.96 (1H, m, 26-$H_a$), 3.00 (1H, m, 26-$H_b$), 1.22 (2H, m, 27-H), 1.32 (2H, m, 28-H), 1.45 (1H, m, 29-$H_a$), 1.62 (1H, m, 29-$H_b$), 4.10 (1H, m, 30-H), 6.96 (1H, s, 32-$H_a$), 7.30 (1H, m, 32-$H_b$), 7.86 (1H, m, 33-H), 2.14 (2H, t, J=8.0 Hz, 35-H), 1.75 (1H, m, 36-$H_a$), 1.99 (1H, m, 36-$H_b$), 4.11 (1H, m, 37-H), 7.10 (1H, s, 39-$H_a$), 7.30 (1H, m, 39-$H_b$), 8.19 (1H, d, J=8.0 Hz, 40-H), 4.36 (1H, m, 42-H), 1.25 (3H, d, J=7.0 Hz, 43-H), 8.22 (1H, d, J=6.5 Hz, 44-H), 6.51 (1H, d, J=15.5 Hz, 46-H), 7.32 (1H, d, J=15.5 Hz, 47-H), 7.46 (2H, d, J=8.5 Hz, 49 and 53-H), 6.78 (2H, d, J=8.5 Hz, 50 and 52-H), 9.85 (1H, s, 51-OH).

$^{13}$C-NMR (125 MHz, DMSO-$d_6$): 76.7 (1-C), 74.5 (2-C), 46.1 (3-C), 80.3 (4-C), 83.6 (5-C), 36.5 (6-C), 70.4 (7-C), 57.4 (8-C), 202.4 (9-C), 74.7 (10-C), 133.3 (11-C), 139.2 (12-C), 70.4 (13-C), 34.7 (14-C), 42.9 (15-C), 26.3 (16-C), 21.4 (17-C), 13.9 (18-C), 9.8 (19-C), 75.3 (20-C), 165.2 (2-OCO), 169.6, 22.6 (4-OCOCH$_3$), 168.8, 20.7 (10-OCOCH$_3$), 169.2 (1'-C), 74.4 (2'-C), 54.0 (3'-C), 166.4 (3'-NHCO), 137.4 (ph-q-C), 127.7 (ph-o-C), 128.3 (ph-m-C), 131.5 (ph-p-C), 129.9 (NBz-q-C), 127.5 (NBz-o-C), 129.0 (NBz-m-C), 128.2 (NBz-p-C), 134.3 (OBz-q-C), 129.6 (OBz-o-C), 128.7 (OBz-m-C), 133.5 (OBz-p-C), 172.0 (21-C), 28.8 (22-C), 29.5 (23-C), 170.0 (24-C), 38.5 (26-C), 28.5 (27-C), 22.9 (28-C), 31.6 (29-C), 52.4 (30-C), 173.9 (31-C), 171.6 (34-C), 31.8 (35-C), 27.7 (36-C), 52.1 (37-C), 173.3 (38-C), 172.3 (41-C), 48.8 (42-C), 18.0 (43-C), 164.7 (45-C), 118.2 (46-C), 137.4 (47-C), 125.8 (48-C), 127.5 (49 and 53-C), 115.8 (50 and 52-C), 158.9 (51-C).

IR: 3324.4 ($v_{OH}$ and $v_{NH}$), 3075.1 ($v_{=CH}$), 1740.6, 1657.2 ($v_{C=O}$), 1603.9, 1518.3, 1450.8 ($v_{C=C}$), 1243.4 ($v_{C-O-C}$), 980.6, 710.3 ($\delta_{=CH}$).

ESI-MS: 1426.31 [M+H]$^+$, 1449.03 [M+Na+H]$^{2+}$.

HR-MS(TOF): 1426.5974 [M+H]$^+$, 1448.5786 [M+Na]$^+$, $C_{74}H_{87}N_7O_{22}$.

Example 25

Liquid-Phase Synthesis of Conjugate MTC-302

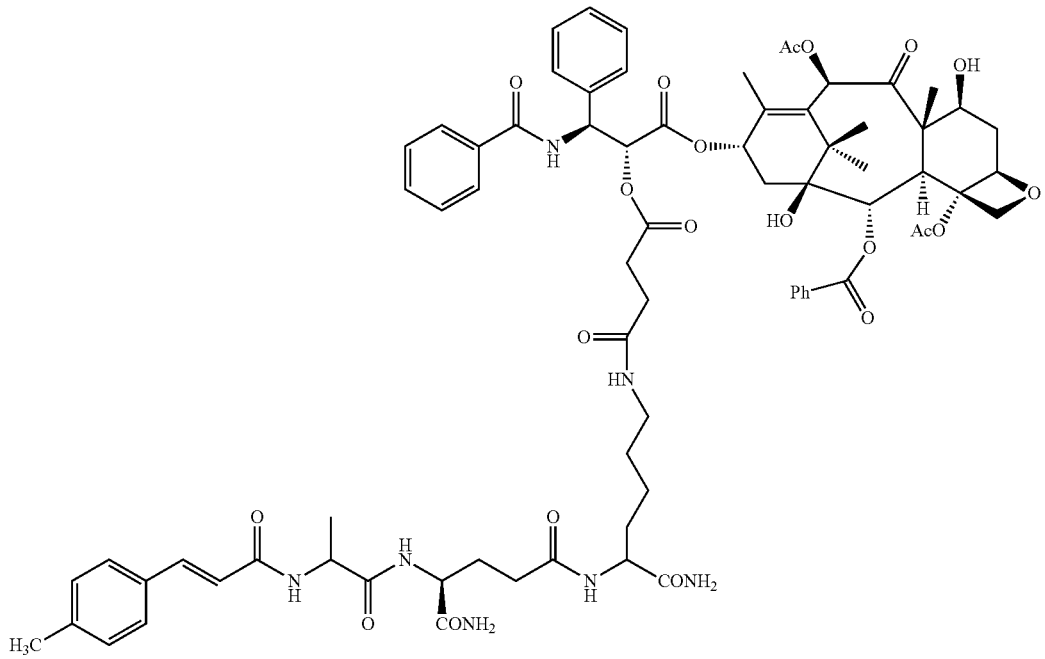

953 mg (1.0 eq) pcatiaxel-2'-O-succinic acid monoester, 115 mg (1.0 eq) HOSu and 192 mg (1.0 eq) EDC.HCl were dissolved in DMSO, and stirred at r.t for 4 hours. 488 mg (1.0 eq) muramyl dipeptide analogue MDA-202 was sparingly added to the mixture in a few portions. The pH of the mixture was adjusted to 7~8 with N-methyl morpholine, and continued to stir for 4 hours. After the completion of the reaction, plenty of water was added to the mixture, and white solid precipitated. The mixture was filtered and the crude product was obtained. The crude product was purified by ODS column chromatography, 1.09 g solid product was obtained through lyophilization. Yield, 77%, m.p.=172~174° C.

$^1$H-NMR (500 MHz, DMSO-$d_6$): 4.63 (1H, br.s, 1-OH), 5.40 (1H, d, J=7.0 Hz, 2-H), 3.56 (1H, d, J=7.0 Hz, 3-H), 4.89 (1H, m, 5-H), 1.62 (1H, m, 6-$H_a$), 2.31 (1H, m, 6-$H_b$), 4.12 (1H, m, 7-H), 4.91 (1H, m, 7-OH), 6.28 (1H, s, 10-H), 5.81 (1H, t, J=9.5 Hz, 13-H), 1.46 (1H, m, 14-$H_a$), 1.79 (1H, m, 14-$H_b$), 0.98 (3H, s, 16-H), 1.01 (3H, s, 17-H), 1.75 (3H, s, 18-H), 1.48 (3H, s, 19-H), 3.99 (1H, d, J=8.0 Hz, 20-$H_a$), 4.01

(1H, d, J=8.0 Hz, 20-H$_b$), 2.23 (3H, s, 4-OCOCH$_3$), 2.09 (3H, s, 10-OCOCH$_3$), 5.34 (1H, d, J=9.0 Hz, 2'-H), 5.52 (1H, t, J=9.0 Hz, 3'-H), 9.21 (1H, d, J=8.5 Hz, 3'-NH), 7.49 (2H, m, ph-o-H), 7.48 (2H, m, ph-m-H), 7.55 (1H, d, J=7.5 Hz, ph-p-H), 7.85 (2H, m, NBz-o-H), 7.46 (2H, m, NBz-m-H), 7.18 (1H, m, NBz-p-H), 7.97 (2H, d, J=8.0 Hz, OBz-o-H), 7.65 (2H, d, J=7.5 Hz, OBz-m-H), 7.72 (1H, d, J=7.0 Hz, OBz-p-H), 2.60 (2H, m, 22-H), 2.36 (2H, m, 23-H), 7.84 (1H, m, 25-H), 2.91 (1H, m, 26-H$_a$), 2.96 (1H, m, 26-H$_b$), 1.22 (2H, m, 27-H), 1.32 (2H, m, 28-H), 1.44 (1H, m, 29-H$_a$), 1.62 (1H, m, 29-H$_b$), 4.11 (1H, m, 30-H$_a$), 6.96 (1H, s, 32-H$_b$), 7.30 (1H, m, 32-H$_b$), 7.86 (1H, m, 33-H), 2.16 (2H, m, 35-H), 1.75 (1H, m, 36-H$_a$), 1.99 (1H, m, 36-H$_b$), 4.12 (1H, m, 37-H), 7.10 (1H, s, 39-H$_a$), 7.22 (1H, m, 39-H$_b$), 8.21 (1H, d, J=8.0 Hz, 40-H), 4.37 (1H, m, 42-H), 1.28 (3H, d, J=7.0 Hz, 43-H), 8.31 (1H, d, J=6.5 Hz, 44-H), 6.68 (1H, d, J=15.5 Hz, 46-H), 7.43 (1H, dc J=16.0 Hz, 47-H), 7.57 (1H, m, 49 and 53-H), 7.49 (1H, m, 50 and 52-H), 2.31 (3H, m, 51-CH$_3$).

$^{13}$C-NMR (125 MHz, DMSO-d$_6$): 76.7 (1-C), 74.5 (2-C), 46.1 (3-C), 80.2 (4-C), 83.6 (5-C), 36.5 (6-C), 70.4 (7-C), 57.4 (8-C), 202.4 (9-C), 74.7 (10-C), 133.3 (11-C), 139.4 (12-C), 70.7 (13-C), 34.7 (14-C), 42.9 (15-C), 26.3 (16-C), 21.4 (17-C), 13.9 (18-C), 9.8 (19-C), 75.3 (20-C), 165.2 (2-OCO), 169.7, 22.6 (4-OCOCH$_3$), 168.8, 20.7 (10-OCOCH$_3$), 169.1 (1'-C), 74.6 (2'-C), 54.0 (3'-C), 166.4 (3'-NHCO), 137.4 (ph-q-C), 127.7 (ph-o-C), 128.3 (ph-m-C), 131.5 (ph-p-C), 129.9 (NBz-q-C), 127.5 (NBz-o-C), 129.0 (NBz-m-C), 128.3 (NBz-p-C), 134.3 (OBz-q-C), 129.6 (OBz-o-C), 128.7 (OBz-m-C), 133.5 (OBz-p-C), 172.0 (21-C), 28.8 (22-C), 29.5 (23-C), 170.0 (24-C), 38.5 (26-C), 28.7 (27-C), 23.0 (28-C), 31.6 (29-C), 52.3 (30-C), 173.9 (31-C), 171.5 (34-C), 31.7 (35-C), 27.7 (36-C), 52.1 (37-C), 173.3 (38-C), 172.4 (41-C), 48.8 (42-C), 18.1 (43-C), 165.1 (45-C), 120.8 (46-C), 137.4 (47-C), 132.1 (48-C), 129.6 (49 and 53-C), 128.7 (50 and 52-C), 138.9 (51-C), 20.9 (51-CH$_3$).

IR: 3324.5 ($\nu_{OH}$ and $\nu_{NH}$), 3066.3 ($\nu_{=CH}$), 2938.3 ($\nu_{—CH}$), 1740.3, 1724.1, 1657.2 ($\nu_{C=O}$), 1603.9, 1535.1, 1451.8 ($\nu_{C=C}$), 1242.8 ($\nu_{C—O—C}$), 981.3, 709.7 ($\delta_{=CH}$).

ESI-MS: 1424.33 [M+H]$^+$, 1446.55 [M+Na]$^+$.

HR-MS(TOF): 1424.6184 [M+H]$^+$, 1446.5996 [M+Na]$^+$, C$_{75}$H$_{89}$N$_7$O$_{21}$.

Example 26

Liquid-Phase Synthesis of Conjugate MTC-303

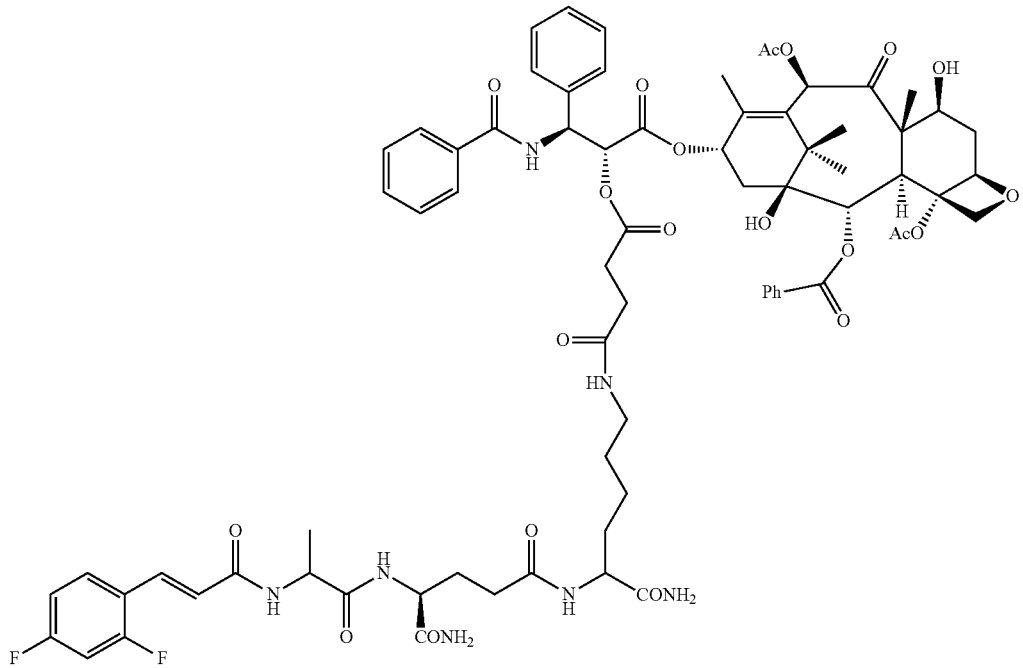

953 mg (1.0 eq) pcatiaxel-2'-O-succinic acid monoester, 115 mg (1.0 eq) HOSu and 192 mg (1.0 eq) EDC.HCl were dissolved in DMSO, and stirred at r.t for 4 hours. 510 mg (1.0 eq) muramyl dipeptide analogue MDA-203 was sparingly added to the mixture in a few portions. The pH of the mixture was adjusted to 7~8 with N-methyl morpholine, and continued to stir for 4 hours. After the completion of the reaction, plenty of water was added to the mixture, and white solid precipitated. The mixture was filtered and the crude product was obtained. The crude product was purified by ODS column chromatography, 1.29 g solid product was obtained through lyophilization. Yield, 89%, m.p.=178~180° C.

$^1$H-NMR (500 MHz, DMSO-d$_6$): 4.62 (1H, br.s, 1-OH), 5.40 (1H, d, J=7.0 Hz, 2-H), 3.56 (1H, d, J=7.0 Hz, 3-H), 4.91 (1H, m, 5-H), 1.62 (1H, m, 6-H$_a$), 2.31 (1H, m, 6-H$_b$), 4.13 (1H, m, 7-H), 4.92 (1H, m, 7-OH), 6.28 (1H, s, 10-H), 5.80 (1H, t, J=7.5 Hz, 13-H), 1.45 (1H, m, 14-H$_a$), 1.77 (1H, m, 14-H$_b$), 0.98 (3H, s, 16-H), 1.01 (3H, s, 17-H), 1.75 (3H, s, 18-H), 1.48 (3H, s, 19-H), 3.98 (1H, d, J=8.0 Hz, 20-H$_a$), 4.00 (1H, d, J=8.0 Hz, 20-H$_b$), 2.23 (3H, s, 4-OCOCH$_3$), 2.10 (3H, s, 10-OCOCH$_3$), 5.33 (1H, d, J=9.0 Hz, 2'-H), 5.52 (1H, t, J=9.0 Hz, 3'-H), 9.21 (1H, d, J=8.5 Hz, 3'-NH), 7.48 (2H, m, ph-o-H), 7.46 (2H, m, ph-m-H), 7.55 (1H, t, J=7.5 Hz, ph-p-H), 7.82 (2H, m, NBz-o-H), 7.44 (2H, m, NBz-m-H), 7.18 (1H, m, NBz-p-H), 7.97 (2H, d, J=7.5 Hz, OBz-o-H), 7.67 (2H, m, OBz-m-H), 7.72 (1H, d, J=8.0 Hz, OBz-p-H), 2.60 (2H, m, 22-H), 2.36 (2H, m, 23-H), 7.82 (1H, m, 25-H), 2.90 (1H, m, 26-H$_a$), 2.96 (1H, m, 26-H$_b$), 1.22 (2H, m, 27-H), 1.32 (2H, m, 28-H), 1.45 (1H, m, 29-H$_a$), 1.62 (1H, m,

29-H$_b$), 4.11 (1H, m, 30-H), 7.06 (1H, s, 32-H$_a$), 7.29 (1H, m, 32-H$_b$), 7.87 (1H, m, 33-H), 2.14 (2H, m, 35-H), 1.75 (1H, m, 36-H$_a$), 2.06 (1H, m, 36-H$_b$), 4.13 (1H, m, 37-H), 7.11 (1H, s, 39-H$_a$), 7.29 (1H, m, 39-H$_b$), 8.23 (1H, d, J=8.5 Hz, 40-H), 4.40 (1H, m, 42-H), 1.27 (3H, m, 43-H), 8.47 (1H, d, J=6.5 Hz, 44-H), 6.89 (1H, d, J=17.0 Hz, 46-H), 7.41 (1H, d, J=16.0 Hz, 47-H), 7.34 (1H, td, J=11.5 and 2.0 Hz, 50-H), 7.17 (1H, m, 52-H), 7.74 (1H, m, 53-H).

$^{13}$C-NMR (125 MHz, DMSO-d$_6$): 76.7 (1-C), 74.5 (2-C), 46.1 (3-C), 80.2 (4-C), 83.6 (5-C), 36.5 (6-C), 70.4 (7-C), 57.4 (8-C), 202.4 (9-C), 74.7 (10-C), 133.3 (11-C), 139.6 (12-C), 70.7 (13-C), 34.7 (14-C), 42.9 (15-C), 26.3 (16-C), 21.4 (17-C), 13.9 (18-C), 9.8 (19-C), 75.3 (20-C), 165.2 (2-OCO), 169.7, 22.6 (4-OCOCH$_3$), 168.8, 20.7 (10-OCOCH$_3$), 169.1 (1'-C), 74.6 (2'-C), 54.0 (3'-C), 166.4 (3'-NHCO), 137.4 (ph-q-C), 127.7 (ph-o-C), 128.3 (ph-m-C), 131.5 (ph-p-C), 129.9 (NBz-q-C), 127.5 (NBz-o-C), 129.0 (NBz-m-C), 128.2 (NBz-p-C), 134.3 (OBz-q-C), 129.6 (OBz-o-C), 128.7 (OBz-m-C), 133.5 (OBz-p-C), 172.0 (21-C), 28.8 (22-C), 29.5 (23-C), 170.0 (24-C), 38.5 (26-C), 28.7 (27-C), 23.0 (28-C), 31.6 (29-C), 52.3 (30-C), 173.9 (31-C), 171.5 (34-C), 31.7 (35-C), 27.7 (36-C), 52.1 (37-C), 173.3 (38-C), 172.3 (41-C), 48.9 (42-C), 18.1 (43-C), 164.6 (45-C), 124.4 (s, 46-C), 137.4 (s, 47-C), 118.5 (m, 48-C), 161.7 (m, 49-C), 104.6 (t, J=26.1 Hz, 50-C), 163.7 (m, 51-C), 112.4 (d, J=19.9 Hz, 52-C), 130.5 (m, 53-C).

IR: 3309.5 ($\nu_{OH}$ and $\nu_{NH}$), 3067.0 ($\nu_{=CH}$), 2945.0 ($\nu_{-CH}$), 1722.0, 1653.8 ($\nu_{C=O}$), 1531.1, 1451.5 ($\nu_{C=C}$), 1239.9 ($\nu_{C-O-C}$), 977.1, 708.3 ($\delta_{=CH}$).

ESI-MS: 1446.03[M+H]$^+$, 1468.26 [M+Na]$^+$.
HR-MS(TOF): 1446.5877 [M+H]$^+$, 1468.5646 [M+Na]$^+$, C$_{74}$H$_{85}$F$_2$N$_7$O$_{21}$

Example 27

Liquid-Phase Synthesis of Conjugate MTC-304 dissolved in DMSO, and stirred at r.t for 4 hours. 526 mg (1.0 eq) muramyl dipeptide analogue MDA-204 was sparingly added to the mixture in a few portions. The pH of the mixture was adjusted to 7~8 with N-methyl morpholine, and continued to stir for 4 hours. After the completion of the reaction, plenty of water was added to the mixture, and white solid precipitated. The mixture was filtered and the crude product was obtained. The crude product was purified by ODS column chromatography, 1.26 g solid product was obtained through lypophilization. Yield, 86%, m.p.=179~180° C.

$^1$H-NMR (500 MHz, DMSO-d$_6$): 4.63 (1H, br.s, 1-OH), 5.40 (1H, d, J=7.5 Hz, 2-H), 3.56 (1H, d, J=7.0 Hz, 3-H), 4.91 (1H, m, 5-H), 1.62 (1H, m, 6-H$_a$), 2.31 (1H, m, 6-H$_b$), 4.12 (1H, m, 7-H), 4.91 (1H, m, 7-OH), 6.28 (1H, s, 10-H), 5.80 (1H, t, J=9.0 Hz, 13-H), 1.45 (1H, m, 14-H$_a$), 1.78 (1H, m, 14-H$_b$), 0.98 (3H, s, 16-H), 1.01 (3H, s, 17-H), 1.77 (3H, s, 18-H), 1.48 (3H, s, 19-H), 3.98 (1H, d, J=8.0 Hz, 20-H$_a$), 4.01 (1H, d, J=8.0 Hz, 20-H), 2.23 (3H, s, 4-OCOCH$_3$), 2.10 (3H, s, 10-OCOCH$_3$), 5.33 (1H, d, J=9.0 Hz, 2'-H), 5.52 (1H, t, J=9.0 Hz, 3'-H), 9.21 (1H, d, J=8.5 Hz, 3'-NH), 7.48 (2H, m, ph-o-H), 7.45 (2H, m, ph-m-H), 7.55 (1H, m, ph-p-H), 7.84 (2H, m, NBz-o-H), 7.44 (2H, m, NBz-m-H), 7.16 (1H, m, NBz-p-H), 7.97 (2H, d, J=7.0 Hz, OBz-o-H), 7.66 (2H, m, OBz-m-H), 7.74 (1H, d, J=7.5 Hz, OBz-p-H), 2.61 (2H, m, 22-H), 2.35 (2H, m, 23-H), 7.84 (1H, m, 25-H), 2.91 (1H, m, 26-H$_a$), 2.96 (1H, m, 26-H$_b$), 1.21 (2H, m, 27-H), 1.32 (2H, m, 28-H), 1.45 (1H, m, 29-H$_a$), 1.62 (1H, m, 29-H$_b$), 4.11 (1H, m, 30-H), 6.96 (1H, s, 32-H$_a$), 7.30 (1H, m, 32-H$_b$), 7.87 (1H, m, 33-H), 2.14 (2H, m, 35-H), 1.75 (1H, m, 36-H$_a$), 1.98 (1H, m, 36-H$_b$), 4.13 (1H, m, 37-H), 7.10 (1H, s, 39-H$_a$), 7.30 (1H, m, 39-H$_b$), 8.23 (1H, d, J=8.0 Hz, 40-H), 4.40 (1H, m, 42-H), 1.29 (3H, m 43-H), 8.51 (1H, d, J=6.5 Hz, 44-H), 6.85 (1H, d, J=16.0 Hz, 46-H), 7.43 (1H, d, J=16.0 Hz, 47-H), 7.54 (1H, m, 50-H), 7.35 (1H, dd, J=8.5 and 2.0 Hz, 52-H), 7.71 (1H, m, 53-H).

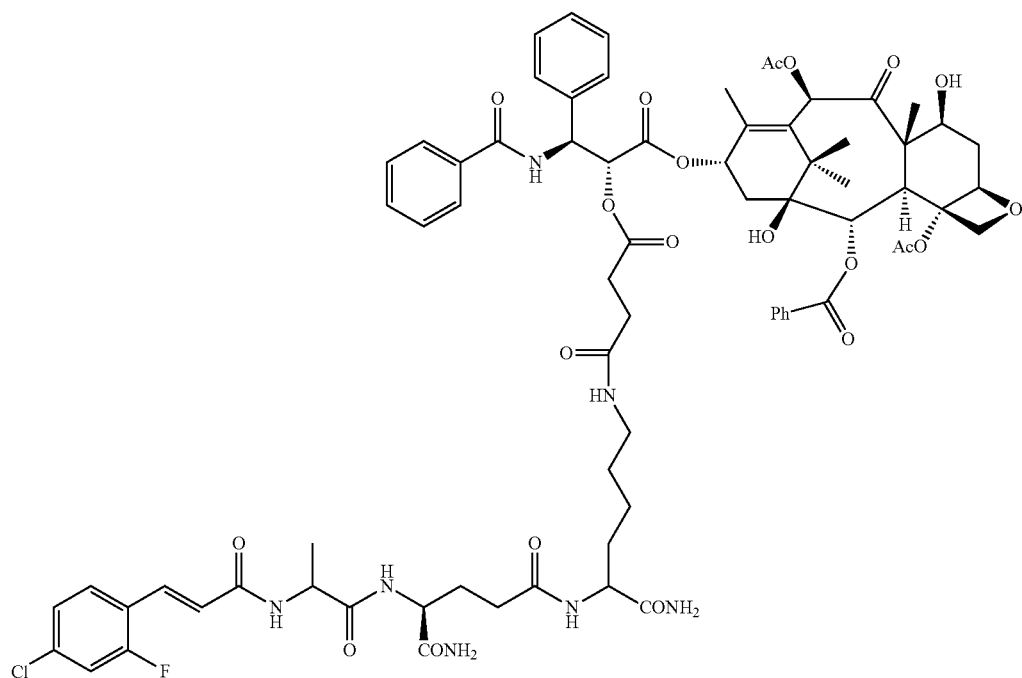

953 mg (1.0 eq) pcatiaxel-2'-O-succinic acid monoester, 115 mg (1.0 eq) HOSu and 192 mg (1.0 eq) EDC.HCl were $^{13}$C-NMR (125 MHz, DMSO-d$_6$): 76.7 (1-C), 74.5 (2-C), 46.1 (3-C), 80.2 (4-C), 83.6 (5-C), 36.5 (6-C), 70.4 (7-C), 57.4 (8-C), 202.3 (9-C), 74.7 (10-C), 133.3 (11-C), 139.4 (12-C), 70.7 (13-C), 34.4 (14-C), 42.9 (15-C), 26.3 (16-C), 21.4 (17-C), 13.9 (18-C), 9.7 (19-C), 75.2 (20-C), 165.2 (2-OCO), 169.6, 22.5 (4-OCOCH$_3$), 168.7, 20.6 (10-OCOCH$_3$), 169.1 (1'-C), 74.7 (2'-C), 54.0 (3'-C), 166.4 (3'-NHCO), 137.3 (ph-q-C), 127.6 (ph-o-C), 128.3 (ph-m-C), 131.4 (ph-p-C), 129.9 (NBz-q-C), 127.4 (NBz-o-C), 129.0 (NBz-m-C), 128.1 (NBz-p-C), 134.2 (OBz-q-C), 129.5 (OBz-o-C), 128.6 (OBz-m-C), 133.5 (OBz-p-C), 172.0 (21-C), 28.8 (22-C), 29.5 (23-C), 170.0 (24-C), 38.5 (26-C), 28.7 (27-C), 22.9 (28-C), 31.6 (29-C), 52.3 (30-C), 173.9 (31-C), 171.5 (34-C), 31.7 (35-C), 27.7 (36-C), 52.1 (37-C), 173.2 (38-C), 172.2 (41-C), 48.9 (42-C), 18.0 (43-C), 164.4 (45-C), 125.3 (m, 46-C), 137.3 (m, 47-C), 122.1 (d. J=11.8 Hz, 48-C), 160.2 (d, J=252.6 Hz, 49-C), 116.7 (d, J=25.5 Hz, 50-C), 134.6 (d, J=10.9 Hz, 51-C), 125.4 (s, 52-C), 130.3 (s, 53-C).

IR: 3324.5 ($v_{OH}$ and $v_{NH}$), 3066.4 ($v_{=CH}$), 2939.7 ($v_{—CH}$), 1739.5, 1724.2, 1657.7 ($v_{C=O}$), 1604.5, 1534.2, 1451.8 ($v_{C=C}$), 1242.6 ($v_{C—O—C}$), 981.6, 708.7 ($\delta_{=CH}$).

ESI-MS: 1462.59 [M+H]$^+$, 1484.93 [M+Na]$^+$.

HR-MS(TOF): 1462.5540 [M+H]$^+$, 1484.5361 [M+Na]$^+$, C$_{74}$H$_{86}$ClFN$_7$O$_{21}$.

Example 28

Liquid-Phase Synthesis of Conjugate MTC-30 umn chromatography, 1.18 g solid product was obtained through lyophilization. Yield, 81%, m.p.=171~172° C.

$^1$H-NMR (500 MHz, DMSO-d$_6$): 4.63 (1H, br.s, 1-OH), 5.40 (1H, d, J=7.0 Hz, 2-H), 3.56 (1H, d, J=7.0 Hz, 3-H), 4.91 (1H, m, 5-H), 1.62 (1H, m, 6-H$_a$), 2.31 (1H, m, 6-H$_b$), 4.12 (1H, m, 7-H), 4.92 (1H, m, 7-OH), 6.28 (1H, s, 10-H), 5.80 (1H, t, J=9.0 Hz, 13-H), 1.46 (1H, m, 14-H$_a$), 1.77 (1H, m, 14-H$_b$), 0.98 (3H, s, 16-H), 1.01 (3H, s, 17-H), 1.75 (3H, s, 18-H), 1.48 (3H, s, 19-H), 3.99 (1H, d, J=8.0 Hz, 20-H$_a$), 4.02 (1H, d, J=8.0 Hz, 20-H$_b$), 2.23 (3H, s, 4-OCOCH$_3$), 2.10 (3H, s, 10-OCOCH$_3$), 5.34 (1H, d, J=9.0 Hz, 2'-H), 5.52 (1H, t, J=9.0 Hz, 3'-H), 9.21 (1H, d, J=8.5 Hz, 3'-NH), 7.48 (2H, m, ph-o-H), 7.47 (2H, m, ph-m-H), 7.55 (1H, m, ph-p-H), 7.84 (2H, m, NBz-o-H), 7.44 (2H, m, NBz-m-H), 7.18 (1H, m, NBz-p-H), 7.97 (2H, d, J=7.5 Hz, OBz-o-H), 7.66 (2H, m OBz-m-H), 7.74 (1H, m, OBz-p-H), 2.58 (2H, m, 22-H), 2.33 (2H, t, J=7.0 Hz, 23-H), 7.82 (1H, m, 25-H), 2.91 (1H, m, 26-H$_a$), 2.96 (1H, m, 26-H$_b$), 1.23 (2H, m, 27-H), 1.33 (2H, m, 28-H), 1.45 (1H, m, 29-H$_a$), 1.62 (1H, m, 29-H$_b$), 4.11 (1H, m, 30-H), 6.96 (1H, s, 32-H$_a$), 7.30 (1H, m, 32-H$_b$), 7.86 (1H, m, 33-H), 2.15 (2H, t, J=8.0 Hz, 35-H), 1.71 (1H, m, 36-H$_a$), 1.99 (1H, m, 36-H$_b$), 4.13 (1H, m, 37-H), 7.12 (1H, s, 39-H$_a$), 7.30 (1H, m, 39-H$_b$), 8.25 (1H, d, J=8.5 Hz, 40-H), 4.41 (1H, m, 42-H), 1.28 (3H, d, J=7.0 Hz, 43-H), 8.45 (1H, d, J=6.5 Hz, 44-H), 6.77 (1H, d, J=16.0 Hz, 46-H), 7.66 (1H, d, J=16.0 Hz, 47-H), 7.54 (1H, m, 50-H), 7.33 (1H, td, J=8.5 and 1.5 Hz, 52-H), 7.76 (1H, m, 53-H).

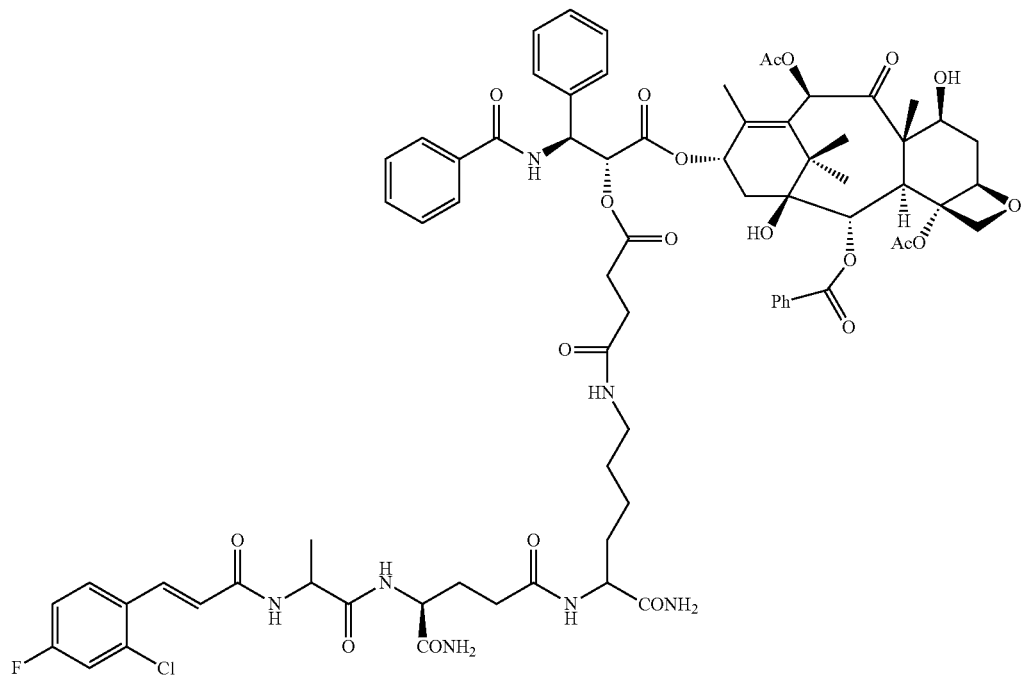

953 mg (1.0 eq) pcatiaxel-2'-O-succinic acid monoester, 115 mg (1.0 eq) HOSu and 192 mg (1.0 eq) EDC.HCl were dissolved in DMSO, and stirred at r.t for 4 hours. 526 mg (1.0 eq) muramyl dipeptide analogue MDA-205 was sparingly added to the mixture in a few portions. The pH of the mixture was adjusted to 7~8 with N-methyl morpholine, and continued to stir for 4 hours. After the completion of the reaction, plenty of water was added to the mixture, and white solid precipitated. The mixture was filtered and the crude product was obtained. The crude product was purified by ODS col- $^{13}$C-NMR (125 MHz, DMSO-d$_6$): 76.7 (1-C), 74.5 (2-C), 46.1 (3-C), 80.2 (4-C), 83.6 (5-C), 36.5 (6-C), 70.4 (7-C), 57.4 (8-C), 202.4 (9-C), 74.7 (10-C), 133.3 (11-C), 139.4 (12-C), 70.7 (13-C), 34.7 (14-C), 42.9 (15-C), 26.3 (16-C), 21.4 (17-C), 13.9 (18-C), 9.8 (19-C), 75.3 (20-C), 165.2 (2-OCO), 169.7, 22.6 (4-OCOCH$_3$), 168.8, 20.7 (10-OCOCH$_3$), 169.1 (1'-C), 74.6 (2'-C), 54.0 (3'-C), 166.4 (3'-NHCO), 137.4 (ph-q-C), 127.7 (ph-o-C), 128.3 (ph-m-C), 131.5 (ph-p-C), 129.9 (NBz-q-C), 127.5 (NBz-o-C), 129.1 (NBz-m-C), 128.3 (NBz-p-C), 134.3 (OBz-q-C), 129.6

(OBz-o-C), 128.7 (OBz-m-C), 133.5 (OBz-p-C), 172.0 (21-C), 28.8 (22-C), 29.5 (23-C), 170.0 (24-C), 38.5 (26-C), 28.7 (27-C), 23.0 (28-C), 31.6 (29-C), 52.3 (30-C), 173.9 (31-C), 171.5 (34-C), 31.7 (35-C), 27.7 (36-C), 52.1 (37-C), 173.2 (38-C), 172.2 (41-C), 48.8 (42-C), 18.2 (43-C), 164.2 (45-C), 124.9 (46-C), 137.4 (47-C), 128.8 (48-C), 134.3 (49-C), 115.4 (d, J=21.5 Hz, 50-C), 162.2 (d, J=249.1 Hz, 51-C), 117.2 (d, J=25.1 Hz, 52-C), 129.9 (53-C).

IR: 3315.4 ($v_{OH}$ and $v_{NH}$), 3069.3 ($v_{=CH}$), 2935.0 ($v_{-CH}$), 1722.8, 1656.5 ($v_{C=O}$), 1601.8, 1534.3, 1451.5 ($v_{C=C}$), 1239.3 ($v_{C-O-C}$), 978.5, 709.7 ($\delta_{=CH}$).

ESI-MS: 1462.89 [M+H]$^+$, 1484.21 [M+Na]$^+$.

HR-MS(TOF): 1462.5541 [M+H]$^+$, 1484.5350 [M+Na]$^+$, $C_{74}H_{85}ClFN_7O_{21}$.

Example 29

Liquid-Phase Synthesis of Conjugate MTC-306

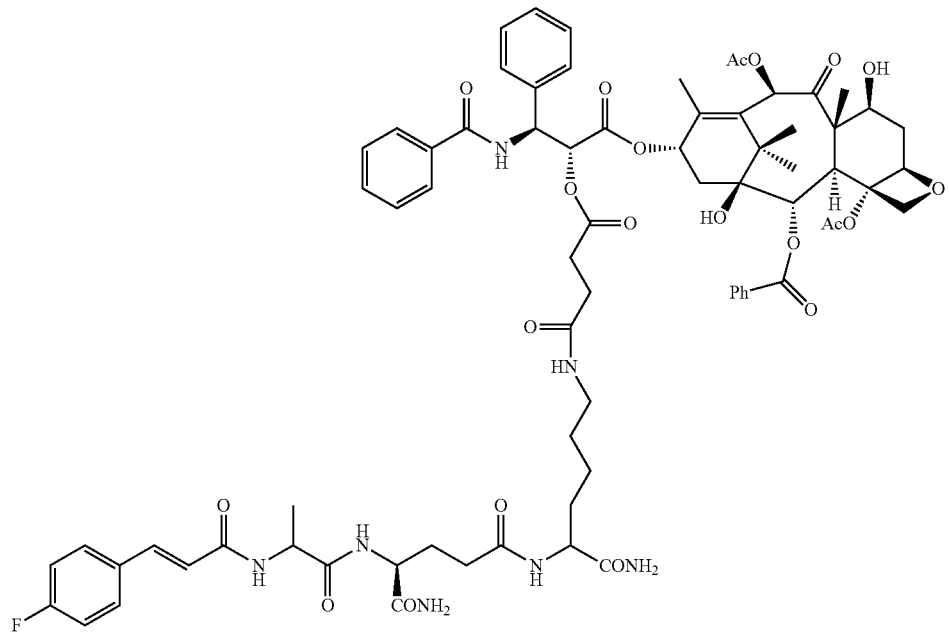

953 mg (1.0 eq) pcatiaxel-2'-O-succinic acid monoester, 115 mg (1.0 eq) HOSu and 192 mg (1.0 eq) EDC.HCl were dissolved in DMSO, and stirred at r.t for 4 hours. 492 mg (1.0 eq) muramyl dipeptide analogue MDA-206 was sparingly added to the mixture in a few portions. The pH of the mixture was adjusted to 7~8 with N-methyl morpholine, and continued to stir for 4 hours. After the completion of the reaction, plenty of water was added to the mixture, and white solid precipitated. The mixture was filtered and the crude product was obtained. The crude product was purified by ODS column chromatography, 1.24 g solid product was obtained through lyophilization. Yield, 87%, m.p.=176~178° C.

$^1$H-NMR (500 MHz, DMSO-$d_6$): 4.61 (1H, br.s, 1-OH), 5.41 (1H, d, J=6.0 Hz, 2-H), 3.56 (1H, d, J=5.5 Hz, 3-H), 4.91 (1H, m, 5-H), 1.62 (1H, m, 6-H$_a$), 2.30 (1H, m, 6-H$_b$), 4.11 (1H, m, 7-H), 4.91 (1H, m, 7-OH), 6.28 (1H, s, 10-H), 5.81 (1H, m, 13-H), 1.49 (1H, m, 14-H$_a$), 1.82 (1H, m, 14-H$_b$), 0.99 (3H, s, 16-H), 1.01 (3H, s, 17-H), 1.76 (3H, s, 18-H), 1.49 (3H, s, 19-H), 3.99 (1H, d, J=5.5 Hz, 20-H$_a$), 4.00 (1H, d, J=5.5 Hz, 20-H$_b$), 2.23 (3H, s, 4-OCOCH$_3$), 2.10 (3H, s, 10-OCOCH$_3$), 5.33 (1H, d, J=8.5 Hz, 2'-H), 5.52 (1H, t, J=8.5 Hz, 3'-H), 9.20 (1H, d, J=8.0 Hz, 3'-NH), 7.48 (2H, m, ph-o-H), 7.46 (2H, m, ph-m-H), 7.52 (1H, m, ph-p-H), 7.84 (2H, m, NBz-o-H), 7.43 (2H, m, NBz-m-H), 7.19 (1H, m, NBz-p-H), 7.98 (2H, d, J=7.5 Hz, OBz-o-H), 7.67 (2H, m, OBz-m-H), 7.72 (1H, m, OBz-p-H), 2.59 (2H, m, 22-H), 2.35 (2H, m, 23-H), 7.81 (1H, m, 25-H), 2.91 (1H, m, 26-H$_a$), 2.96 (1H, m, 26-H$_b$), 1.22 (2H, m, 27-H), 1.32 (2H, m, 28-H), 1.45 (1H, m, 29-H$_a$), 1.62 (1H, m, 29-H$_b$), 4.11 (1H, m, 30-H), 6.94 (1H, s, 32-H$_a$), 7.28 (1H, m, 32-H$_b$), 7.85 (1H, m, 33-H), 2.15 (2H, m, 35-H), 1.76 (1H, m, 36-H$_a$), 1.98 (1H, m, 36-H$_b$), 4.13 (1H, m, 37-H), 7.09 (1H, s, 39-H$_a$), 7.28 (1H, m, 39-H$_b$), 8.20 (1H, d, J=7.5 Hz, 40-H), 4.40 (1H, m, 42-H), 1.26 (3H, m, 43-H), 8.35 (1H, d, J=4.5 Hz, 44-H), 6.79 (1H, d, J=15.5 Hz, 46-H), 7.40 (1H, d, J=15.5 Hz, 47-H), 7.81 (2H, m, 49 an 53-H), 7.39 (2H, m, 50 snd 52-H).

$^{13}$C-NMR (125 MHz, DMSO-$d_6$): 76.7 (1-C), 74.5 (2-C), 46.1 (3-C), 80.2 (4-C), 83.6 (5-C), 36.5 (6-C), 70.4 (7-C), 57.4 (8-C), 202.3 (9-C), 74.7 (10-C), 133.3 (11-C), 139.4 (12-C), 70.7 (13-C), 34.7 (14-C), 42.9 (15-C), 26.3 (16-C), 21.4 (17-C), 13.9 (18-C), 9.7 (19-C), 75.3 (20-C), 165.2 (2-OCO), 169.6, 22.5 (4-OCOCH$_3$), 168.8, 20.6 (10-OCOCH$_3$), 169.1 (1'-C), 74.7 (2'-C), 54.0 (3'-C), 166.4 (3'-NHCO), 137.3 (ph-q-C), 127.6 (ph-o-C), 128.3 (ph-m-C), 131.5 (ph-p-C), 129.9 (NBz-q-C), 127.4 (NBz-o-C), 129.0 (NBz-m-C), 128.3 (NBz-p-C), 134.2 (OBz-q-C), 129.5 (OBz-o-C), 128.6 (OBz-m-C), 133.5 (OBz-p-C), 172.0 (21-C), 28.8 (22-C), 29.5 (23-C), 170.0 (24-C), 38.5 (26-C), 28.7 (27-C), 23.0 (28-C), 31.6 (29-C), 52.3 (30-C), 173.9 (31-C), 171.5 (34-C), 31.7 (35-C), 27.7 (36-C), 52.1 (37-C), 173.2 (38-C), 172.3 (41-C), 48.9 (42-C), 18.1 (43-C), 164.5 (45-C), 123.5 (s, 46-C), 137.4 (s, 47-C), 133.5 (s, 48-C), 130.9 (d, J=8.3 Hz, 49 and 53-C), 116.2 (d. J=21.2 Hz, 50 and 52-C), 162.4 (d, J=242.4 Hz, 51-C).

IR: 3310.1 ($v_{OH}$ and $v_{NH}$), 3063.6 ($v_{=CH}$), 2939.5 ($v_{-CH}$), 1740.5, 1724.1, 1658.2 ($v_{C=O}$), 1582.5, 1536.0, 1450.0 ($v_{C=C}$), 1243.5 ($v_{C-O-C}$), 978.0, 779.7, 709.5 ($\delta_{=CH}$).

ESI-MS: 1429.41 [M+2H]$^{2+}$, 1451.54 [M+Na+H]$^{2+}$.

HR-MS(TOF): 1428.5950 [M+H]$^+$, 1450.5743 [M+Na]$^+$, $C_{74}H_{86}FN_7O_{21}$.

Example 30

Liquid-Phase Synthesis of Conjugate MTC-307

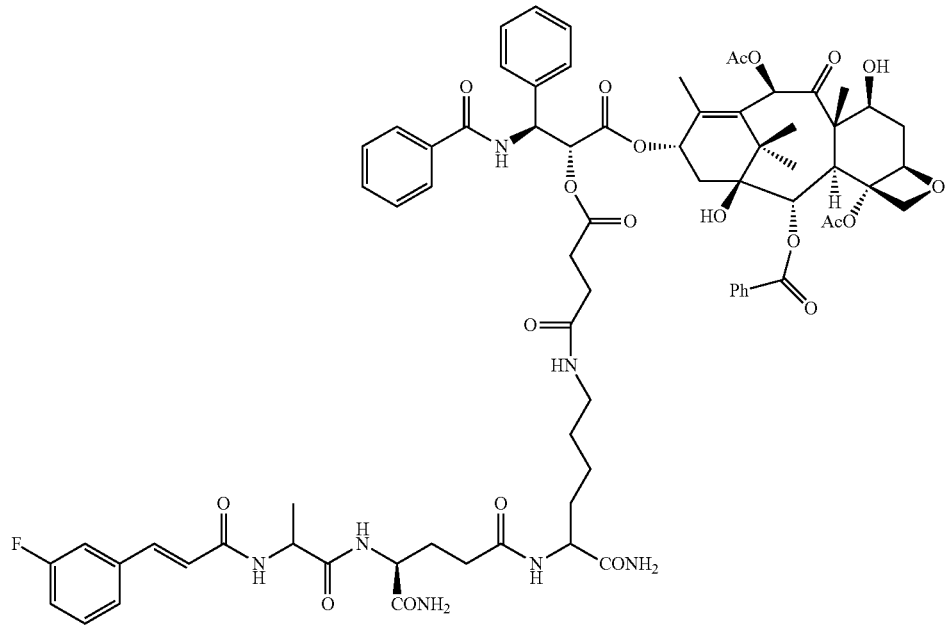

953 mg (1.0 eq) pcatiaxel-2'-O-succinic acid monoester, 115 mg (1.0 eq) HOSu and 192 mg (1.0 eq) EDC.HCl were dissolved in DMSO, and stirred at r.t for 4 hours. 492 mg (1.0 eq) muramyl dipeptide analogue MDA-207 was sparingly added to the mixture in a few portions. The pH of the mixture was adjusted to 7~8 with N-methyl morpholine, and continued to stir for 4 hours. After the completion of the reaction, plenty of water was added to the mixture, and white solid precipitated. The mixture was filtered and the crude product was obtained. The crude product was purified by ODS column chromatography, 1.21 g solid product was obtained through lyophilization. Yield, 85%, m.p.=167~168° C.

$^1$H-NMR (500 MHz, DMSO-$d_6$): 4.63 (1H, br.s, 1-OH), 5.40 (1H, d, J=7.0 Hz, 2-H), 3.56 (1H, d, J=7.0 Hz, 3-H), 4.91 (1H, m, 5-H), 1.62 (1H, m, 6-$H_a$), 2.30 (1H, m, 6-$H_b$), 4.12 (1H, m, 7-H), 4.92 (1H, m, 7-OH), 6.28 (1H, s, 10-H), 5.81 (1H, t, J=7.5 Hz, 13-H), 1.46 (1H, m, 14-$H_a$), 1.78 (1H, m, 14-$H_b$), 0.98 (3H, s, 16-H), 1.01 (3H, s, 17-H), 1.77 (3H, s, 18-H), 1.48 (3H, s, 19-H), 3.98 (1H, d, J=8.5 Hz, 20-$H_a$), 4.01 (1H, d, J=8.5 Hz, 20-$H_b$), 2.23 (3H, s, 4-OCOCH$_3$), 2.09 (3H, s, 10-OCOCH$_3$), 5.32 (1H, d, J=9.0 Hz, 2'-H), 5.52 (1H, t, J=9.0 Hz, 3'-H), 9.21 (1H, d, J=8.5 Hz, 3'-NH), 7.48 (2H, m, ph-o-H), 7.44 (2H, m, ph-m-H), 7.55 (1H, t, J=7.5 Hz, ph-p-H), 7.84 (2H, m, NBz-o-H), 7.43 (2H, m, NBz-m-H), 7.19 (1H, m, NBz-p-H), 7.97 (2H, d, J=7.0 Hz, OBz-o-H), 7.65 (2H, t, J=8.0 Hz, OBz-m-H), 7.72 (1H, t, J=7.5 Hz, OBz-p-H), 2.60 (2H, m, 22-H), 2.35 (2H, t, J=7.0 Hz, 23-H), 7.82 (1H, m, 25-H), 2.90 (1H, m, 26-$H_a$), 3.00 (1H, m, 26-$H_b$), 1.22 (2H, m, 27-H), 1.33 (2H, m, 28-H), 1.46 (1H, m, 29-$H_a$), 1.62 (1H, m, 29-$H_b$), 4.11 (1H, m, 30-H), 6.96 (1H, s, 32-$H_a$), 7.32 (1H, m, 32-$H_b$), 7.87 (1H, m, 33-H), 2.15 (2H, t, J=8.0 Hz, 35-H), 1.71 (1H, m, 36-$H_a$), 1.99 (1H, m, 36-$H_b$), 4.13 (1H, m, 37-H), 7.11 (1H, s, 39-$H_a$), 7.30 (1H, m, 39-$H_b$), 8.22 (1H, d, J=8.0 Hz, 40-H), 4.40 (1H, m, 42-H), 1.26 (3H, d, J=7.0 Hz, 43-H), 8.37 (1H, d, J=6.5 Hz, 44-H), 6.79 (1H, d, J=16.0 Hz, 46-H), 7.49 (1H, d, J=16.0 Hz, 47-H), 7.38 (1H, m, 49-H), 7.22 (1H, m, 51-H), 7.47 (1H, m, 52-H), 7.41 (1H, m, 53-H).

$^{13}$C-NMR (125 MHz, DMSO-$d_6$): 76.7 (1-C), 74.5 (2-C), 46.1 (3-C), 80.2 (4-C), 83.6 (5-C), 36.5 (6-C), 70.4 (7-C), 57.4 (8-C), 202.4 (9-C), 74.7 (10-C), 133.3 (11-C), 139.4 (12-C), 70.7 (13-C), 34.7 (14-C), 42.9 (15-C), 26.3 (16-C), 21.4 (17-C), 13.9 (18-C), 9.8 (19-C), 75.3 (20-C), 165.2 (2-OCO), 169.7, 22.6 (4-OCOCH$_3$), 168.8, 20.6 (10-OCOCH$_3$), 169.1 (1'-C), 74.4 (2'-C), 54.0 (3'-C), 166.4 (3'-NHCO), 137.5 (ph-q-C), 127.7 (ph-o-C), 128.3 (ph-m-C), 131.5 (ph-p-C), 129.9 (NBz-q-C), 127.5 (NBz-o-C), 129.0 (NBz-m-C), 128.2 (NBz-p-C), 134.3 (OBz-q-C), 129.6 (OBz-o-C), 128.7 (OBz-m-C), 133.5 (OBz-p-C), 172.0 (21-C), 28.8 (22-C), 29.5 (23-C), 170.0 (24-C), 38.5 (26-C), 28.5 (27-C), 23.0 (28-C), 31.6 (29-C), 52.3 (30-C), 173.9 (31-C), 171.5 (34-C), 31.7 (35-C), 27.7 (36-C), 52.1 (37-C), 173.3 (38-C), 172.3 (41-C), 48.8 (42-C), 18.1 (43-C), 164.6 (45-C), 123.5 (46-C), 137.5 (47-C), 133.5 (48-C), 113.9 (d, J=21.6 Hz, 49-C), 162.9 (d, J=242.3 Hz, 50-C), 116.7 (d, J=21.0 Hz, 51-C), 130.9 (d, J=8.5 Hz, 52-C), 123.6 (d, J=2.5 Hz, 53-C).

IR: 3320.5 ($\nu_{OH}$ and $\nu_{NH}$), 3063.6 ($\nu_{=CH}$), 2939.0 ($\nu_{-CH}$), 1740.0, 1721.0, 1657.2 ($\nu_{C=O}$), 1582.7, 1536.7, 1450.0 ($\nu_{C=C}$), 1243.6 ($\nu_{C-O-C}$), 979.4, 780.5, 709.5 ($\delta_{=CH}$).

ESI-MS: 1429.41 [M+2H]$^{2+}$, 1451.54 [M+Na+H]$^{2+}$.

HR-MS(TOF): 1428.5950 [M+H]$^+$, 1450.5736 [M+Na]$^+$, $C_{74}H_{86}FN_7O_{21}$.

Example 31

Liquid-Phase Synthesis of Conjugate MTC-308

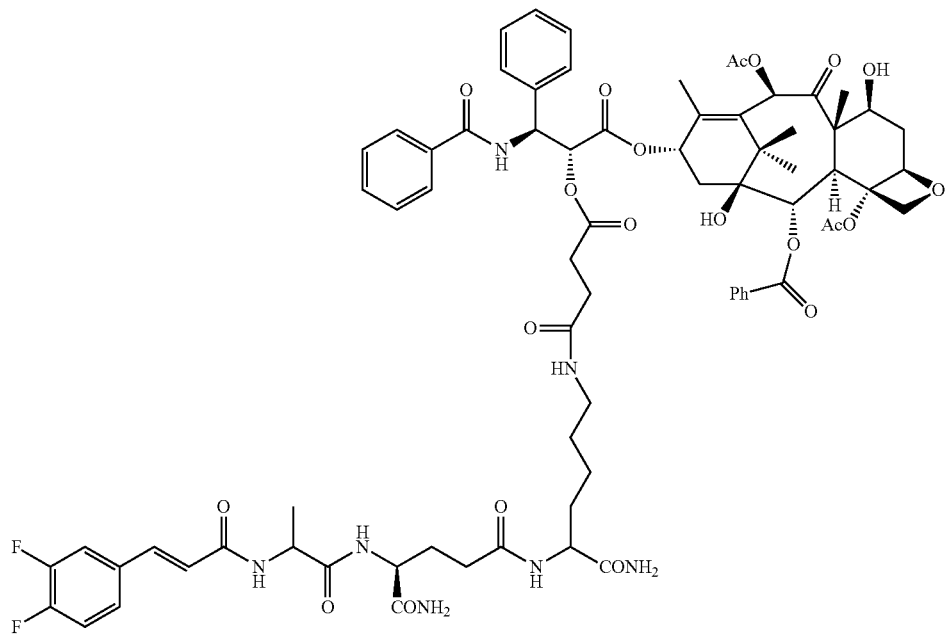

953 mg (1.0 eq) pcatiaxel-2'-O-succinic acid monoester, 115 mg (1.0 eq) HOSu and 192 mg (1.0 eq) EDC-HC were dissolved in DMSO, and stirred at r.t for 4 hours. 510 mg (1.0 eq) muramyl dipeptide analogue MDA-208 was sparingly added to the mixture in a few portions. The pH of the mixture was adjusted to 7~8 with N-methyl morpholine, and continued to stir for 4 hours. After the completion of the reaction, plenty of water was added to the mixture, and white solid precipitated. The mixture was filtered and the crude product was obtained. The crude product was purified by ODS column chromatography, 1.14 g solid product was obtained through lyophilization. Yield, 79%, m.p.=167~168° C.

$^1$H-NMR (500 MHz, DMSO-$d_6$): 4.62 (1H, br.s, 1-OH), 5.40 (1H, d, J=6.5 Hz, 2-H), 3.56 (1H, d, J=7.0 Hz, 3-H), 4.91 (1H, m, 5-H), 1.62 (1H, m, 6-$H_a$), 2.31 (1H, m, 6-$H_b$), 4.12 (1H, m, 7-H), 4.92 (1H, m, 7-OH), 6.27 (1H, s, 10-H), 5.81 (1H, t, J=8.0 Hz, 13-H), 1.48 (1H, m, 14-$H_a$), 1.80 (1H, m, 14-$H_b$), 0.98 (3H, s, 16-H), 1.01 (3H, s, 17-H), 1.75 (3H, s, 18-H), 1.48 (3H, s, 19-H), 3.99 (1H, m, 20-$H_a$), 4.00 (1H, m, 20-$H_b$), 2.22 (3H, s, 4-OCOCH$_3$), 2.13 (3H, s, 10-OCOCH$_3$), 5.32 (1H, d, J=8.5 Hz, 2'-H), 5.51 (1H, t, J=8.5 Hz, 3'-H), 9.21 (1H, d, J=8.5 Hz, 3'-NH), 7.49 (2H, m, ph-o-H), 7.47 (2H, m, ph-m-H), 7.55 (1H, m, ph-p-H), 7.84 (2H, m, NBz-o-H), 7.43 (2H, m, NBz-m-H), 7.17 (1H, m, NBz-p-H), 8.06 (2H, d, J=7.0 Hz, OBz-o-H), 7.67 (2H, m, OBz-m-H), 7.72 (1H, d, J=8.0 Hz, OBz-p-H), 2.59 (2H, m, 22-H), 2.35 (2H, m, 23-H), 7.84 (1H, m, 25-H), 2.90 (1H, m, 26-$H_a$), 3.00 (1H, m, 26-$H_b$), 1.22 (2H, m, 27-H), 1.31 (2H, m, 28-H), 1.48 (1H, m, 29-$H_a$), 1.64 (1H, m, 29-$H_b$), 4.11 (1H, m, 30-H), 6.96 (1H, s, 32-$H_a$), 7.30 (1H, m, 32-$H_b$), 7.87 (1H, m, 33-H), 2.14 (2H, m, 35-H), 1.70 (1H, m, 36-$H_a$), 1.98 (1H, m, 36-$H_b$), 4.13 (1H, m, 37-H), 7.11 (1H, s, 39-$H_a$), 7.30 (1H, m, 39-$H_b$), 8.22 (1H, d, J=8.0 Hz, 40-H), 4.40 (1H, m, 42-H), 1.37 (3H, d, J=7.5 Hz, 43-H), 8.34 (1H, d, J=6.5 Hz, 44-H), 6.73 (1H, d, J=15.5 Hz, 46-H), 7.40 (1H, d, J=15.5 Hz, 47-H), 7.67 (1H, m, 50-H), 7.43 (1H, m, 52-H), 7.48 (1H, m, 53-H).

$^{13}$C-NMR (125 MHz, DMSO-$d_6$): 76.7 (1-C), 74.5 (2-C), 46.1 (3-C), 80.2 (4-C), 83.6 (5-C), 36.5 (6-C), 70.4 (7-C), 57.4 (8-C), 202.4 (9-C), 74.7 (10-C), 133.3 (11-C), 139.5 (12-C), 70.7 (13-C), 34.7 (14-C), 42.9 (15-C), 26.3 (16-C), 21.4 (17-C), 13.9 (18-C), 9.8 (19-C), 75.3 (20-C), 165.2 (2-OCO), 169.7, 22.6 (4-OCOCH$_3$), 168.8, 20.7 (10-OCOCH$_3$), 169.2 (1'-C), 74.6 (2'-C), 54.0 (3'-C), 166.4 (3'-NHCO), 137.4 (ph-q-C), 127.7 (ph-o-C), 128.3 (ph-m-C), 131.5 (ph-p-C), 129.9 (NBz-q-C), 127.5 (NBz-o-C), 129.0 (NBz-m-C), 128.2 (NBz-p-C), 134.3 (OBz-q-C), 129.6 (OBz-o-C), 128.7 (OBz-m-C), 133.5 (OBz-p-C), 172.0 (21-C), 28.8 (22-C), 29.5 (23-C), 170.0 (24-C), 38.5 (26-C), 28.5 (27-C), 23.0 (28-C), 31.6 (29-C), 52.3 (30-C), 173.9 (31-C), 171.5 (34-C), 31.7 (35-C), 27.7 (36-C), 52.1 (37-C), 173.3 (38-C), 172.3 (41-C), 48.8 (42-C), 18.2 (43-C), 164.7 (45-C), 123.3 (s, 46-C), 137.4 (s, 47-C), 133.3 (m, 48-C), 118.6 (m, 49-C), 151.2 (m, 50-C), 149.3 (m, 51-C), 116.7 (m, 52-C), 125.1 (m, 53-C).

IR: 3306.6 ($v_{OH}$ and $v_{NH}$), 3066.4 ($v_{=CH}$), 2932.6 ($v_{-CH}$), 1739.8, 1720.2 1658.2 ($v_{C=O}$), 1535.1, 1518.5, 1450.2 ($v_{C=C}$), 1274.4, 1243.6 ($v_{C-O-C}$), 979.7, 775.8, 709.5 ($\delta_{=CH}$).

ESI-MS: 1446.25 [M+H]$^+$, 1468.77 [M+Na]$^+$.

HR-MS(TOF): 1446.5861 [M+H]$^+$, 1468.5651 [M+Na]$^+$, $C_{74}H_{85}F_2N_7O_{21}$.

Example 32

Liquid-Phase Synthesis of Conjugate MTC-213

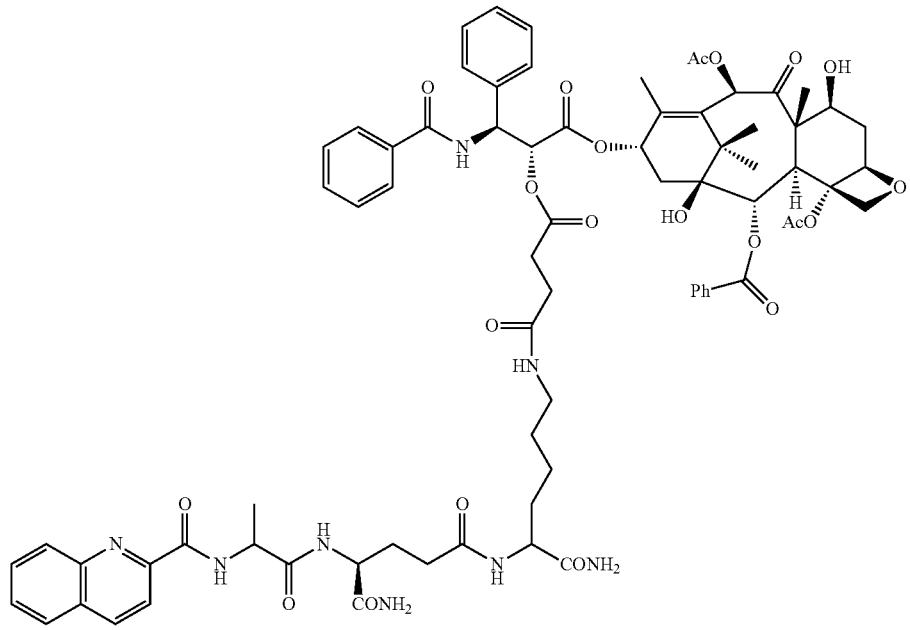

953 mg (1.0 eq) pcatiaxel-2'-O-succinic acid monoester, 115 mg (1.0 eq) HOSu and 192 mg (1.0 eq) EDC.HCl were dissolved in DMSO, and stirred at r.t for 4 hours. 499 mg (1.0 eq) muramyl dipeptide analogue MDA-113 was sparingly added to the mixture in a few portions. The pH of the mixture was adjusted to 7~8 with N-methyl morpholine, and continued to stir for 4 hours. After the completion of the reaction, plenty of water was added to the mixture, and white solid precipitated. The mixture was filtered and the crude product was obtained. The crude product was purified by ODS column chromatography, 1.18 g solid product was obtained through lyophilization. Yield, 82%, m.p.=167~168° C.

$^1$H-NMR (600 MHz, DMSO-d$_6$): 4.64 (1H, br.s, 1-OH), 5.40 (1H, d, J=7.2 Hz, 2-H), 3.56 (1H, d, J=7.2 Hz, 3-H), 4.91 (1H, m, 5-H), 1.62 (1H, m, 6-H$_a$), 2.31 (1H, m, 6-H$_b$), 4.13 (1H, m, 7-H), 4.92 (1H, m, 7-OH), 6.28 (1H, s, 10-H), 5.81 (1H, t, J=9.0 Hz, 13-H), 1.45 (1H, m, 14-H$_a$), 1.79 (1H, m, 14-H$_b$), 0.98 (3H, s, 16-H), 0.99 (3H, s, 17-H), 1.76 (3H, s, 18-H), 1.51 (3H, s, 19-H), 3.98 (1H, d, J=8.4 Hz, 20-H$_a$), 4.01 (1H, d, J=8.4 Hz, 20-H$_b$), 2.22 (3H, s, 4-OCOCH$_3$), 2.09 (3H, s, 10-OCOCH$_3$), 5.34 (1H, d, J=9.0 Hz, 2'-H), 5.52 (1H, t, J=9.0 Hz, 3'-H), 9.20 (1H, d, J=9.0 Hz, 3'-NH), 7.48 (2H, d, J=7.8 Hz, ph-o-H), 7.46 (2H, m, ph-m-H), 7.55 (1H, t, J=7.8 Hz, ph-p-H), 7.82 (2H, m, NBz-o-H), 7.43 (2H, m, NBz-m-H), 7.17 (1H, m, NBz-p-H), 7.97 (2H, d, J=7.8 Hz, OBz-o-H), 7.65 (2H, t, J=7.8 Hz, OBz-m-H), 7.72 (1H, t, J=7.8 Hz, OBz-p-H), 2.61 (2H, m, 22-H), 2.35 (2H, t, J=7.2 Hz, 23-H), 7.82 (1H, m, 25-H), 2.90 (1H, m, 26-H$_a$), 2.98 (1H, m, 26-H$_b$), 1.22 (2H, m, 27-H), 1.32 (2H, m, 28-H), 1.45 (1H, m, 29-H$_a$), 1.64 (1H, m, 29-H$_b$), 4.11 (1H, m, 30-H), 6.96 (1H, s, 32-H$_a$), 7.29 (1H, s, 32-H$_b$), 7.87 (1H, m, 33-H), 2.11 (2H, t, J=7.2 Hz, 35-H), 1.71 (1H, m, 36-H$_a$), 1.99 (1H, m, 36-H$_b$), 4.19 (1H, m, 37-H), 7.09 (1H, s, 39-H$_a$), 7.29 (1H, s, 39-H$_b$), 8.16 (1H, d, J=8.4 Hz, 40-H), 4.62 (1H, m, 42-H), 1.27 (3H, d, J=6.6 Hz, 43-H), 8.37 (1H, d, J=7.8 Hz, 44-H), 8.58 (1H, d, J=8.4 Hz, 47-H), 8.92 (1H, d, J=8.4 Hz, 48-H), 7.88 (1H, m, 50-H), 7.49 (1H, m, 51-H), 7.74 (1H, m, 52-H), 8.08 (1H, d, J=8.4 Hz, 53-H).

$^{13}$C-NMR (150 MHz, DMSO-d$_6$): 76.7 (1-C), 74.6 (2-C), 46.1 (3-C), 80.3 (4-C), 83.6 (5-C), 36.5 (6-C), 70.4 (7-C), 57.4 (8-C), 202.4 (9-C), 74.7 (10-C), 133.3 (11-C), 139.5 (12-C), 70.7 (13-C), 34.4 (14-C), 42.9 (15-C), 26.3 (16-C), 21.4 (17-C), 13.9 (18-C), 9.8 (19-C), 75.3 (20-C), 165.2 (2-OCO), 169.7, 22.6 (4-OCOCH$_3$), 168.8, 20.7 (10-OCOCH$_3$), 169.1 (1'-C), 74.5 (2'-C), 54.0 (3'-C), 166.5 (3'-NHCO), 137.4 (ph-q-C), 127.7 (ph-o-C), 128.3 (ph-m-C), 131.5 (ph-p-C), 129.9 (NBz-q-C), 127.5 (NBz-o-C), 128.9 (NBz-m-C), 128.2 (NBz-p-C), 134.3 (OBz-q-C), 129.6 (OBz-o-C), 128.7 (OBz-m-C), 133.5 (OBz-p-C), 171.9 (21-C), 28.8 (22-C), 29.5 (23-C), 170.0 (24-C), 38.5 (26-C), 28.8 (27-C), 23.0 (28-C), 31.6 (29-C), 52.3 (30-C), 173.9 (31-C), 171.5 (34-C), 31.7 (35-C), 27.8 (36-C), 52.2 (37-C), 173.2 (38-C), 172.0 (41-C), 48.6 (42-C), 19.0 (43-C), 163.3 (45-C), 149.6 (46-C), 118.5 (47-C), 138.0 (48-C), 128.1 (49-C), 128.6 (50-C), 129.2 (51-C), 130.7 (52-C), 130.3 (53-C), 146.0 (54-C).

IR: 3324.9 ($v_{OH}$ and $v_{NH}$), 2938.5 ($v_{-CH}$), 1739.6, 1721.9, 1655.0 (vC=O), 1529.9, 1500.2, 1451.7, 1428.7 (vC=C), 1371.6, 1242.5, 1177.0, 1070.8 ($\delta_{-CH}$), 980.0, 776.8, 708.9 ($\delta_{=CH}$).

ESI-MS: 1436.75 [M+2H]$^{2+}$.

HR-MS(TOF): 1435.6001 [M+H]$^+$, 1457.5774 [M+Na]$^+$, $C_{75}H_{86}N_8O_{21}$.

Example 33

Liquid-Phase Synthesis of Conjugate MTC-219

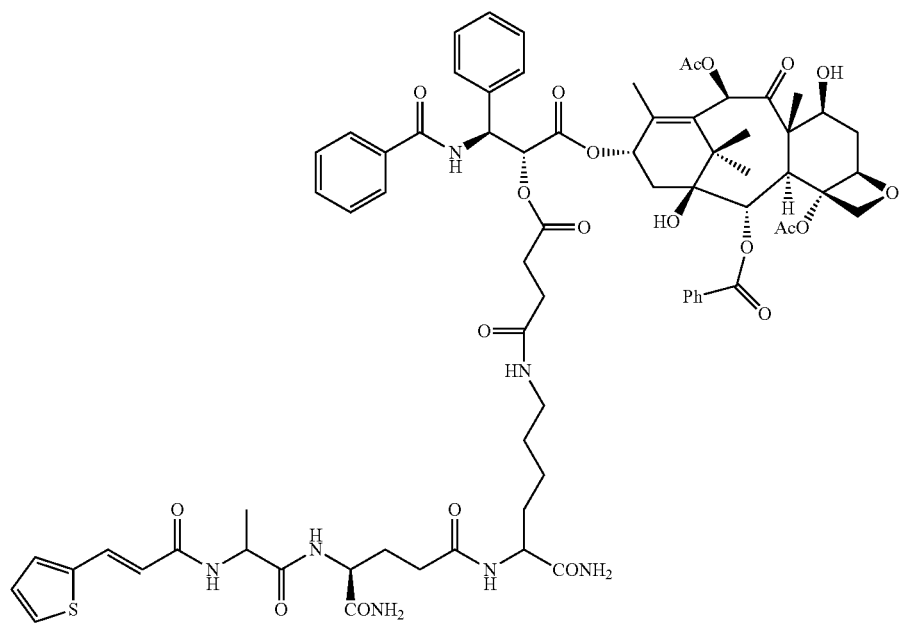

953 mg (1.0 eq) pcatiaxel-2'-O-succinic acid monoester, 115 mg (1.0 eq) HOSu and 192 mg (1.0 eq) EDC.HCl were dissolved in DMSO, and stirred at r.t for 4 hours. 480 mg (1.0 eq) muramyl dipeptide analogue MDA-119 was sparingly added to the mixture in a few portions. The pH of the mixture was adjusted to 7~8 with N-methyl morpholine, and continued to stir for 4 hours. After the completion of the reaction, plenty of water was added to the mixture, and white solid precipitated. The mixture was filtered and the crude product was obtained. The crude product was purified by ODS column chromatography, 1.12 g solid product was obtained through lypophilization. Yield, 79%, m.p.=169~171° C.

$^1$H-NMR (500 MHz, DMSO-$d_6$): 4.61 (1H, br.s, 1-OH), 5.41 (1H, d, J=7.0 Hz, 2-H), 3.56 (1H, d, J=8.5 Hz, 3-H), 4.89 (1H, J=10 Hz 5-H), 1.62 (1H, m, 6-$H_a$), 2.31 (1H, m, 6-$H_b$), 4.09 (1H, m, 7-H), 4.91 (1H, m, 7-OH), 6.28 (1H, s, 10-H), 5.81 (1H, t, J=9.0 Hz, 13-H), 1.44 (1H, m, 14-$H_a$), 1.78 (1H, m, 14-$H_b$), 1.01 (3H, s, 16-H), 0.99 (3H, s, 17-H), 1.76 (3H, s, 18-H), 1.49 (3H, s, 19-H), 3.98 (1H, m, 20-$H_a$), 4.00 (1H, m, 20-$H_b$), 2.22 (3H, s, 4-OCOCH$_3$), 2.09 (3H, s, 10-OCOCH$_3$), 5.32 (1H, d, J=9.0 Hz, 2'-H), 5.52 (1H, t, J=8.5 Hz, 3'-H), 9.19 (1H, d, J=8.5 Hz, 3'-NH), 7.48 (2H, m, ph-o-H), 7.43 (2H, m, ph-m-H), 7.55 (1H, m, ph-p-H), 7.84 (2H, m, NBz-o-H), 7.49 (2H, m, NBz-m-H), 7.18 (1H, m, NBz-p-H), 7.96 (2H, d, J=8.0 Hz, OBz-o-H), 7.65 (2H, m, OBz-m-H), 7.72 (1H, m, OBz-p-H), 2.63 (2H, m, 22-H), 2.35 (2H, m, 23-H), 7.88 (1H, m, 25-H), 2.93 (1H, m, 26-$H_a$), 3.21 (1H, m, 26-$H_b$), 1.23 (2H, m, 27-H), 1.38 (2H, m, 28-H), 1.45 (1H, m, 29-$H_a$), 1.62 (1H, m, 29-$H_b$), 4.10 (1H, m, 30-H), 6.95 (1H, s, 32-$H_a$), 7.29 (1H, s, 32-$H_b$), 7.87 (1H, m, 33-H), 2.26 (2H, m, 35-H), 1.76 (1H, m, 36-$H_a$), 1.95 (1H, m, 36-$H_b$), 4.12 (1H, m, 37-H), 7.03 (1H, s, 39-$H_a$), 7.29 (1H, s, 39-$H_b$), 8.24 (1H, d, J=8.0 Hz, 40-H), 4.37 (1H, m, 42-H), 1.25 (3H, m, 43-H), 8.39 (1H, m, 44-H), 6.97 (1H, d, J=15.0 Hz, 46-H), 7.45 (1H, d, J=15.0 Hz, 47-H), 8.17 (1H, m, 50-H), 7.59 (1H, m, 51-H), 7.72 (1H, m, 52-H).

IR: 3331.9 ($v_{OH}$ and $v_{NH}$), 2963.6, 2936.7 ($v_{-CH}$), 1739.2, 1712.5, 1649.9 ($v_{C=O}$), 1538.4, 1452.3, 1438.2 ($v_{C-C}$), 1370.7, 1243.8, 1172.5, 1144.1 ($\delta_{-CH}$), 980.0, 833.2, 706.6 ($\delta_{=CH}$).

ESI-MS: 1417.21 [M+2H]$^{2+}$.

HR-MS(TOF): 1416.5542 [M+H]$^+$, 1438.5365 [M+Na]$^+$, $C_{72}H_{85}N_7O_{21}S$.

Example 34

Liquid-Phase Synthesis of Conjugate MTC-230

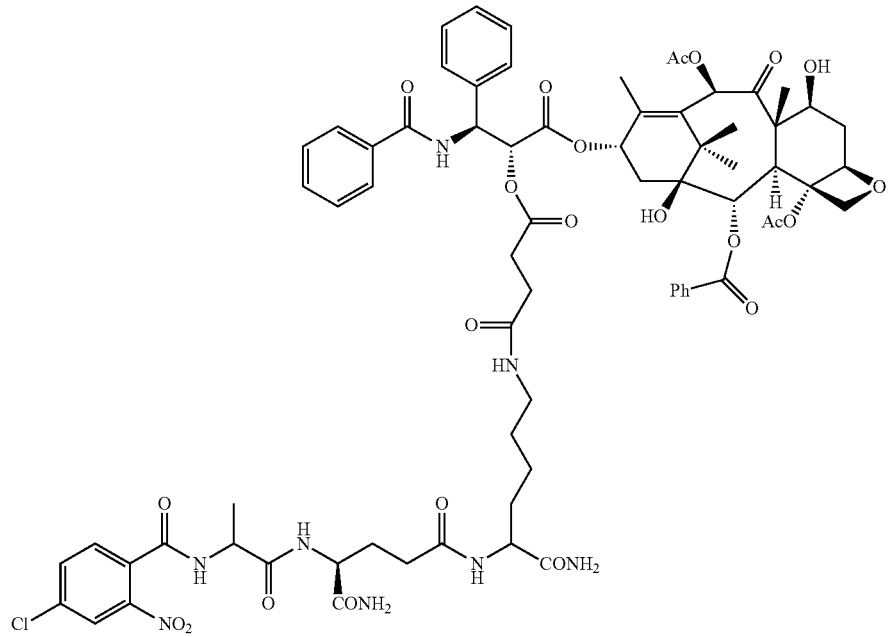

953 mg (1.0 eq) pcatiaxel-2'-O-succinic acid monoester, 115 mg (1.0 eq) HOSu and 192 mg (1.0 eq) EDC.HCl were dissolved in DMSO, and stirred at r.t for 4 hours. 553 mg (1.0 eq) muramyl dipeptide analogue MDA-130 was sparingly added to the mixture in a few portions. The pH of the mixture was adjusted to 7~8 with N-methyl morpholine, and continued to stir for 4 hours. After the completion of the reaction, plenty of water was added to the mixture, and white solid precipitated. The mixture was filtered and the crude product was obtained. The crude product was purified by ODS column chromatography, 1.28 g solid product was obtained through lyophilization. Yield, 86%, m.p.=172~173° C.

$^1$H-NMR (600 MHz, DMSO-d$_6$): 4.62 (1H, br.s, 1-OH), 5.40 (1H, d, J=7.2 Hz, 2-H), 3.56 (1H, d, J=7.2 Hz, 3-H), 4.90 (1H, m, 5-H), 1.62 (1H, m, 6-H$_a$), 2.31 (1H, m, 6-H$_b$), 4.12 (1H, m, 7-H), 4.91 (1H, m, 7-OH), 6.28 (1H, s, 10-H), 5.81 (1H, t, J=9.0 Hz, 13-H), 1.51 (1H, m, 14-H$_a$), 1.79 (1H, m, 14-H$_b$), 0.98 (3H, s, 16-H), 0.99 (3H, s, 17-H), 1.75 (3H, s, 18-H), 1.48 (3H, s, 19-H), 3.98 (1H, d, J=7.8 Hz, 20-H$_a$), 4.00 (1H, d, J=7.8 Hz, 20-H$_b$), 2.23 (3H, s, 4-OCOCH$_3$), 2.09 (3H, s, 10-OCOCH$_3$), 5.33 (1H, d, J=7.8 Hz, 2'-H), 5.52 (1H, t, J=9.0 Hz, 3'-H), 9.20 (1H, d, J=9.0 Hz, 3'-NH), 7.48 (2H, m, ph-o-H), 7.43 (2H, m, ph-m-H), 7.55 (1H, t, J=7.8 Hz, ph-p-H), 7.83 (2H, m, NBz-o-H), 7.42 (2H, m, NBz-m-H), 7.18 (1H, m, NBz-p-H), 7.98 (2H, d, J=7.2 Hz, OBz-o-H), 7.66 (2H, t, J=7.2 Hz, OBz-m-H), 7.72 (1H, t, J=7.2 Hz, OBz-p-H), 2.60 (2H, m, 22-H), 2.35 (2H, m, 23-H), 7.82 (1H, m, 25-H), 2.91 (1H, m, 26-H$_a$), 2.96 (1H, m, 26-H$_b$), 1.22 (2H, m, 27-H), 1.30 (2H, m, 28-H), 1.44 (1H, m, 29-H$_a$), 1.62 (1H, m, 29-H$_b$), 4.11 (1H, m, 30-H), 6.95 (1H, s, 32-H$_a$), 7.29 (1H, s, 32-H$_b$), 7.87 (1H, m, 33-H), 2.17 (2H, t, J=7.8 Hz, 35-H), 1.72 (1H, m, 36-H$_a$), 1.97 (1H, m, 36-H$_b$), 4.12 (1H, m, 37-H), 7.09 (1H, s, 39-H$_a$), 7.29 (1H, s, 39-H$_b$), 8.16 (1H, d, J=7.8 Hz, 40-H), 4.46 (1H, m, 42-H), 1.30 (3H, d, J=6.6 Hz, 43-H), 8.52 (1H, d, J=6.6 Hz, 44-H), 7.70 (1H, m, 47-H), 7.84 (1H, m, 48-H), 8.97 (1H, m, 50-H).

$^{13}$C-NMR (150 MHz, DMSO-d$_6$): 76.7 (1-C), 74.5 (2-C), 46.1 (3-C), 80.2 (4-C), 83.6 (5-C), 36.5 (6-C), 70.4 (7-C), 57.4 (8-C), 202.4 (9-C), 74.7 (10-C), 133.3 (11-C), 139.4 (12-C), 70.7 (13-C), 34.7 (14-C), 42.9 (15-C), 26.3 (16-C), 21.5 (17-C), 13.9 (18-C), 9.8 (19-C), 75.3 (20-C), 165.2 (2-OCO), 169.6, 22.5 (4-OCOCH$_3$), 169.6, 20.6 (10-OCOCH$_3$), 169.1 (1'-C), 74.4 (2'-C), 54.0 (3'-C), 166.4 (3'-NHCO), 137.4 (ph-q-C), 127.7 (ph-o-C), 128.7 (ph-m-C), 131.5 (ph-p-C), 129.9 (NBz-q-C), 127.4 (NBz-o-C), 129.0 (NBz-m-C), 128.3 (NBz-p-C), 134.3 (OBz-q-C), 129.5 (OBz-o-C), 128.6 (OBz-m-C), 133.5 (OBz-p-C), 172.0 (21-C), 28.8 (22-C), 29.5 (23-C), 170.0 (24-C), 38.5 (26-C), 28.7 (27-C), 22.9 (28-C), 31.5 (29-C), 52.4 (30-C), 173.9 (31-C), 171.6 (34-C), 31.7 (35-C), 27.8 (36-C), 52.1 (37-C), 173.1 (38-C), 173.2 (41-C), 48.8 (42-C), 19.7 (43-C), 164.4 (45-C), 131.5 (46-C), 130.6 (47-C), 134.5 (48-C), 147.7 (49-C), 124.0 (50-C), 149.7 (51-C).

IR: 3277.6 ($v_{OH}$ and $v_{NH}$), 3065.0 ($v_{=CH}$), 2973.2, 2936.4 ($v_{—CH}$), 1719.3, 1646.9, 1629.8 ($v_{C=O}$), 1537.1, 1452.0 ($v_{C=C}$), 1350.0, 1240.9, 1151.2 ($\delta_{—CH}$), 978.4, 895.0, 706.3 ($\delta_{=CH}$).

ESI-MS: 1463.70 [M+H]$^+$.

HR-MS(TOF): 1463.5293 [M+H]$^+$, 1485.5120 [M+Na]$^+$, C$_{72}$H$_{83}$ClN$_8$O$_{23}$.

Example 35

Liquid-Phase Synthesis of Conjugate MTC-233

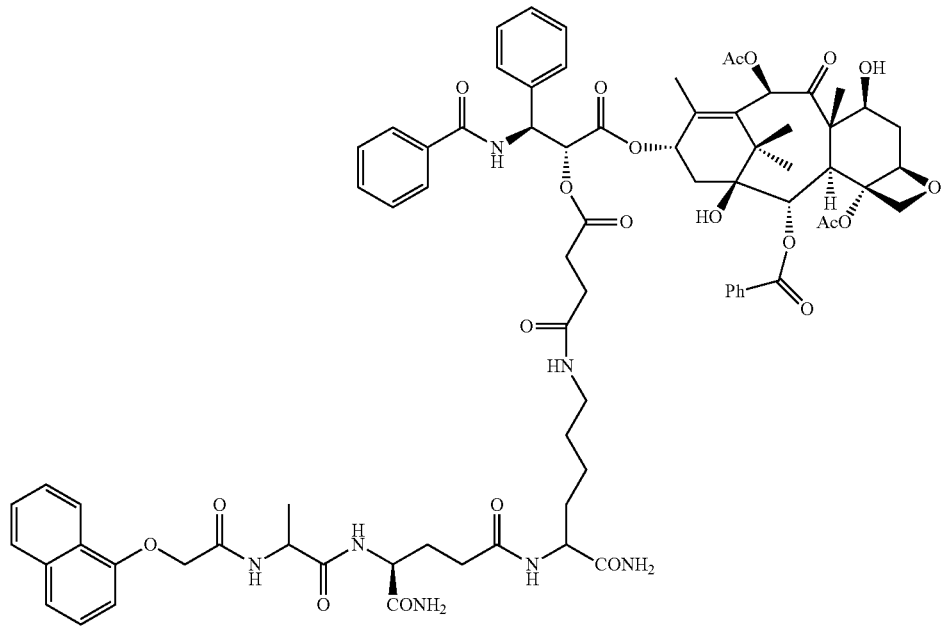

953 mg (1.0 eq) pcatiaxel-2'-O-succinic acid monoester, 115 mg (1.0 eq) HOSu and 192 mg (1.0 eq) EDC.HCl were dissolved in DMSO, and stirred at r.t. for 4 hours. 528 mg (1.0 eq) muramyl dipeptide analogue MDA-133 was sparingly added to the mixture in a few portions. The pH of the mixture was adjusted to 7~8 with N-methyl morpholine, and continued to stir for 4 hours. After the completion of the reaction, plenty of water was added to the mixture, and white solid precipitated. The mixture was filtered and the crude product was obtained. The crude product was purified by ODS column chromatography, 1.17 g solid product was obtained through lypophilization. Yield, 80%, m.p.=155~156° C.

$^1$H-NMR (600 MHz, DMSO-$d_6$): 4.61 (1H, br.s, 1-OH), 5.40 (1H, d, J=7.2 Hz, 2-H), 3.56 (1H, d, J=7.2 Hz, 3-H), 4.90 (1H, m, 5-H), 1.62 (1H, m, 6-$H_a$), 2.31 (1H, m, 6-$H_b$), 4.12 (1H, m, 7-H), 4.91 (1H, m, 7-OH), 6.28 (1H, s, 10-H), 5.81 (1H, t, J=9.0 Hz, 13-H), 1.48 (1H, m, 14-$H_a$), 1.79 (1H, m, 14-$H_b$), 0.98 (3H, s, 16-H), 0.99 (3H, s, 17-H), 1.75 (3H, s, 18-H), 1.49 (3H, s, 19-H), 3.98 (1H, d, J=8.4 Hz, 20-$H_a$), 4.00 (1H, d, J=8.4 Hz, 20-$H_b$), 2.22 (3H, s, 4-OCOCH$_3$), 2.09 (3H, s, 10-OCOCH$_3$), 5.33 (1H, d, J=9.0 Hz, 2'-H), 5.52 (1H, t, J=9.0 Hz, 3'-H), 9.19 (1H, d, J=9.0 Hz, 3'-NH), 7.48 (2H, m, ph-o-H), 7.43 (2H, m, ph-m-H), 7.56 (1H, m, ph-p-H), 7.83 (2H, m, NBz-o-H), 7.42 (2H, m, NBz-m-H), 7.18 (1H, m, NBz-p-H), 7.97 (2H, d, J=7.2 Hz, OBz-o-H), 7.66 (2H, m, OBz-m-H), 7.72 (1H, m, OBz-p-H), 2.60 (2H, m, 22-H), 2.35 (2H, t, J=7.2 Hz, 23-H), 7.82 (1H, m, 25-H), 2.90 (1H, m, 26-$H_a$), 2.96 (1H, m, 26-$H_b$), 1.22 (2H, m, 27-H), 1.33 (2H, m, 28-H), 1.44 (1H, m, 29-$H_a$), 1.62 (1H, m, 29-$H_b$), 4.11 (1H, m, 30-H), 6.94 (1H, s, 32-$H_a$), 7.37 (1H, s, 32-$H_b$), 7.87 (1H, m, 33-H), 2.15 (2H, t, J=7.8 Hz, 35-H), 1.70 (1H, m, 36-$H_a$), 1.97 (1H, m, 36-$H_b$), 4.12 (1H, m, 37-H), 7.09 (1H, s, 39-$H_a$), 7.32 (1H, s, 39-$H_b$), 8.21 (1H, d, J=8.4 Hz, 40-H), 4.43 (1H, m, 42-H), 1.29 (3H, d, J=6.6 Hz, 43-H), 8.28 (1H, d, J=7.8 Hz, 44-H), 4.73 (1H, s, 46-H), 6.20 (1H, d, J=7.8 Hz, 48-H), 7.32 (1H, m, 49-H), 7.38 (1H, m, 50-H), 7.97 (1H, m, 52-H), 7.49 (1H, m, 53-H), 7.54 (1H, m, 54-H), 8.30 (1H, m, 55-H).

$^{13}$C-NMR (150 MHz, DMSO-$d_6$): 76.7 (1-C), 74.5 (2-C), 46.1 (3-C), 80.2 (4-C), 83.6 (5-C), 36.5 (6-C), 70.4 (7-C), 57.4 (8-C), 202.3 (9-C), 74.7 (10-C), 133.3 (11-C), 139.4 (12-C), 70.7 (13-C), 34.4 (14-C), 42.9 (15-C), 26.3 (16-C), 21.4 (17-C), 13.9 (18-C), 9.8 (19-C), 75.3 (20-C), 165.2 (2-OCO), 169.6, 22.5 (4-OCOCH$_3$), 168.8, 20.6 (10-OCOCH$_3$), 169.1 (1'-C), 74.4 (2'-C), 54.0 (3'-C), 166.4 (3'-NHCO), 137.4 (ph-q-C), 127.7 (ph-o-C), 128.3 (ph-m-C), 131.5 (ph-p-C), 129.9 (NBz-q-C), 127.4 (NBz-o-C), 129.0 (NBz-m-C), 128.2 (NBz-p-C), 134.3 (OBz-q-C), 129.6 (OBz-o-C), 128.7 (OBz-m-C), 133.5 (OBz-p-C), 172.0 (21-C), 28.8 (22-C), 29.5 (23-C), 170.0 (24-C), 38.5 (26-C), 28.7 (27-C), 22.9 (28-C), 31.6 (29-C), 52.4 (30-C), 173.9 (31-C), 171.5 (34-C), 31.7 (35-C), 27.7 (36-C), 52.2 (37-C), 173.2 (38-C), 173.3 (41-C), 48.2 (42-C), 18.4 (43-C), 167.2 (45-C), 67.2 (46-C), 153.1 (47-C), 105.7 (48-C), 126.1 (49-C), 120.7 (50-C), 134.0 (51-C), 127.6 (52-C), 126.1 (53-C), 125.4 (54-C), 121.7 (55-C), 127.4 (56-C).

IR: 3289.3 ($v_{OH}$ and $v_{NH}$), 3065.7 ($v_{=CH}$), 2937.8 ($v_{-CH}$), 1739.5, 1720.9, 1647.6 ($v_{C=O}$), 1577.5, 1537.2, 1450.4 ($v_{C=C}$), 1265.1, 1239.5, 1154.1 ($\delta_{-CH}$), 905.9, 853.3, 792.9, 771.3, 707.4 ($\delta_{=CH}$).

ESI-MS: 1465.32 [M+2H]$^{2+}$.

HR-MS(TOF): 1464.6128 [M+H]$^+$, 1486.5942 [M+Na]$^+$, $C_{77}H_{89}N_7O_{22}$.

Example 36

Liquid-phase synthesis of docetaxel-2'-O-succinic acid monoester

The synthetic route was shown as below:

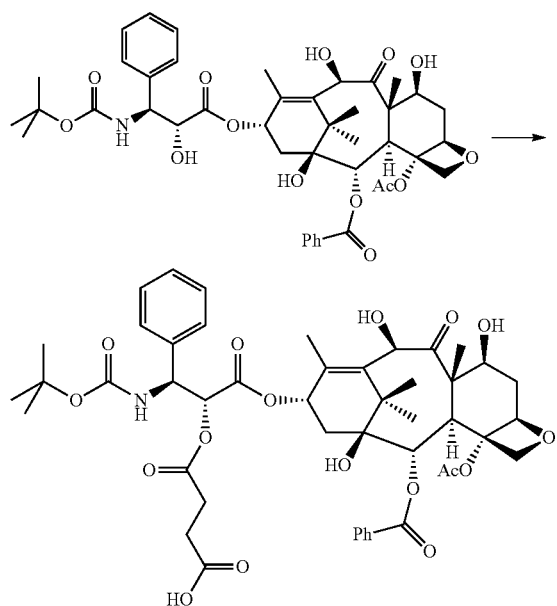

Reagents and conditions: succinic anhydride, DMAP, r.t, 2 h.

8.07 g (1.0 eq) docetaxel, 1.2 g (1.2 eq) succinic anhydride and 0.61 g (0.5 eq) DMAP were dissolved in DMF, and the mixture was stirred at r.t for 2 hours. After the completion of the reaction, the mixture was diluted with DCM, and the DCM layer was washed with 2 N HCl aqueous solution 3 times, and water for 1 time in sequence. The DCM layer was separated, and evaporated under vacuum. Large amount of water was added to the residue, and white solids precipitated. The mixture was filtered, and 7.9 g target compound was obtained through lypophilization. Yield 87%, m.p.=181~182° C.

$^1$H-NMR (600 MHz, DMSO-$d_6$): 4.43 (1H, br.s, 1-OH), 5.39 (1H, d, J=7.2 Hz, 2-H), 3.62 (1H, d, J=7.2 Hz, 3-H), 4.89 (1H, d, J=9.6 Hz, 5-H), 1.62 (1H, m, 6-$H_a$), 2.22 (1H, d, J=9.6 Hz, 6-$H_b$), 4.04 (1H, m, 7-H), 5.09 (1H, s, 10-H), 5.77 (1H, t, J=9.0 Hz, 13-H), 1.62 (1H, m, 14-$H_a$), 1.85 (1H, dd, J=15.0 and 9.0 Hz, 14-$H_b$), 0.97 (3H, s, 16-H), 0.99 (3H, s, 17-H), 1.73 (3H, s, 18-H), 1.51 (3H, s, 19-H), 3.98 (1H, d, J=9.0 Hz, 20-$H_a$), 4.02 (1H, d, J=9.0 Hz, 20-$H_b$), 2.26 (3H, s, 4-OCOCH$_3$), 5.06 (1H, m, 2'-H), 5.07 (1H, m, 3'-H), 7.86 (1H, d, J=8.4 Hz, 3'-NH), 7.35 (2H, d, J=7.8 Hz, ph-o-H), 7.40 (2H, t, J=7.8 Hz, ph-m-H), 7.17 (1H, t, J=7.8 Hz, ph-p-H), 7.97 (2H, d, J=7.8 Hz, OBz-o-H), 7.63 (2H, d, J=7.8 Hz, OBz-m-H), 7.71 (1H, d, J=7.8 Hz, OBz-p-H), 1.37 (9H, s, —C(CH$_3$)$_3$), 2.50 (2H, m, —CH$_2$—CH$_2$—COOH), 2.60 (2H, m, —CH$_2$-CH$_2$—COOH), 12.23 (1H, br.s, —CH$_2$—CH$_2$—COOH).

$^{13}$C-NMR (150 MHz, DMSO-$d_6$): 76.8 (1-C), 74.8 (2-C), 46.0 (3-C), 80.3 (4-C), 83.7 (5-C), 36.5 (6-C), 70.8 (7-C), 56.9 (8-C), 209.3 (9-C), 73.7 (10-C), 135.9 (11-C), 136.8 (12-C), 71.7 (13-C), 34.7 (14-C), 42.9 (15-C), 26.4 (16-C), 20.8 (17-C), 13.7 (18-C), 9.8 (19-C), 75.4 (20-C), 165.3 (2-OCO), 169.5, 22.5 (4-OCOCH$_3$), 168.3 (1'-C), 75.1 (2'-C), 57.4 (3'-C), 155.2 (3'-NHCO), 78.5, 28.1 (—C(CH$_3$)$_3$), 137.4 (ph-q-C), 127.4 (ph-o-C), 128.5 (ph-m-C), 128.0 (ph-p-C), 130.0 (OBz-q-C), 129.5 (OBz-o-C), 128.7 (OBz-m-C), 133.4 (OBz-p-C), 171.5, 28.4, 28.5, 172.9 (—CO—CH$_2$—CH$_2$—COOH).

ESI-MS: 930.31 [M+Na]$^+$.
HR-MS(TOF): 930.3507 [M+Na]$^+$, C$_{47}$H$_{57}$NO$_{17}$.

Examples 37-43

Liquid-Phase Synthesis of Conjugate MDC

Example 37

Liquid-Phase Synthesis of Conjugate MDC 400

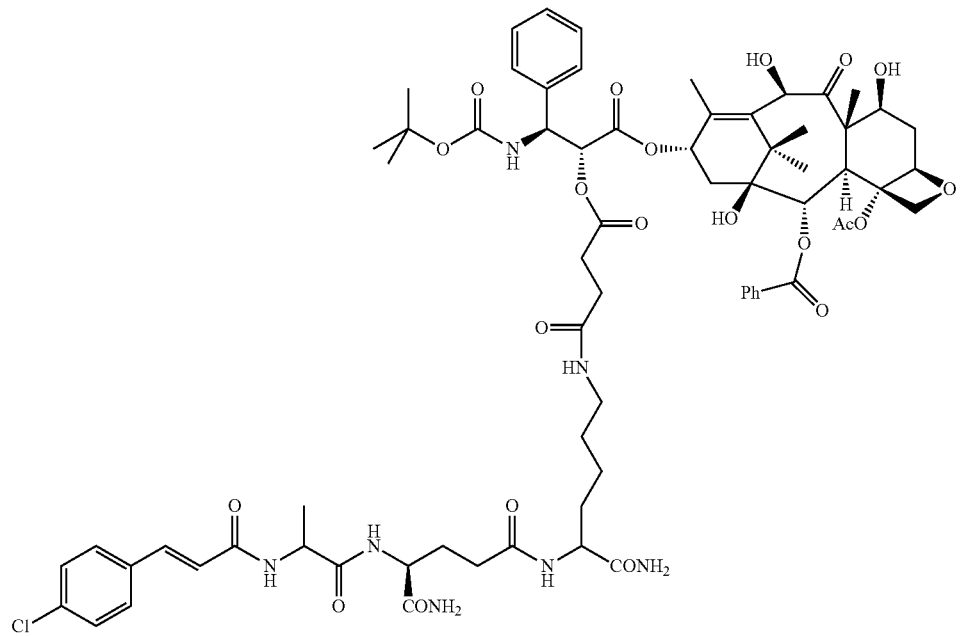

90.7 mg (1.0 eq) docetaxel-2'-O-succinic acid monoester, 11.5 mg (1.0 eq) HOSu and 19.2 mg (1.0 eq) EDC.HCl were dissolved in DMSO, and the mixture was stirred at r.t for 4 hours. 50.8 mg (1.0 eq) of muramyl dipeptide analogue MDA was sparingly added to the mixture in a few portions, and the pH of the mixture was adjusted to 7~8 with N-methyl morphine. The mixture was continued to stir for 4 hours. After the completion of the reaction, a plenty of water was added to the mixture, and white solids precipitated. The mixture was filtered, and the crude product was obtained. The crude product was purified by ODS column chromatography, and 124 mg solid product was obtained through lyophilization. Yield 89%, m.p.=180~181° C.

$^1$H-NMR (600 MHz, DMSO-d$_6$): 4.41 (1H, br.s, 1-OH), 5.39 (1H, d, J=6.6 Hz, 2-H), 3.62 (1H, d, J=6.6 Hz, 3-H), 4.89 (1H, d, J=10.2 Hz, 5-H), 1.66 (1H, m, 6-H$_a$), 2.26 (1H, m, 6-H$_b$), 4.04 (1H, m, 7-H), 5.07 (1H, s, 10-H), 5.77 (1H, t, J=9.0 Hz, 13-H), 1.64 (1H, m, 14-H$_a$), 1.82 (1H, dd, J=15.6 and 9.0 Hz, 14-H$_b$), 0.96 (3H, s, 16-H), 0.97 (3H, s, 17-H), 1.68 (3H, s, 18-H), 1.50 (3H, s, 19-H), 3.99 (1H, m, 20-H$_a$), 4.01 (1H, d, J=9.0 Hz, 20-H$_b$), 2.22 (3H, s, 4-OCOCH$_3$), 5.04 (1H, m, 2'-H), 5.06 (1H, m, 3'-H), 7.86 (1H, m, 3'-NH), 7.30 (2H, m, ph-o-H), 7.35 (2H, d, J=7.8 Hz, ph-m-H), 7.16 (1H, t, J=7.2 Hz, ph-p-H), 7.97 (2H, d, J=7.8 Hz, OBz-o-H), 7.64 (2H, t, J=7.8 Hz, OBz-m-H), 7.71 (1H, t, J=7.2 Hz, OBz-p-H), 1.36 (9H, s, —C(CH$_3$)$_3$), 2.59 (2H, m, 22-H), 2.36 (2H, m, 23-H), 7.83 (1H, m, 25-H), 2.92 (1H, m, 26-H$_a$), 3.00 (1H, m, 26-H$_b$), 1.21 (2H, m, 27-H), 1.27 (2H, m, 28-H), 1.52 (1H, m, 29-H$_a$), 1.63 (1H, m, 29-H$_b$), 4.11 (1H, m, 30-H), 6.96 (1H, s, 32-H$_a$), 7.30 (1H, s, 32-H$_b$), 7.90 (1H, m, 33-H), 2.15 (2H, m, 35-H), 1.72 (1H, m, 36-H$_a$), 1.99 (1H, m, 36-H$_b$), 4.13 (1H, m, 37-H), 7.02 (1H, s, 39-H$_a$), 7.30 (1H, s, 39-H$_b$), 8.29 (1H, m, 40-H), 4.38 (1H, m, 42-H), 1.26 (3H, d, J=6.6 Hz, 43-H), 8.38 (1H, d, J=6.6 Hz, 44-H), 6.75 (1H, d, J=16.2 Hz, 46-H), 7.37 (1H, d, J=16.3 Hz, 47-H), 7.57 (2H, d, J=8.4 Hz, 49 and 53-H), 7.46 (2H, d, J=8.4 Hz, 50 and 52-H).

$^{13}$C-NMR (150 MHz, DMSO-d$_6$): 76.8 (1-C), 74.8 (2-C), 46.1 (3-C), 80.3 (4-C), 83.7 (5-C), 36.5 (6-C), 70.7 (7-C), 57.0 (8-C), 209.3 (9-C), 73.7 (10-C), 136.0 (11-C), 136.8 (12-C), 71.1 (13-C), 34.7 (14-C), 42.9 (15-C), 26.5 (16-C), 20.8 (17-C), 13.6 (18-C), 9.8 (19-C), 75.3 (20-C), 165.3 (2-OCO), 169.6, 22.5 (4-OCOCH$_3$), 168.9 (1'-C), 75.0 (2'-C), 55.1 (3'-C), 155.2 (3'-NHCO), 78.5, 28.1 (—C(CH$_3$)$_3$), 137.5 (ph-q-C), 127.4 (ph-o-C), 128.5 (ph-m-C), 128.0 (ph-p-C), 130.0 (OBz-q-C), 129.6 (OBz-o-C), 128.7 (OBz-m-C), 133.4 (OBz-p-C), 171.9 (21-C), 28.9 (22-C), 29.6 (23-C), 170.0 (24-C), 38.5 (26-C), 28.9 (27-C), 23.0 (28-C), 31.4 (29-C), 52.1 (30-C), 174.1 (31-C), 171.6 (34-C), 31.7 (35-C), 27.7 (36-C), 52.4 (37-C), 173.4 (38-C), 172.3 (41-C), 48.8 (42-C), 18.1 (43-C), 164.7 (45-C), 122.7 (46-C), 137.6 (47-C), 133.8 (48-C), 129.0 (49 and 53-C), 129.2 (50 and 52-C), 134.0 (51-C).

IR: 3320.6 ($v_{OH}$ and $v_{NH}$), 2976.8, 2933.5 ($v_{-CH}$), 1739.7, 1658.6 ($v_{C=O}$), 1531.5, 1496.5, 1452.4 ($v_{C=C}$), 1246.2 ($v_{C-O-C}$), 983.5, 707.9 ($\delta_{=CH}$).

ESI-MS: 1398.14 [M+H]$^+$, 1420.32 [2M+Na]$^+$.

HR-MS(TOF): 1398.5791 [M+H]$^+$, 1420.5609 [M+Na]$^+$, C$_{70}$H$_{88}$ClN$_7$O$_{21}$.

Example 38

Liquid-Phase Synthesis of Conjugate MDC 403

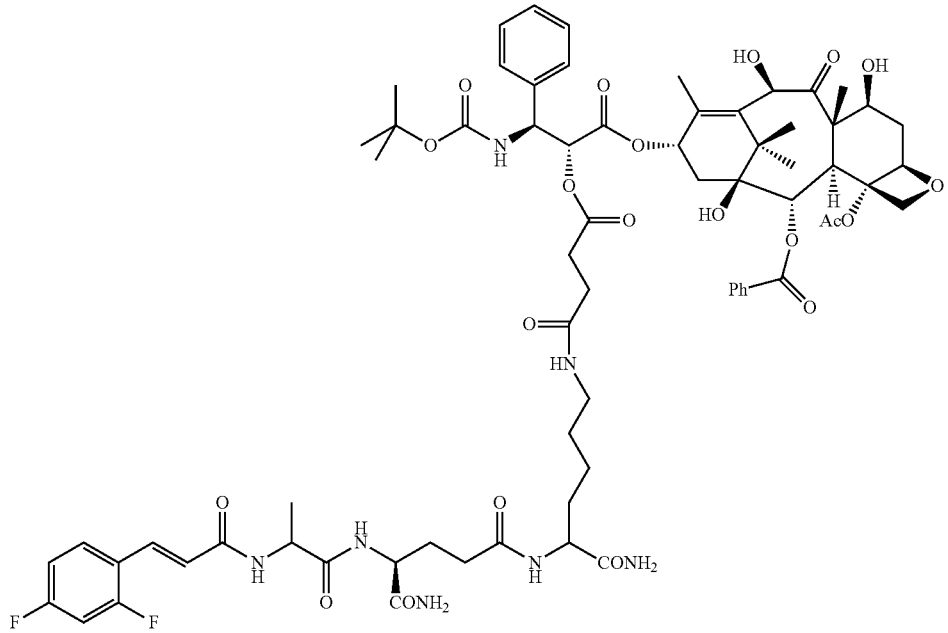

90.7 mg (1.0 eq) docetaxel-2'-O-succinic acid monoester, 11.5 mg (1.0 eq) HOSu and 19.2 mg (1.0 eq) EDC.HCl were dissolved in DMSO, and the mixture was stirred at r.t for 4 hours. 51 mg (1.0 eq) of muramyl dipeptide analogue MDA-203 was sparingly added to the mixture in a few portions, and the pH of the mixture was adjusted to 7~8 with N-methyl morphine. The mixture was continued to stir for 4 hours. After the completion of the reaction, a plenty of water was added to the mixture, and white solids precipitated. The mixture was filtered, and the crude product was obtained. The crude product was purified by ODS column chromatography, and 114 mg solid product was obtained through lyophilization. Yield 80%, m.p.=165~166° C.

$^1$H-NMR (500 MHz, DMSO-d$_6$): 4.45 (1H, br.s, 1-OH), 5.44 (1H, d, J=6.0 Hz, 2-H), 3.64 (1H, d, J=6.0 Hz, 3-H), 4.89

(1H, m, 5-H), 1.66 (1H, m, 6-H$_a$), 2.25 (1H, m, 6-H$_b$), 4.03 (1H, m, 7-H), 5.09 (1H, s, 10-H), 5.80 (1H, m, 13-H), 1.64 (1H, m, 14-H$_a$), 1.82 (1H, m, 14-H$_b$), 0.96 (3H, s, 16-H), 0.96 (3H, s, 17-H), 1.68 (3H, s, 18-H), 1.52 (3H, s, 19-H), 3.99 (1H, m, 20-H$_a$), 4.01 (1H, m, 20-H$_b$), 2.22 (3H, s, 4-OCOCH$_3$), 5.04 (1H, m, 2'-H), 5.06 (1H, m, 3'-H), 7.86 (1H, m, 3'-NH), 7.31 (2H, m, ph-o-H), 7.38 (2H, min. ph-m-H), 7.19 (1H, m, ph-p-H), 7.99 (2H, d, J=6.5 Hz, OBz-o-H), 7.66 (2H, m, OBz-m-H), 7.72 (1H, m, OBz-p-H), 1.39 (9H, s, —C(CH$_3$)$_3$), 2.62 (2H, m, 22-H), 2.39 (2H, m, 23-H), 7.83 (1H, m, 25-H), 3.01 (2H, br.s, 26-H), 1.21 (2H, m, 27-H), 1.29 (2H, m, 28-H), 1.52 (1H, br.s, 29-H$_a$), 1.63 (1H, br.s, 29-H$_b$), 4.14 (1H, m, 30-H), 6.96 (1H, s, 32-H$_a$), 7.31 (1H, s, 32-H$_b$), 7.90 (1H, m, 33-H), 2.17 (2H, m, 35-H), 1.70 (1H, m, 36-H$_a$), 1.99 (1H, m, 36-H$_b$), 4.13 (1H, m, 37-H), 7.02 (1H, s, 39-H$_a$), 7.30 (1H, s, 39-H$_b$), 8.22 (1H, m, 40-H), 4.38 (1H, m, 42-H), 1.26 (3H, m, 43-H), 8.47 (1H, d, J=6.0 Hz, 44-H), 6.82 (1H, d, J=16.0 Hz, 46-H), 7.37 (1H, m, 47-H), 7.18 (1H, m, 51-H), 7.70 (1H, m, 53-H).

$^{13}$C-NMR (125 MHz, DMSO-d$_6$): 77.2 (1-C), 75.2 (2-C), 46.4 (3-C), 80.8 (4-C), 84.2 (5-C), 36.9 (6-C), 71.2 (7-C), 57.4 (8-C), 209.3 (9-C), 74.2 (10-C), 136.0 (11-C), 136.8 (12-C), 71.2 (13-C), 35.2 (14-C), 43.3 (15-C), 26.9 (16-C), 21.2 (17-C), 14.1 (18-C), 10.3 (19-C), 75.3 (20-C), 165.1 (2-OCO), 170.5, 22.9 (4-OCOCH$_3$), 168.9 (1'-C), 75.0 (2'-C), 55.6 (3'-C), 155.2 (3'-NHCO), 79.0, 28.1 (—C(CH$_3$)$_3$), 137.5 (ph-q-C), 127.9 (ph-o-C), 128.5 (ph-m-C), 128.0 (ph-p-C), 130.0 (OBz-q-C), 129.2 (OBz-o-C), 128.7 (OBz-m-C), 133.4 (OBz-p-C), 172.0 (21-C), 28.6 (22-C), 29.3 (23-C), 170.0 (24-C), 39.0 (26-C), 28.6 (27-C), 23.4 (28-C), 31.4 (29-C), 52.1 (30-C), 174.1 (31-C), 171.6 (34-C), 31.7 (35-C), 27.7 (36-C), 52.6 (37-C), 173.7 (38-C), 172.3 (41-C), 49.4 (42-C), 18.5 (43-C), 164.7 (45-C), 122.7 (46-C), 137.6 (47-C), 118.5 (m, 48-C), 161.7 (m, 49-C), 104.6 (m, 50-C), 163.7 (m, 51-C), 112.4 (m, 52-C), 130.5 (m, 53-C).

IR: 3323.9 ($v_{OH}$ and $v_{NH}$), 2977.6, 2937.6 ($v_{—CH}$), 1739.5, 1659.3 ($v_{C=O}$), 1532.5, 1504.2, 1452.5 ($v_{C=C}$), 1368.2, 1272.7, 1246.8, 1161.2, 1069.2 ($\delta_{—CH}$), 983.0, 852.5, 708.8 ($\delta_{=CH}$).

ESI-MS: 1400.98 [M+H]$^+$, 1422.43 [M+Na]$^+$.

HR-MS(TOF): 1400.6008 [M+H]$^+$, 1422.5824 [M+Na]$^+$, C$_{70}$H$_{87}$F$_2$N$_7$O$_{21}$.

Example 39

Liquid-Phase Synthesis of Conjugate MDC 404

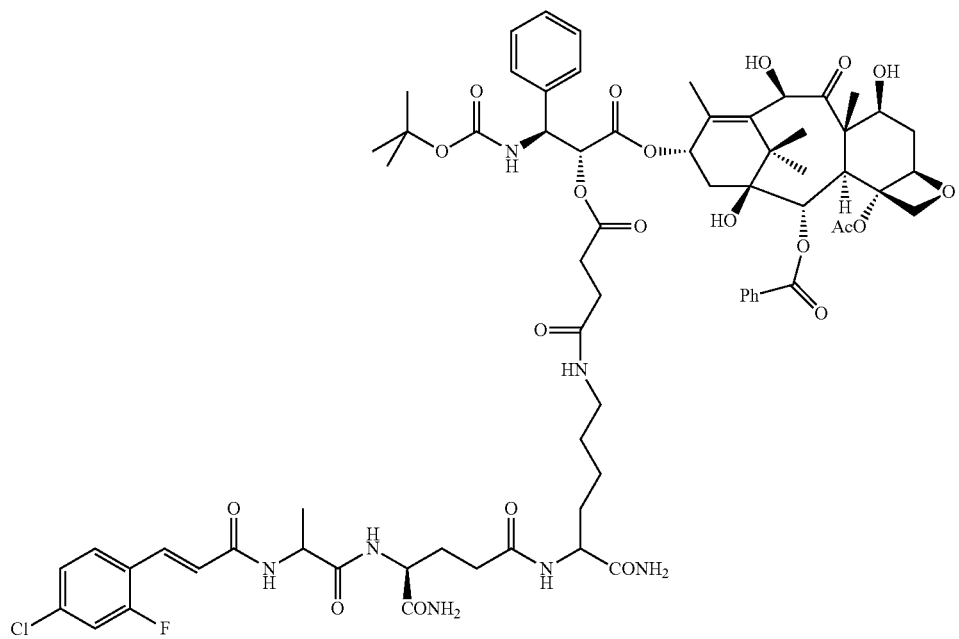

90.7 mg (1.0 eq) docetaxel-2'-O-succinic acid monoester, 11.5 mg (1.0 eq) HOSu and 19.2 mg (1.0 eq) EDC.HCl were dissolved in DMSO, and the mixture was stirred at r.t for 4 hours. 52.6 mg (1.0 eq) of muramyl dipeptide analogue MDA-204 was sparingly added to the mixture in a few portions, and the pH of the mixture was adjusted to 7~8 with N-methyl morphine. The mixture was continued to stir for 4 hours. After the completion of the reaction, a plenty of water was added to the mixture, and white solids precipitated. The mixture was filtered, and the crude product was obtained. The crude product was purified by ODS column chromatography, and 116 mg solid product was obtained through lypophilization. Yield, 82%, m.p.=175~176° C.

$^1$H-NMR (500 MHz, DMSO-d$_6$): 4.42 (1H, br.s, 1-OH), 5.41 (1H, d, J=7.0 Hz, 2-H), 3.65 (1H, d, J=7.0 Hz, 3-H), 4.90 (1H, m, 5-H), 1.63 (1H, m, 6-H$_a$), 2.28 (1H, m, 6-H$_b$), 4.05 (1H, m, 7-H), 5.09 (1H, s, 10-H), 5.78 (1H, t, J=8.5 Hz, 13-H), 1.63 (1H, m, 14-H$_a$), 1.83 (1H, m, 14-H$_b$), 0.99 (3H, s, 16-H), 1.02 (3H, s, 17-H), 1.68 (3H, s, 18-H), 1.51 (3H, s, 19-H), 4.00 (1H, m, 20-H$_a$), 4.02 (1H, m, 20-H$_b$), 2.23 (3H, s, 4-OCOCH$_3$), 5.02 (1H, m, 2'-H), 5.09 (1H, m, 3'-H), 7.86 (1H, m, 3-NH), 7.30 (2H, m, ph-o-H), 7.37 (2H, m, ph-m-H), 7.18 (1H, m, ph-p-H), 7.99 (2H, d, J=7.5 Hz, OBz-o-H), 7.65 (2H, m, OBz-m-H), 7.71 (1H, m, OBz-p-H), 1.36 (9H, s, —C(CH$_3$)$_3$), 2.61 (2H, m, 22-H), 2.37 (2H, m, 23-H), 7.83 (1H, m, 25-H), 3.00 (1H, m, 26-H$_a$), 3.01 (1H, m, 26-H$_b$), 1.20 (2H, m, 27-H), 1.29 (2H, m, 28-H), 1.52 (1H, m, 29-H$_a$), 1.63 (1H, m, 29-H$_b$), 4.11 (1H, m, 30-H), 6.96 (1H, s, 32-H$_a$), 7.30 (1H, s, 32-H$_b$), 7.88 (1H, m, 33-H), 2.16 (2H, m, 35-H), 1.74 (1H, m, 36-H$_a$), 2.00 (1H, m, 36-H$_b$), 4.13 (1H, m,

37-H), 7.01 (1H, s, 39-H$^a$), 7.30 (1H, s, 39-H$_b$), 8.24 (1H, d, J=8.5 Hz, 40-H), 4.40 (1H, m, 42-H), 1.28 (3H, m, 43-H), 8.51 (1H, d, J=7.0 Hz, 44-H), 6.86 (1H, d, J=16.0 Hz, 46-H), 7.38 (1H, d, J=16.0 Hz, 47-H), 7.54 (1H, dd, J=11.0 and 2.0 Hz, 50-H), 7.37 (1H, m, 52-H), 7.7 (1H, m, 53-H).

$^{13}$C-NMR (125 MHz, DMSO-d$_6$): 76.8 (1-C), 75.3 (2-C), 46.4 (3-C), 80.8 (4-C), 84.2 (5-C), 36.9 (6-C), 71.2 (7-C), 57.4 (8-C), 209.8 (9-C), 74.2 (10-C), 136.5 (11-C), 137.3 (12-C), 71.5 (13-C), 35.2 (14-C), 42.6 (15-C), 26.9 (16-C), 21.3 (17-C), 14.1 (18-C), 10.3 (19-C), 75.5 (20-C), 165.7 (2-OCO), 169.4, 23.4 (4-OCOCH$_3$), 168.9 (1'-C), 75.3 (2'-C), 55.6 (3'-C), 155.7 (3'-NHCO), 79.0, 28.2 (—C(CH$_3$)$_3$), 137.3 (ph-q-C), 127.4 (ph-o-C), 128.4 (ph-m-C), 128.0 (ph-p-C), 130.8 (OBz-q-C), 129.0 (OBz-o-C), 128.4 (OBz-m-C), 133.7 (OBz-p-C), 172.0 (21-C), 28.9 (22-C), 29.3 (23-C), 170.0 (24-C), 38.5 (26-C), 28.6 (27-C), 22.9 (28-C), 32.1 (29-C), 52.7 (30-C), 174.4 (31-C), 172.0 (34-C), 32.2 (35-C), 28.1 (36-C), 52.8 (37-C), 173.6 (38-C), 172.3 (41-C), 49.4 (42-C), 18.5 (43-C), 164.9 (45-C), 122.2 (46-C), 138.0 (47-C), 122.1 (d, J=11.8 Hz, 48-C), 160.7 (d, J=252.5 Hz, 49-C), 117.3 (d, J=28.8 Hz, 50-C), 130.3 (d, J=10.9 Hz, 51-C), 125.2 (s, 52-C), 130.4 (s, 53-C).

IR: 3324.6 ($v_{OH}$ and $v_{NH}$), 2977.0, 2935.8 ($v_{—CH}$), 1739.5, 1660.5 ($v_{C=O}$), 1533.3, 1452.6 ($v_{C=C}$), 1368.2, 1269.0, 1248.3, 1162.0, 1070.6 ($\delta_{—CH}$), 984.2, 856.3, 708.8 ($\delta_{=CH}$).

ESI-MS: 1416.05 [M+H]$^+$, 1438.05 [M+Na]$^+$.

HR-MS(TOF): 1416.5693 [M+H]$^+$, 1438.5511 [M+Na]$^+$, C$_{70}$H$_{87}$ClFN$_7$O$_{21}$.

Example 40

Liquid-Phase Synthesis of Conjugate MDC 405

N-methyl morphine. The mixture was continued to stir for 4 hours. After the completion of the reaction, a plenty of water was added to the mixture, and white solids precipitated. The mixture was filtered, and the crude product was obtained. The crude product was purified by ODS column chromatography, and 99 mg solid product was obtained through lypophilization. Yield 70%, m.p.=174~175° C.

$^1$H-NMR (500 MHz, DMSO-d$_6$): 4.42 (1H, br.s, 1-OH), 5.41 (1H, d, J=7.0 Hz, 2-H), 3.65 (1H, d, J=7.0 Hz, 3-H), 4.90 (1H, m, 5-H), 1.64 (1H, m, 6-H$_a$), 2.28 (1H, m, 6-H$_b$), 4.05 (1H, m, 7-H), 5.09 (1H, s, 10-H), 5.80 (1H, t, J=8.5 Hz, 13-H), 1.63 (1H, m, 14-H$_a$), 1.83 (1H, m, 14-H$_b$), 0.99 (3H, s, 16-H), 1.02 (3H, s, 17-H), 1.70 (3H, s, 18-H), 1.51 (3H, s, 19-H), 4.00 (1H, m, 20-H$_a$), 4.02 (1H, m, 20-H$_b$), 2.25 (3H, s, 4-OCOCH$_3$), 5.09 (1H, m, 2'-H), 5.09 (1H, m, 3'-H), 7.86 (1H, m, 3'-NH), 7.31 (2H, m, ph-o-H), 7.35 (2H, m, ph-m-H), 7.19 (1H, t, J=7.0 Hz, ph-p-H), 8.00 (2H, d, J=7.5 Hz, OBz-o-H), 7.65 (2H, m, OBz-m-H), 7.71 (1H, m, OBz-p-H), 1.36 (9H, s, —C(CH$_3$)$_3$), 2.59 (2H, m, 22-H), 2.36 (2H, m, 23-H), 7.87 (1H, m, 25-H), 3.00 (1H, m, 26-H$_a$), 3.01 (1H, m, 26-H$_b$), 1.20 (2H, m, 27-H), 1.29 (2H, m, 28-H), 1.52 (1H, m, 29-H$_a$), 1.63 (1H, m, 29-H$_b$), 4.11 (1H, m, 30-H), 6.97 (1H, s, 32-H$_a$), 7.32 (1H, s, 32-H$_b$), 7.88 (1H, m, 33-H), 2.16 (2H, m, 35-H), 1.72 (1H, m, 36-H$_a$), 1.99 (1H, m, 36-H$_b$), 4.13 (1H, m, 37-H), 7.11 (1H, s, 39-H$_a$), 7.31 (1H, s, 39-H$_b$), 8.25 (1H, d, J=8.0 Hz, 40-H), 4.38 (1H, m, 42-H), 1.26 (3H, m, 43-H), 8.45 (1H, d, J=7.0 Hz, 44-H), 6.79 (1H, d, J=16.0 Hz, 46-H), 7.38 (1H, d, J=16.0 Hz, 47-H), 7.56 (1H, dd, J=9.0 and 3.0 Hz, 50-H), 7.33 (1H, m, 52-H), 7.75 (1H, m, 53-H).

$^{13}$C-NMR (125 MHz, DMSO-d$_6$): 77.3 (1-C), 75.3 (2-C), 46.4 (3-C), 80.8 (4-C), 84.2 (5-C), 36.9 (6-C), 71.2 (7-C), 57.0 (8-C), 209.3 (9-C), 74.2 (10-C), 136.5 (11-C), 137.3

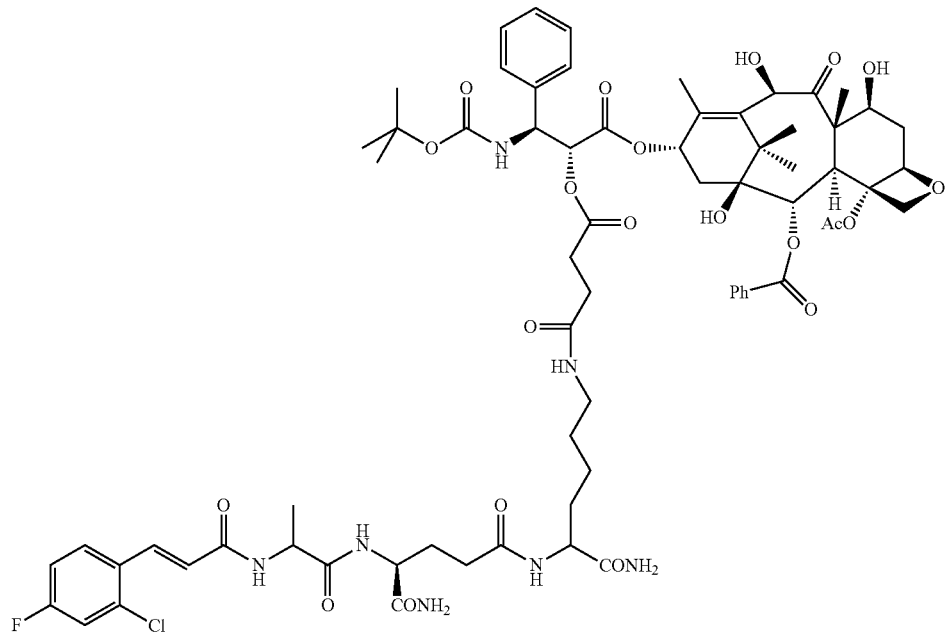

90.7 mg (1.0 eq) docetaxel-2'-O-succinic acid monoester, 11.5 mg (1.0 eq) HOSu and 19.2 mg (1.0 eq) EDC.HCl were dissolved in DMSO, and the mixture was stirred at r.t. for 4 hours. 52.6 mg (1.0 eq) of muramyl dipeptide analogue MDA-205 was sparingly added to the mixture in a few portions, and the pH of the mixture was adjusted to 7~8 with (12-C), 71.6 (13-C), 35.2 (14-C), 43.3 (15-C), 26.9 (16-C), 21.2 (17-C), 14.1 (18-C), 10.3 (19-C), 75.9 (20-C), 165.7 (2-OCO), 170.0, 22.9 (4-OCOCH$_3$), 169.4 (1'-C), 75.5 (2'-C), 55.5 (3'-C), 155.7 (3'-NHCO), 78.9, 28.2 (—C(CH$_3$)$_3$), 137.3 (ph-q-C), 127.9 (ph-o-C), 129.0 (ph-m-C), 129.1 (ph-p-C), 130.5 (OBz-q-C), 130.0 (OBz-o-C), 129.1 (OBz-m-C), 133.6

(OBz-p-C), 172.0 (21-C), 29.3 (22-C), 30.1 (23-C), 170.4 (24-C), 38.5 (26-C), 28.6 (27-C), 23.4 (28-C), 32.1 (29-C), 52.6 (30-C), 174.4 (31-C), 172.3 (34-C), 32.2 (35-C), 26.9 (36-C), 52.8 (37-C), 173.7 (38-C), 172.7 (41-C), 49.3 (42-C), 18.7 (43-C), 164.7 (45-C), 125.4 (46-C), 133.9 (47-C), 129.2 (48-C), 134.6 (49-C), 115.8 (d, J=21.6 Hz, 50-C), 162.7 (d, J=249.6 Hz, 51-C), 117.6 (d, J=24.9 Hz, 52-C), 129.6 (53-C).

IR: 3316.8 ($v_{OH}$ and $v_{NH}$), 2977.3, 2938.6 ($v_{-CH}$), 1739.5, 1659.2 ($v_{C=O}$), 1533.0, 1490.7 ($v_{C=C}$), 1368.3, 1241.6, 1161.7, 1068.6 ($\delta_{-CH}$), 982.1, 858.0, 708.6 ($\delta_{=CH}$).

ESI-MS: 1416.52 [M+H]$^+$, 1438.42 [M+Na]$^+$.

HR-MS(TOF): 1416.5725 [M+H]$^+$, 1438.5523 [M+Na]$^+$, $C_{70}H_{87}ClFN_7O_{21}$.

Example 41

Liquid-Phase Synthesis of Conjugate MDC 406

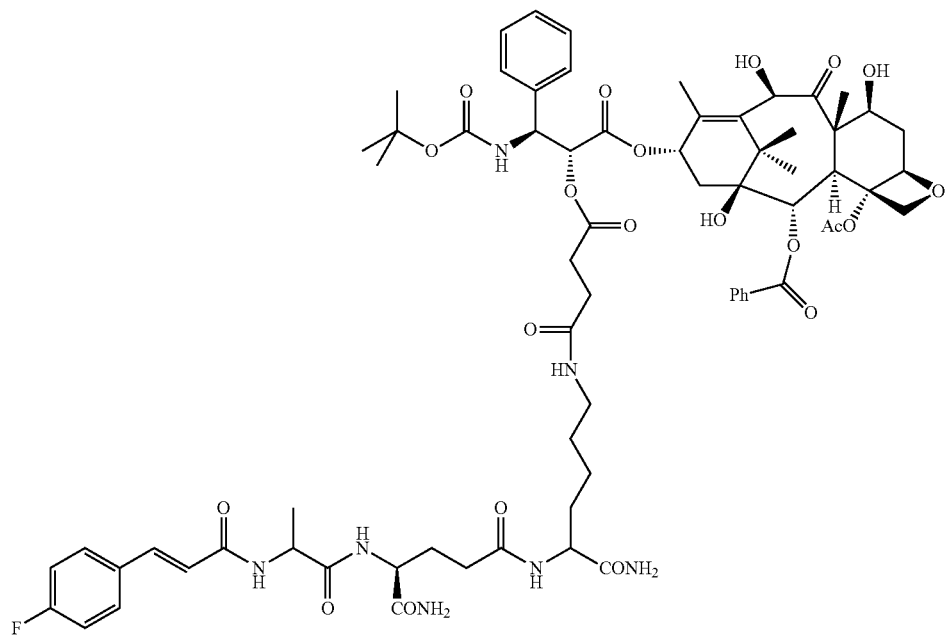

90.7 mg (1.0 eq) docetaxel-2'-O-succinic acid monoester, 11.5 mg (1.0 eq) HOSu and 19.2 mg (1.0 eq) EDC.HCl were dissolved in DMSO, and the mixture was stirred at r.t for 4 hours. 49.2 mg (1.0 eq) of muramyl dipeptide analogue MDA-206 was sparingly added to the mixture in a few portions, and the pH of the mixture was adjusted to 7~8 with N-methyl morphine. The mixture was continued to stir for 4 hours. After the completion of the reaction, a plenty of water was added to the mixture, and white solids precipitated. The mixture was filtered, and the crude product was obtained. The crude product was purified by ODS column chromatography, and 125.6 mg solid product was obtained through lypophilization. Yield 91%, m.p.=162~163° C.

$^1$H-NMR (500 MHz, DMSO-d$_6$): 4.41 (1H, br.s, 1-OH), 5.42 (1H, d, J=7.0 Hz, 2-H), 3.65 (1H, d, J=7.0 Hz, 3-H), 4.90 (1H, m, 5-H), 1.66 (1H, m, 6-H$_a$), 2.25 (1H, m, 6-H$_b$), 4.03 (1H, m, 7-H), 5.09 (1H, s, 10-H), 5.80 (1H, t, J=8.5 Hz, 13-H), 1.64 (1H, m, 14-H$_a$), 1.82 (1H, m, 14-H$_b$), 0.99 (3H, s, 16-H), 0.99 (3H, s, 17-H), 1.68 (3H, s, 18-H), 1.50 (3H, s, 19-H), 3.99 (1H, m, 20-H$_a$), 4.01 (1H, m, 20-H$_b$), 2.22 (3H, s, 4-OCOCH$_3$), 5.09 (1H, m, 2'-H), 5.09 (1H, m, 3'-H), 7.86 (1H, m, 3'-NH), 7.30 (2H, m, ph-o-H), 7.35 (2H, m, ph-m-H), 7.16 (1H, t, J=7.0 Hz, ph-p-H), 7.99 (2H, d, J=7.5 Hz, OBz-o-H), 7.65 (2H, m, OBz-m-H), 7.71 (1H, m, OBz-p-H), 1.36 (9H, s, —C(CH$_3$)$_3$), 2.55 (2H, m, 22-H), 2.34 (2H, m, 23-H), 7.83 (1H, m, 25-H), 3.01 (2H, br.s, 26-H), 1.21 (2H, m, 27-H), 1.27 (2H, m, 28-H), 1.52 (1H, m, 29-H$_a$), 1.64 (1H, m, 29-H$_b$), 4.11 (1H, m, 30-H), 6.97 (1H, s, 32-H$_a$), 7.31 (1H, s, 32-H$_b$), 7.86 (1H, m, 33-H), 2.17 (2H, m, 35-H), 1.79 (1H, m, 36-H$_a$), 2.00 (1H, m, 36-H$_b$), 4.15 (1H, m, 37-H), 7.11 (1H, s, 39-H$_a$), 7.31 (1H, s, 39-H$_b$), 8.22 (1H, d, J=8.0 Hz, 40-H), 4.38 (1H, m, 42-H), 1.26 (3H, m, 43-H), 8.35 (1H, d, J=8.0 Hz, 44-H), 6.71 (1H, d, J=16.0 Hz, 46-H), 7.38 (1H, d, J=16.0 Hz, 47-H), 7.87 (2H, m, 49 an 53-H), 7.38 (2H, m, 50 snd 52-H).

$^{13}$C-NMR (125 MHz, DMSO-d$_6$): 77.3 (1-C), 75.3 (2-C), 46.4 (3-C), 80.7 (4-C), 84.2 (5-C), 36.9 (6-C), 71.2 (7-C), 57.4 (8-C), 209.8 (9-C), 74.2 (10-C), 136.5 (11-C), 137.2 (12-C), 71.6 (13-C), 35.1 (14-C), 43.3 (15-C), 26.9 (16-C), 21.2 (17-C), 14.1 (18-C), 10.3 (19-C), 75.9 (20-C), 165.8 (2-OCO), 170.0, 22.9 (4-OCOCH$_3$), 169.4 (1'-C), 75.5 (2'-C), 55.5 (3'-C), 155.7 (3'-NHCO), 79.0, 28.5 (—C(CH$_3$)$_3$), 137.9 (ph-q-C), 127.9 (ph-o-C), 129.2 (ph-m-C), 128.5 (ph-p-C), 130.5 (OBz-q-C), 130.1 (OBz-o-C), 129.3 (OBz-m-C), 133.6 (OBz-p-C), 172.3 (21-C), 29.3 (22-C), 30.0 (23-C), 170.5 (24-C), 38.7 (26-C), 29.2 (27-C), 23.4 (28-C), 32.1 (29-C), 52.6 (30-C), 174.4 (31-C), 172.0 (34-C), 32.2 (35-C), 28.2 (36-C), 52.8 (37-C), 173.7 (38-C), 172.8 (41-C), 49.3 (42-C), 18.6 (43-C), 165.3 (45-C), 122.3 (46-C), 137.9 (47-C), 133.9 (48-C), 131.9 (m, 49 and 53-C), 116.4 (d, J=21.8 Hz, 50 and 52-C), 163.2 (d, J=245.3 Hz, 51-C).

IR: 3318.8 ($v_{OH}$ and $v_{NH}$), 2977.6, 2938.0 ($v_{-CH}$), 1659.3 ($v_{C=O}$), 1535.1, 1511.9, 1452.6 ($v_{C=C}$), 1368.5, 1246.7, 1160.7, 1069.1 ($\delta_{-CH}$), 983.0, 832.9, 708.1 ($\delta_{=CH}$).

ESI-MS: 1382.00 [M+H]$^+$, 1404.60 [M+Na]$^+$.

HR-MS(TOF): 1382.6064 [M+H]$^+$, 1404.5900 [M+Na]$^+$, $C_{70}H_{88}FN_7O_{21}$.

Example 42

Liquid-Phase Synthesis of Conjugate MDC 407

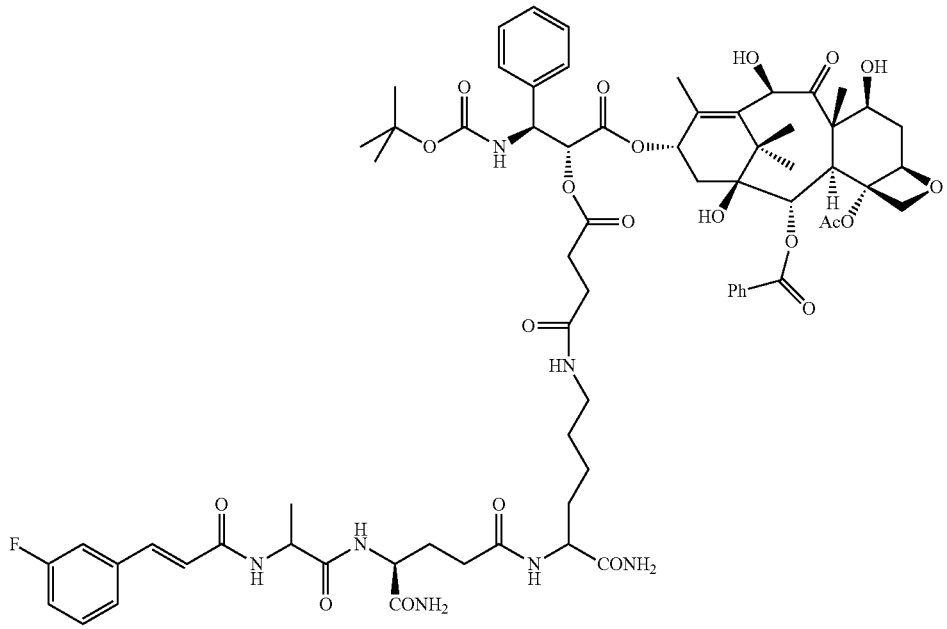

90.7 mg (1.0 eq) docetaxel-2'-O-succinic acid monoester, 11.5 mg (1.0 eq) HOSu and 19.2 mg (1.0 eq) EDC.HCl were dissolved in DMSO, and the mixture was stirred at r.t for 4 hours. 49.2 mg (1.0 eq) of muramyl dipeptide analogue MDA-207 was sparingly added to the mixture in a few portions, and the pH of the mixture was adjusted to 7~8 with N-methyl morphine. The mixture was continued to stir for 4 hours. After the completion of the reaction, a plenty of water was added to the mixture, and white solids precipitated. The mixture was filtered, and the crude product was obtained. The crude product was purified by ODS column chromatography, and 117.4 mg solid product was obtained through lypophilization. Yield 85%, m.p.=174~175° C.

$^1$H-NMR (500 MHz, DMSO-d$_6$): 4.43 (1H, br.s, 1-OH), 5.41 (1H, d, J=7.5 Hz, 2-H), 3.65 (1H, d, J=7.5 Hz, 3-H), 4.91 (1H, m, 5-H), 1.66 (1H, m, 6-H$_a$), 2.25 (1H, m, 6-H$_b$), 4.05 (1H, m, 7-H), 5.09 (1H, s, 10-H), 5.80 (1H, m, 13-H), 1.64 (1H, m, 14-H$_a$), 1.82 (1H, m, 14-H$_b$), 0.99 (3H, s, 16-H), 102 (3H, s, 17-H), 1.68 (3H, s, 18-H), 1.51 (3H, s, 19-H), 4.02 (1H, m, 20-H$_a$), 4.05 (1H, d, J=9.0 Hz, 20-H$_b$), 2.22 (3H, s, 4-OCOCH$_3$), 5.09 (1H, m, 2'-H), 5.09 (1H, m, 3'-H), 7.86 (1H, m, 3'-NH), 7.31 (2H, m, ph-o-H), 7.37 (2H, d, J=7.5 Hz, ph-m-H), 7.17 (1H, m, ph-p-H), 7.99 (2H, d, J=7.5 Hz, OBz-o-H), 7.65 (2H, t, J=7.5 Hz, OBz-m-H), 7.74 (1H, m, OBz-p-H), 1.39 (9H, s, —C(CH$_3$)$_3$), 2.62 (2H, m, 22-H), 2.36 (2H, m, 23-H), 7.83 (1H, m, 25-H), 3.00 (2H, br.s, 26-H), 1.25 (2H, m, 27-H), 1.26 (2H, m, 28-H), 1.57 (1H, m, 29-H$_a$), 1.64 (1H, m, 29-H$_b$), 4.11 (1H, m, 30-H), 6.97 (1H, s, 32-H$_a$), 7.31 (1H, s, 32-H$_b$), 7.92 (1H, m, 33-H), 2.16 (2H, m, 35-H), 1.74 (1H, m, 36-H$_a$), 2.00 (1H, m, 36-H$_b$), 4.14 (1H, m, 37-H), 7.11 (1H, s, 39-H$_a$), 7.31 (1H, s, 39-H$_b$), 8.23 (1H, d, J=8.5 Hz, 40-H), 4.39 (1H, m, 42-H), 1.28 (3H, m, 43-H), 8.37 (1H, d, J=6.5 Hz, 44-H), 6.81 (1H, d, J=16.5 Hz, 46-H), 7.38 (1H, d, J=16.5 Hz, 47-H), 7.37 (1H, m, 49-H), 7.22 (1H, m, 51-H), 7.47 (1H, m, 52-H), 7.41 (1H, m, 53-H).

$^{13}$C-NMR (125 MHz, DMSO-d$_6$): 77.3 (1-C), 75.3 (2-C), 46.4 (3-C), 80.8 (4-C), 84.2 (5-C), 36.9 (6-C), 71.2 (7-C), 57.4 (8-C), 209.8 (9-C), 74.2 (10-C), 136.5 (11-C), 137.3 (12-C), 71.6 (13-C), 35.2 (14-C), 43.3 (15-C), 26.9 (16-C), 21.2 (17-C), 14.1 (18-C), 10.3 (19-C), 75.9 (20-C), 165.1 (2-OCO), 170.0, 22.9 (4-OCOCH$_3$), 169.4 (1'-C), 75.5 (2'-C), 55.6 (3'-C), 155.7 (3'-NHCO), 78.9, 28.6 (—C(CH$_3$)$_3$), 137.9 (ph-q-C), 127.9 (ph-o-C), 129.2 (ph-m-C), 128.5 (ph-p-C), 130.5 (OBz-q-C), 130.1 (OBz-o-C), 129.3 (OBz-m-C), 133.9 (OBz-p-C), 172.3 (21-C), 29.3 (22-C), 30.1 (23-C), 170.6 (24-C), 38.7 (26-C), 29.3 (27-C), 23.4 (28-C), 32.1 (29-C), 52.6 (30-C), 174.4 (31-C), 172.0 (34-C), 32.2 (35-C), 28.2 (36-C), 52.8 (37-C), 173.7 (38-C), 172.8 (41-C), 49.3 (42-C), 18.6 (43-C), 165.8 (45-C), 124.0 (46-C), 138.0 (47-C), 133.9 (48-C), 114.4 (d, J=21.4 Hz, 49-C), 162.9 (d, J=242.4 Hz, 50-C), 116.7 (d, J=21.3 Hz, 51-C), 131.4 (d, J=8.5 Hz, 52-C), 124.1 (d, J=2.5 Hz, 53-C).

IR: 3301.8 ($v_{OH}$ and $v_{NH}$), 2969.9, 2932.2 ($v_{-CH}$), 1656.3 ($v_{C=O}$), 1529.6, 1449.4 ($v_{C=C}$), 1367.3, 1245.0, 1159.9, 1069.2 ($\delta_{-CH}$), 981.7, 783.2, 707.7 ($\delta_{=CH}$).

ESI-MS: 1382.83 [M+H]$^+$, 1404.64 [M+Na]$^+$.

HR-MS(TOF): 1382.6118 [M+H]$^+$, 1404.5942 [M+Na]$^+$, $C_{70}H_{88}FN_7O_{21}$.

Example 43

Liquid-Phase Synthesis of Conjugate MDC 408

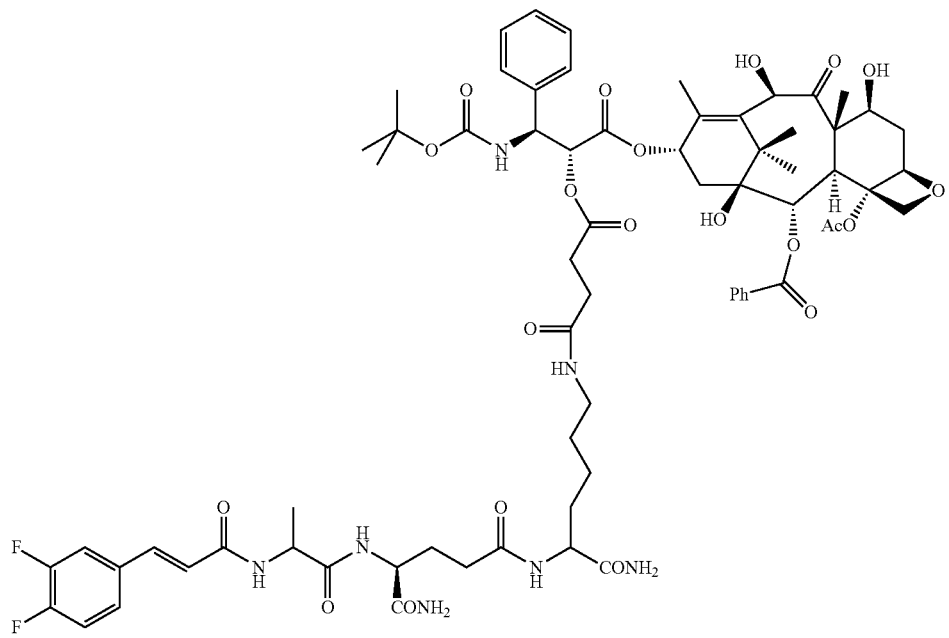

90.7 mg (1.0 eq) docetaxel-2'-O-succinic acid monoester, 11.5 mg (1.0 eq) HOSu and 19.2 mg (1.0 eq) EDC.HCl were dissolved in DMSO, and the mixture was stirred at r.t for 4 hours. 51 mg (1.0 eq) of muramyl dipeptide analogue MDA-208 was sparingly added to the mixture in a few portions, and the pH of the mixture was adjusted to 7~8 with N-methyl morphine. The mixture was continued to stir for 4 hours. After the completion of the reaction, a plenty of water was added to the mixture, and white solids precipitated. The mixture was filtered, and the crude product was obtained. The crude product was purified by ODS column chromatography, and 117.5 mg solid product was obtained through lyophilization. Yield 84%, m.p.=172~173° C.

$^1$H-NMR (500 MHz, DMSO-$d_6$): 4.43 (1H, br.s, 1-OH), 5.41 (1H, d, J=7.0 Hz, 2-H), 3.64 (1H, d, J=7.5 Hz, 3-H), 4.90 (1H, m, 5-H), 1.66 (1H, m, 6-$H_a$), 2.25 (1H, m, 6-$H_b$), 4.02 (1H, m, 7-H), 5.09 (1H, s, 10-H), 5.80 (1H, m, 13-H), 1.64 (1H, m, 14-$H_a$), 1.82 (1H, m, 14-$H_b$), 0.99 (3H, s, 16-H), 1.02 (3H, s, 17-H), 1.70 (3H, s, 18-H), 1.51 (3H, s, 19-H), 4.02 (1H, m, 20-$H_a$), 4.05 (1H, m, 20-$H_b$), 2.25 (3H, s, 4-OCOCH$_3$), 5.09 (1H, m, 2'-H), 5.09 (1H, m, 3'-H), 7.87 (1H, m, 3'-NH), 7.31 (2H, m, ph-o-H), 7.37 (2H, d, J=7.5 Hz, ph-m-H), 7.19 (1H, m, ph-p-H), 7.99 (2H, d, J=7.0 Hz, OBz-o-H), 7.66 (2H, t, J=7.0 Hz, OBz-m-H), 7.73 (1H, m, OBz-p-H), 1.39 (9H, s, —C(CH$_3$)$_3$), 2.62 (2H, m, 22-H), 2.39 (2H, m, 23-H), 7.83 (1H, m, 25-H), 3.01 (2H, br.s, 26-H), 1.25 (2H, m, 27-H), 1.26 (2H, m, 28-H), 1.64 (1H, m, 29-$H_a$), 1.67 (1H, m, 29-$H_b$), 4.13 (1H, m, 30-H), 6.97 (1H, s, 32-$H_a$), 7.31 (1H, s, 32-$H_b$), 7.92 (1H, m, 33-H), 2.16 (2H, m, 35-H), 1.78 (1H, m, 36-$H_a$), 2.00 (1H, m, 36-$H_b$), 4.14 (1H, m, 37-H), 7.11 (1H, s, 39-$H_a$), 7.31 (1H, s, 39-$H_b$), 8.22 (1H, d, J=8.0 Hz, 40-H), 4.40 (1H, m, 42-H), 1.28 (3H, m, 43-H), 8.34 (1H, d, J=7.0 Hz, 44-H), 6.74 (1H, d, J=15.5 Hz, 46-H), 7.38 (1H, d, J=15.5 Hz, 47-H), 7.68 (1H, m, 50-H), 7.45 (1H, m, 52-H), 7.49 (1H, m, 53-H).

$^{13}$C-NMR (125 MHz, DMSO-$d_6$): 77.3 (1-C), 75.3 (2-C), 46.4 (3-C), 80.8 (4-C), 84.2 (5-C), 37.0 (6-C), 71.2 (7-C), 57.4 (8-C), 209.8 (9-C), 74.2 (10-C), 136.5 (11-C), 137.3 (12-C), 71.6 (13-C), 35.2 (14-C), 43.3 (15-C), 26.9 (16-C), 21.2 (17-C), 14.1 (18-C), 10.3 (19-C), 75.9 (20-C), 165.0 (2-OCO), 170.0, 22.9 (4-OCOCH$_3$), 169.4 (1'-C), 75.5 (2'-C), 55.6 (3'-C), 155.7 (3'-NHCO), 79.0, 28.6 (—C(CH$_3$)$_3$), 138.0ph-q-C), 127.9 (ph-o-C), 129.1 (ph-m-C), 128.5 (ph-p-C), 130.5 (OBz-q-C), 130.0 (OBz-o-C), 129.1 (OBz-m-C), 133.9 (OBz-p-C), 172.3 (21-C), 29.3 (22-C), 30.1 (23-C), 170.4 (24-C), 38.7 (26-C), 29.3 (27-C), 23.4 (28-C), 32.1 (29-C), 52.6 (30-C), 174.4 (31-C), 172.0 (34-C), 32.2 (35-C), 28.2 (36-C), 52.8 (37-C), 173.7 (38-C), 172.7 (41-C), 49.3 (42-C), 18.7 (43-C), 165.7 (45-C), 123.8 (s, 46-C), 137.3 (s, 47-C), 133.3 (m, 48-C), 118.6 (d, J=17.1 Hz, 49-C), 151.2 (m, 50-C), 149.3 (dd, J=34.8 and 13.0 Hz, 51-C), 116.7 (d, J=17.6 Hz, 52-C), 125.1 (m, 53-C).

IR: 3308.5 ($v_{OH}$ and $v_{NH}$), 2977.6, 2936.9 ($v_{—CH}$), 1659.6 ($v_{C=O}$), 1517.9, 1452.4 ($v_{C=C}$), 1368.3, 1274.8, 1247.4, 1161.3 ($\delta_{—CH}$), 981.7, 775.8, 707.9 ($\delta_{=CH}$).

ESI-MS: 1400.82 [M+H]$^+$, 1422.63 [M+Na]$^+$.

HR-MS(TOF): 1400.6014 [M+H]$^+$, 1422.5825 [M+Na]$^+$, $C_{70}H_{87}F_2N_7O_{21}$.

Biological Example

Activity Test In Vitro Part

Example 44

In the invention, six compounds, MTC-220, MTC-302, MTC-213, MTC-219, MTC-233 and MDC-400 were sent to the U.S. National Cancer Institute (NCI) for screening their antitumor activity in vitro. The experimental results show that, the 50% growth inhibition (GI$_{50}$) activity of those conjugates in 60 human tumor cell lines was in the same magnitude range as paclitaxel, and the 50% lethal concentration ($LC_{50}$) were more than 10 μM. The experimental results refer to FIGS. 1-12.

In the invention, the compounds, MTC-301, MTC-302, MTC-303, MTC-304, MTC-305, MTC-306, MTC-307, MDC-308, MDC-403, MDC-404, MDC-405. MDC-406, MDC-407 and MDC-408 were screened their antitumor activity in 10 human tumor cell lines. The 50% growth inhibition ($GI_{50}$) activity of those conjugated compounds was in the same magnitude range as paclitaxel or docetaxel. The experimental results refer to FIGS. 13-16.

Biological Evaluation In Vivo

Example 45

The Tumor Growth Inhibition Activity of MTC-220 in Nude Mice Xenograft Models Using Human Breast Cancer Line MDA-MB-231

Experiment Materials and Test Animals:
1. MTC-220, a colorless and clear liquid had the concentration of 1.0 mg/mL, 1.5 mg/mL, 2.0 mg/mL, was repackaged in a sterile condition, and can be used directly, stored at 4° C. Drug administration dose were set as: 10 mg/kg, 15 mg/kg, and 20 mk/kg, drug administration volume was 0.2 mL/20 g.
2. Paclitaxel Injection, the products of Beijing Union Pharmaceutical Factory, Approval Number: H10980069, product lot number: 080704, specifications 5 mL: 30 mg.
3. Taxol+MDA [Peptide MDA(P) 0.54 mg/mL (0.001M)+Taxol (T) 0.9 mg/mL (0.001M)], were prepared by the commission, can be directly used after the repackaging in a sterile condition, stored at 4° C.
4. MDA [Peptide (P) 0.54 mg/mL (0.001M), Example 10], a colorless and clear liquid, was prepared by the commission, can be directly used after the repackaging in a sterile condition, stored at 4° C. Tumor lines: Highly metastatic human breast cancer line MDA-MB-231 were implanted in nude mice, and the tumor-bearing mice were obtained from Crown Bioscience Co. Ltd. (Beijing), and were cultured and preserved by our laboratory.

Animals: BALB/c nu mice, ♀, 4~5 weeks old, were obtained from the Instititute of laboratory animal, Chinese Academy of Medical Science. Certificate NO. SCXK (BeiJing) 2005-0013.

Feeding facilities: Experimental Animal Center, Chinese Academy of Medical Sciences, SPF level Animal Lab, Certificate NO. SYSK (BeiJing) 2004-0001.

Experiment Methods:
The tumor-bearing mice with good tumor growth and good general physical condition were selected and sacrificed. Tumor was isolated in a sterile condition and cut into fragments (diameter for about 2-3 mm) by surgical knife. The fragments were then hypodermically inoculated in posterior axillary of nude mice by means of a trocar. The tumor was grown normally. The mice were divided into groups and administrated drug after 11 days. The length and width of tumor were measured using vernier calipers, and divided into groups by the tumor volume.

The mice were divided into eight groups, each group had 6-8 mice. The groups contained Negative control. Paclitaxel group, were injected paclitaxel injection in dose 24 mg/kg intermittently, three MTC groups, were administrated with MTC-220 in a dose of 10 mg/kg, 15 mg/kg and 20 mg/kg respectively, MDA group; and Taxol+MDA group. The tumors sizes of the above 7 groups mice were similar with the average volume of about 140 $mm^3$. Mice with relatively larger tumor volumes than usual (with an average volume of 340 $mm^3$) were administrated with MTC-220 in a dose of 30 mg/kg (MTC-220 30 mg/kg group). After grouping, all mice were administrated with drug by intraperitoneal injection once a day depends on their body weight.

The day of grouping and administration of drug was defined as D1, the tumors sizes (length and width) and body weights of mice were measured once every three days. The paclitaxel control group was intermittently administered for 4 times, while the MTC-220 with 30 mg/kg group was withdrawn from drug after administration successively for 12 times. Other groups were administered with drugs for 24 times successively. The experiment was completed 24 h after the last administration.

The mice were sacrificed, and tumors were isolated and their weight was measured, and the inhibition rate of tumor growth by drugs were calculated. Statistical significance of the tumor weight, tumor volume and RTV level were evaluated by t-test. Calculation methods and formula were omitted.

Anti-tumor activities were evaluated by Tumor Relative proliferation Rate T/C (%)

Therapeutic effect evaluation standard: T/C (%)>40, was judged as invalid;

T/C (%)≤40, and through statistical evaluation P<0.05, was judged as invalid valid.

Experiment Results:
During the observation of the experiment, the body weight of mice in negative control group gradually increased. The average body weight increased by 3.5 g compared to the beginning of the division. Paclitaxel control group was administrated intermittently, the body weight maintained in the tolerated range of toxic and side effects. The MTC-220 30 mg/kg dose group was administrated 12 times successively in 12 days, and the body weight of mice maintained essentially the same as the that at the beginning of the grouping, but the body weight gradually increased after withdrawal of drug, and at the end of the experiment the body weight increased by 2.6 g compared to the beginning of the grouping. The increase of body weight in MTC-220 30 mg/kg doses group was the same as MTC-220 15 mg/kg dose group which was treated for 24 times (the latter group body weight was increased by 2.7 g), the two groups had similar total administration dose. While the MTC-220 20 mg/kg dose group was administrated successively for 24 days, the body weight of this group increased by 1.9 g, less than the body weight of negative group. The body weight of T (0.9 mg/mL)+P (0.54 mg/mL) group under administration successively was close to the body weight of Paclitaxel group in early stage, but the toxic and side effects appeared gradually during the continued administration, which included abdominal distention, less movement, weight loss, etc. At the twentieth day, ⅔ mice of this group had been died.

The mice tumor growth curve indicated, the tumor growth rate in MDA liquid [P (0.54 mg/mL)] administered group was slower than the tumor growth rate of the negative control group, and the tumor relative proliferation rate (T/C) was 83.5%. The tumor growth was significantly related to the administration dose of MTC-220 10 mg/kg, 15 mg/kg and 20 mg/kg. At the end of experiment, the tumor growth inhibition rate of the three groups were 37.3%, 57.4% and 72.2%, respectively, and tumor relative proliferation rate were 70.0%, 39.5% and 29.4% respectively, wherein the MTC-220 15 mg/kg group and MTC-220 20 mg/kg group were judged as valid.

MTC-220 30 mg/kg group which were administrated successively for 12 times, the total dose was the same as the MTC 15 mg/kg group which were administrated successively for 24 times. Even though the tumor volume of MTC-220 30 mg/kg group was a little bigger at the beginning of the experiment, it became smaller gradually during the administration. The growth rate was also quite slow after withdrawal of drug. At the end of experiment, the tumor growth inhibition activity of MTC-220 30 mg/kg group increased significantly (MTC-220 15 mg/kg group was 57.4%, MTC-220 30 mg/kg group was >87%), and the tumor relative proliferation rate (T/C) decreased significantly (MTC-220 15 mg/kg group was 37.5%, MTC-220 30 mg/kg group was >6.16%). Compared MTC-220 30 mg/kg dose group, which administered successively for 12 times, with MTC-220 20 mg/kg dose group, which was administered successively for 24 times, the amount administered in MTC-220 30 mg/kg group was smaller, but the inhibition rate of MTC-220 30 mg/kg group was higher, the tumor relative proliferation rate (TIC) of MTC-220 30 mg/kg group was also decreased significantly, and the mice physical conditions in MTC-220 30 mg/kg group were better. All above indicated that if the tumor bearing mice were administered with suitable dose, not only the tumor growth can be controlled, but also less dose and shorter treatment is needed, and further the toxic and side effects are decreased.

Experiment conclusion: The inhibition of human breast cancer MDA-MB-231 in tumor bearing nude mice was significant after the mice were injected intraperitonealy with MTC-220 10 mg/kg, 15 mg/kg and 20 mg/kg successively. The growth of MDA-MB-231 tumor line was inhibited significantly, and the inhibition effects were related to the administration dose. The administration effects of 15 mg/kg and 20 mg/kg were judged as valid in this lot experiment.

MTC-220 30 mg/kg group were administrated successively for 12 times, the inhibition of the tumor growth of MDA-MB-231 was significant. The tumor grew slowly after withdrawal of drug, and the physical condition recovered well. The treatment period was shorter, and the effect of tumor inhibition was more significant compared to the MTC-220 15 mg/kg group. The experiment results refer to FIGS. 11-14 and Table 1-2.

TABLE 1

The effect of MTC-220 in MDA-MB-231 xenograft tumor nude mice (1)

| Group | Mice NO. Beginning | Mice NO. End | Body weight (g) Beginning | Body weight (g) End | Tumor weight (g) | TGI (%) |
|---|---|---|---|---|---|---|
| NC | 7 | 7 | 19.0 ± 1.14 | 22.5 ± 1.92 | 2.84 ± 1.205 | |
| Paclitaxel 24 mg/kg × 4 | 8 | 8 | 17.7 ± 1.50 | 19.5 ± 0.94 | 0.43 ± 0.416*** | 84.9 |
| MTC-220 10 mg/kg × 24 | 6 | 6 | 17.4 ± 1.47 | 20.6 ± 1.64 | 1.78 ± 1.016 | 37.3 |
| MTC-220 15 mg/kg × 24 | 6 | 6 | 17.9 ± 0.88 | 20.6 ± 0.91 | 1.21 ± 0.813* | 57.4 |
| MTC-220 20 mg/kg × 24 | 7 | 7 | 17.0 ± 1.11 | 18.9 ± 1.58 | 0.79 ± 0.654** | 72.2 |
| MTC-220 30 mg/kg × 12 | 6 | 6 | 17.5 ± 1.09 | 20.1 ± 0.98 | 0.37 ± 0.413*** | >87.0 |
| Taxol + MDA × 24 | 6 | 2 | 17.4 ± 1.09 | 19.2 ± 0.05 | 0.77 ± 0.440 | 72.9 |
| MDA × 24 | 6 | 6 | 18.5 ± 1.05 | 21.4 ± 0.90 | 1.98 ± 0.744 | 30.3 |

*P < 0.05, Compared to NC.
**P < 0.01, Compared to NC.
***P < 0.001, Compared to NC.
(TGI, Tumor Growth Inhibition; NC, Negative Control)

TABLE 2

The effect of MTC-220 in MDA-MB-231 xenograft tumor nude mice (2)

| Group | Tumor Volume (mm$^3$) Beginning | Tumor Volume (mm$^3$) End | RTV | T/C (%) |
|---|---|---|---|---|
| NC | 138 ± 48.4 | 2388 ± 1073.6 | 18.03 ± 6.108 | |
| Paclitaxel 24 mg/kg × 4 | 133 ± 39.8 | 422 ± 404.6 | 3.18 ± 2.735*** | 17.64 |
| MTC-220 10 mg/kg × 24 | 135 ± 70.6 | 1655 ± 929.4 | 12.62 ± 5.924 | 70.00 |
| MTC-220 15 mg/kg × 24 | 148 ± 80.5 | 967 ± 590.4 | 7.12 ± 4.064** | 39.49 |
| MTC-220 20 mg/kg × 24 | 133 ± 57.6 | 642 ± 482.3 | 4.58 ± 2.456*** | 25.40 |
| MTC-220 30 mg/kg × 12 | 340 ± 58.4 | 391 ± 480.5 | 1.11 ± 1.366*** | 6.16 |
| Taxol + MDA × 24 | 136 ± 40.7 | 1093 ± 343.3 | 11.70 ± 0.299* | 64.9 |
| MDA × 24 | 141 ± 61.1 | 1898 ± 775.4 | 15.06 ± 5.292 | 83.5 |

*P < 0.05, Compared to NC.
**P < 0.01, Compared to NC.
***P < 0.001, Compared to NC.
(TGI, Tumor Growth Inhibition; NC, Negative Control)

Example 46

The Growth Inhibition of MTC-220 in Human Lung Cancer H460 Xenograft Tumor Nude Mice Experiment Materials and Test Animals:
MTC-220: It was prepared by the commission, three concentrations of 1.0 mg % mL, 1.5 mg/mL and 2.0 mg/mL, was colorless and clear liquid, was dispensed in a sterile condition and can be used directly, stored at 4° C.
Paclitaxel Injection: the product of Beijing Union Pharmaceutical Factory, Approval Number: H10980069, product lot number: 080704, specifications 5 mL: 30 mg. Solvent Vehicle: (the physiological saline solution mixture contained 5% DMSO and 5% polyoxyethylene alcohol castor oil (Cremphor EL)), was dispensed in a sterile condition and can be used directly, stored at 4° C.
Tumor lines: Human lung cancer H460 cell lines were obtained from ATCC, and was cultured and preserved in the Lab. Through cell culture in vitro, the tumor was inoculated on nude mice, the tumor grew and passaged for the experiment use.
Animals: BALB/c nude mice, ♀, 4~5 weeks old, were obtained from the Experimental Lab, Chinese Academy of Medical Science, Certificate NO. SCXK (BeiJing) 2005-0013.
Feeding facilities: Experimental Animal Center SPF level Animal Lab, Chinese Academy of Medical Sciences, Certificate NO. SYSK (Beijing) 2004-0001.
Experiment Method:
The tumor-bearing mice with good tumor growth and good general physical condition were selected and sacrificed. Tumor was isolated in a sterile condition and cut into fragments (diameter for about 2-3 mm) by surgical knife. The fragments were then hypodermically inoculated in posterior axillary of nude mice by means of a trocar.
After the tumors grew naturally for eight days, the average volume of tumors reaches 130 mm$^3$. The length and width of tumor was measured using vernier calipers, and divided into groups by the tumor volume.
The mice were divided into five groups for observation, each groups had eight mice. The negative control group was administered with solvent vehicle, and the other three dose groups were administered with MTC-220 5 mg/kg, 10 mg/kg, 20 mg/kg, respectively. The positive control group was administered with paclitaxel injection in a dose of 24 mg/kg once every three days. Respective drug was administrated for each group from the grouping day.
The grouping day was defined as D1, the administration of the paclitaxel control group was administered intermittently for 4 times, while MTC-220 groups were administered for 25 times successively. The experiment was terminated 24 hours after the last administration.
During the experimentation, the tumors sizes (length and width) and body weights of mice were measured once every three days. The tumor volume (TV) and relative tumor volume (RTV) were calculated according to the method for references, and the tumor volume growth tendency chart was plotted.
At the end of the experiment, the mice were sacrificed. Tumors were removed and weighed, and the inhibition rate of the tumor growth by drugs was calculated. Statistical significance of the tumor weight, tumor volume and RTV level were evaluated by t-test.
Calculation formula:

$$\text{Tumor growth inhibition}(\%) = \frac{C-T}{C} \times 100\%$$

(C, average tumor weight of control group; T, average tumor weight of administrated group)

Tumor Volume (TV)=length×width$^2$/2.
Relative Tumor Volume (RTV) formula: Vt/Vo
(Vo is the volume of TV at the beginning of the grouping, and Vt is the volume of TV at measure time)
Anti-tumor activities were evaluated by Tumor Relative proliferation Rate T/C (%)

$$T/C(\%) = \frac{\text{Administrated Group } (T) \; RTV}{\text{Negative control group } (C) \; RTV} \times 100\%$$

Therapeutic effect evaluation standard: T/C (%)>40, was judged as invalid;
T/C (%)≤40, and through statistical evaluation P<0.05, was judged as valid.
Experiment Results:
The observed results demonstrated that, during the 25 days, the body weight of negative control group gradually increased, and general status had no change. H460 tumor grew faster, compared with the tumor volume at the beginning of the grouping, the average of negative control relative tumor volume was 33.3 at the end of the experiment.
Positive control group which was administered with paclitaxel in dose of 24 mg/kg twice a day, indicated its inhibition of the growth of H460 tumor. The tumor growth inhibition rate gradually increased with the increase of administration times. Compared with negative control group the tumor growth inhibition rate was 65% after the fourth administration. The therapeutic effects maintained for one week after withdrawal of drug, and decreased gradually thereafter. At the end of the experiment, the statistics results indicated the inhibition rate of tumor weight was 61%, and the tumor relative proliferation rate (T/C) was 35.6%. The therapeutic effect of the positive control group was better than the negative control group. It was also observed in the experiment that, after the administration with paclitaxel in the dose of 24 mg/kg twice intermittently, the mice started losing weight and the weight lost gradually by 2 compared with the average weight at the beginning of grouping. The body weight started to recover one week after withdrawal drug.
Twenty days before the administration, the mouse weight was essentially the same between the negative control group and two groups which were treated with MTC-200 10 mg/kg and 5 mg/kg, respectively. The body weight of the two treated groups decreased somewhat compared to the negative control group during the continued administration. After 25 days of the successive administration with a dose of MTC-220 5 mg/kg, the growth rate of tumor volume was not significantly different compared to that of the negative control. After 2 weeks of the successive administration with a dose of 10 mg/kg, the measured result of H460 tumor volume was different from that of the negative control. At the end of the experiment, the tumor volume inhibition of 10 mg/kg dose group was 18.8%, and the tumor weight inhibition rate was 17.3%.
After 10 days of treatment with MTC-220 in a dose of 20 mg/kg, the measured result of tumor volume was different from that of the negative control group. Tumor grew slowly during the continued administration, and the inhibition of tumor growth gradually increased. Until the end of experiment, the inhibition of tumor weight was 52.9%, and the tumor relative proliferation Rate (T/C) was 50.1%, it was significant in statistics compared with the negative control group. Experiment results refer to FIGS. 15-16 and table 3-4.

TABLE 3

MTC-220 effects H460 tumor growth inhibition (1)

| Group | Mice NO. Beginning | Mice NO. End | Body weight (g) Beginning | Body weight (g) End | Tumor weight (g) | TGI (%) |
|---|---|---|---|---|---|---|
| NC | 8 | 8 | 18.3 ± 0.71 | 22.6 ± 1.30 | 2.98 ± 0.626 | |
| MTC-220 5 mg/kg × 25 | 8 | 8 | 18.0 ± 0.95 | 21.9 ± 1.10 | 2.91 ± 0.695 | 2.15 |
| MTC-220 10 mg/kg × 25 | 8 | 8 | 18.2 ± 0.70 | 21.4 ± 1.15 | 2.46 ± 0.624 | 17.3 |
| MTC-220 20 mg/kg × 25 | 8 | 6 | 17.8 ± 1.10 | 18.9 ± 2.49 | 1.40 ± 0.466** | 52.9 |
| Paclitaxel injection 24 mg/kg × 4 | 8 | 8 | 18.9 ± 1.28 | 18.6 ± 1.41 | 1.16 ± 0.410** | 61.0 |

**$P < 0.05$, compared to negative group.
(TGI, Tumor Growth Inhibition; NC, Negative Control)

TABLE 4

MTC-220 effects H460 tumor growth inhibition (2)

| Group | Tumor volume (mm³) Beginning | Tumor volume (mm³) End | RTV | T/C (%) |
|---|---|---|---|---|
| Negative control | 133 ± 39.1 | 4032 ± 751.0 | 33.3 ± 13.21 | |
| MTC-220 5 mg/kg × 25 | 125 ± 36.8 | 3737 ± 591.0 | 32.0 ± 8.27 | 96.2 |
| MTC-220 10 mg/kg × 25 | 125 ± 43.0 | 3274 ± 797.0 | 27.7 ± 6.81 | 83.1 |
| MTC-220 20 mg/kg × 25 | 123 ± 44.6 | 1963 ± 641.9 | 16.7 ± 9.93** | 50.1 |
| Paclitaxel injection 24 mg/kg × 4 | 130 ± 36.7 | 1583 ± 507.2 | 11.9 ± 3.16** | 35.6 |

**$P < 0.05$, compared to negative group
(RTV, Relative Tumor Volume)

Experiment result: Human lung tumor H460 bearing mice were injected intraperitoneally by the successive administration with MTC-220 in dose of 5 mg/kg, 10 mg/kg, 20 mg/kg for 25 days respectively. The MTC sample inhibited the growth of H460 tumor, and the inhibition effects of anti-tumor were related to the drug dosage. At the end of experiment, the inhibition of tumor weight of the 20 mg/kg dose group was 52.9%, relative tumor proliferation rate was 50.1%, they were significantly different in statistics compared with them of the negative group.

Example 47

The Screening Results of MTC-220 in Xenograft Tumor Nude Mice Using the Sensitive Tumor Lines Experiment Purpose: To test the effect of MTC-220 in xenograft tumor nude mice using breast cancer, lung cancer and ovarian cancer tumor cell lines in vivo. The tumor lines which were significantly sensitive to MTC-220 was screened, and the response of nude mice during the successive administration was observed.

Experiment Animals: BALB/c nu mice were obtained from the institute of Laboratory Animal, Chinese Academy of Medical Science. Certificate NO. SCXK (BeiJing) 2005-0013.

Cell lines: The tumor cell lines were passaged and cultured by our Lab, some of them was obtained from ATCC.

The tumor cell lines included: Human breast cancer MX-1 and MCF-7.

Human ovarian cancer A2780, and clear Human ovarian cell cancer ES-2,

Human lung cancer H1975 and A549.

Experiment Method:

1. The mice were only divided into negative group and MTC-220 administration group.

2. The method was essentially the same as Example 52 and Example 53, which is not described in detail here.

3. The administration dose and treatment progress was determined based from the preliminary experiments, which had solid effects and the shortest treatment period—the dose of 30 mg/kg/day, and the administration duration time of every lot experiment was not more than 12 days.

Experiment results (1): After the administration of MTC-220, the MCF-7 tumor of mice became smaller. At the tenth administration, the tumor volume was very small, then drug was withdrawn and the MCF-7 tumor of mice was under observation. After another week, the tumor of the group disappeared one after another. There was no tumor discovered during the following three weeks of the continued observation. Only the breast cancer MCF-7 tumor grew slowly. Fifty days after inoculation, the tumor volume of negative group was no more than 600 mm. The observation was terminated because the experiment result was clear.

Figure 17:
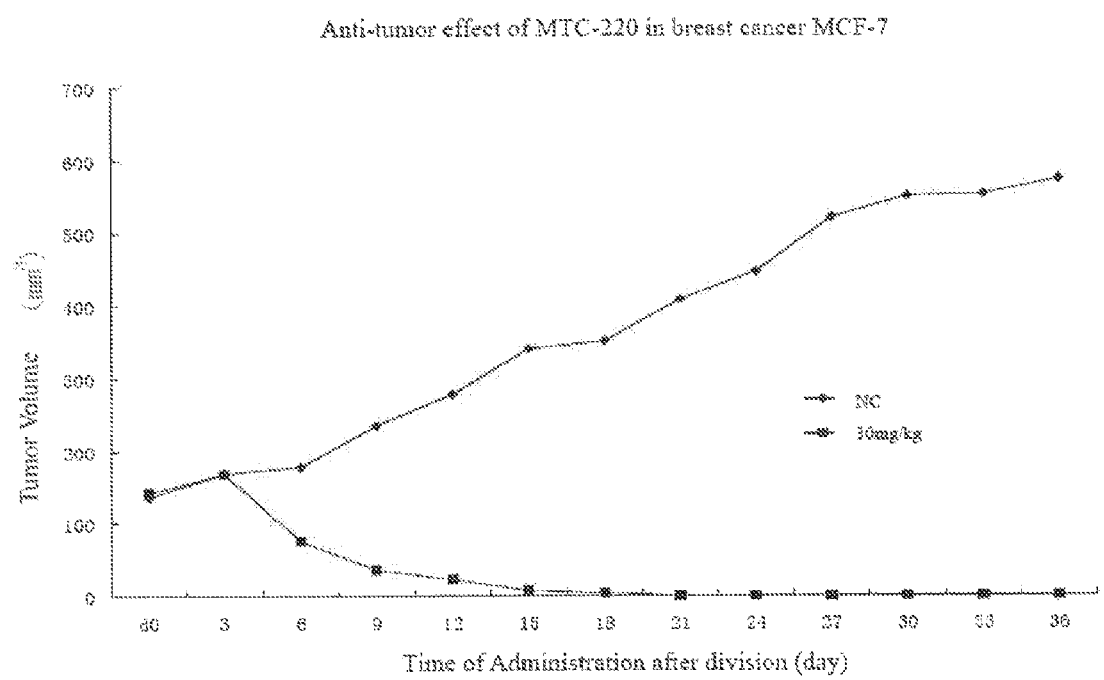
FIG. 17 The growth inhibition of MTC-220 in MCF-7 tumor bearing mice.
Figure 18:
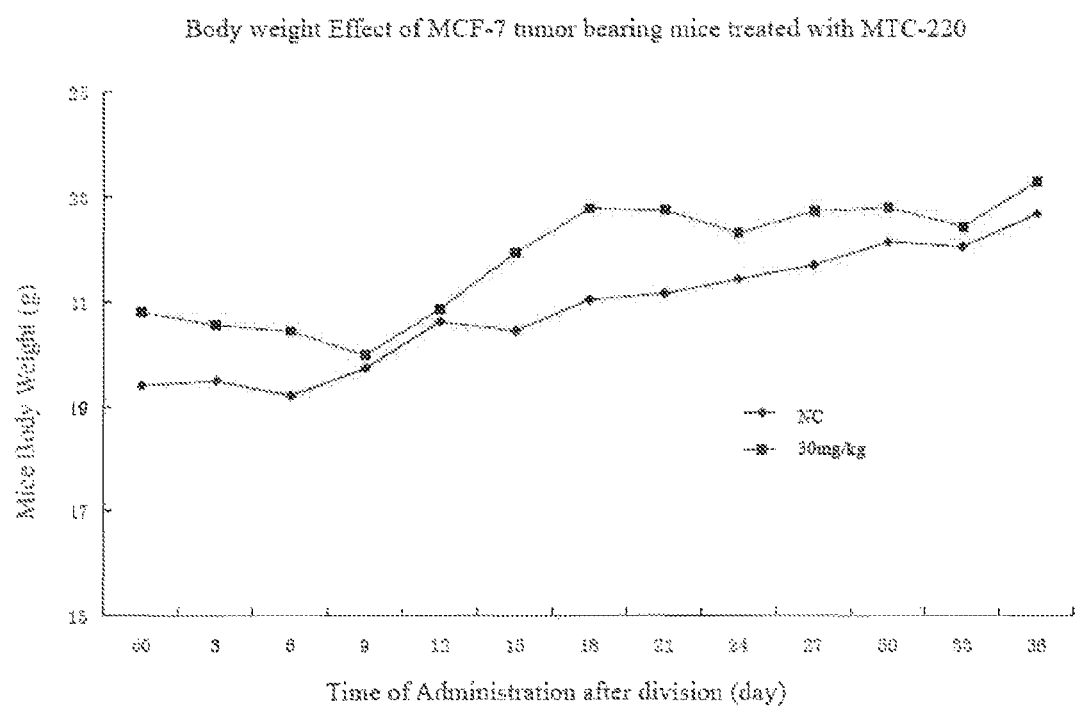
FIG. 18 The effect on body weight of MTC-220 in MCF-7 tumor bearing mice.

The change in body weight can be found in the Figures, and the drug had certain effect on the body weight, the body weight had a tendency of decrease during the administration. The body weight increased after drug withdrawal, and the change was essentially parallel as negative control group. Experiment results refer to FIGS. 17-18 and Table 5-6.

TABLE 5

The body weight at the beginning and end of the experiment,
and the MCF-7 tumor weight at the end of the experiment (1)

| Group | Mice NO. Beginning | End | Body weight (g) Beginning | End | Tumor Weight (g) | TGI (%) |
|---|---|---|---|---|---|---|
| NC | 6 | 5 | 19.4 ± 1.72 | 22.7 ± 1.21 | 0.558 ± 0.275 | |
| MTC-220 30 mg/kg × 12 | 6 | 6 | 20.8 ± 1.14 | 23.3 ± 1.22 | 0** | 100 |

**P < 0.05
(TGI, Tumor Growth Inhibition; NC, Negative Control)

TABLE 6

The MCF-7 tumor volume at the beginning
and end of the experiment (2)

| Group | Tumor volume (mm³) Beginning | End | RTV | T/C (%) |
|---|---|---|---|---|
| NC | 136 ± 73.1 | 573 ± 286.4 | 5.29 ± 1.432 | |
| MTC-220 30 mg/kg × 12 | 142 ± 73.5 | 0 | 0** | 0 |

**P < 0.05;
(RTV, Relative Tumor volume; NC, Negative Control)

Experiment results (2): During the administration of MTC-220, A549 tumor became smaller and smaller, but didn't disappear. One week after withdrawal of drug, the tumor of one mouse disappeared. Within two weeks after withdrawal of drug, the average volume of MTC-220 administration group was maintained at the level at the time of drug withdrawal, it didn't increase.

Figure 19:
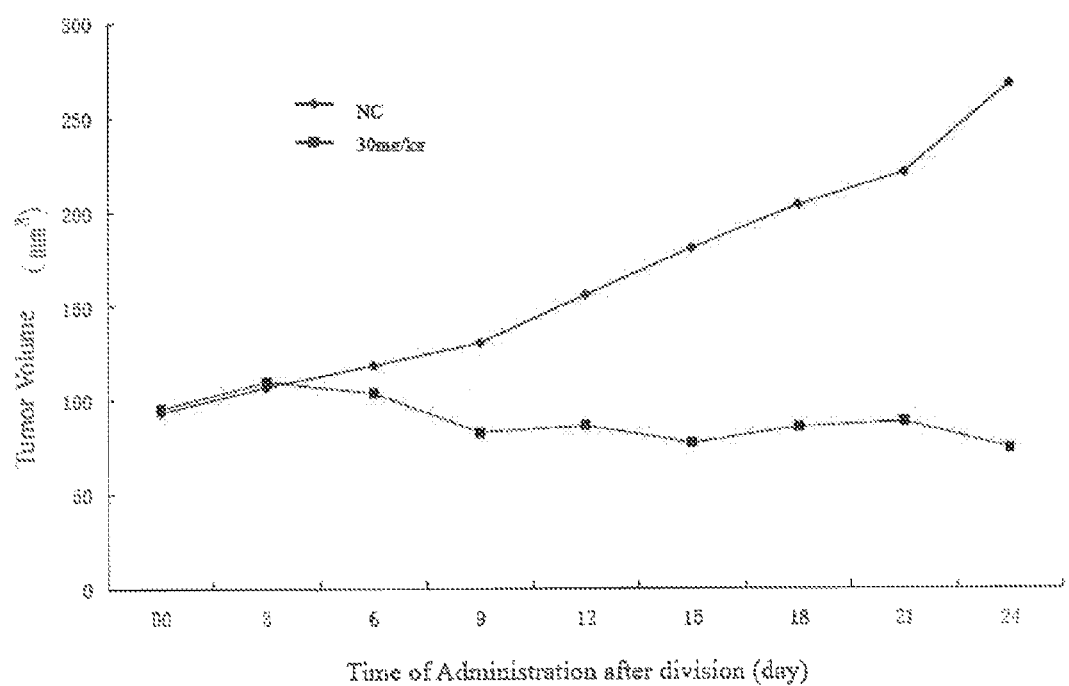
FIG. 19 The growth inhibition of MTC-220 in A549 tumor bearing mice.
Figure 20:
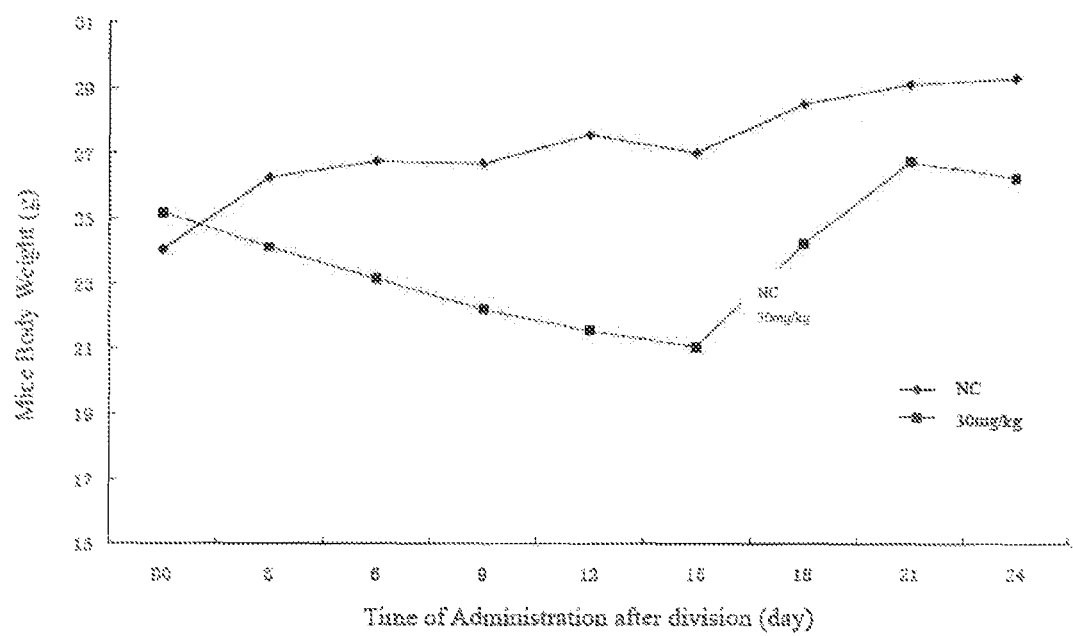
FIG. 20 The effect on body weight of MTC-220 in A549 tumor bearing mice.

The change of body weight was shown in the Figures, and the drug had an observable effect on the body weight, the body weight decreased continuously during the administration. The body weight kept decreasing within several days after drug withdrawal, one mouse died one week after drug withdrawal, and the body weight of other mice recovered gradually. Experiment results were shown FIGS. 19-20 and Table 7-8.

TABLE 7

The body weight at the beginning and end of the experiment and
the tumor weight of A549 at the end of the experiment (1)

| Group | Mice No. Beginning | End | Body weight (g) Beginning | End | Tumor weight (g) | TGI (%) |
|---|---|---|---|---|---|---|
| NC | 6 | 6 | 24.1 ± 1.90 | 29.3 ± 1.82 | 0.31 ± 0.100 | |
| MTC-220 30 mg/kg × 12 | 6 | 5 | 25.2 ± 1.31 | 26.3 ± 1.51 | 0.062 ± 0.041** | 79.9 |

**P < 0.05
(TGI, Tumor Growth Inhibition; NC, Negative Control)

TABLE 8

The tumor volume of A549 at the beginning
and end of the experiment (2)

| Group | Tumor volume (mm³) Beginning | End | RTV | T/C (%) |
|---|---|---|---|---|
| NC | 93 ± 29.5 | 268 ± 100.5 | 2.87 ± 0.562 | |
| MTC-220 30 mg/kg × 12 | 95 ± 27.7 | 74 ± 55.2 | 0.67 ± 0.411** | 23.3** |

**P < 0.05;
(RTV, Relative Tumor volume; NC, Negative Control)

Figure 21:
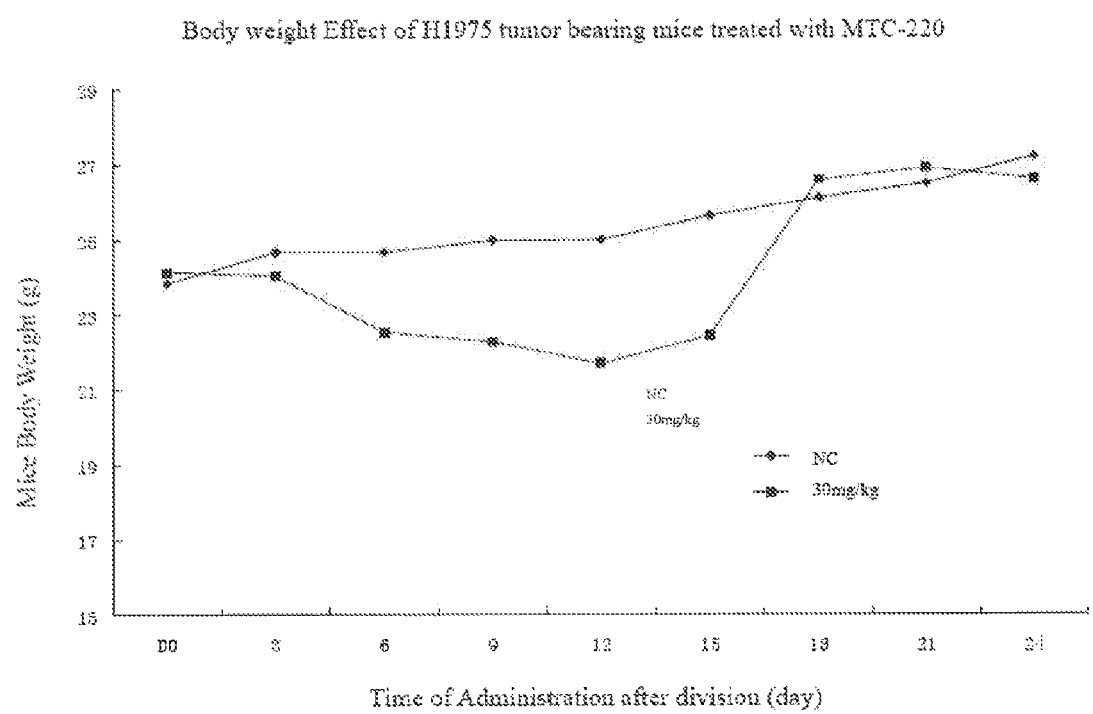
FIG. 21 The effect on body weight of MTC-220 in H1975 tumor bearing mice.
Figure 22:
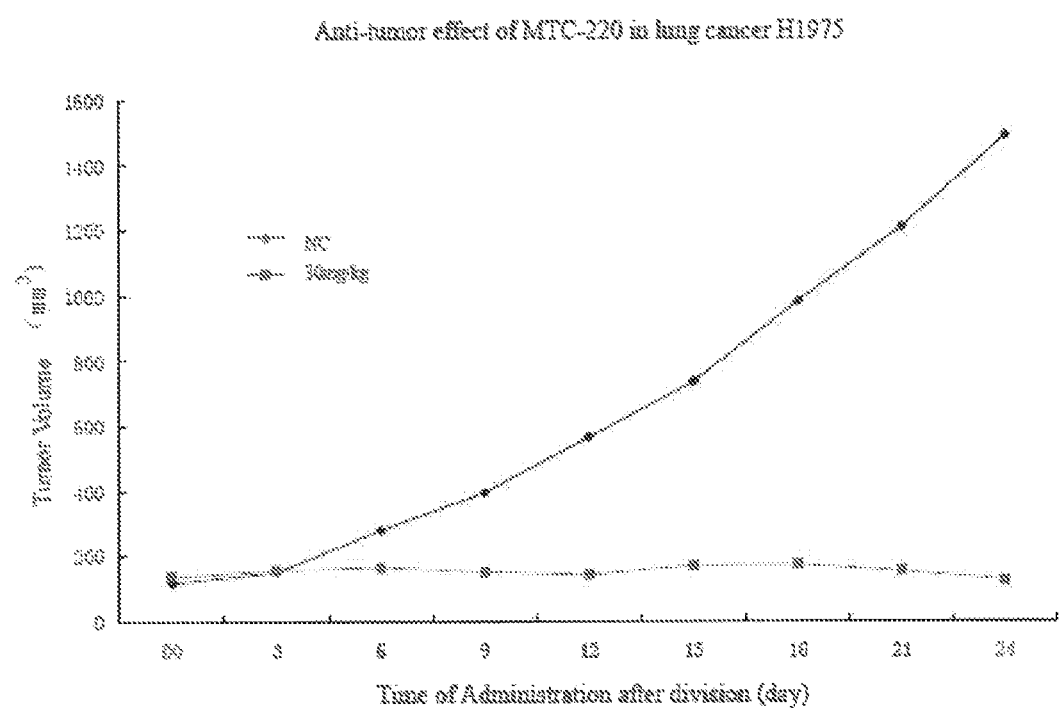
FIG. 22 The growth inhibition of MTC-220 in H1975 tumor bearing mice.

Experiment results (3): The MTC-220 administration significantly inhibited H1975 tumor growth of. During the administration, the tumor volume of treated group became smaller and smaller, and then the tumor in some mice disappeared. Experiment results were shown in FIGS. 21-22, and Table 9-10.

TABLE 9

The tumor weight of H1975 at the beginning and end of the experiment (1)

| Group | Mice NO. Beginning | Mice NO. End | Body weight (g) Beginning | Body weight (g) End | Tumor weight (g) | TGI (%) |
|---|---|---|---|---|---|---|
| NC | 7 | 7 | 23.8 ± 1.43 | 27.2 ± 1.23 | 1.91 ± 0.909 | |
| MTC-220 30 mg/kg × 12 | 7 | 5 | 24.1 ± 1.20 | 26.6 ± 0.76 | 0.13 ± 0.103** | 93.1 |

**$P < 0.05$
(TGI, Tumor Growth Inhibition; NC, Negative Control)

TABLE 10

The experiment beginning and end H1975 tumor volume (2)

| Group | Tumor volume (mm³) Beginning | Tumor volume (mm³) End | RTV | T/C (%) |
|---|---|---|---|---|
| NC | 117 ± 60.0 | 1490 ± 621.2 | 13.08 ± 2.541 | |
| MTC-220 30 mg/kg × 12 | 135 ± 50.6 | 127 ± 106.1 | 0.66 ± 0.464** | 5.0 |

**$P < 0.05$;
(TGI, Relative Tumor volume; NC, Negative Control)

The conclusion of screening MTC-220 on tumor:

MTC-220 was applied on human breast cancer, lung cancer, ovarian cancer of xenograft tumor nude mice, the screening results of preliminary experiments indicated, mice injected intraperitoneally with MTC-220 in the dose of 30 mg/kg for 10~12 times demonstrated that the MTC samples had inhibition effects on the growth of the selected tumor with different degrees in the screening experiment.

It was observed that from the experiment, the inhibition of MTC-220 on the growth of breast cancer MX-1 was weak, the inhibition of MTC-220 on ovarian cancer A2780 and ES-2 tumor was at certain degree, but didn't attain the valid standard. MTC-220 demonstrated significant inhibition effects on breast cancer MCF-7, lung cancer A549 and H1975 tumor. The observed result indicated that, in MTC-220 sensitive tumor lines, the tumor volume of bearing mice became smaller during administration, after drug withdrawal the tumor volume kept decreasing, and the tumors in some mice disappeared. At the end of the experiment, the inhibition of A549 and H1975 tumor growth were above 80%, their tumor relative proliferation rates were below 30%, which were significantly statistically different compared with the negative control group. The MTC-220 inhibited MCF-7 tumor growth significantly, and the tumor of treated mice group disappeared after successive administration for 10 times.

Conclusion: MTC-220 inhibited breast cancer and lung cancer significantly, it is most sensitive to the tumor lines of MDA-MB-231, MCF-7, H460, H1975 and A549.

Example 48

Anti-Natural Metastasis Effect of MTC-220 on Breast Cancer in Mice

Mice breast cancer cell line (4T1, ATCC CRL2539) was a generous gift from Prof. Wei Liang of the Institute of biophysics, Chinese Academy of Sciences. The cell was cultured in the 1640 medium (Gibco) containing 10% fetal bovine serum (FBS), 1% glutamine and 1% penicillin.

4T1 cells in logarithmic phase were collected and the concentration was adjusted to $2 \times 10^6$/mL. 4T1 tumors were introduced in female BALB/c mice by injecting subcutaneously into the fourth fat pad area of the right abdominal mammary gland with the dose of $2 \times 10^5$/0.1 mL. Five days after the implantation of 4T1 tumor cells, the mice were divided into five groups randomly, each group had eight mice, and the mice were respectivelyly received intraperitoneal administration of paclitaxel (3 mg/kg), MTC-220 (2.5 mg/kg, 5 mg/kg, 10 mg/kg) or control vehicle once daily. From the 9th day after implantation, tumor growth was measured every 2 days with vernier calipers for determining the long diameter and short diameter of tumor. Tumor volume was calculated by the formula (½)×long diameter×short diameter². Drug was withdrawn on the twenty-eight days after the implantation, all mice were then sacrificed and the body weight were measured. The tumors, spleen and lung were removed and weighed. The lungs were fixed in Bouin's fixative for 24 h. The numbers of lung metastasis nodule were counted, the statistics was evaluated using Mann-Whitney U test.

Figure 23:
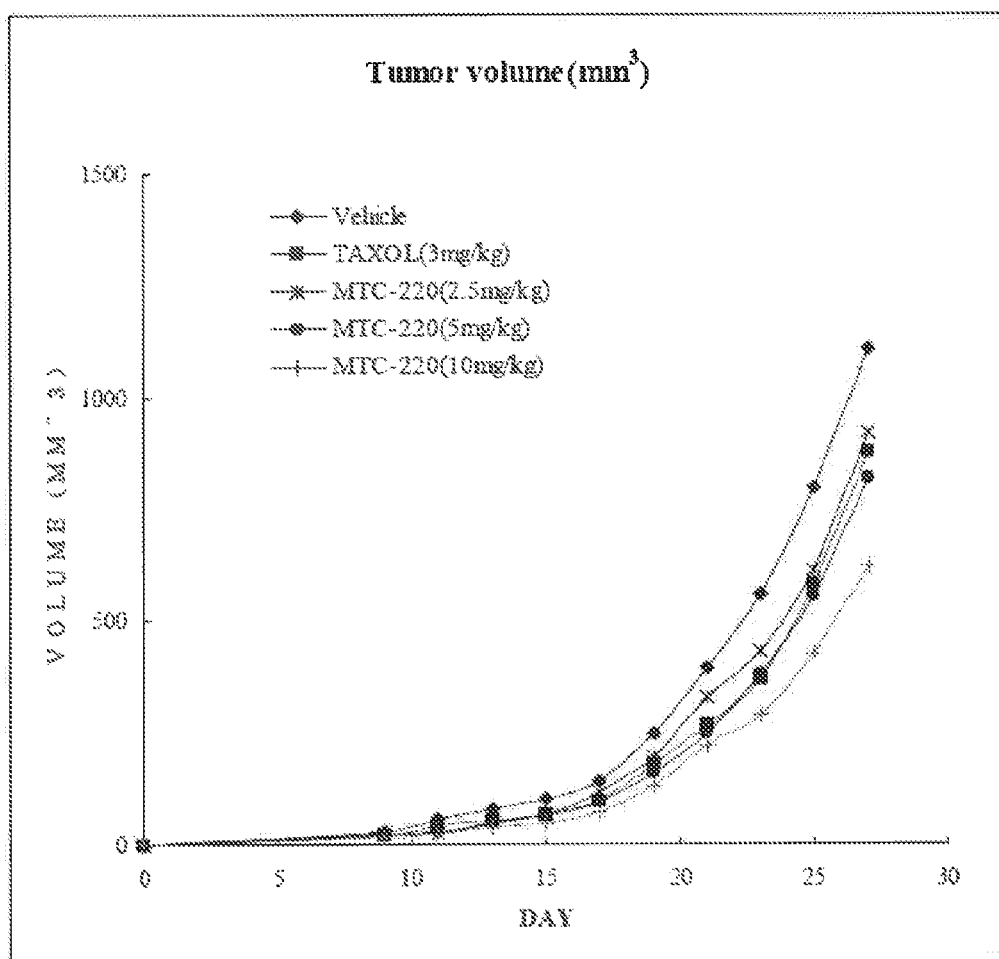
FIG. 23 The growth inhibition of MTC-220 in breast cancer mice (1).
Figure 24:
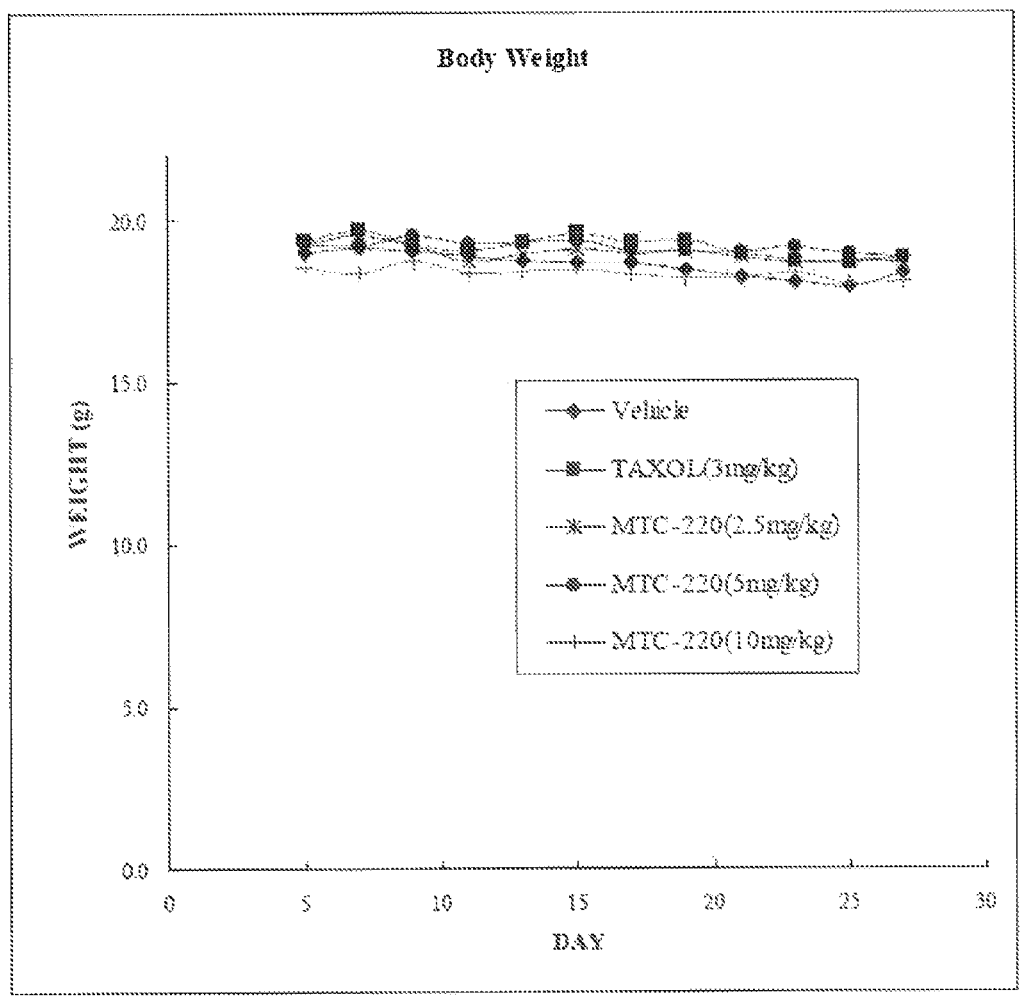
FIG. 24 The effect on body weight of MTC-220 in breast cancer mice (2).
Figure 25:
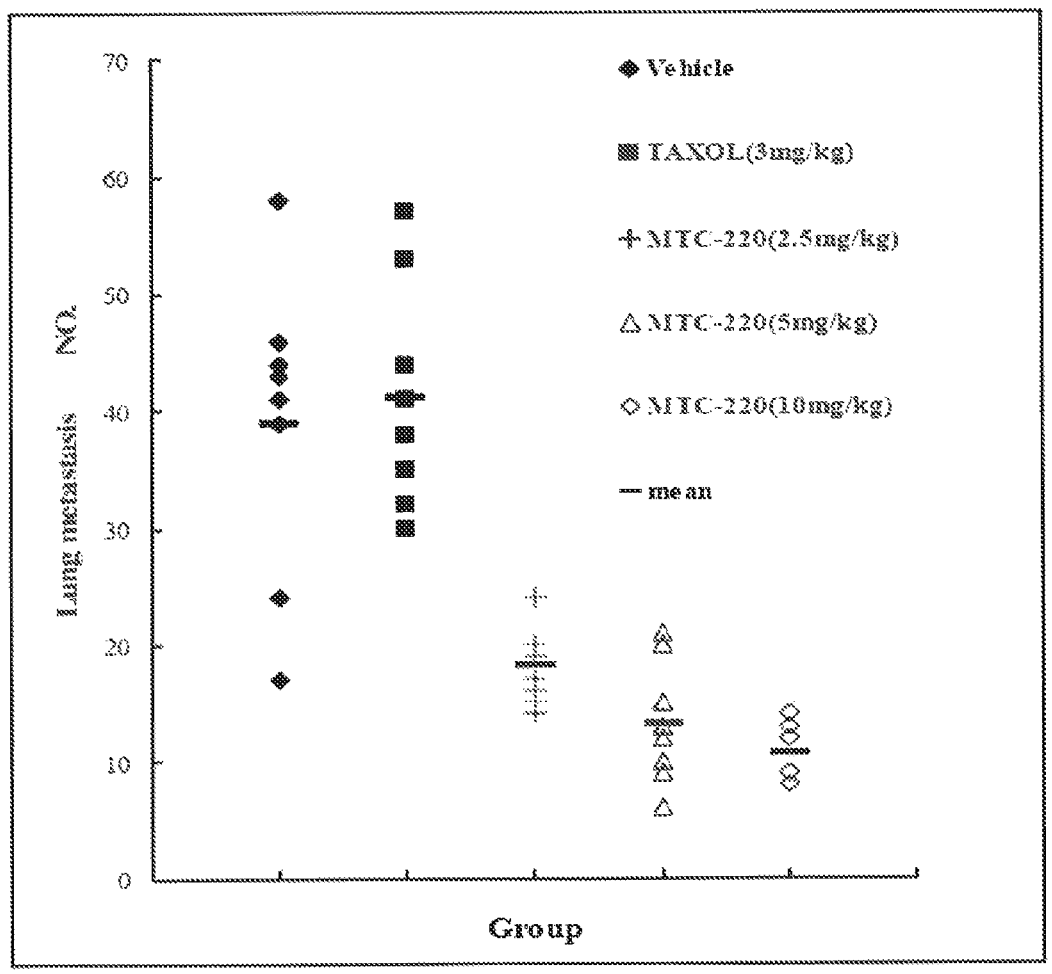
FIG. 25 Anti-tumor natural metastasis activities of MTC-220 in breast cancer mice (3).

The results indicated that, MTC-220 significantly decreased the lung metastasis nodule numbers of 4T1 mice with statistical significance ($p < 0.01$) compared to vehicle control group, and the result depended on the administration dosage. There was no significant improvement of lung metastasis nodule in the Taxol group. MTC-220 and Taxol both significantly inhibited the growth of tumor compared to vehicle control group. During the observation of the experiment, there was no toxic and side effects of MTC-220 observed. Experiment results were shown in FIGS. 23-25 and Table 11.

TABLE 11

MTC-220 Anti-natural metastasis activities of mice breast cancer

| Group | Tumor weight (g) | Lung weight (mg) | Lung metastasis nodule counts |
|---|---|---|---|
| Vehicle | 1.08 ± 0.3 | 163 ± 11 | 39 ± 13 |
| TAXOL (3 mg/kg) | 0.80* ± 0.2 | 190 ± 49 | 41.2 ± 9 |
| MTC-220 (2.5 mg/kg) | 0.84* ± 0.2 | 153 ± 18 | 18.1**△△▽▽ ± 3 |
| MTC-220 (5.0 mg/kg) | 0.77* ± 0.2 | 160 ± 15 | 13.3**△△▽▽ ± 5 |
| MTC-220 (10 mg/kg) | 0.71** ± 0.2 | 147*△▽ ± 17 | 10.6**△△▽▽ ± 3 |

Compared to vehicle control group:
**$P < 0.01$,
*$P < 0.05$;
Compared to Taxol group:
△△$P < 0.01$,
△$P < 0.05$;

Example 49

Anti-Natural Metastasis Effect of MTC-220 on Lung Cancer in Mice

C57Bl/6 mice with lewis lung cancer were sacrificed and the tumor was removed. The tumor cell suspension ($5 \times 10^6$ cell/mL) was prepared in a sterile condition. The suspension (0.2 mL/mice, 1×10$^6$ tumor cell) was inoculated subcutaneously into the axillary of 24 C57Bl/6 mice. Three days after the implantation, the mice were divided into three groups randomly, each group had eight mice, and the mice separately received intraperitoneally administration of paclitaxel (6 mg/kg), MTC-220 (10 mg/kg), or control vehicle once daily. From the 7th day after the implantation, the long diameter and short diameter of tumor was measured every 2 days. Tumor volume was calculated by the formula (½)×long diameter× short diameter$^2$. Drug was withdrawn on the eighteenth day after the implantation. All mice were then sacrificed and the body weight was measured. The tumors, spleen and lung were removed and weighed. The lungs were fixed in Bouin's fixative for 24 h. The numbers of lung metastasis nodule were counted, and the statistics was evaluated by Mann-Whitney U test.

Figure 26:
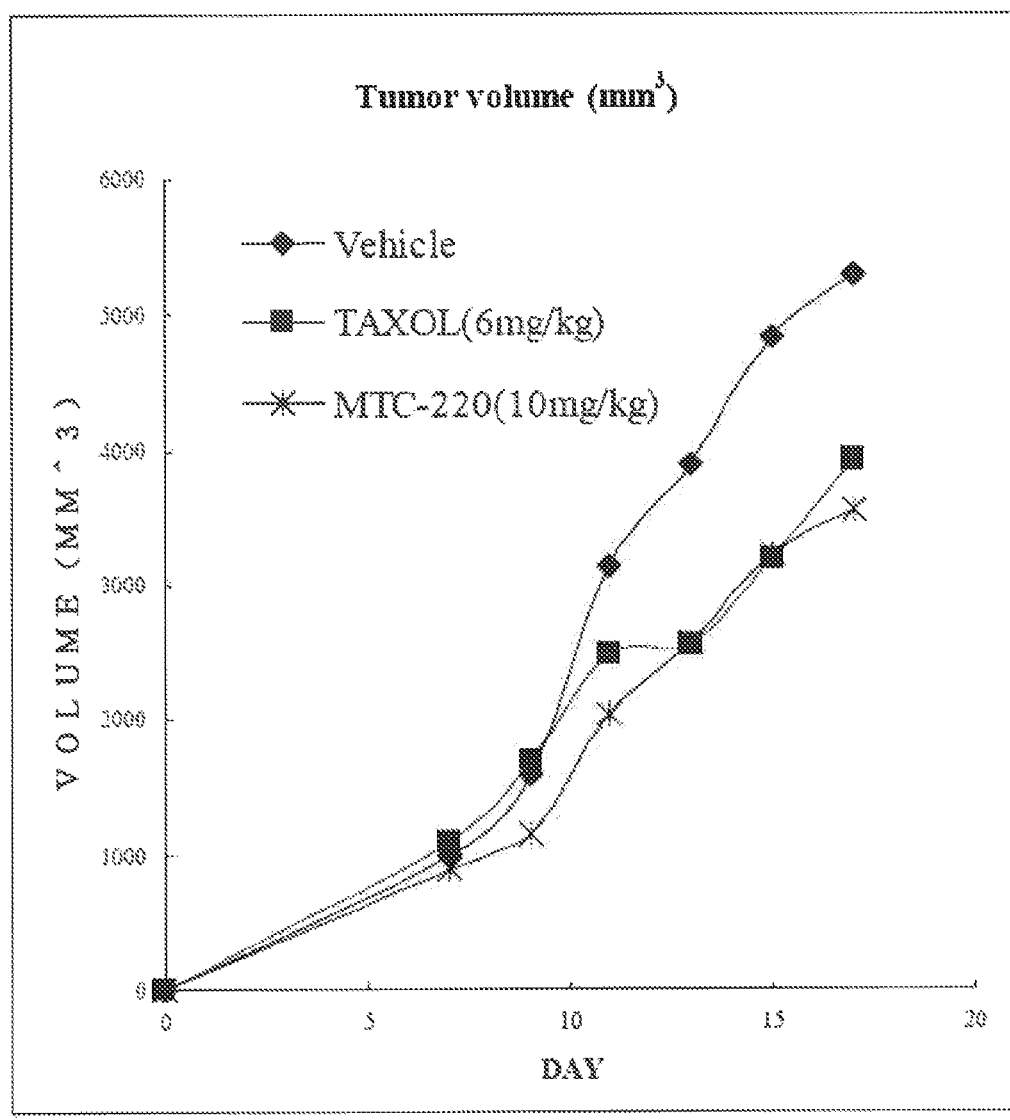
FIG. 26 The growth inhibition activity of MTC-220 in Lewis lung cancer mice (1).
Figure 27:
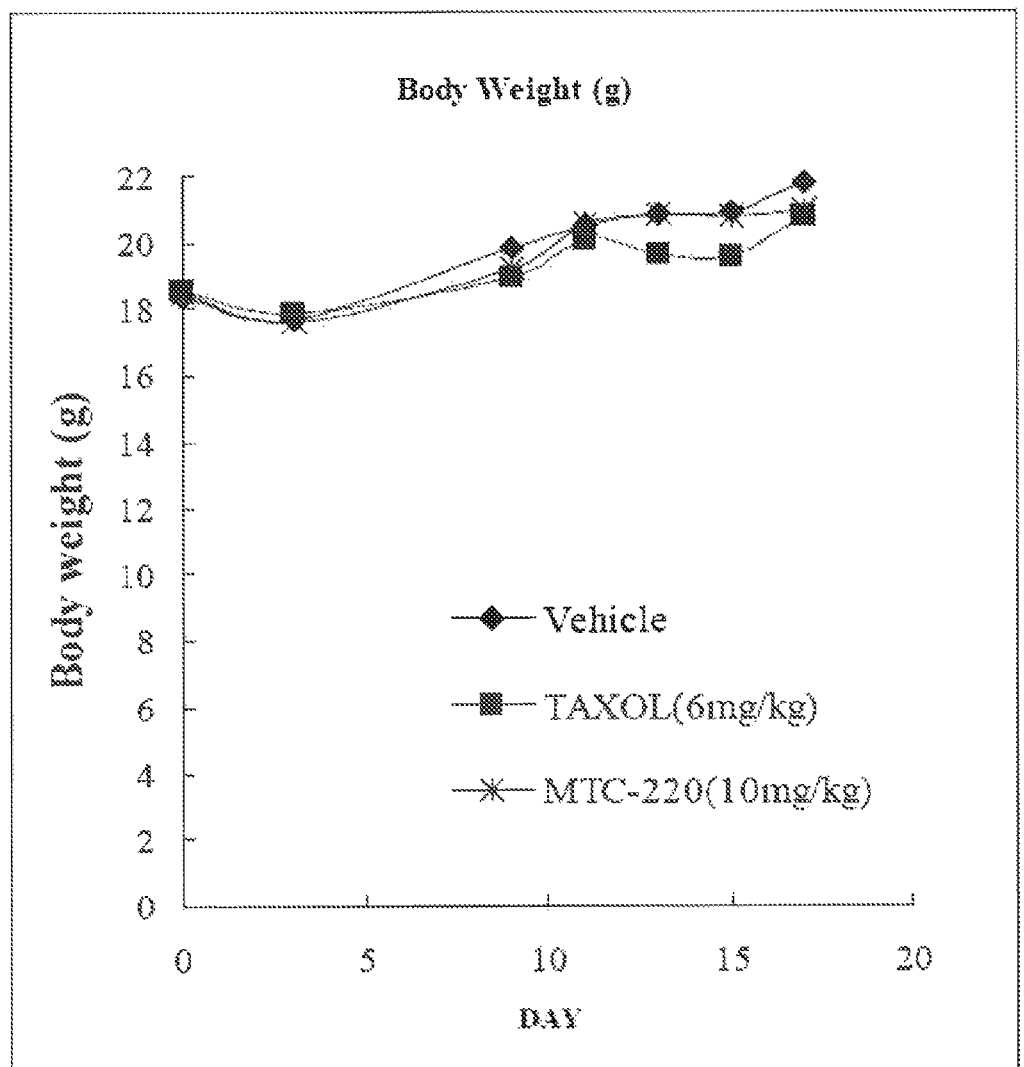
FIG. 27 The effect on body weight of MTC-220 in Lewis lung cancer mice (2).
Figure 28:
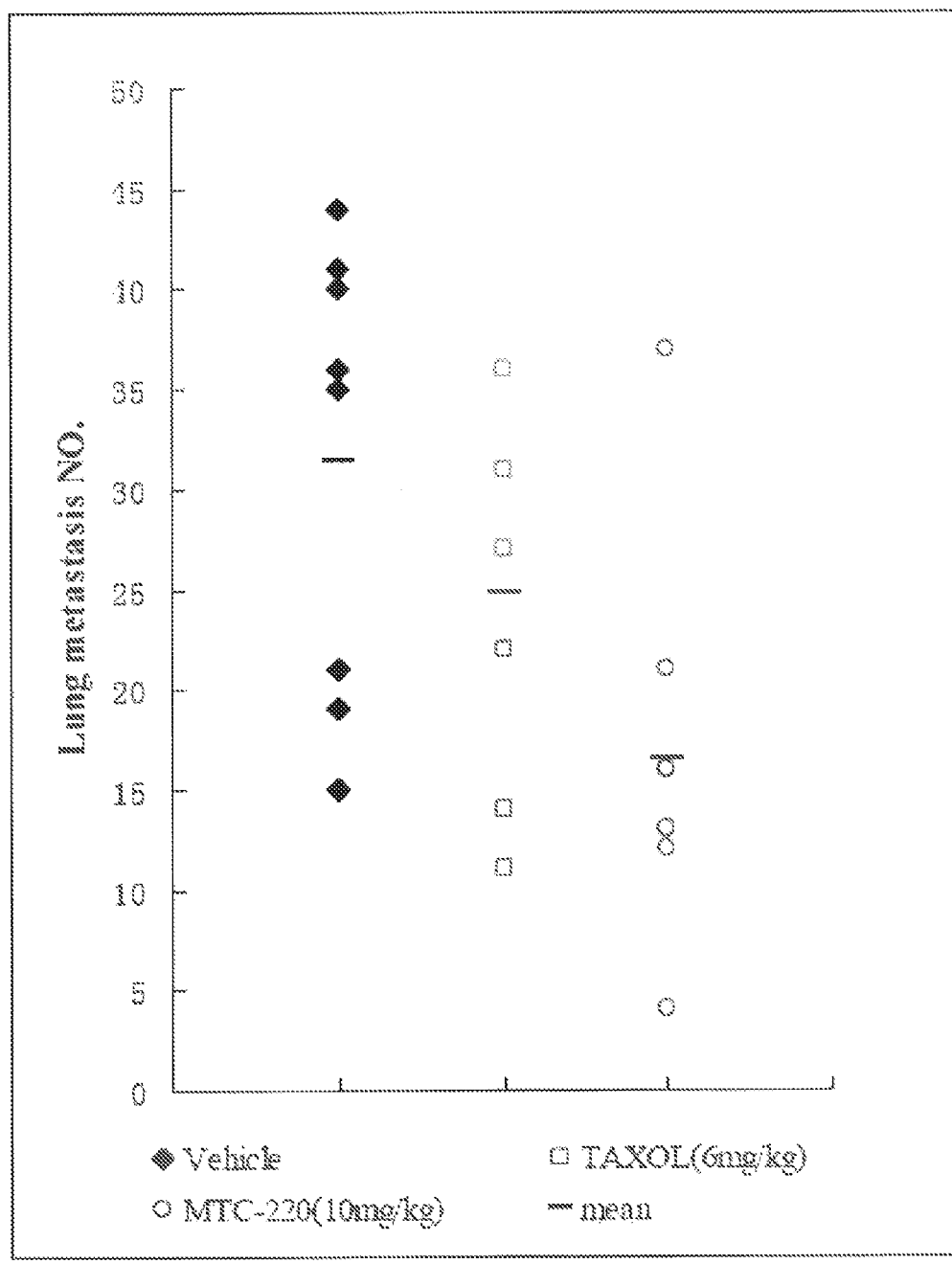
FIG. 28 Anti-tumor natural metastasis activities of MTC-220 in Lewis lung cancer mice (3).

The results indicated that, MTC-220 significantly decreased the lung metastasis nodule number of LLC mice with statistical significance ($p<0.05$) compared to vehicle control group. There was no significant improvement of lung metastasis nodule in the Taxol group. MTC-220 and Taxol both significantly inhibited the growth of tumor compared to vehicle control group. During the observation of the experiment, there was no toxic and side effect by MTC-220, and the body weight of mice increased gradually. Experiment results were shown in FIGS. 26-28 and Table 12.

TABLE 12

Anti-natural metastasis activities of MTC-220 in Lewis lung cancer mice

| Group | Tumor weight (g) | Lung weight (mg) | Lung metastasis nodule counts |
|---|---|---|---|
| Vehicle | 5.75 ± 1.6 | 205 ± 121 | 31.4 ± 11 |
| TAXOL (6 mg/kg) | 4.21* ± 1.1 | 161 ± 27 | 24.9 ± 9 |
| MTC-220 10 mg/kg | 3.84* ± 1.4 | 152 ± 37 | 16.5*$^{\Delta V}$ ± 9 |

Compared to vehicle control group:
**P < 0.01,
*P < 0.05;
Compared to Taxol group:
$^{\Delta\Delta}$P < 0.01,
$^{\Delta}$P < 0.05.

Example 50

Anti-Artificial Metastasis of MTC-220 on Lewis Lung Cancer in Mice

C57Bl/6 mice with Lewis lung cancer were sacrificed and the tumor was removed. The tumor cell suspension (5×10$^6$ cell/mL) was prepared in a sterile condition. The suspension (0.2 mL/mice, 3×10$^5$ tumor cell) was inoculated intravenously into the tails of fifty C57Bl/6 mice. Two days after the implantation, the mice were divided into five groups randomly, each group had ten mice, and the mice separately received intraperitoneally administration of paclitaxel (3 mg/kg), MTC-220 (2.5 mg/kg, 5 mg/kg or 10 mg/kg), or control vehicle. Drug was withdrawn on the twenty-eighth day after the successive administration, all mice were then sacrificed and the body weight was measured. The tumors, spleen and lung were removed and weighed. The lungs were fixed in Bouin's fixative for 24 h. The number of lung metastasis nodule was counted, and the statistics was evaluated by Mann-Whitney U test.

Figure 29:
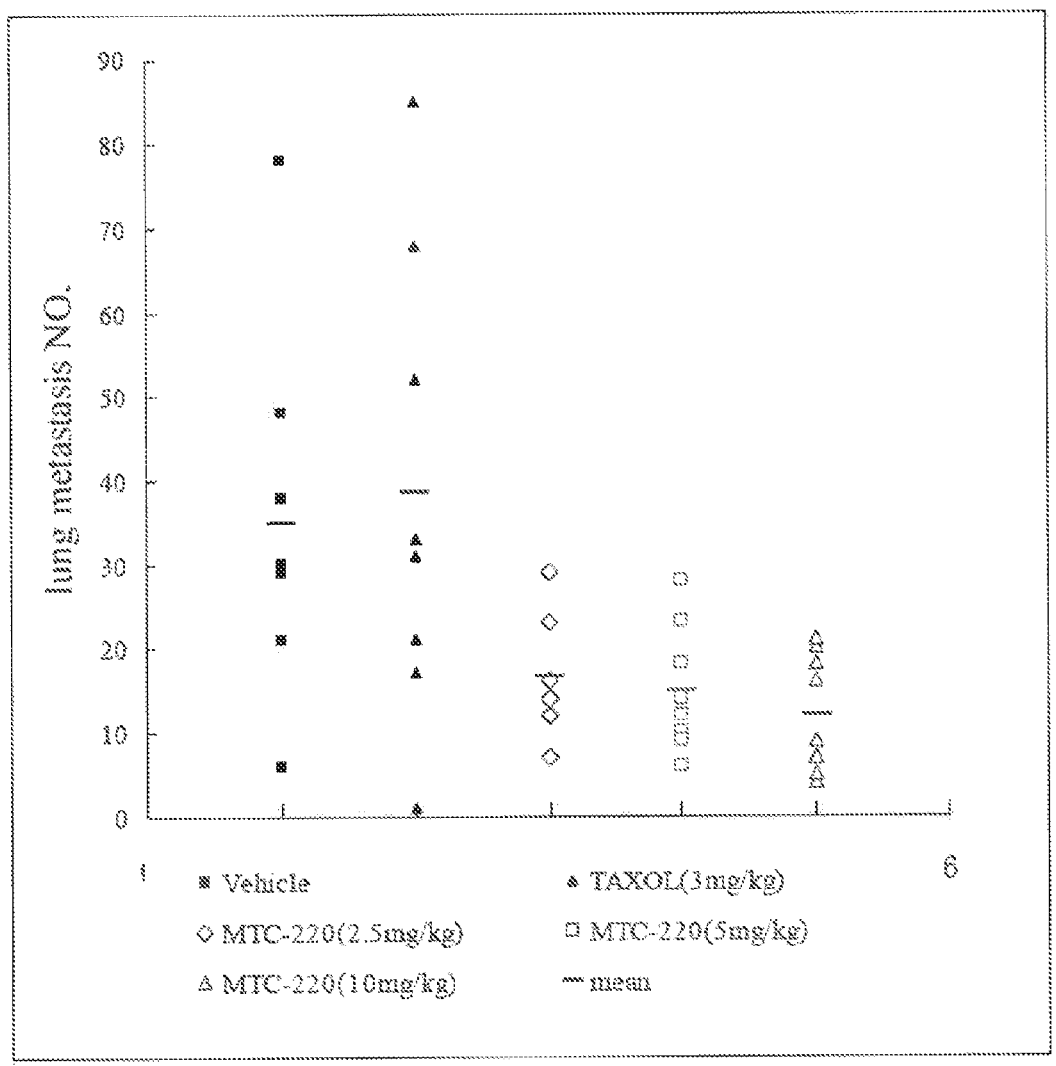
FIG. 29 Anti-tumor artificial metastasis activities of MTC-220 in Lewis lung cancer mice.

The results indicated that, MTC-220 significantly decreased the lung metastasis nodule number of LLC mice with statistical significance compared to vehicle control group, and the result depended on the administration dosage. There was no significant improvement of lung metastasis nodule in the Taxol group. Experiment results were shown in FIG. 29 and Table 13.

TABLE 13

Antiarticial metastasis activities of MTC-220 on Lewis lung cancer in mice

| Group | Body weight (g) | Lung weight (mg) | Lung metastasis nodule counts |
|---|---|---|---|
| Vehicle | 19.3 ± 1.3 | 397 ± 301 | 35.0 ± 21 |
| TAXOL (3 mg/kg) | 17.1* ± 2.8 | 497 ± 491 | 38.5 ± 28 |
| MTC-220 (2.5 mg/kg) | 19.0 ± 1.9 | 334 ± 217 | 16.4* ± 7 |
| MTC-220 (5 mg/kg) | 18.4 ± 2.3 | 492 ± 353 | 15.0* ± 7 |
| MTC-220 (10 mg/kg) | 17.4** ± 1.5 | 393 ± 326 | 11.8** ± 6.8 |

Compared to vehicle control group:
**P < 0.01,
*P < 0.05

Example 51

The Toxicity Test of MTC-220 by Single Dose

Experiment Methods:

In light of the publication "technical guidelines for cytotoxic anticancer drugs in non-clinical studies" and "technical guidelines for studies on chemical drugs with acute toxicities" by State Food and Drug Administration, the toxicity study on MTC-220 was conducted at maximal administration dosage in the ICR mice with a single dose was intravenously injected.

Experiment Results:

After the intravenous injection of MTC-220 in a dose of 112.5 mg·kg$^{-1}$ the voluntary activities of mice in administered group were reduced, some mice showed jumping symptoms, which then recovered about 10 min later. There was no unusual phenomenon in the Vehicle group (Epoxidized castor oil:DMSO:Normal Saline=5:5:90, volume ratio) and Control group. After continued observation for 14 days, the animal behavior, voluntary activities and physical sign of each group were normal, and no death occured.

The body weight of each administered group and vehicle group was not significantly different compared with that of the control group. Anatomical examination results: animal heart, liver, spleen, lung, kidney, gastrointestinal and other various organs showed no sign of abnormal changes.

Experimental Results:

After the intravenous injection to ICR mice tail with MTC-220 in a single dose of 112.5 mg·kg$^{-1}$, there was no significant symptoms of toxicity or death. It was thought that the MTD of MTC-220 by intravenous injection into the tested ICR mice was higher than its maximum administration dose (112.5 mg·kg$^{-1}$).

Pharmacology experiment results above, as well as single-dose toxicity test result showed that the design concept of the conjugate of taxane anti-tumor agent and Muramyl Dipeptide Analogue was right. It was a series of safe and new compounds, which can be developed as new drugs with the dual anti-tumor and anti metastasis functions.

What is claimed is:
1. A compound of formula I, and/or a pharmaceutically acceptable salt thereof,

I wherein when A is phenyl, B is acetoxy; when A is tert-butoxy, B is hydroxy; n=2, 3, 4, 5, 6, 7, 8, 9, 10, 11 or 12;
wherein X is chosen from $C_{1-6}$ alkyl, $C_{1-6}$ alkylene and $C_{1-6}$ alkyl comprising at least one heteroatom, wherein the at least one heteroatom is independently chosen from oxygen, sulfur and nitrogen; or X is a single bond;
wherein M is chosen from aryl and heteroaryl;
wherein R is chosen from hydrogen, substituted or unsubstituted straight or branched $C_{1-6}$ alkyl, hydroxy, substituted or unsubstituted straight or branched $C_{1-6}$ alkoxy, thiol, substituted or unsubstituted straight or branched $C_{1-6}$ alkylthio, $C_{1-6}$ alkoxy-$C_{1-6}$ alkyl, amino; substituted or unsubstituted straight or branched $C_{1-6}$ mono- and di-alkylamino; aldehyde group, substituted or unsubstituted straight or branched $C_{1-6}$ alkylcarbonyl, carboxyl, substituted or unsubstituted straight or branched $C_{1-6}$ alkylcarboxyl, carbamoyl, substituted or unsubstituted straight or branched $C_{1-6}$ alkylamide, $C_{2-6}$ alkene, halogen, nitro and cyano;
wherein the substituent(s) on $C_1$-$C_6$ straight chain or branched chain described herein is independently chosen from hydroxyl, thiol, amino, aldehyde group, carboxyl, carbamoyl, halogen, nitro and cyano.

2. The compound and/or pharmaceutically acceptable salt thereof according to claim 1, wherein n=2, 3, 4, 5, 6, 7, 8, 9 or 10.

3. The compound and/or pharmaceutically acceptable salt thereof according to claim 2, wherein n=2, 3, 4, 5, 6, 7 or 8.

4. The compound and/or pharmaceutically acceptable salt thereof according to claim 3, wherein n=2, 3, 4 or 5.

5. The compound and/or pharmaceutically acceptable salt thereof according to claim 1, wherein X is chosen from $C_{1-4}$ alkyl, $C_{1-4}$ alkylene and $C_{1-4}$ alkyl comprising at least one heteroatom, wherein the at least one heteroatom is independently chosen from oxygen and sulfur; or X is a single bond.

6. The compound and/or pharmaceutically acceptable salt thereof according to claim 5, wherein X is chosen from $C_{1-3}$ alkyl, $C_{1-3}$ alkylene and $C_{1-3}$ alkyl comprising at least one heteroatom, wherein the heteroatom is oxygen; or X is a single bond.

7. The compound and/or pharmaceutically acceptable salt thereof according to claim 6, wherein X is chosen from —C≡C—, —CH$_2$—CH$_2$—, —O—CH$_2$— and a single bond.

8. The compound and/or pharmaceutically acceptable salt thereof according to claim 1, wherein the aryl is chosen from five membered to fourteen membered aryl.

9. The compound and/or pharmaceutically acceptable salt thereof according to claim 8, wherein the aryl is chosen from five-membered aryl, six-membered aryl, nine-membered fused ring aryl, ten-membered fused ring aryl, thirteen-membered fused ring aryl and fourteen-membered fused ring aryl.

10. The compound and/or pharmaceutically acceptable salt thereof according to claim 9,
wherein the six-membered aryl is

;

wherein the nine-membered fused ring aryl is chosen from

;

wherein the ten-membered fused ring aryl is

.

11. The compound and/or pharmaceutically acceptable salt thereof according to claim 1, wherein the heteroaryl is chosen from heterocyclic aromatic ring comprising one, two, three or four heteroatoms in the ring, wherein the heteroatom(s) is independently chosen from nitrogen, oxygen and sulfur.

12. The compound and/or pharmaceutically acceptable salt thereof according to claim 11, wherein the heteroaryl is chosen from five membered to fourteen membered heterocyclic aromatic ring comprising one, two, three or four heteroatoms in the ring, wherein the heteroatom(s) is independently chosen from nitrogen, oxygen and sulfur.

13. The compound and/or pharmaceutically acceptable salt thereof according to claim 12, wherein the heteroaryl is chosen from five-membered heterocyclic aromatic ring, six-membered heterocyclic aromatic ring, eight-membered fused heterocyclic aromatic ring, nine-membered fused heterocyclic aromatic ring and ten-membered fused heterocyclic aromatic ring, wherein the aromatic ring comprising one, two, three or four heteroatoms in the ring, wherein the heteroatom(s) is independently chosen from nitrogen, oxygen and sulfur.

14. The compound and/or pharmaceutically acceptable salt thereof according to claim 13, wherein the five-membered heterocyclic aromatic ring is chosen from

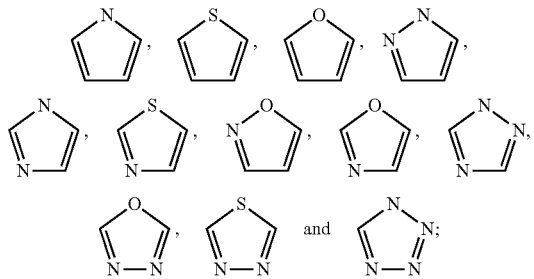

wherein the six-membered heterocyclic aromatic ring is chosen from

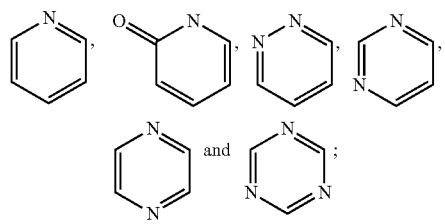

wherein the eight-membered fused heterocyclic aromatic ring is chosen from

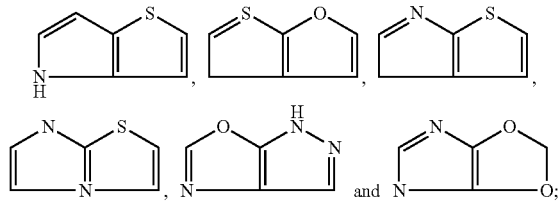

wherein the nine-membered fused heterocyclic aromatic ring is chosen from

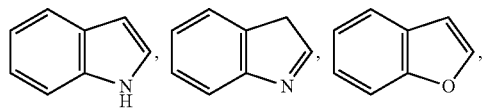

-continued

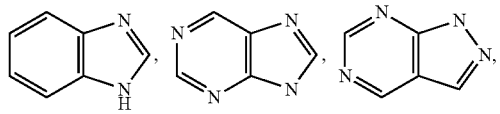

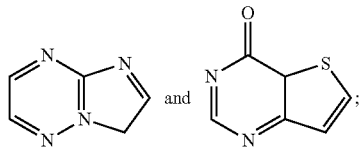

wherein the ten-membered fused heterocyclic aromatic ring is chosen from

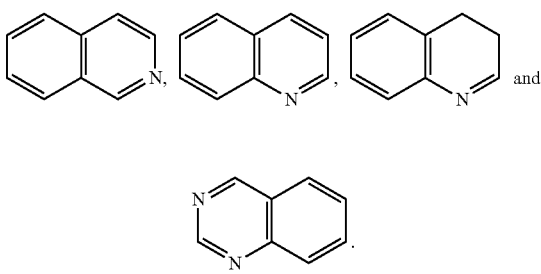

15. The compound and/or pharmaceutically acceptable salt thereof according to claim 1, wherein R is chosen from hydrogen, substituted or unsubstituted straight or branched $C_{1-4}$ alkyl, hydroxy, substituted or unsubstituted straight or branched $C_{1-4}$ alkoxy, $C_{1-4}$ alkoxy-$C_{1-4}$ alkyl, thiol, substituted or unsubstituted straight or branched $C_{1-4}$ alkylthio, amino, substituted or unsubstituted straight or branched mono- and di-$C_{1-4}$ alkylamino, aldehyde group, substituted or unsubstituted straight or branched $C_{1-4}$ alkylcarbonyl, carboxyl, substituted or unsubstituted straight or branched $C_{1-4}$ alkylcarboxyl, carbamoyl, substituted or unsubstituted straight or branched $C_{1-4}$ alkylamide, $C_{2-4}$ alkene, halogen, nitro and cyano; wherein the substituent(s) on straight or branched $C_{1-4}$ alkyl is independently chosen from hydroxyl, thiol, amino, aldehyde group, carboxyl, carbamoyl, fluorine, chlorine, bromine, nitro and cyano.

16. The compound and/or pharmaceutically acceptable salt thereof according to claim 15, wherein R is chosen from hydrogen, straight or branched $C_{1-4}$ alkyl, hydroxy, straight or branched $C_{1-4}$ alkoxy, thiol, straight or branched $C_{1-4}$ alkylthio, amino, straight or branched $C_{1-4}$ alkylamino, halogen, nitro and cyano.

17. The compound and/or pharmaceutically acceptable salt thereof according to claim 16, wherein R is chosen from hydrogen, hydroxyl, thiol, amino, fluorine, chlorine, bromine, nitro, cyano, methyl, ethyl, n-propyl, iso-propyl, methoxy, ethoxy, n-propoxy and iso-propoxy.

18. The compound and/or pharmaceutically acceptable salt thereof according to claim 1, wherein the compound is chosen from compounds of formula IA

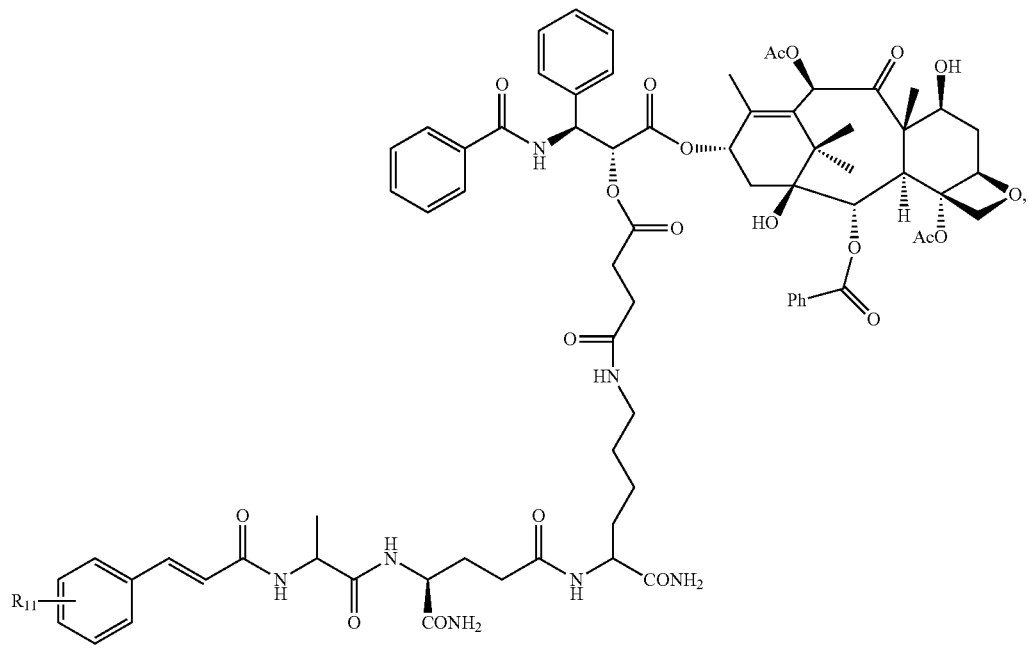

IA wherein $R_{11}$ is at least one group independently chosen from hydrogen, hydroxyl, thiol, amino, aldehyde group, carboxyl, carbamoyl, halogen, nitro, cyano, $C_{1-4}$ alkyl, $C_{1-4}$ alkoxy, $C_{1-4}$ alkyl amino and $C_{1-4}$ alkoxy-$C_{1-4}$ alkyl.

19. The compound and/or pharmaceutically acceptable salt thereof according to claim 1, wherein the compound is chosen from compounds of formula IB wherein $R_{12}$ is at least one group independently chosen from hydrogen, hydroxyl, thiol, amino, aldehyde group, carboxyl, carbamoyl, halogen, nitro, cyano, $C_{1-4}$ alkyl, $C_{1-4}$ alkoxy, $C_{1-4}$ alkyl amino and $C_{1-4}$ alkoxy-$C_{1-4}$ alkyl.

20. The compound and/or pharmaceutically acceptable salt thereof according to claim 1, wherein the compound is chosen from compounds of formula IC

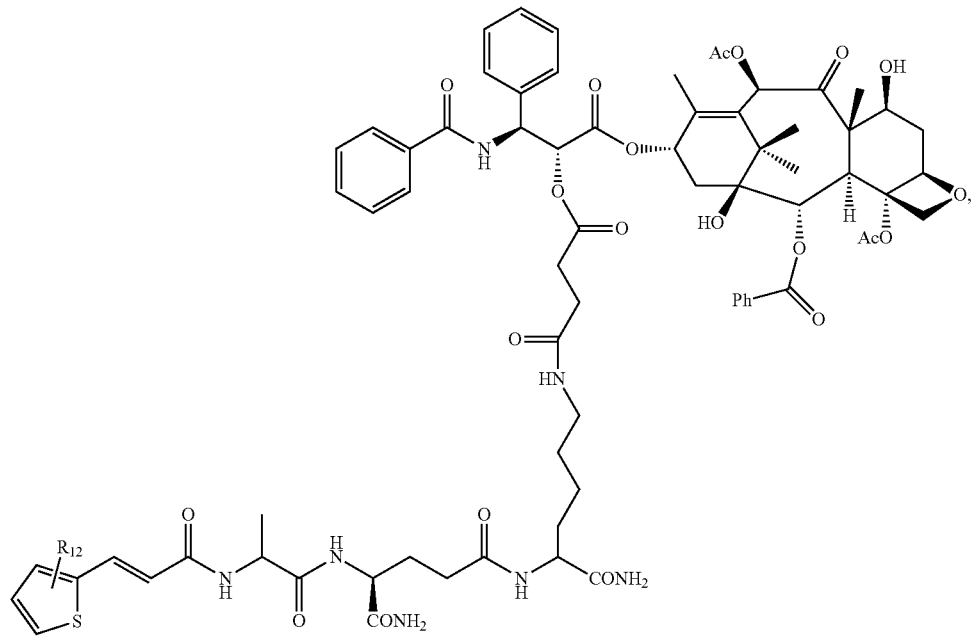

IB

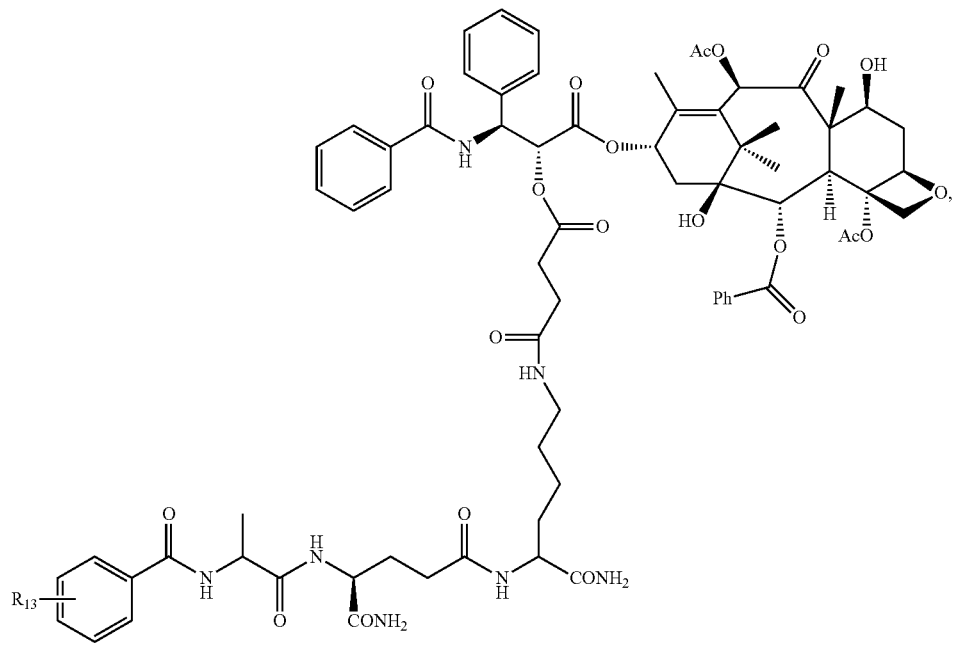

IC wherein $R_{13}$ is at least one group independently chosen from hydrogen, hydroxyl, thiol, amino, aldehyde group, carboxyl, carbamoyl, halogen, nitro, cyano, $C_{1-4}$ alkyl, $C_{1-4}$ alkoxy, $C_{1-4}$ alkyl amino and $C_{1-4}$ alkoxy-$C_{1-4}$ alkyl.

21. The compound and/or pharmaceutically acceptable salt thereof according to claim 1, wherein the compound is chosen from compounds of formula ID wherein $R_{14}$ is at least one group independently chosen from hydrogen, hydroxyl, thiol, amino, aldehyde group, carboxyl, carbamoyl, halogen, nitro, cyano, $C_{1-4}$ alkyl, $C_{1-4}$ alkoxy, $C_{1-4}$ alkyl amino and $C_{1-4}$ alkoxy-$C_{1-4}$ alkyl.

22. The compound and/or pharmaceutically acceptable salt thereof according to claim 1, wherein the compound is chosen from compounds of formula IE

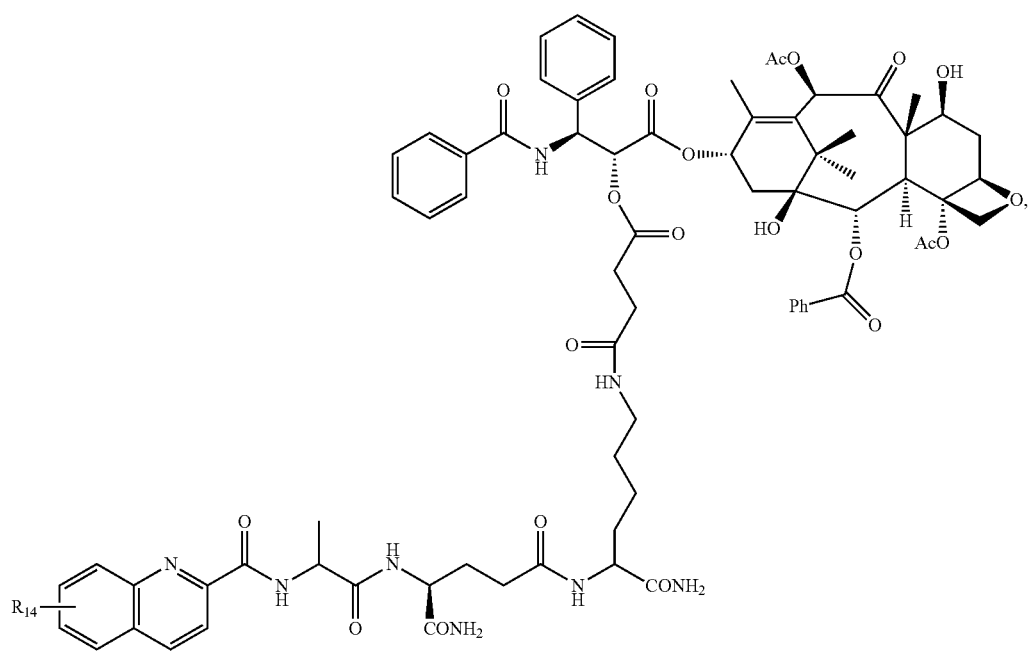

ID

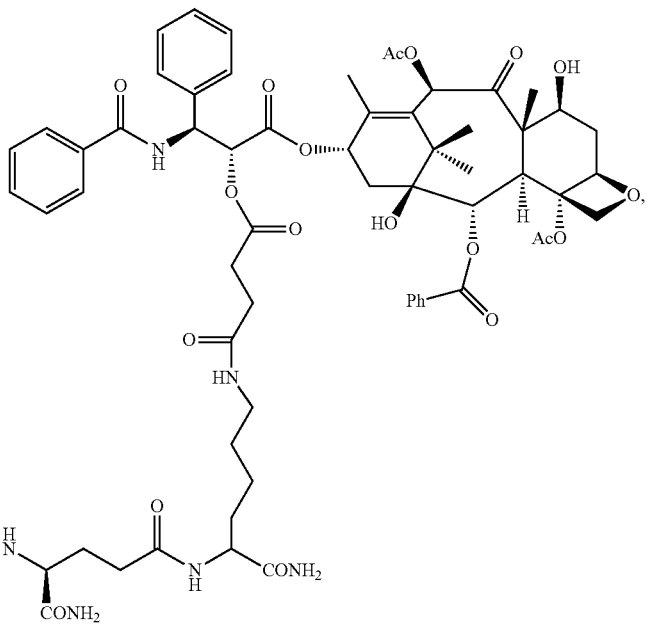

IE

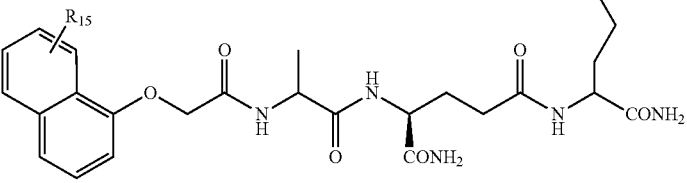

wherein $R_{15}$ is at least one group independently chosen from hydrogen, hydroxyl, thiol, amino, aldehyde group, carboxyl, carbamoyl, halogen, nitro, cyano, $C_{1-4}$ alkyl, $C_{1-4}$ alkoxy, $C_{1-4}$ alkyl amino and $C_{1-4}$ alkoxy-$C_{1-4}$ alkyl.

23. The compound and/or pharmaceutically acceptable salt thereof according to claim 1, wherein the compound is chosen from compounds of formula IF wherein $R_{21}$ is at least one group independently chosen from hydrogen, hydroxyl, thiol, amino, aldehyde group, carboxyl, carbamoyl, halogen, nitro, cyano, $C_{1-4}$ alkyl, $C_{1-4}$ alkoxy, $C_{1-4}$ alkyl amino and $C_{1-4}$ alkoxy-$C_{1-4}$ alkyl.

24. The compound and/or pharmaceutically acceptable salt thereof according to claim 1, wherein the compound is chosen from:

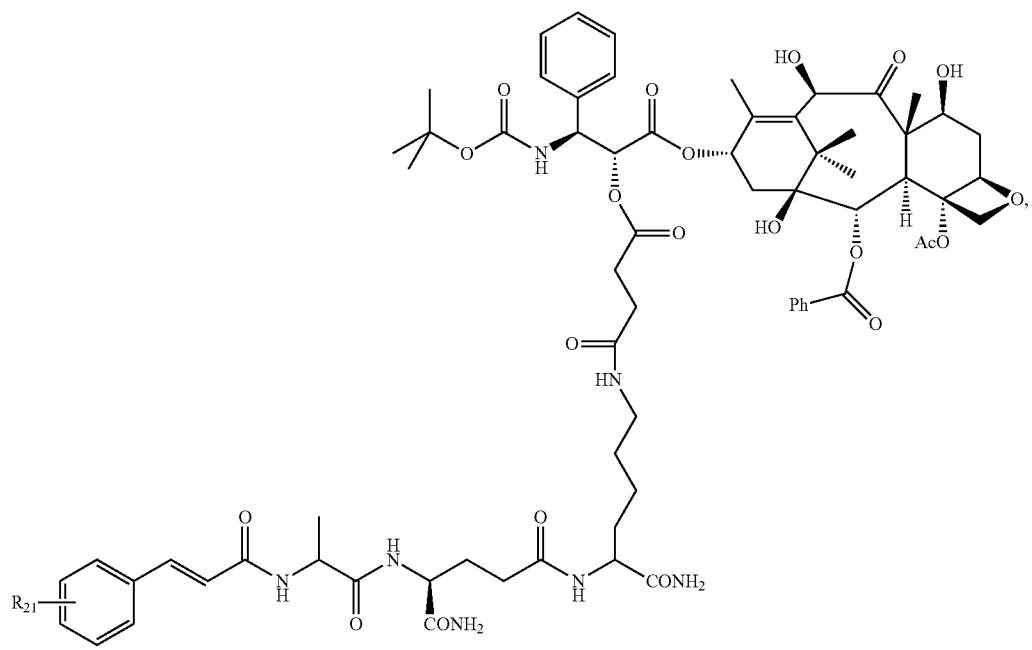

IF

113
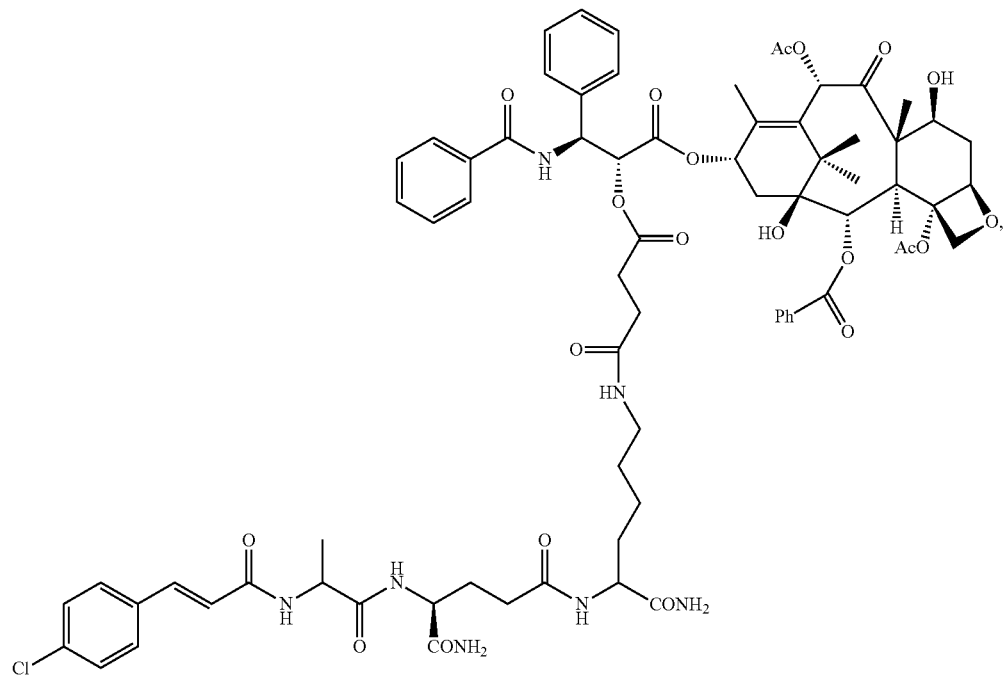
114
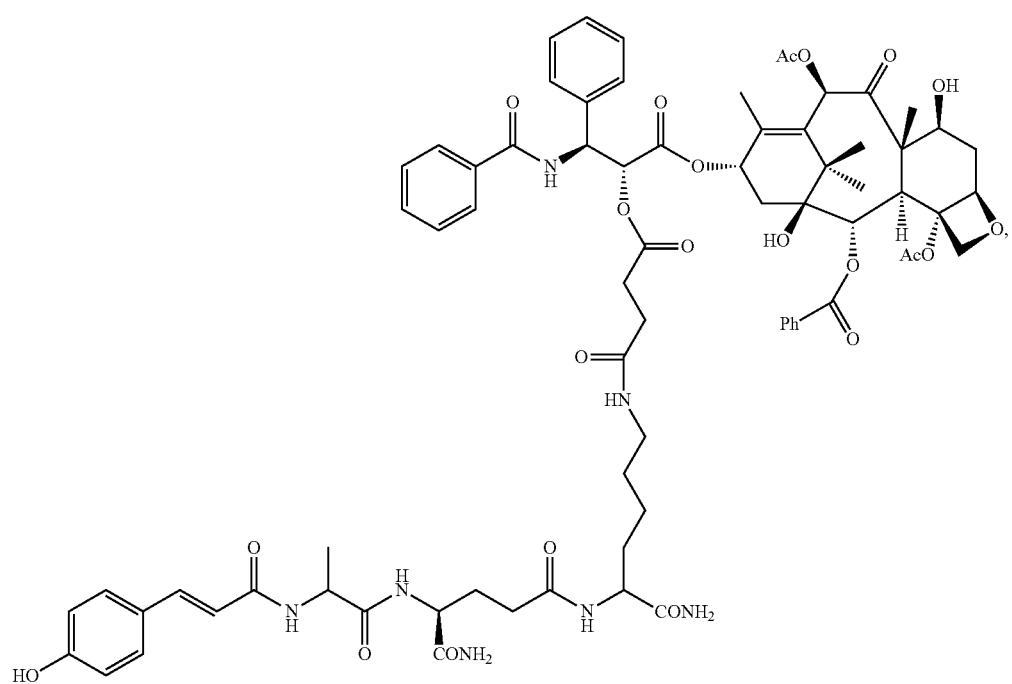

-continued
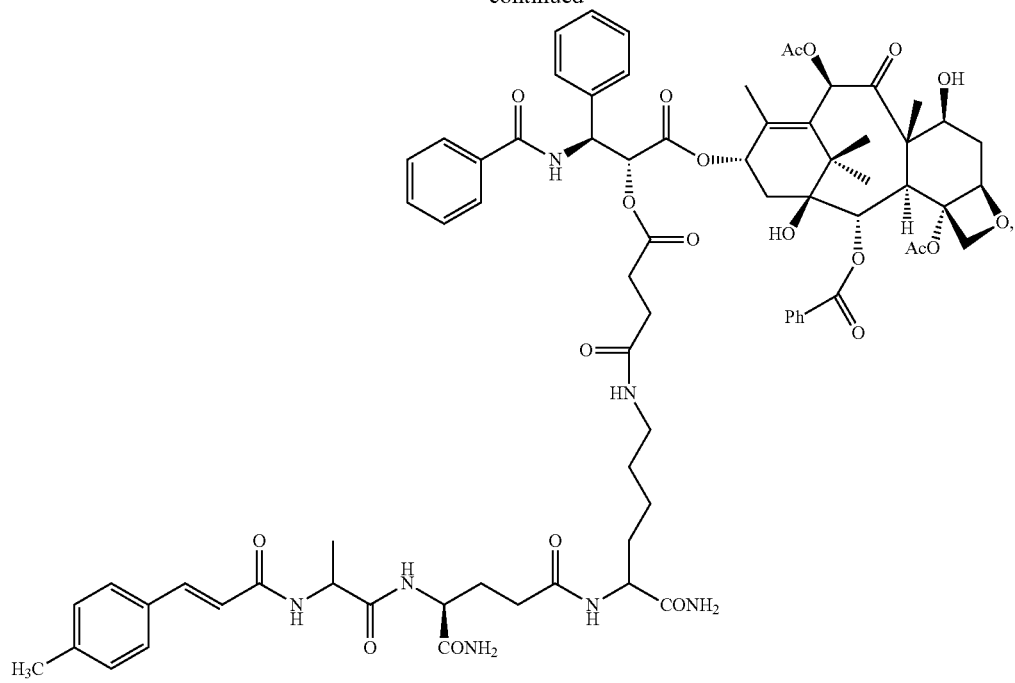
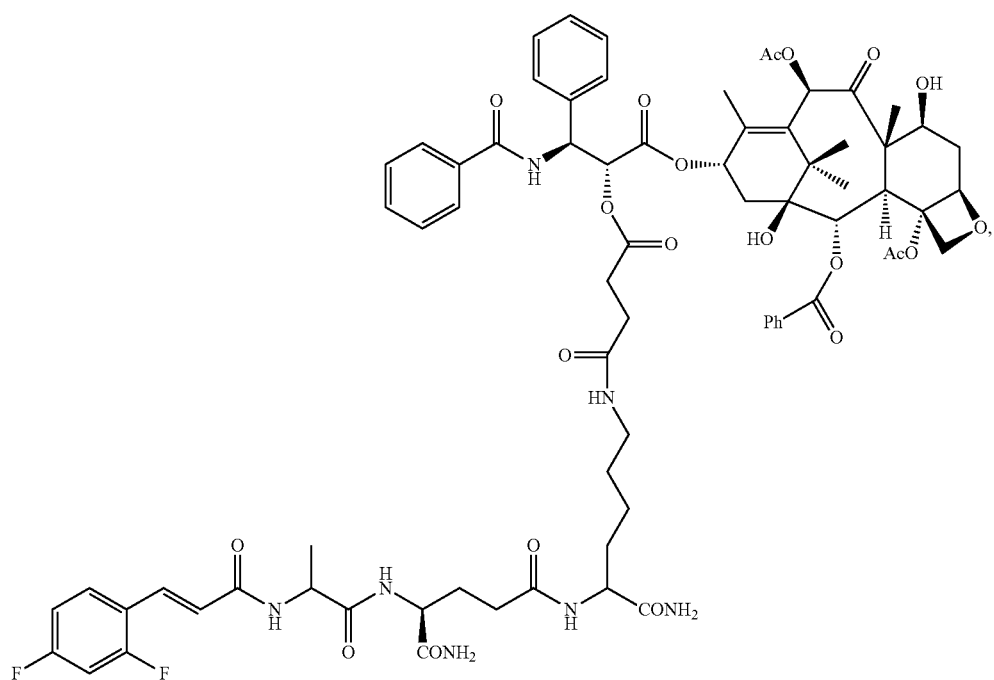

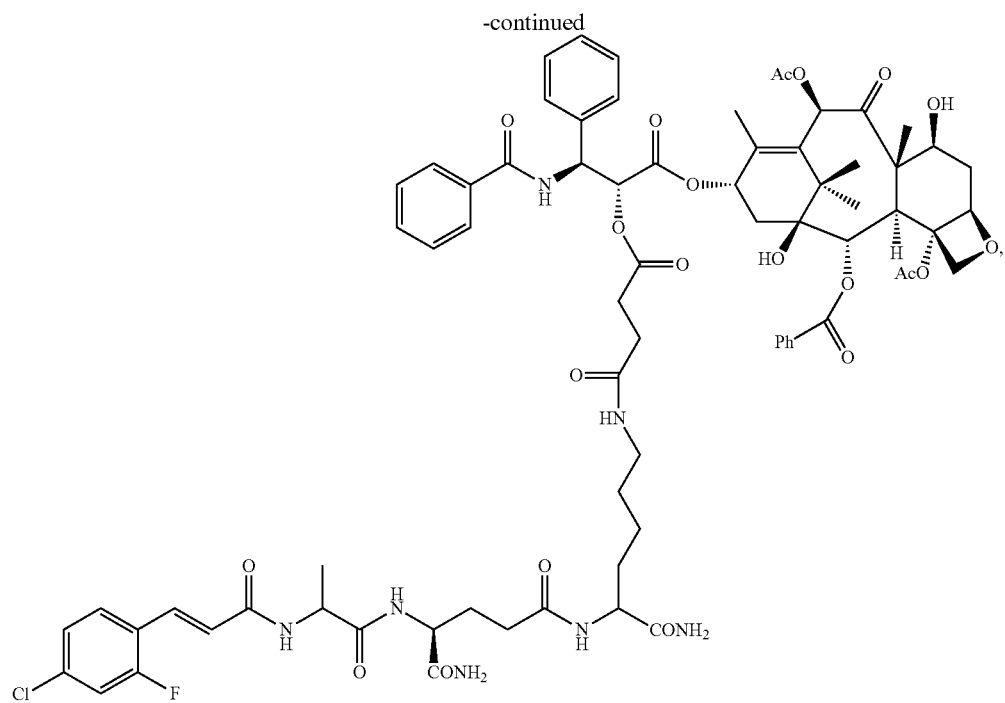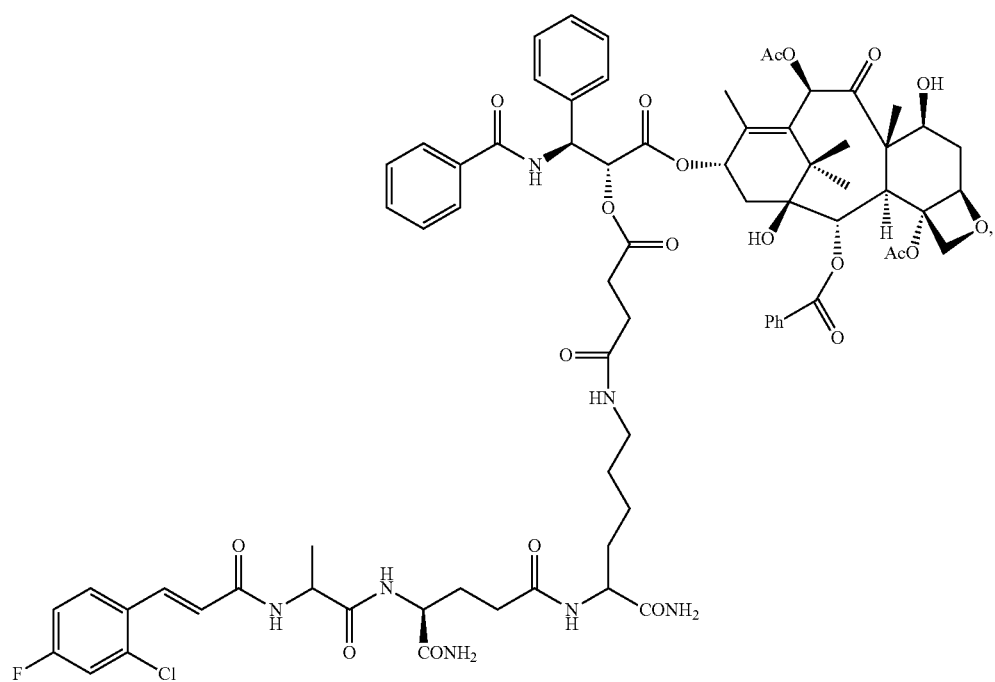

-continued
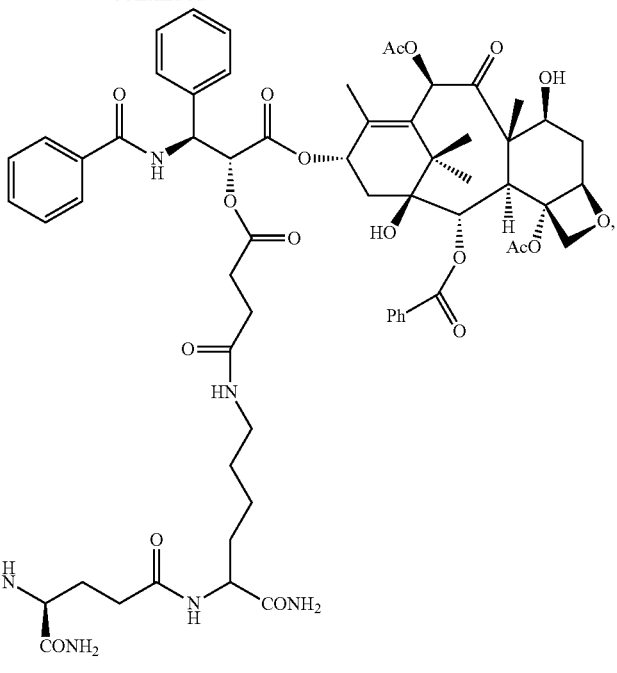
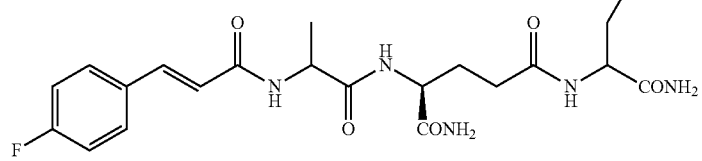
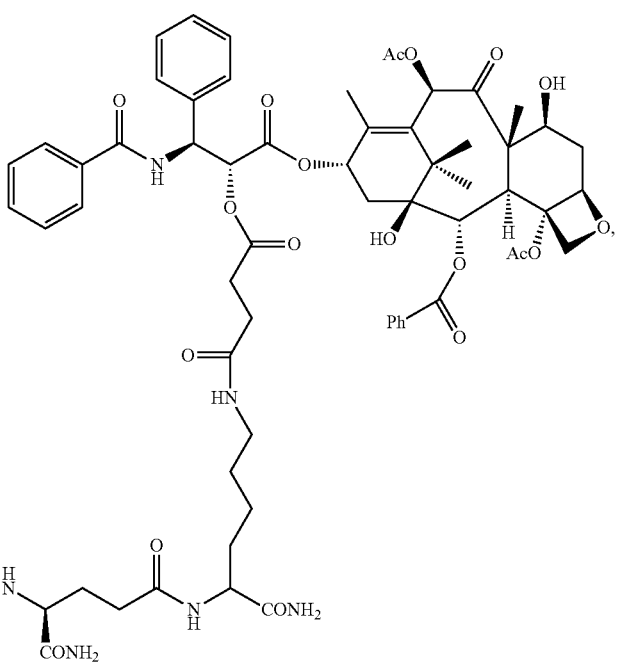
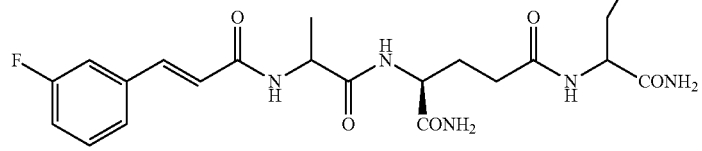

-continued
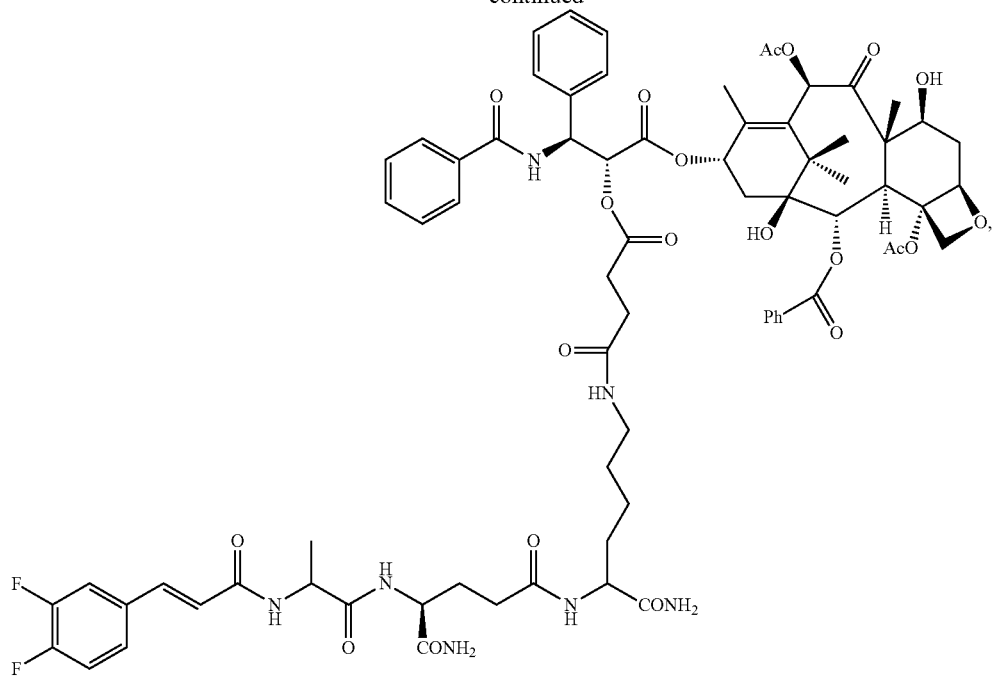
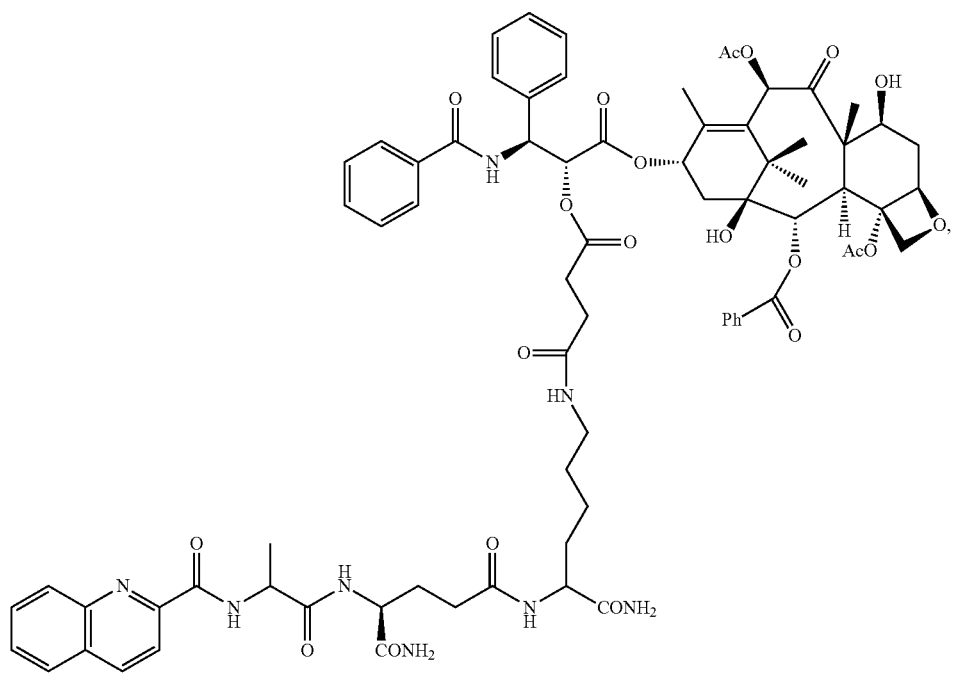

-continued
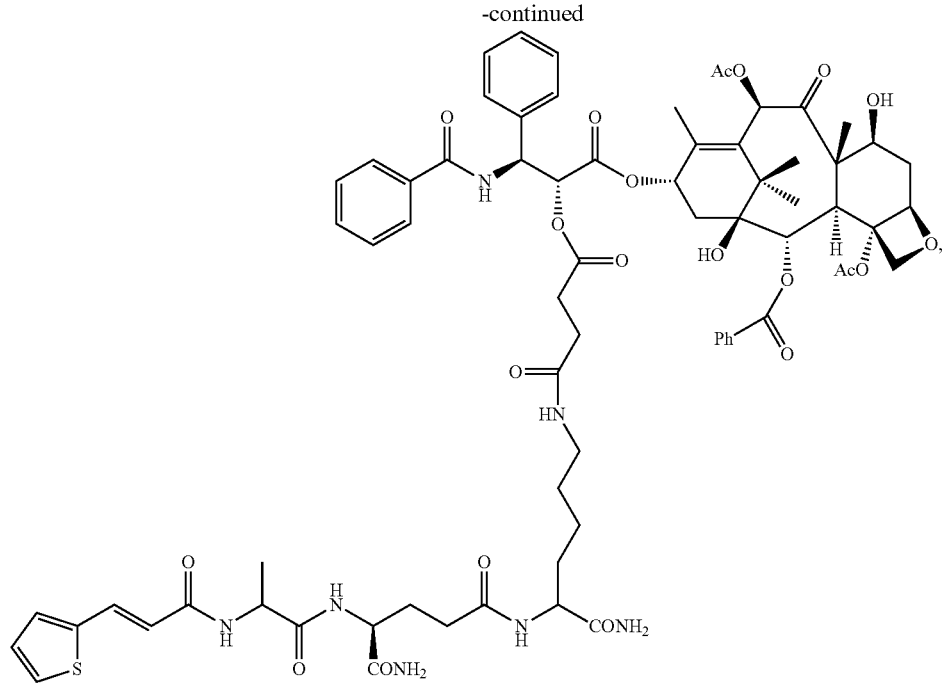
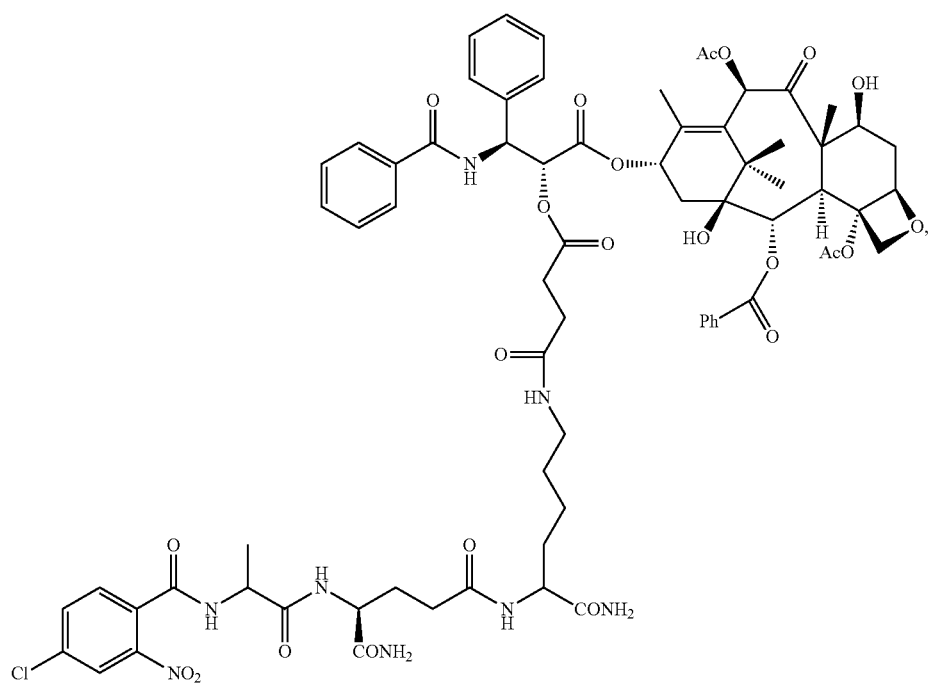

-continued
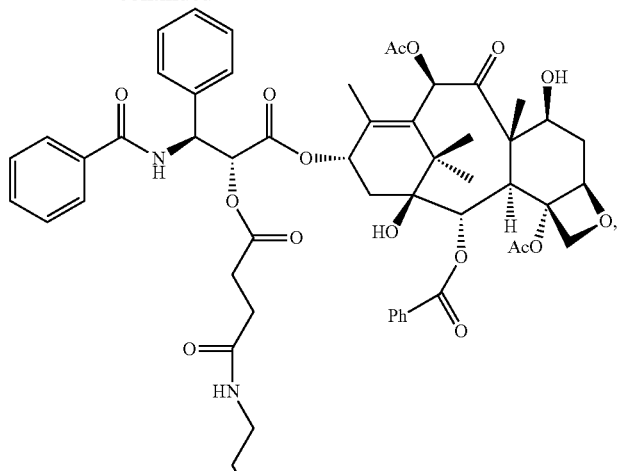
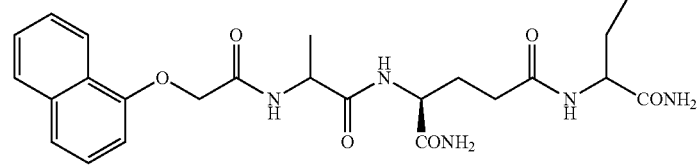
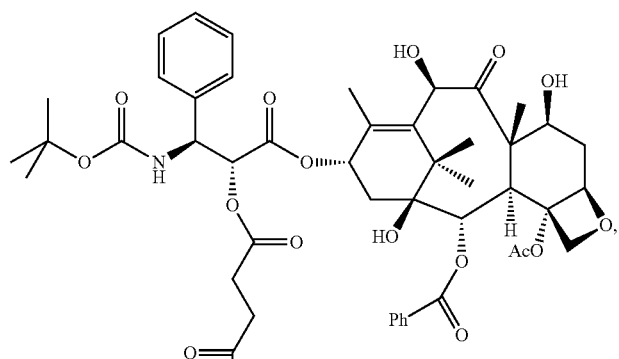
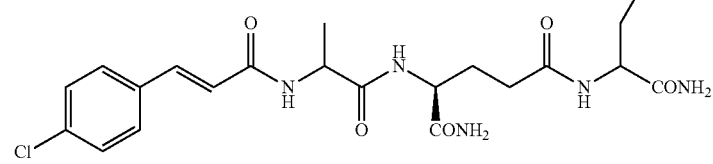

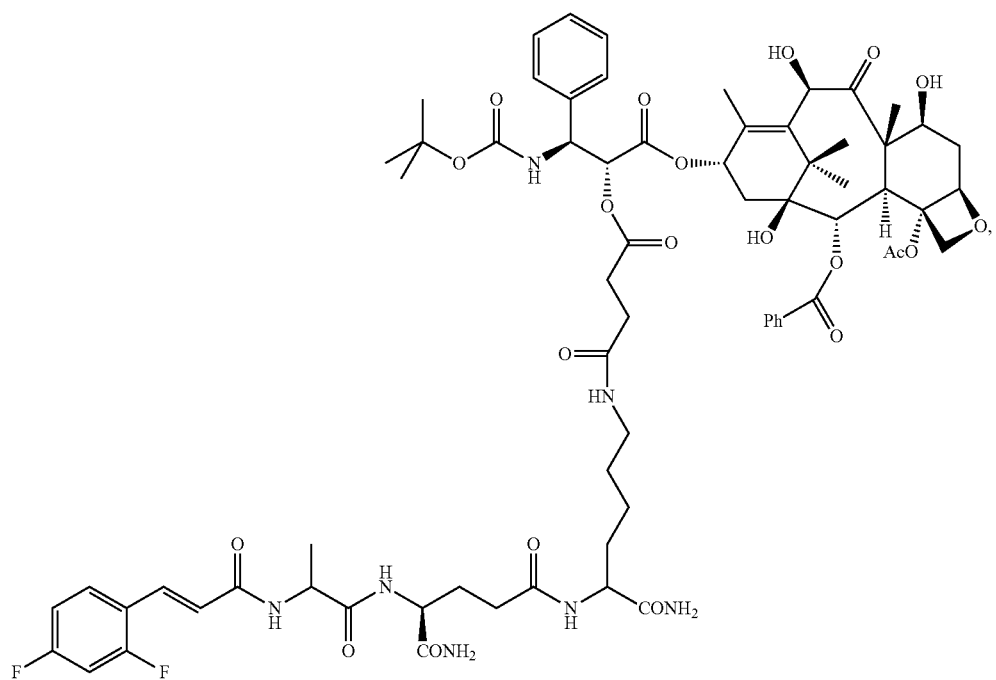
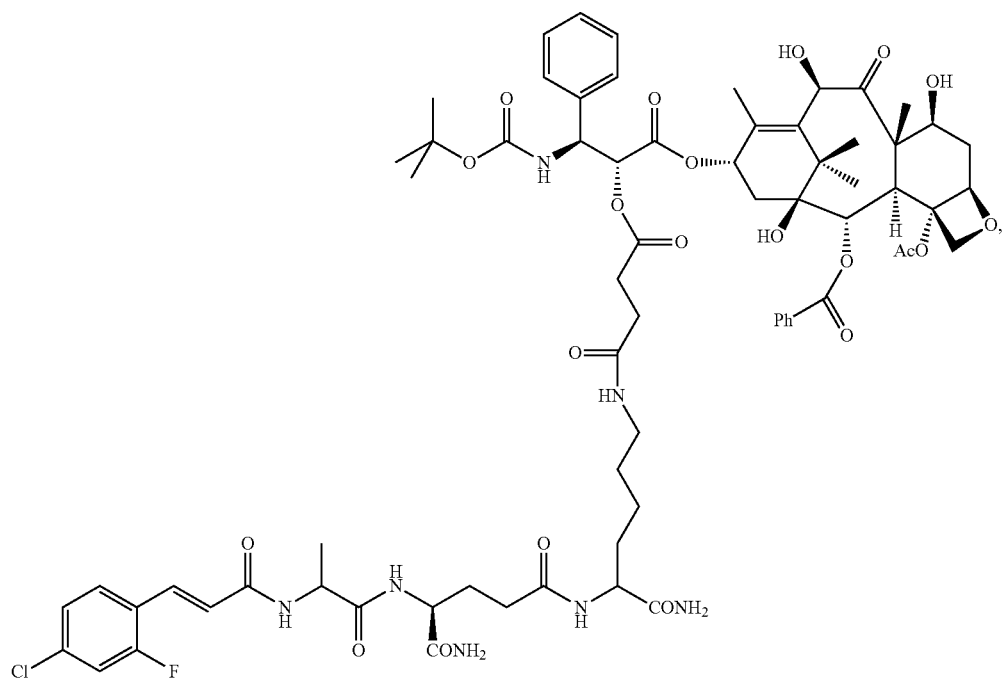

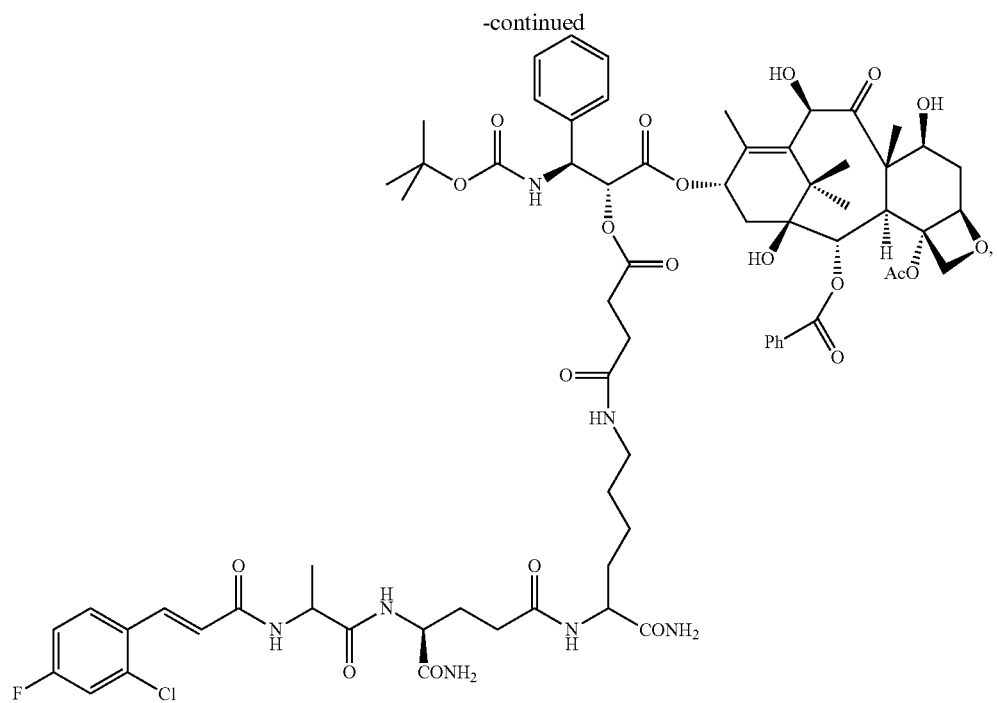
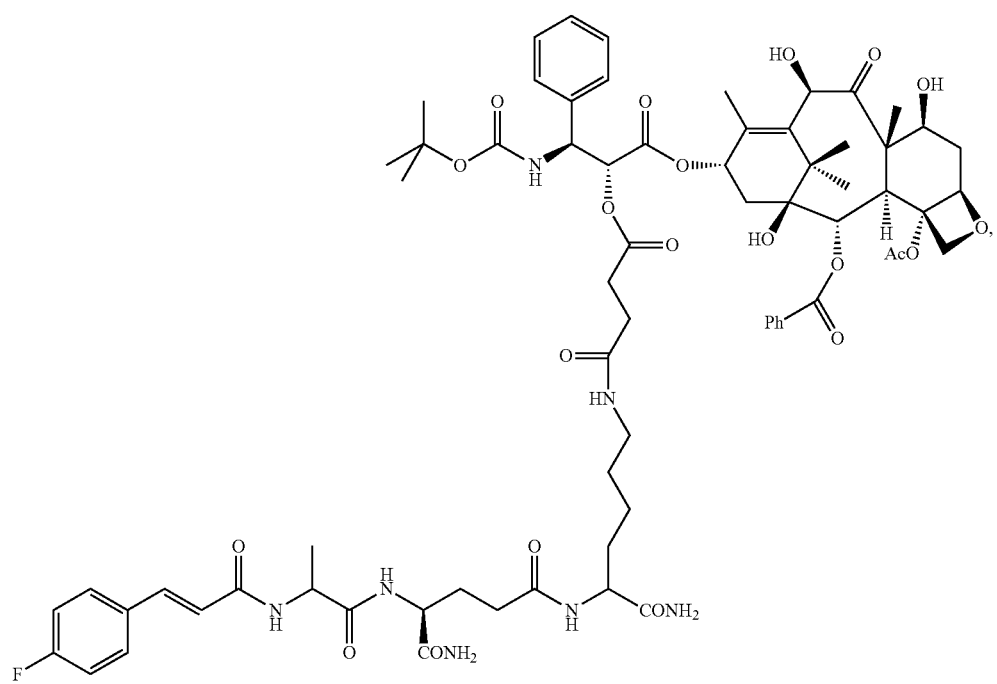

-continued
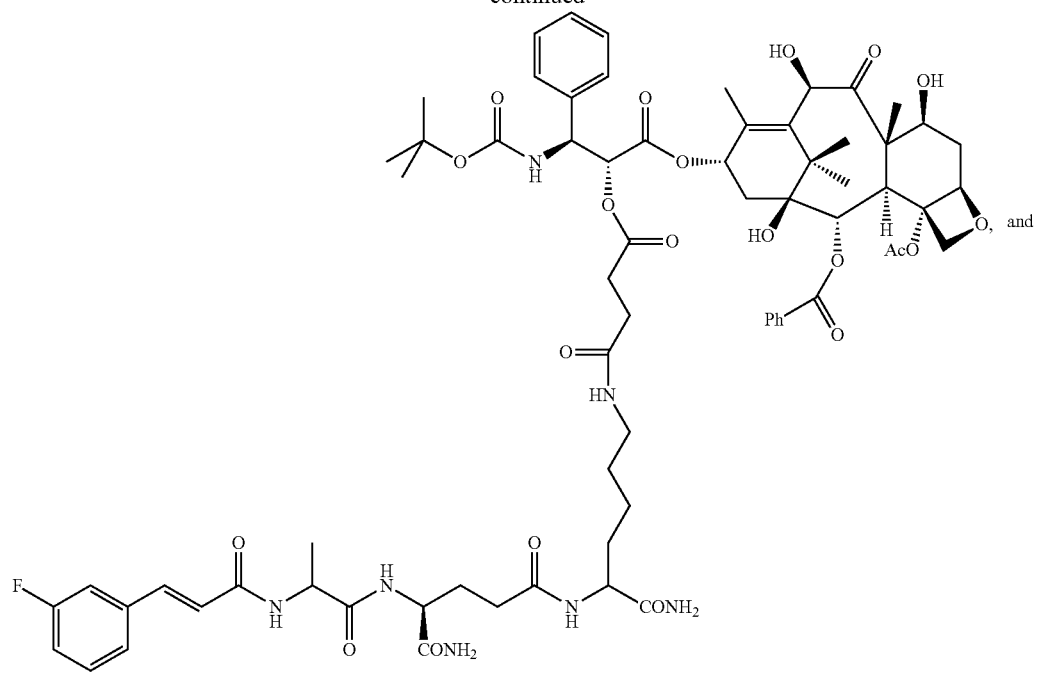
and
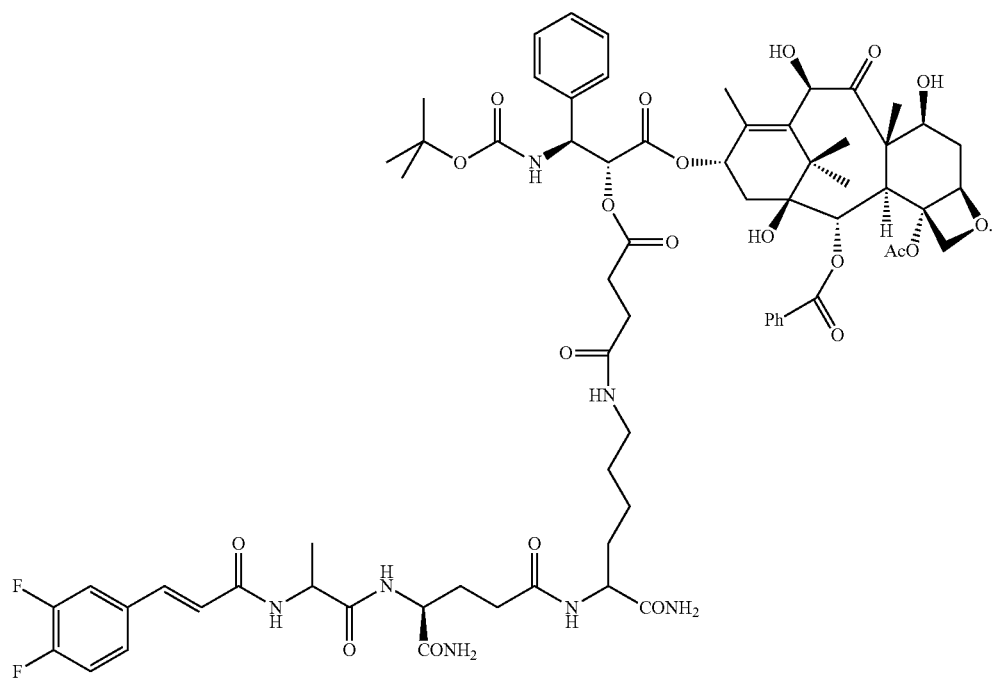

25. The compound and/or pharmaceutically acceptable salt thereof according to claim 1, wherein the pharmaceutically acceptable salt is chosen from hydrochloride, hydrobromide, sulfate, phosphate, nitrate, oxalate, fumarate, maleate, succinate, citrate, tartrate, mesylate and p-toluenesulfonate.

26. A pharmaceutical composition comprising the compound and/or pharmaceutically acceptable salt thereof according to claim 1 and at least one pharmaceutically accepted carrier.

27. A method for treating immune regulation comprising administering to the subject a therapeutic amount of the compound and/or pharmaceutically acceptable salt thereof according to claim 1.

28. A method for preventing and/or treating cancer comprising administering to the subject a therapeutic amount of compound and/or pharmaceutically acceptable salt thereof according to claim 1
wherein the cancer is chosen from melanoma, gastric cancer, lung cancer, breast cancer, renal cancer, liver cancer, oral cavity epidermal carcinoma, cervical cancer, oophoroma, pancreatic cancer, prostatic cancer and colonic cancer.

29. A method for preparing the compound and/or pharmaceutically acceptable salt thereof according to claim 1, comprising:
1) synthesizing Paclitaxel-2'-O-alkane-di-acid monoester or docetaxel-2'-O-alkane-di-acid monoester in liquid-phase;
2) synthesizing Muramyl dipeptide Analogue on solid-phase or in liquid-phase;
3) synthesizing conjugates of Muramyl Dipeptide Analogue and paclitaxel, or conjugates of Muramyl Dipeptide Analogue and docetaxel in liquid-phase.

30. The method according to claim 29, wherein the step 1) of the method for preparing paclitaxel-2'-O-alkane-di-acid monoester comprises:
(1) dissolving Paclitaxel, alkane-di-anhydride and 4-N,N-dimethyl pyridine in pyridine, and stirring for 4 h at room temperature;
(2) diluting the pyridine solution with acetic ether, then washing the acetic ether layer with saturated $CuSO_4$ aqueous solution and $H_2O$ sequentially;
(3) separating and concentrating the acetic ether layer under vacuum, adding abundant water into the residue, then filtering and lyophilizing the white solid to obtain paclitaxel-2'-O-alkane-di-acid monoester.

31. The method according to claim 29, wherein step 1) of the method for preparing docetaxel-2'-O-alkane-di-acid monoester comprises:
(1) dissolving docetaxel, alkane-di-anhydride and 4-N,N-dimethyl pyridine in N,N-dimethylformamide, and stirring for 2 h at room temperature;
(2) diluting the N,N-dimethylformamide solution with dichloromethane, then washing the dichloromethane layer with 2N HCl aqueous solution and $H_2O$ sequentially;
(3) separating and concentrating the dichloromethane layer under vacuum, dissolving the residue in a small amount of methanol, then adding abundant water into the residue, then filtering and lyophilizing the white solid to obtain docetaxel-2'-O-alkane-di-acid monoester.

32. The method according to claim 29, wherein step 2) of the method for preparing muramyl dipeptide analogue comprises:

1) Solid-phase synthesis:
(1) Firstly, synthesizing the intermediate Fmoc-D-iso-Gln-OH in liquid-phase;
(2) Then, introducing Fmoc-L-Lys(Boc)-COOH, Fmoc-D-iso-Gln-COOH, Fmoc-L-Ala-COOH and carboxylic acid to the solid phase carrier of aminoresin of Rink-Amide AM by solid-phase synthesis wherein the condensation reaction is a conventional amide condensation reaction, the condensation reaction is reacted completely by adding the excess amount of the above three amino acids or anyone carboxylic acid and any condensing agent of HATU or HBTU, BOP or PyBOP, and obtaining muramyl dipeptide analogue by the steps comprising washing and cleaving the resin thoroughly, and purifying the crude product;

2) Liquid-phase synthesis:
(1) Firstly, synthesizing the intermediate of Boc-D-Glu(OBzl)-$NH_2$ and Boc-Lys(Z)-$NH_2$;
(2) Then, synthesizing the dipeptide fragment of Boc-Ala-D-Glu(OBzl)-$NH_2$ and the tripeptide fragment of R-Ala-D-Glu(OBzl)-$NH_2$ by the active ester method, and removing the Bzl protective group by the acetic acid solution of hydrobromic acid or other acid or base, synthesizing the tertrapeptide of R-Ala-D-iso-Gln-Lys(Z)-$NH_2$ by the active ester method;
(3) At last, removing the Z protective group by the mixed solution of boron trifluoride ethylether, trifluoroacetic acid and ethanethiol (v/v/v=9:9:2) to obtain the crude product, and purifying the crude product to obtain muramyl dipeptide analogue.

33. The method according to claim 32, wherein the amino acids of Fmoc-L-Lys(Boc)-COOH, Fmoc-D-iso-Gln-COOH, Fmoc-L-Ala-COOH in the solid-phase synthesis can be replaced by any natural or unnatural amino acid.

34. The method according to claim 29, wherein the method for preparing the conjugates of muramyl dipeptide analogue and paclitaxel or conjugates of muramyl dipeptide analogue and docetaxel comprises:
1) Firstly, dissolving paclitaxel-2'-O-alkane-di-acid monoester or docetaxel-2'-O-alkane-di-acid monoester, HOSu and DIC with molar ratio (2:1-1:2) in the solution of dimethyl sulfoxide or N,N-dimethyl formamide or N-methyl pyrrolidone, then allowing the solution to react for 1-10 hours at the temperature of −20° C. to +50° C.;
2) Then, adding equimolar proportions of muramyl dipeptide analogue to the solution of dimethyl sulfoxide or N,N-dimethyl formamide or N-methyl pyrrolidone, adjusting the pH of the reaction system to 6 to 8 by alkalescence reagent N-methyl morpholine, allowing the reaction to continue for 1-10 hours, obtaining the conjugate after reaction completed;
3) At last, adding any one of water, methanol, ethanol, diethyl ether, petroleum ether and ethyl butyl ether to the reaction solution, and filtering the precipitated solid, and purifying the crude product by preparative HPLC or recrystallization and obtaining the target product.

35. A compound of formula I, and/or a pharmaceutically acceptable salt thereof,

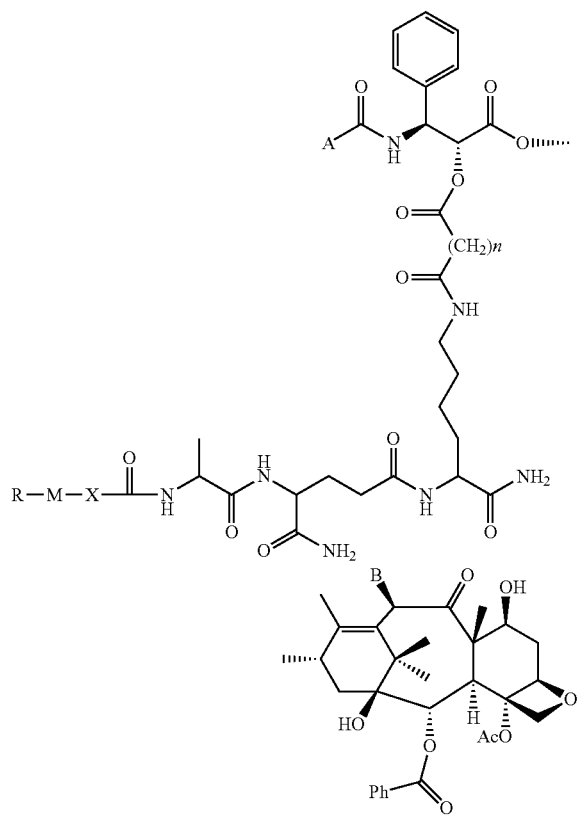

I wherein when A is phenyl, B is acetoxy; when A is tert-butoxy, B is hydroxy; n=2, 3, 4, 5, 6, 7, 8, 9, 10, 11 or 12;

wherein X is chosen from $C_{1-6}$ alkyl, $C_{1-6}$ alkylene and $C_{1-6}$ alkyl comprising at least one heteroatom, wherein the at least one heteroatom is independently chosen from oxygen, sulfur and nitrogen; or X is a single bond;

wherein M is chosen from

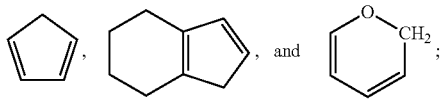

wherein R is chosen from hydrogen, substituted or unsubstituted straight or branched $C_{1-6}$ alkyl, hydroxy, substituted or unsubstituted straight or branched $C_{1-6}$ alkoxy, thiol, substituted or unsubstituted straight or branched $C_{1-6}$ alkylthio, $C_{1-6}$ alkoxy-$C_{1-6}$ alkyl, amino; substituted or unsubstituted straight or branched $C_{1-6}$ mono- and di-alkylamino; aldehyde group, substituted or unsubstituted straight or branched $C_{1-6}$ alkylcarbonyl, carboxyl, substituted or unsubstituted straight or branched $C_{1-6}$ alkylcarboxyl, carbamoyl, substituted or unsubstituted straight or branched $C_{1-6}$ alkylamide, $C_{2-6}$ alkene, halogen, nitro and cyano;

wherein the substituent(s) on $C_1$-$C_6$ straight chain or branched chain described herein is independently chosen from hydroxyl, thiol, amino, aldehyde group, carboxyl, carbamoyl, halogen, nitro and cyano.

* * * * *